US008293902B2

(12) United States Patent
Hennequin

(10) Patent No.: US 8,293,902 B2
(45) Date of Patent: Oct. 23, 2012

(54) QUINAZOLINE COMPOUNDS

(75) Inventor: Laurent Francois Andre Hennequin, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 1379 days.

(21) Appl. No.: 11/705,035

(22) Filed: Feb. 12, 2007

(65) Prior Publication Data

US 2008/0027069 A1 Jan. 31, 2008

Related U.S. Application Data

(63) Continuation of application No. 10/502,538, filed as application No. PCT/GB03/00343 on Jan. 28, 2003, now Pat. No. 7,268,230.

(30) Foreign Application Priority Data

Feb. 1, 2002 (EP) .................................. 02290242

(51) Int. Cl.
*C07D 239/02* (2006.01)
*C07D 401/12* (2006.01)
(52) U.S. Cl. ...................................... 544/280; 544/288
(58) Field of Classification Search .................. None
See application file for complete search history.

(56) References Cited

U.S. PATENT DOCUMENTS

| 5,120,782 A | 6/1992 | Hubsch et al. |
| 5,212,195 A | 5/1993 | Clark et al. |
| 5,338,849 A | 8/1994 | Festal et al. |
| 5,380,739 A | 1/1995 | Clark et al. |
| 5,409,930 A | 4/1995 | Spada et al. |
| 5,411,963 A | 5/1995 | Dreilcorn et al. |
| 5,480,883 A | 1/1996 | Spada et al. |
| 5,646,153 A | 7/1997 | Spada et al. |
| 5,710,158 A | 1/1998 | Myers et al. |
| 5,714,493 A | 2/1998 | Myers et al. |
| 5,714,495 A | 2/1998 | Viaud et al. |
| 5,721,237 A | 2/1998 | Myers et al. |
| 5,736,534 A | 4/1998 | Arnold et al. |
| RE36,256 E | 7/1999 | Spada et al. |
| 5,962,458 A | 10/1999 | Lohmann et al. |
| 6,046,206 A | 4/2000 | Pamukcu et al. |
| 6,057,320 A | 5/2000 | Spada et al. |
| 6,071,921 A | 6/2000 | Lohmann et al. |
| 6,153,617 A | 11/2000 | Bridges |
| 6,162,804 A | 12/2000 | Bilodeau et al. |
| 6,184,225 B1 | 2/2001 | Thomas et al. |
| 6,225,318 B1 | 5/2001 | Sobolov-Jaynes et al. |
| 6,258,951 B1 | 7/2001 | Lohmann et al. |
| 6,265,411 B1 | 7/2001 | Thomas et al. |
| 6,291,455 B1 | 9/2001 | Thomas et al. |
| 6,294,532 B1 | 9/2001 | Thomas et al. |
| 6,362,336 B1 | 3/2002 | Lohmann et al. |
| 6,414,148 B1 | 7/2002 | Thomas et al. |
| 6,514,971 B1 | 2/2003 | Thomas et al. |
| 6,531,491 B1 | 3/2003 | Kania et al. |
| 6,645,969 B1 | 11/2003 | Myers et al. |
| 6,673,803 B2 | 1/2004 | Thomas et al. |
| 6,809,097 B1 | 10/2004 | Thomas et al. |
| 6,887,874 B2 | 5/2005 | Hennequin |
| 6,897,210 B2 | 5/2005 | Thomas et al. |
| 7,049,438 B2 | 5/2006 | Hennequin et al. |
| 7,074,800 B1 | 7/2006 | Stokes et al. |
| 7,087,602 B2 | 8/2006 | Thomas et al. |
| 7,117,615 B2 | 10/2006 | Gerber |
| 7,160,889 B2 | 1/2007 | Hennequin et al. |
| 7,173,038 B1 | 2/2007 | Thomas et al. |
| 7,262,201 B1 | 8/2007 | Hennequin et al. |
| 7,268,230 B2 | 9/2007 | Hennequin et al. |
| 7,371,765 B2 | 5/2008 | Hennequin |
| 7,696,214 B2 | 4/2010 | Hennequin et al. |
| 7,851,623 B2 | 12/2010 | Arnott et al. |
| 7,989,460 B2 * | 8/2011 | Hennequin ................ 514/266.1 |
| 2002/0177601 A1 | 11/2002 | Himmelsbach et al. |
| 2003/0144298 A1 | 7/2003 | Curwen et al. |
| 2003/0191308 A1 | 10/2003 | Hennequin et al. |
| 2003/0199491 A1 | 10/2003 | Hennequin |
| 2003/0199513 A1 | 10/2003 | Thomas et al. |
| 2003/0207878 A1 | 11/2003 | Hennequin |
| 2003/0225111 A1 | 12/2003 | Hennequin et al. |
| 2005/0043336 A1 | 2/2005 | Hennequin et al. |

(Continued)

FOREIGN PATENT DOCUMENTS

DE 19614718 10/1997

(Continued)

OTHER PUBLICATIONS

Flaugh et al, Synthesis and Evaluation of the Antiovulatory Activity of a Variety of Melatonin Analogues, J. Med. Chem., 22(1); 63-69 (1979).

Gazit et al., Tyrophostins IV—Highly Potent Inhibitors . . . Relationship Study of 4-Anilidoquinazolines, Bioorganic & Medicinal Chemistry, vol. 4. No. 8, 1996, pp. 1203-1207.

Gibson et al., Epidermal growth factor receptor tyrosine kinase: structure-activity relationships and antitumour activity of novel quinazolines, Bioorganic & Medicinal Chemistry, vol. 7, No. 21, 1997, 2723-2728.

(Continued)

*Primary Examiner* — Noble Jarrell

(74) *Attorney, Agent, or Firm* — Morgan, Lewis & Bockius LLP

(57) ABSTRACT

The invention relates to compounds of the formula (I) wherein ring C, Z, m, n, $R^1$ and $R^2$ are defined herein and salts thereof; their use in the manufacture of a medicament for use in the production of an antiangiogenic and/or vascular permeability reducing effect in warm-blooded animals; processes for the preparation of such compounds; intermediates used in such processes; processes for making such intermediates; pharmaceutical compositions containing a compound of formula I or a pharmaceutically acceptable salt thereof and methods of treating disease states involving angiogenesis by administering a compound of formula I or a pharmaceutically acceptable salt thereof.

7 Claims, No Drawings

U.S. PATENT DOCUMENTS

| | | |
|---|---|---|
| 2005/0043395 A1 | 2/2005 | Wedge |
| 2005/0054662 A1 | 3/2005 | Hennequin et al. |
| 2005/0085465 A1 | 4/2005 | Hennequin |
| 2005/0222183 A1 | 10/2005 | Wedge |
| 2005/0239777 A1 | 10/2005 | Thomas et al. |
| 2006/0004017 A1 | 1/2006 | Stokes |
| 2006/0148819 A1 | 7/2006 | Hennequin |
| 2006/0235042 A1 | 10/2006 | Graczyk et al. |
| 2007/0027145 A1 | 2/2007 | Hennequin |
| 2007/0066633 A1 | 3/2007 | Hennequin |
| 2007/0082921 A1 | 4/2007 | Hennequin et al. |
| 2007/0088044 A1 | 4/2007 | Hennequin et al. |
| 2007/0129387 A1 | 6/2007 | McCabe |
| 2008/0058342 A1 | 3/2008 | Hennequin |
| 2008/0221322 A1 | 9/2008 | Arnott et al. |
| 2009/0156821 A1 | 6/2009 | Hennequin |
| 2009/0203905 A1 | 8/2009 | Blixt et al. |
| 2010/0280042 A1 | 11/2010 | Hennequin et al. |
| 2010/0298357 A1 | 11/2010 | McCabe |
| 2011/0071144 A1 | 3/2011 | Thomas et al. |

FOREIGN PATENT DOCUMENTS

| | | |
|---|---|---|
| EP | 0326330 | 8/1989 |
| EP | 0602851 | 6/1994 |
| EP | 0837063 | 4/1998 |
| EP | 1029853 | 8/2000 |
| GB | 2345486 | 7/2000 |
| WO | WO 87/04321 | 7/1987 |
| WO | WO 92/20642 | 11/1992 |
| WO | WO 95/15758 | 6/1995 |
| WO | WO 95/19169 | 7/1995 |
| WO | WO 95/23141 | 8/1995 |
| WO | WO 95/24190 | 9/1995 |
| WO | WO 96/29301 | 9/1996 |
| WO | WO 96/39145 | 12/1996 |
| WO | WO 97/03069 | 1/1997 |
| WO | WO 97/17329 | 5/1997 |
| WO | WO 97/22596 | 6/1997 |
| WO | WO 97/30034 | 8/1997 |
| WO | WO 97/30035 | 8/1997 |
| WO | WO 97/32856 | 9/1997 |
| WO | WO 97/34876 | 9/1997 |
| WO | WO 97/42187 | 11/1997 |
| WO | WO 98/02434 | 1/1998 |
| WO | WO 98/13350 | 4/1998 |
| WO | WO 98/13354 | 4/1998 |
| WO | WO 98/54093 | 12/1998 |
| WO | WO 99/06396 | 2/1999 |
| WO | WO 99/10349 | 3/1999 |
| WO | WO 99/21859 | 5/1999 |
| WO | WO 99/35132 | 7/1999 |
| WO | WO 99/35146 | 7/1999 |
| WO | WO 00/06554 | 2/2000 |
| WO | WO 00/12497 | 3/2000 |
| WO | WO 00/21955 | 4/2000 |
| WO | WO 00/44728 | 8/2000 |
| WO | WO 00/47212 | 8/2000 |
| WO | WO 00/55141 | 9/2000 |
| WO | WO 01/02369 | 1/2001 |
| WO | WO 01/29025 | 4/2001 |
| WO | WO 01/32651 | 5/2001 |
| WO | WO 01/66099 | 9/2001 |
| WO | WO 01/74360 | 10/2001 |
| WO | WO 01/77085 | 10/2001 |
| WO | WO 01/94341 | 12/2001 |
| WO | WO 02/12226 | 2/2002 |
| WO | WO 02/12227 | 2/2002 |
| WO | WO 02/12228 | 2/2002 |
| WO | WO 02/16352 | 2/2002 |
| WO | WO 03/020699 | 3/2003 |
| WO | WO 03/037252 | 5/2003 |
| WO | WO 03/039551 | 5/2003 |
| WO | WO 03/040108 | 5/2003 |
| WO | WO 03/040109 | 5/2003 |
| WO | WO 2004/014383 | 2/2004 |
| WO | WO 2004/014426 | 2/2004 |
| WO | WO 2004/032937 | 4/2004 |
| WO | WO 2004/071397 | 8/2004 |
| WO | WO 2005/013998 | 2/2005 |
| WO | WO 2005/014582 | 2/2005 |
| WO | WO 2005/061488 | 7/2005 |
| WO | WO 2007/036713 | 4/2007 |

OTHER PUBLICATIONS

Hara et al., On the Amination of Azaheterocycles. A New Procedure for the Introduction of an Amino Group (I), J. Heterocyclic Chem. vol. 19, 1982, pp. 1285-1287.

Karminski et al., The Synthesis of Some Quinazoline Derivatives and Their Biological Properties; J. Environ. Sci. Health, vol. B18, 1983, pp. 599-610.

Sinyak, et al., Synthesis and Biological Properties of Derivatives of 4-Heterylmercaptoquinazoline, Zaporozh'e Medical Institute pp. 103-106, translated from Khimiko-farmatsevticheskii Zhurnal, vol. 20, No. 2, Feb. 1986, 168-171, original article submitted Dec. 29, 1984.

Mazeas et al. "Synthesis of new melatoninergic ligands including azaindole moiety" Heterocycles 50(2): 1065-1080 (1999).

* cited by examiner

QUINAZOLINE COMPOUNDS

This application is a continuation of U.S. Ser. No. 10/502,538, filed Jul. 28, 2004 (now U.S. Pat. No. 7,268,230), which is a 371 of PCT/GB03/00343 filed Jan. 28, 2003, which claims priority from EP02290242.3 filed on Feb. 1, 2002.

The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al., 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al., 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844). Basic FGF (bFGF) is a potent stimulator of angiogenesis (e.g. Hayek et al, 1987, Biochem. Biophys. Res. Commun. 147: 876-880) and raised levels of FGFs have been found in the serum (Fujimoto et al, 1991, Biochem Biophys. Res. Commun. 180: 386-392) and urine (Nguyen et al, 1993, J. Natl. Cancer. Inst. 85: 241-242) of patients with cancer.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt-1, the kinase insert domain-containing receptor, KDR (also referred to as Flk-1), and another fms-like tyrosine kinase receptor, Flt-4. Two of these related RTKs, Flt-1 and KDR, have been shown to bind VEGF with high affinity (De Vries et al, 1992, Science 255: 989-991; Tennan et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

The present invention is based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation including macular degeneration.

VEGF is a key stimulus for vasculogenesis and angiogenesis. This cytokine induces a vascular sprouting phenotype by inducing endothelial cell proliferation, protease expression and migration, and subsequent organisation of cells to form a capillary tube (Keck, P. J., Hauser, S. D., Krivi, G., Sanzo, K., Warren, T., Feder, J., and Connolly, D. T., Science (Washington D.C.), 246: 1309-1312, 1989; Lamoreaux, W. J., Fitzgerald, M. E., Reiner, A., Hasty, K. A., and Charles, S. T., Microvasc. Res., 55: 29-42, 1998; Pepper, M. S., Montesano, R., Mandroita, S. J., Orci, L. and Vassalli, J. D., Enzyme Protein, 49: 138-162, 1996.). In addition, VEGF induces significant vascular permeability (Dvorak, H. F., Detinar, M., Claffey, K. P., Nagy, J. A., van de Water, L., and Senger, D. R., (Int. Arch Allergy Immunol., 107: 233-235, 1995; Bates, D. O., Heald, R. I., Curry, F. E. and Williams, B. J. Physiol. (Lond.), 533: 263-272, 2001), promoting formation of a hyper-permeable, immature vascular network which is characteristic of pathological angiogenesis.

It has been shown that activation of KDR alone is sufficient to promote all of the major phenotypic responses to VEGF, including endothelial cell proliferation, migration, and survival, and the induction of vascular permeability (Meyer, M., Clauss, M., Lepple-Wienhues, A., Waltenberger, J., Augustin, H. G., Ziche, M., Lanz, C., Büttner, M., Rziha, H-J., and Dehio, C., EMBO J., 18: 363-374, 1999; Zeng, H., Sanyal, S, and Mukhopadhyay, D., J. Biol. Chem., 276: 32714-32719, 2001; Gille, H., Kowalski, J., Li, B., LeCouteri, J., Moffat, B, Zioncheck, T. F., Pelletier, N. and Ferrara, N., J. Biol. Chem., 276: 3222-3230, 2001).

International patent application publication number WO 00/47212 describes VEGF receptor tyrosine kinase inhibitors. Compounds of WO 00/47212 possess activity against VEGF receptor tyrosine kinase (RTK) such that they may be used in an amount sufficient to inhibit VEGF RTK whilst demonstrating no significant activity against EGF RTK. Their VEGF RTK inhibitory activity is due both to activity against KDR and against Flt-1, but generally they are more potent against KDR. Generally they have extended plasma pharmacokinetics. Some VEGF RTK inhibitors have been found to act as potassium channel blockers and are positive in a hERG assay; such activity may give rise to ECG (electrocardiogram) changes in vivo. Compounds of WO 00/47212 have predominantly basic side chains.

Surprisingly we have now found compounds of the present invention to be very potent KDR inhibitors but to have less activity against Flt-1 than compounds of WO 00/47212, to have less extended plasma pharmacokinetics than compounds of WO 00/47212 and to be inactive or only weakly active in a hERG assay. Compounds of the present invention have predominantly neutral side chains. Compounds of the present invention have a beneficial toxicological profile compared to compounds of WO 00/47212.

According to one aspect of the present invention there is provided the use of a compound of the formula I:

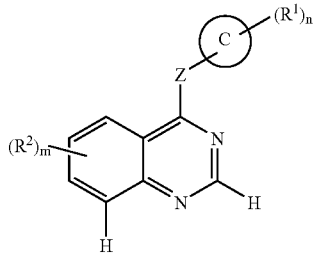

wherein:
ring C is an 8, 9, 10, 12 or 13-membered bicyclic or tricyclic moiety which moiety may be saturated or unsaturated, which may be aromatic or non-aromatic, and which optionally may contain 1-3 heteroatoms selected independently from O, N and S;
Z is —O—, —NH— or —S—;
n is 0, 1, 2, 3, 4 or 5;
m is 0, 1, 2 or 3;
$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —$NR^3R^4$ (wherein $R^3$ and $R^4$, which may be the same or different, each represents hydrogen or $C_{1-3}$alkyl), or $R^5X^1$— (wherein $X^1$ represents a direct bond, —O—, —$CH_2$—, —OC(O)—, —C(O)—, —S—, —SO—, —$SO_2$—, —$NR^6C(O)$—, —$C(O)NR^7$—, —$SO_2NR^8$—, —$NR^9SO_2$— or —$NR^{10}$— (wherein $R^6$, $R^7$, $R^8$, $R^9$ and $R^{10}$ each independently represents hydrogen, $C_{1-3}$alkyl or $C_{1-3}$alkoxy$C_{2-3}$alkyl), and $R^5$ is selected from one of the following twenty-two groups:
1) hydrogen, oxiranyl$C_{1-4}$alkyl or $C_{1-5}$alkyl which may be unsubstituted or which may be substituted with one or more groups selected from hydroxy, fluoro, chloro, bromo and amino;
2) $C_{1-5}$alkyl$X^2C(O)R^{11}$ (wherein $X^2$ represents —O— or —$NR^{12}$— (in which $R^{12}$ represents hydrogen, $C_{1-3}$alkyl or $C_{1-3}$alkoxy$C_{2-3}$alkyl) and $R^{11}$ represents $C_{1-3}$alkyl, —$NR^{13}R^{14}$ or —$OR^{15}$ (wherein $R^{13}$, $R^{14}$ and $R^{15}$ which may be the same or different each represents hydrogen, $C_{1-5}$alkyl or $C_{1-3}$alkoxy$C_{2-3}$alkyl));
3) $C_{1-5}$alkyl$X^3R^{16}$ (wherein $X^3$ represents —O—, —S—, —SO—, —$SO_2$—, —OC(O)—, —$NR^{17}C(O)$—, —C(O)$NR^{11}$—, —$SO_2NR^{19}$—, —$NR^{20}SO_2$ or —$NR^{2}$— (wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl) and $R^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
4) $C_{1-5}$alkyl$X^4C_{1-5}$alkyl$X^5R^{22}$ (wherein $X^4$ and $X^5$ which may be the same or different are each —O—, —S—, —SO—, —$SO_2$—, —$NR^{23}C(O)$—, —C(O)$NR^{24}$—, —$SO_2NR^{25}$—, $NR^{26}SO_2$ or $NR^{27}$—(wherein $R^{23}$, $R^{24}$, $R^{25}$, $R^{26}$ and $R^{27}$ each independently represents hydrogen, $C_{1-3}$alkyl or $C_{1-3}$alkoxy$C_{2-3}$alkyl) and $R^{22}$ represents hydrogen, $C_{1-3}$alkyl or $C_{1-3}$alkoxy$C_{2-3}$alkyl);
5) $R^{28}$ (wherein $R^{28}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
6) $C_{1-5}$alkyl$R^{28}$ (wherein $R^{28}$ is as defined hereinbefore);
7) $C_{2-5}$alkenyl$R^{28}$ (wherein $R^{28}$ is as defined hereinbefore);
8) $C_{2-5}$alkynyl$R^{28}$ (wherein $R^{28}$ is as defined hereinbefore);
9) $R^{29}$ (wherein $R^{29}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from oxo, hydroxy, halogeno, amino, $C_{1-4}$alkyl, $C_{1-4}$alkoxy, $C_{1-4}$hydroxyalkyl, $C_{1-4}$aminoayl, $C_{1-4}$alkylamino, $C_{1-4}$hydroxyalkoxy, carboxy, trifluoromethyl, cyano, —C(O)$NR^{30}R^{31}$, —$NR^{32}C(O)R^{33}$ (wherein $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
10) $C_{1-5}$alkyl$R^{29}$ (wherein $R^{29}$ is as defined hereinbefore);
11) $C_{2-5}$alkenyl$R^{29}$ (wherein $R^{29}$ is as defined hereinbefore);
12) $C_{2-5}$alkynyl$R^{29}$ (wherein $R^{29}$ is as defined hereinbefore);
13) $C_{1-5}$alkyl$X^6R^{29}$ (wherein $X^6$ represents —O—, —S—, —SO—, —$SO_2$—, —$NR^{34}C(O)$—, —C(O)$NR^{35}$, $SO_2NR^{36}$, —$NR^{37}SO_2$— or —$NR^{38}$— (wherein $R^{34}$, $R^3$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);
14) $C_{2-5}$alkenyl$X^7R^{29}$ (wherein $X^7$ represents —O—, —S—, —SO—, —$SO_2$—, —$NR^{39}C(O)$—, —C(O)$NR^{40}$—, —$SO_2NR^{41}$—, —$NR^{42}SO_2$ or —$NR^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);
15) $C_{2-5}$alkynyl$X^8R^{29}$ (wherein $X^8$ represents —O—, —S—, —SO—, —$SO_2$—, —$NR^{44}C(O)$—, —C(O)$NR^{45}$—, —$SO_2NR^{46}$—, —$NR^{47}SO_2$— or —$NR^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);
16) $C_{1-4}$alkyl$X^9C_{1-4}$alkyl$R^{29}$ (wherein $X^9$ represents —O—, —S—, —SO—, —$SO_2$—, —$NR^{49}C(O)$—, —C(O)$NR^{50}$—, —SO₂NR⁵¹—, —NR⁵²SO₂— or —NR⁵³— (wherein R⁴⁹, R⁵⁰, R⁵¹, R⁵² and R¹³ each independently represents hydrogen, $C_{1-3}$alkyl or $C_{1-3}$alkoxy$C_{2-3}$alkyl) and R²⁹ is as defined hereinbefore);

17) $C_{1-4}$alkylX⁹$C_{1-4}$alkylR²⁸ (wherein X⁹ and R²⁸ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenylX⁹$C_{1-4}$alkylR²⁸ (wherein X⁹ and R²⁸ are as defined hereinbefore);

21) $C_{2-5}$alkynylX⁹$C_{1-4}$alkylR²⁸ (wherein X⁹ and R²⁸ are as defined hereinbefore); and 22) $C_{1-4}$alkylR⁵⁴($C_{1-4}$alkyl)$_q$(X⁹)$_r$R⁵⁵ (wherein X⁹ is as defined hereinbefore, q is 0 or 1, r is 0 or 1, and R⁵⁴ and R⁵⁵ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl), with the proviso that R⁵⁴ cannot be hydrogen);

and additionally wherein any $C_{1-5}$alkyl, $C_{2-5}$alkenyl or $C_{2-5}$alkynyl group in R⁵X¹— which is linked to X¹ may bear one or more substituents selected from hydroxy, halogeno and amino); R¹ represents hydrogen, oxo, halogeno, hydroxy, $C_{1-4}$alkoxy, $C_{1-4}$alkyl, $C_{1-4}$alkoxymethyl, $C_{1-4}$alkanoyl, $C_{1-4}$haloalkyl, cyano, amino, $C_{2-5}$alkenyl, $C_{2-5}$alkynyl, $C_{1-3}$alkanoyloxy, nitro, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, N—($C_{1-4}$alkylsulphonyl)amino, N—($C_{1-4}$alkylsulphonyl)-N—($C_{1-4}$alkyl)amino, N,N-di($C_{1-4}$alkylsulphonyl)amino, a $C_{3-7}$alkylene chain joined to two ring C carbon atoms, $C_{1-4}$alkanoylamino$C_{1-4}$alkyl, carboxy or a group R⁵⁶X¹⁰ (wherein X¹⁰ represents a direct bond, —O—, —CH₂—, —OC(O)—, —C(O)—, —S—, —SO—, —SO₂—, —NR⁵⁷C(O)—, —C(O)NR¹⁸—, —SO₂NR⁵⁹—, —NR⁶⁰SO₂— or —NR⁶¹— (wherein R⁵⁷, R⁵⁸, R⁵⁹, R⁶⁰ and R⁶¹ each independently represents hydrogen, $C_{1-3}$alkyl or $C_{1-3}$alkoxy$C_{2-3}$alkyl), and R⁵⁶ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;

2) $C_{1-5}$alkylX¹¹C(O)R⁶² (wherein X¹¹ represents —O— or —NR⁶³— (in which R⁶³ represents hydrogen, $C_{1-3}$alkyl or $C_{1-3}$alkoxy$C_{2-3}$alkyl) and R⁶² represents $C_{1-3}$alkyl, —NR⁶⁴R⁶⁵ or —OR⁶⁶ (wherein R⁶⁴, R⁶⁵ and R⁶⁶ which may be the same or different each represents hydrogen, $C_{1-5}$alkyl or $C_{1-3}$alkoxy$C_{2-3}$alkyl));

3) $C_{1-5}$alkylX¹²R⁶⁷ (wherein X¹² represents —O—, —S—, —SO—, —SO₂—, —OC(O)—, —NR⁶⁸C(O)—, —C(O)NR⁶⁹—, —SO₂NR⁷⁰—, —NR⁷¹SO₂— or —NR⁷²— (wherein R⁶⁸, R⁶⁹, R⁷⁰, R⁷¹ and R⁷² each independently represents hydrogen, $C_{1-3}$alkyl or $C_{1-3}$alkoxy$C_{2-3}$alkyl) and R⁶⁷ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

4) $C_{1-5}$alkylX¹³$C_{1-5}$alkylX¹⁴R⁷³ (wherein X¹³ and X¹⁴ which may be the same or different are each —O—, —S—, —SO—, —SO₂—, —NR⁷⁴C(O)—, —C(O)NR¹⁵—, —SO₂NR⁷⁶—, —NR⁷⁷SO₂— or —NR⁷⁸— (wherein R⁷⁴, R⁷⁵, R⁷⁶, R⁷⁷ and R⁷⁸ each independently represents hydrogen, $C_{1-3}$alkyl or $C_{1-3}$alkoxy$C_{2-3}$alkyl) and R⁷³ represents hydrogen, $C_{1-3}$alkyl or $C_{1-3}$alkoxy$C_{2-3}$alkyl);

5) R⁷⁹ (wherein R⁷⁹ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

6) $C_{1-5}$alkylR⁷⁹ (wherein R⁷⁹ is as defined hereinbefore);

7) $C_{2-5}$alkenylR⁷⁹ (wherein R⁷⁹ is as defined hereinbefore);

8) $C_{2-5}$alkynylR⁷⁹ (wherein R⁷⁹ is as defined hereinbefore);

9) R⁸⁰ (wherein R⁸⁰ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from oxo, hydroxy, halogeno, amino, $C_{1-4}$alkyl, $C_{1-4}$alkoxy, $C_{1-4}$hydroxyalkyl, $C_{1-4}$-aminoalkyl, $C_{1-4}$alkylamino, $C_{1-4}$hydroxyalkoxy, carboxy, trifluoromethyl, cyano, —C(O)NR⁸¹R⁸², —NR⁸³C(O)R⁴ (wherein R⁸¹, R⁸², R⁸³ and R⁴, which may be the same or different, each represents hydrogen, $C_{1-4}$alkyl or $C_{1-3}$alkoxy$C_{2-3}$alkyl) and a group —(—O—)$_f$($C_{1-4}$-alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

10) $C_{1-5}$alkyl$R^{80}$ (wherein $R^{80}$ is as defined hereinbefore);

10) $C_{2-5}$alkenyl$R^{80}$ (wherein $R^{80}$ is as defined hereinbefore);

12) $C_{2-5}$alkynyl$R^{80}$ (wherein $R^{80}$ is as defined hereinbefore);

13) $C_{1-5}$alkyl$X^{15}R^{80}$ (wherein $X^{15}$ represents —O—, —S—, —SO—, —SO$_2$—, —NR$^{85}$C(O)—, —C(O)NR$^{86}$—, —SO$_2$NR$^{87}$—, —NR$^{88}$SO$_2$— or —NR$^{89}$— (wherein $R^{85}$, $R^{86}$, $R^{87}$, $R^{88}$ and $R^{89}$ each independently represents hydrogen, $C_{1-3}$alkyl or $C_{1-3}$alkoxy$C_{2-3}$alkyl) and $R^{80}$ is as defined hereinbefore);

14) $C_{2-5}$alkenyl$X^{16}R^{10}$ (wherein $X^{16}$ represents —O—, —S—, —SO—, —SO$_2$—, —NR$^{90}$C(O)—, —C(O)NR$^{91}$—, —SO$_2$NR$^{92}$—, —NR$^{93}$SO$_2$— or —NR$^{94}$— (wherein $R^{90}$, $R^{91}$, $R^{92}$, $R^{93}$ and $R^{94}$ each independently represents hydrogen, $C_{1-3}$alkyl or $C_{1-3}$alkoxy$C_{2-3}$alkyl) and $R^{80}$ is as defined hereinbefore);

15) $C_{2-5}$alkynyl$X^{17}R^{80}$ (wherein $X^{17}$ represents —O—, —S—, —SO—, —SO$_2$—, —NR$^{95}$C(O)—, —C(O)NR$^{96}$—, —SO$_2$NR$^{97}$—, —NR$^{98}$SO$_2$— or —NR$^{99}$— (wherein $R^{95}$, $R^{96}$, $R^{97}$, $R^{93}$ and $R^{99}$ each independently represents hydrogen, $C_{1-3}$alkyl or $C_{1-3}$alkoxy$C_{2-3}$alkyl) and $R^{80}$ is as defined hereinbefore);

16) $C_{1-4}$alkyl$X^{18}C_{1-4}$alkyl$R^{80}$ (wherein $X^{18}$ represents —O—, —S—, —SO—, —SO$_2$—, —NR$^{100}$C(O)—, —C(O)NR$^{101}$—, —SO$_2$NR$^{102}$—, —NR$^{103}$SO$_2$ or —NR$^{104}$— (wherein $R^{100}$, $R^{101}$, $R^{102}$, $R^{103}$ and $R^{104}$ each independently represents hydrogen, $C_{1-3}$alkyl or $C_{1-3}$alkoxy$C_{2-3}$alkyl) and $R^{80}$ is as defined hereinbefore);

17) $C_{1-4}$alkyl$X^{18}C_{1-4}$alkyl$R^{79}$ (wherein $X^{18}$ and $R^{79}$ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphouyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^{18}C_{1-4}$alkyl$R^{79}$ (wherein $X^{18}$ and $R^{79}$ are as defined hereinbefore);

21) $C_{2-5}$alkynyl$X^{18}C_{1-4}$alkyl$R^{79}$ (wherein $X^{18}$ and $R^{79}$ are as defined hereinbefore); and 22) $C_{1-4}$alkyl$R^{105}(C_{1-4}$alkyl$)_x(X''^8)_yR^{106}$ (wherein $X^{18}$ is as defined hereinbefore, x is 0 or 1, y is 0 or 1, and $R^{105}$ and $R^{106}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl) with the proviso that $R^{105}$ cannot be hydrogen);

and additionally wherein any $C_{1-5}$alkyl, $C_{2-5}$alkenyl or $C_{2-5}$alkynyl group in $R^{56}X^{10}$— which is linked to $X^{10}$ may bear one or more substituents selected from hydroxy, halogeno and amino); with the proviso that one or more $R^1$ and/or one or more $R^2$ are selected from one of the following five groups:

(i) $Q^1X^1$ wherein $X^1$ is as defined hereinbefore and $Q^1$ is selected from one of the following ten groups:

1) $Q^2$ (wherein $Q^2$ is a 5-6-membered saturated or partially unsaturated heterocyclic group with 1-2 heteroatoms, selected independently from O, S and N, which heterocyclic group bears at least one substituent selected from $C_{2-5}$alkenyl, $C_{2-5}$alkynyl, $C_{1-6}$-fluoroalkyl, $C_{1-6}$alkanoyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-4}$alkylsulphonyl and $C_{1-6}$-fluoroalkylsulphonyl and which heterocyclic group may optionally bear a further 1 or 2 substituents selected from $C_{2-5}$alkenyl, $C_{2-5}$alkynyl, $C_{1-6}$-fluoroalkyl, $C_{1-6}$alkanoyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$-fluoroalkanoyl, carbamoyl, $C_{1-4}$alkylcarbamoyl, di($C_{1-4}$alkyl) carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-4}$alkylsulphonyl, $C_{1-6}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylamino$C_{1-4}$alkyl, di($C_{1-4}$alkyl) amino$C_{1-4}$alkyl, $C_{1-4}$alkylamino$C_{1-4}$alkoxy, di($C_{1-4}$alkyl) amino$C_{1-4}$alkoxy and a group —(—O—)$_f(C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which cyclic group may bear one or more substituents selected from $C_{1-4}$alkyl));

2) $C_{1-5}$alkyl$W^1Q^2$ (wherein $W^1$ represents —O—, —S—, —SO—, —SO$_2$—, —OC(O)—, —NQ$^6$C(O)—, —C(O)NQ$^4$-, —SO$_2$NQ$^5$-, —NQ$^6$SO$_2$— or —NQ$^7$- (wherein $Q^3$, $Q^4$, $Q^5$, $Q^6$ and $Q^7$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl) and $Q^2$ is as defined hereinbefore;

3) $C_{1-5}$alkyl$Q^2$ (wherein $Q^2$ is as defined hereinbefore);

4) $C_{2-5}$alkenyl$Q^2$ (wherein $Q^2$ is as defined hereinbefore);

5) $C_{2-5}$alkynyl$Q^2$ (wherein $Q^2$ is as defined hereinbefore);

6) $C_{1-4}$alkyl$W^2C_{1-4}$alkyl$Q^2$ (wherein $W^2$ represents —O—, —S—, —SO—, —SO$_2$—, —NQ$^8$C(O)—, —C(O)NQ$^9$-, —SO$_2$NQ$^{10}$-, —NQ$^{11}$SO$_2$— or —NQ$^{12}$- (wherein $Q^8$, $Q^9$, $Q^{10}$, $Q^{11}$ and $Q^{12}$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl) and $Q^2$ is as defined hereinbefore);

7) $C_{2-5}$alkenyl$W^2C_{1-4}$alkyl$Q^2$ (wherein $W^2$ and $Q^2$ are as defined hereinbefore);

8) $C_{2-5}$alkynyl$W^2C_{1-4}$alkyl$Q^2$ (wherein $W^2$ and $Q^2$ are as defined hereinbefore);

9) $C_{1-4}$alkyl$Q^{13}(C_{1-4}$alkyl$)_j(W^2)_kQ^{14}$ (wherein $W^2$ is as defined hereinbefore, j is 0 or 1, k is 0 or 1, and $Q^{13}$ and $Q^{14}$ are each independently selected from hydrogen, $C_{1-3}$alkyl, cyclopentyl, cyclohexyl and a 5-6-membered saturated or partially unsaturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1, 2 or 3 substituents selected from $C_{2-5}$alkenyl, $C_{2-5}$alkynyl, $C_{1-6}$-fluoroalkyl, $C_{1-6}$alkanoyl, amino$C_{1-6}$ alkanoyl, $C_{1-4}$alkylamino$C_{1-6}$alkanoyl, di($C_{1-4}$alkyl)amino$C_{1-6}$alkanoyl, $C_{1-6}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamnoyl$C_{1-4}$alkyl, di($C_{1-4}$alkyl)carbamoyl$C_{1-6}$alkyl, $C_{1-6}$alkylsulphonyl, $C_{1-6}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl), with the provisos that $Q^{13}$ cannot be hydrogen and one or both of $Q^{13}$ and $Q^{14}$ must be a 5-6-membered saturated or partially unsaturated heterocyclic group as defined hereinbefore which heterocyclic group bears at least one substituent selected from $C_{2-5}$alkenyl, $C_{2-5}$alkynyl, $C_{1-6}$-fluoroalkyl, $C_{1-6}$alkanoyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl and $C_{1-4}$-fluoroalkylsulphonyl and which heterocyclic group optionally bears 1 or 2 further substituents selected from those defined hereinbefore);

10) $C_{1-4}$alkyl$Q^{13}C_{1-4}$alkanoyl$Q^{14n}$ wherein $Q^{13}$ is as defined hereinbefore and is not hydrogen and $Q^{14n}$ is a 5-6-membered saturated or partially unsaturated heterocyclic group containing at least one nitrogen atom and optionally containing a further nitrogen atom wherein $Q^{14n}$ is linked to $C_{1-4}$ alkanoyl through a nitrogen atom and wherein $Q^{14n}$ optionally bears 1, 2 or 3 substituents selected from $C_{2-5}$alkenyl, $C_{2-5}$alkynyl, $C_{1-6}$-fluoroalkyl, $C_{1-6}$alkanoyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl); and additionally wherein any $C_{1-5}$alkyl, $C_{2-5}$alkenyl or $C_{2-5}$alkynyl group in $Q^1X^1$— which is linked to $X^1$ may bear one or more substituents selected from hydroxy, halogeno and amino);

(ii) $Q^{15}W^3$
wherein $W^3$ represents —NQ$^{16}$C(O)—, —C(O)NQ$^{17}$-, —SO$_2$NQ$^{18}$-, —NQ$^{19}$SO$_2$— or —NQ$^{20}$- (wherein $Q^{16}$, $Q^{17}$, $Q^{18}$, $Q^{19}$ and $Q^{20}$ each independently represents $C_{2-5}$alkenyl, $C_{2-5}$alkynyl, $C_{1-4}$haloalkyl), and $Q^{15}$ is $C_{1-6}$haloalkyl, $C_{2-5}$alkenyl or $C_{2-5}$alkynyl;

(iii) $Q^{21}W^4C_{1-5}$alkyl$X^1$— wherein $W^4$ represents —NQ$^{22}$C(O)—, —C(O)NQ$^{23}$-, —SO$_2$NQ$^{24}$-, —NQ$^2$SO$_2$— or —NQ$^{26}$- (Wherein $Q^{22}$, $Q^{23}$, $Q^{24}$, $Q^{25}$ and $Q^{26}$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl), and $Q^{21}$ represents $C_{1-6}$haloalkyl, $C_{2-5}$alkenyl or $C_{2-5}$alkynyl, and $X^1$ is as defined hereinbefore;

(iv) $Q^{28}C_{1-5}$alkyl$X^1$—, $Q^{28}C_{2-5}$alkenyl$X^1$— or $Q^{28}C_{2-5}$alkynyl$X^1$— wherein $X^1$ is as defined hereinbefore and $Q^{28}$ is an imidazolidinyl group which bears two oxo substituents and one $C_{1-6}$alkyl or $C_{3-10}$cycloalkyl group which $C_{1-6}$alkyl or $C_{3-10}$cycloalkyl group may bear a hydroxy substituent on the carbon atom which is linked to the imidazolidinyl group, and wherein the $C_{1-5}$alkyl, $C_{1-5}$alkenyl or $C_{1-5}$alkynyl linked to $X^1$ may bear one or more substituents selected from hydroxy, halogeno and amino; and (v) $Q^{29}C_{1-5}$alkyl$X^1$—, $Q^{29}C_{2-5}$alkenyl$X^1$— or $Q^{29}C_{2-5}$alkynyl$X^1$— wherein $X^1$ is as defined hereinbefore, the $C_{1-5}$alkyl, $C_{1-5}$alkenyl or $C_{1-5}$alkynyl linked to $X^1$ may bear one or more substituents selected from hydroxy, halogeno and amino and $Q^{29}$ is a group 1,4-dioxa-8-azaspiro[4.5]dec-8-yl, which may be represented:

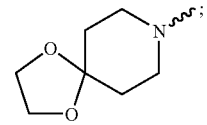

or $R^1$ may be selected from any of the groups defined hereinbefore and $R^2$ is 6,7-methylenedioxy or 6,7-ethylenedioxy; or a salt thereof, or a prodrug thereof for example an ester or an amide, in the manufacture of a medicament for use in the production of an antiangiogenic and/or vascular permeability reducing effect in warm-blooded animals such as humans.

According to one aspect of the present invention there is provided the use of a compound of the formula I:

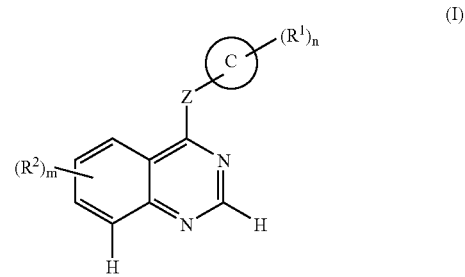

wherein:
ring C is an 8, 9, 10, 12 or 13-membered bicyclic or tricyclic moiety which moiety may be saturated or unsaturated, which may be aromatic or non-aromatic, and which optionally may contain 1-3 heteroatoms selected independently from O, N and S;
Z is —O—, —NH— or —S—;
n is 0, 1, 2, 3, 4 or 5;
m is 0, 1, 2 or 3;
$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —NR$^3$R$^4$ (wherein R$^3$ and R$^4$, which may be the same or different, each represents hydrogen or $C_{1-3}$alkyl), or R$^5$X$^1$— (wherein X$^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^8$—, —NR$^9$SO$_2$— or —NR$^{10}$— (wherein R$^6$, R$^7$, R$^8$, R$^9$ and R$^{10}$ each independently represents hydrogen, $C_{1-3}$alkyl or $C_{1-3}$alkoxy$C_{2-3}$alkyl), and $R^5$ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;

2) $C_{1-5}$alkyl$X^2$C(O)$R^{11}$ (wherein $X^2$ represents —O— or —$NR^{12}$— (in which $R^{12}$ represents hydrogen, $C_{1-3}$alkyl or $C_{1-3}$alkoxy$C_{2-3}$alkyl) and $R^{11}$ represents $C_{1-3}$alkyl, —$NR^{13}R^{14}$ or —$OR^{15}$ (wherein $R^{13}$, $R^{14}$ and $R^{15}$ which may be the same or different each represents hydrogen, $C_{1-5}$alkyl or $C_{1-3}$alkoxy$C_{2-3}$alkyl));

3) $C_{1-5}$alkyl$X^3R^{16}$ (wherein $X^3$ represents —O—, —S—, —SO—, —$SO_2$—, —OC(O)—, —$NR^{17}$C(O)—, —C(O)$NR^{18}$—, —$SO_2NR^{19}$—, —$NR^{20}SO_2$— or —$NR^{21}$— (wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl) and $R^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

4) $C_{1-5}$alkyl$X^4C_{1-5}$alkyl$X^5R^{22}$ (wherein $X^4$ and $X^5$ which may be the same or different are each —O—, —S—, —SO—, —$SO_2$—, —$NR^{23}$C(O)—, —C(O)$NR^{24}$—, —$SO_2NR^{25}$—, —$NR^{26}SO_2$— or —$NR^{27}$— (wherein $R^{23}$, $R^{24}$, $R^{25}$, $R^{26}$ and $R^{27}$ each independently represents hydrogen, $C_{1-3}$alkyl or $C_{1-3}$alkoxy$C_{2-3}$alkyl) and $R^{22}$ represents hydrogen, $C_{1-3}$alkyl or $C_{1-3}$alkoxy$C_{2-3}$alkyl);

5) $R^{28}$ (wherein $R^{28}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

6) $C_{1-5}$alkyl$R^{28}$ (wherein $R^{28}$ is as defined hereinbefore);

7) $C_{2-5}$alkenyl$R^{28}$ (wherein $R^{28}$ is as defied hereinbefore);

8) $C_{2-5}$alkynyl$R^{28}$ (wherein $R^{28}$ is as defined hereinbefore);

9) $R^{29}$ (wherein $R^{29}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from oxo, hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)$NR^{30}R^{31}$, —$NR^{32}$C(O)$R^{33}$ (wherein $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

10) $C_{1-5}$alkyl$R^{29}$ (wherein $R^{29}$ is as defined hereinbefore);

11) $C_{2-5}$alkenyl$R^{29}$ (wherein $R^{29}$ is as defined hereinbefore);

12) $C_{2-5}$alkynyl$R^{29}$ (wherein $R^{29}$ is as defined hereinbefore);

13) $C_{1-5}$alkyl$X^6R^{29}$ (wherein $X^6$ represents —O—, —S—, —SO—, —$SO_2$—, —$NR^{34}$C(O)—, —C(O)$NR^{35}$—, —$SO_2NR^{36}$—, —$NR^{37}SO_2$— or $NR^{38}$ (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);

14) $C_{2-5}$alkenyl$X^7R^{29}$ (wherein $X^7$ represents —O—, —S—, —SO—, —$SO_2$—, —$NR^{39}$C(O)—, —C(O)$NR^{40}$—, —$SO_2NR^{41}$—, $NR^{42}SO_2$— or —$NR^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);

15) $C_{2-5}$alkynyl$X^8R^{29}$ (wherein $X^8$ represents —O—, —S—, —SO—, —$SO_2$—, —$NR^{44}$C(O)—, —C(O)$NR^{45}$—, —$SO_2NR^{46}$—, —$NR^{47}SO_2$— or —$NR^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);

16) $C_{1-4}$alkyl$X^9C_{1-4}$alkyl$R^{29}$ (wherein $X^9$ represents —O—, —S—, —SO—, —$SO_2$—, —$NR^{49}$C(O)—, —C(O)$NR^{50}$—, $SO_2NR^5$—, —$NR^{52}SO_2$— or —$NR^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined hereinbefore);

17) $C_{1-4}$alkyl$X^9C1_{-4}$alkyl$R^{28}$ (wherein $X^9$ and $R^{28}$ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^9C_{1-4}$alkyl$R^{28}$ (wherein $X^9$ and $R^{28}$ are as defined hereinbefore);

21) $C_{2-5}$alkynyl$X^9C_{1-4}$alkyl$R^{28}$ (wherein $X^9$ and $R^{28}$ are as defined hereinbefore); and 22) $C_{1-4}$alkyl$R^{54}(C_{1-4}$alkyl)$_q(X^9)_rR^{55}$ (wherein $X^9$ is as defined hereinbefore, q is 0 or 1, r is 0 or 1, and $R^{54}$ and $R^{55}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylamino$C_{1-4}$alkyl, di($C_{1-4}$alkyl) amino$C_{1-4}$alkyl, $C_{1-4}$alkylamino$C_{1-4}$alkoxy, di($C_{1-4}$alkyl) amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5X^1$— which is linked to $X^1$ may bear one or more substituents selected from hydroxy, halogeno and amino); $R^1$ represents hydrogen, oxo, halogeno, hydroxy, $C_{1-4}$alkoxy, $C_{1-4}$alkyl, $C_{1-4}$alkoxymethyl, $C_{1-4}$alkanoyl, $C_{1-4}$haloalkyl, cyano, amino, $C_{2-5}$alkenyl, $C_{2-5}$alkynyl, $C_{1-3}$alkanoyloxy, nitro, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, N—($C_{1-4}$alkylsulphonyl)amino, N—($C_{1-4}$alkylsulphonyl)-N—($C_{1-4}$alkyl)amino, N,N-di($C_{1-4}$alkylsulphonyl)amino, a $C_{3-7}$alkylene chain joined to two ring C carbon atoms, $C_{1-4}$alkanoylamino$C_{1-4}$alkyl, carboxy or a group $R^{56}X^{10}$ (wherein $X^{10}$ represents a direct bond, —O—, —$CH_2$—, —OC(O)—, —C(O)—, —S—, —SO—, —$SO_2$—, —$NR^{57}$C(O)—, —C(O)$NR^{58}$—, —$SO_2NR^{59}$—, —$NR^{60}SO_2$— or —$NR^{61}$— (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl), and $R^{56}$ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;

2) $C_{1-5}$alkyl$X^{11}$C(O)$R^{62}$ (wherein $X^{11}$ represents —O— or —$NR^{63}$— (in which $R^{63}$ represents hydrogen, $C_{1-3}$alkyl or $C_{1-3}$alkoxy$C_{2-3}$alkyl) and $R^{62}$ represents $C_{1-3}$alkyl, —$NR^{64}R^{65}$ or —$OR^{66}$ (wherein $R^{64}$, $R^{61}$ and $R^{66}$ which may be the same or different each represents hydrogen, $C_{1-5}$alkyl or $C_{1-3}$alkoxy$C_{2-3}$alkyl));

3) $C_{1-5}$alkyl$X^{12}R^{67}$ (wherein $X^{12}$ represents —O—, —S—, —SO—, —$SO_2$—, —OC(O)—, —$NR^{68}$C(O)—, —C(O)$NR^{69}$—, —$SO_2NR^{70}$—, —$NR^{71}SO_2$— or —$NR^{72}$— (wherein $R^{68}$, $R^{69}$, $R^{70}$, $R^{71}$ and $R^{72}$ each independently represents hydrogen, $C_{1-3}$alkyl or $C_{1-3}$alkoxy$C_{2-3}$alkyl) and $R^{67}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

4) $C_{1-5}$alkyl$X^{13}C_{1-5}$alkyl$X^{14}R^{73}$ (wherein $X^{13}$ and $X^{14}$ which may be the same or different are each —O—, —S—, —SO—, —$SO_2$—, —$NR^{74}$C(O)—, —C(O)$NR^{75}$—, —$SO_2NR^{76}$—, —$NR^{77}SO_2$— or —$NR^{78}$— (wherein $R^{74}$, $R^{75}$, $R^{76}$, $R^{77}$ and 78 each independently represents hydrogen, $C_{1-3}$alkyl or $C_{1-3}$alkoxy$C_{2-3}$alkyl) and $R^{73}$ represents hydrogen, $C_{1-3}$alkyl or $C_{1-3}$alkoxy$C_{2-3}$alkyl);

5) $R^{79}$ (wherein $R^{79}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino(alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

6) $C_{1-5}$alkyl$R^{79}$ (wherein $R^{79}$ is as defined hereinbefore);

7) $C_{2-5}$alkenyl$R^{79}$ (wherein $R^{79}$ is as defined hereinbefore);

8) $C_{2-5}$alkynyl$R^{79}$ (wherein $R^{79}$ is as defined hereinbefore);

9) $R^{80}$ (wherein $R^{80}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from oxo, hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)$NR^{81}R^{82}$, —$NR^{83}$C(R)$R^{84}$ (wherein $R^{81}$, $R^{82}$, $R^{83}$ and $R^{84}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

10) $C_{1-5}$alkyl$R^{80}$ (wherein $R^{80}$ is as defined hereinbefore);

11) $C_{2-5}$alkenyl$R^{80}$ (wherein $R^{80}$ is as defined hereinbefore);

12) $C_{2-5}$alkynyl$R^{80}$ (wherein $R^{80}$ is as defined hereinbefore);

13) $C_{1-5}$alkyl$X^{15}R^{80}$ (wherein $X^{15}$ represents —O—, —S—, —SO—, —$SO_2$—, —$NR^{85}$C(O)—, —C(O)$NR^{86}$—, —$SO_2NR^{92}$—, —$NR^{93}SO_2$— or —$NR^{94}$— (wherein $R^{85}$, $R^{86}$, $R^{87}$, $R^{88}$ and $R^{89}$ each independently represents hydrogen, $C_{1-3}$alkyl or $C_{1-3}$alkoxy$C_{2-3}$alkyl) and $R^{80}$ is as defined hereinbefore);

14) $C_{2-5}$alkenyl$X^{16}R^{80}$ (wherein $X^{16}$ represents —O—, —S—, —SO—, —$SO_2$—, —$NR^{90}$C(O)—, —C(O)$NR^{91}$—, —$SO_2NR^{92}$—, —$NR^{93}SO_2$— or —$NR^{94}$— (wherein $R^{90}$, $R^{91}$, $R^{92}$, $R^{93}$ and $R^{94}$ each independently represents hydrogen, $C_{1-3}$alkyl or $C_{1-3}$alkoxy$C_{2-3}$alkyl) and $R^{80}$ is as defined hereinbefore);

15) $C_{2-5}$alkynyl$X^{17}R^{80}$ (wherein $X^{17}$ represents —O—, —S—, —SO—, —$SO_2$—, —$NR^{95}$C(O)—, —C(O)$NR^{96}$—, —$SO_2NR^{97}$—, —$NR^{98}SO_2$— or —$NR^{99}$— (wherein $R^{95}$, $R^{96}$, $R^{97}$, $R^{98}$ and $R^{99}$ each independently represents hydrogen, $C_{1-3}$alkyl or $C_{1-3}$alkoxy$C_{2-3}$alkyl) and $R^{80}$ is as defined hereinbefore);

16) $C_{1-4}$alkyl$X^{18}C_{1-4}$alkyl$R^{80}$ (wherein $X^{18}$ represents —O—, —S—, —SO—, —$SO_2$—, —$NR^{100}$C(O)—, —C(O)$NR^{101}$—, —$SO_2NR^{102}$—, $NR^{103}SO_2$— or —$NR^{104}$— (wherein $R^{100}$, $R^{101}$, $R^{102}$, $R^{103}$ and $R^{104}$ each independently represents hydrogen, $C_{1-3}$alkyl or $C_{1-3}$alkoxy$C_{2-3}$alkyl) and $R^{80}$ is as defined hereinbefore);

17) $C_{1-4}$alkyl$X^{18}C_{1-4}$alkyl$R^{79}$ (wherein $X^{18}$ and $R^{79}$ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^{18}C_{1-4}$alkyl$R^{79}$ (wherein $X^{18}$ and $R^{79}$ are as defined hereinbefore);

21) $C_{2-5}$alkynyl$X^{18}C_{1-4}$alkyl$R^{79}$ (wherein $X^{18}$ and $R^{79}$ are as defined hereinbefore); and 22) $C_{1-4}$alkyl$R^{115}(C_{1-4}$alkyl)$_x(X^{18})_yR^{106}$ (wherein $X^{18}$ is as defined hereinbefore, x is 0 or 1, y is 0 or 1, and $R^{105}$ and $R^{106}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl) with the proviso that $R^{105}$ cannot be hydrogen); and additionally wherein any $C_{1-5}$alkyl, $C_{2-5}$alkenyl or $C_{2-5}$alkynyl group in $R^{56}X^{10}$— which is linked to $X^{10}$ may bear one or more substituents selected from hydroxy, halogeno and amino); with the proviso that one or more $R^1$ and/or one or more $R^2$ are selected from one of the following three groups:

(i) $Q^1X^1$ wherein $X^1$ is as defined hereinbefore and $Q^1$ is selected from one of the following nine groups:

1) $Q^2$ (wherein $Q^2$ is a 5-6-membered saturated or partially unsaturated heterocyclic group with 1-2 heteroatoms, selected independently from O, S and N, which heterocyclic group bears at least one substituent selected from $C_{2-5}$alkenyl, $C_{2-5}$alkynyl, $C_{1-6}$-fluoroalkyl, $C_{1-6}$alkanoyl, $C_{1-6}$-fluoroalkanoyl, $C_{1-6}$alkylsulphonyl and $C_{1-6}$-fluoroalkylsulphonyl and which heterocyclic group may optionally bear a further 1 or 2 substituents selected from $C_{2-5}$alkenyl, $C_{2-5}$alkynyl, $C_{1-6}$-fluoroalkyl, $C_{1-6}$alkanoyl, $C_{1-6}$-fluoroalkanoyl, $C_{1-4}$alkylsulphonyl, $C_{1-6}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which cyclic group may bear one or more substituents selected from $C_{1-4}$alkyl));

2) $C_{1-5}$alkyl$W^1Q^2$ (wherein $W^1$ represents —O—, —S—, —SO—, —$SO_2$—, —OC(O)—, —$NQ^3$C(O)—, —C(O)$NQ^4$-, —$SO_2NQ^5$-, —$NQ^6SO_2$— or —$NQ^7$- (wherein $Q^3$, $Q^4$, $Q^5$, $Q^6$ and $Q^7$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl) and $Q^2$ is as defined hereinbefore;

3) $C_{1-5}$alkyl$Q^2$ (wherein $Q^2$ is as defined hereinbefore);

4) $C_{2-5}$alkenyl$Q^2$ (wherein $Q^2$ is as defined hereinbefore);

5) $C_{2-5}$alkynyl$Q^2$ (wherein $Q^2$ is as defined hereinbefore);

6) $C_{1-4}$alkyl$W^2C_{1-4}$alkyl$Q^2$ (wherein $W^2$ represents —O—, —S—, —SO—, —$SO_2$—, —$NQ^8$C(O)—, —C(O)$NQ^9$-, —$SO_2NQ^{10}$-, —$NQ^{11}SO_2$— or —$NQ^{12}$- (wherein $Q^8$, $Q^9$, $Q^{10}$, $Q^{11}$ and $Q^{12}$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl) and $Q^2$ is as defined hereinbefore);

7) $C_{2-5}$alkenyl$W^2C_{1-4}$alkyl$Q^2$ (wherein $W^2$ and $Q^2$ are as defined hereinbefore);

8) $C_{2-5}$alkynyl$W^2C_{1-4}$alkyl$Q^2$ (wherein $W^2$ and $Q^2$ are as defined hereinbefore); and 9) $C_{1-4}$alkyl$Q^{13}(C_{1-4}$alkyl)$_j(W^2)_kQ^{14}$ (wherein $W^2$ is as defined hereinbefore, j is 0 or 1, k is 0 or 1, and $Q^{13}$ and $Q^{14}$ are each independently selected from hydrogen, $C_{1-3}$alkyl, cyclopentyl, cyclohexyl and a 5-6-membered saturated or partially unsaturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1, 2 or 3 substituents selected from $C_{2-5}$alkenyl, $C_{2-5}$alkynyl, $C_{1-4}$-fluoroalkyl, $C_{1-6}$alkanoyl, $C_{1-6}$-fluoroalkanoyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl), with the provisos that $Q^{13}$ cannot be hydrogen and one or both of $Q^{13}$ and $Q^{14}$ must be a 5-6-membered saturated or partially unsaturated heterocyclic group as defined hereinbefore which heterocyclic group bears at least one substituent selected from $C_{2-5}$alkenyl, $C_{2-5}$alkynyl, $C_{1-6}$-fluoroalkyl, $C_{1-6}$alkanoyl, $C_{1-6}$fluoroalkanoyl, $C_{1-6}$alkylsulphonyl and $C_{1-6}$fluoroalkylsulphouyl and which heterocyclic group optionally bears 1 or 2 further substituents selected from those defined hereinbefore); and additionally wherein any $C_{1-5}$alkyl, $C_{2-5}$alkenyl or $C_{2-5}$alkynyl group in $Q^1X^1$— which is linked to $X^1$ may bear one or more substituents selected from hydroxy, halogeno and amino);

(ii) $Q^{15}W^3$ wherein $W^3$ represents —$NQ^{16}$C(O)—, —C(O)$NQ^{17}$-, —$SO_2NQ^{18}$-, —$NQ^{19}SO_2$— or —$NQ^{20}$- (wherein $Q^{16}$, $Q^{17}$, $Q^{18}$, $Q^{19}$ and $Q^{20}$ each independently represents $C_{2-5}$alkenyl, $C_{2-5}$alkynyl, $C_{1-4}$haloalkyl), and $Q^{15}$ is $C_{1-6}$haloalkyl, $C_{2-5}$alkenyl or $C_{2-5}$alkynyl; and (iii) $Q^{21}W^4C_{1-5}$alkyl$X^1$— wherein $W^4$ represents —$NQ^{22}$C(O)—, —C(O)$NQ^{23}$-, —$SO_2NQ^{24}$-, —$NQ^{25}SO_2$— or —$NQ^{26}$- (Wherein $Q^{22}$, $Q^{23}$, $Q^{24}$, $Q^{25}$ and $Q^{26}$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl), and $Q^{21}$ represents $C_{1-6}$haloalkyl, $C_{2-5}$alkenyl or $C_{2-5}$alkynyl, and $X^1$ is as defined hereinbefore; or a salt thereof, or a prodrug thereof for example an ester or an amide, in the manufacture of a medicament for use in the production of an antiangiogenic and/or vascular permeability reducing effect in warm-blooded animals such as humans.

According to one aspect of the present invention ring C is a 9-10-membered aromatic bicyclic moiety which may optionally contain 1-3 heteroatoms selected independently from O, N and S.

According to one aspect of the present invention ring C is a 9-10-membered heteroaromatic bicyclic moiety which contains 1-3 heteroatoms selected independently from O, N and S.

According to one aspect of the present invention ring C is a 9-10-membered heteroaromatic bicyclic moiety which contains 1 or 2 nitrogen atoms.

According to one aspect of the present invention ring C is indolyl, quinolinyl, indazolyl or azaindolyl.

According to one aspect of the present invention ring C is indolyl, indazolyl or azaindolyl.

According to one aspect of the present invention ring C is indolyl or azaindolyl.

According to one aspect of the present invention ring C is azaindolyl.

According to one aspect of the present invention ring C is indolyl.

According to one aspect of the present invention ring C is indazolyl.

According to one aspect of the present invention ring Z is —O— or —S—.

According to one aspect of the present invention ring Z is —O—.

In one embodiment of the present invention $X^1$ represents a direct bond, —O—, —S—, —$NR^6C(O)$—, —$NR^9SO_2$— or —$NR^{10}$— (wherein $R^6$, $R^9$ and $R^{10}$ each independently represents hydrogen, $C_{1-2}$alkyl or $C_{1-2}$alkoxyethyl).

In one embodiment of the present invention $X^1$ represents a direct bond, —O—, —S—, —$NR^6C(O)$—, —$NR^9SO_2$— (wherein $R^6$ and $R^9$ each independently represents hydrogen or $C_{1-2}$alkyl) or NH.

In one embodiment of the present invention $X^1$ represents —O—, —S—, —$NR^6C(O)$— (wherein $R^6$ represents hydrogen or $C_{1-2}$alkyl) or NH.

In one embodiment of the present invention $X^1$ represents —O— or —$NR^6C(O)$— (wherein $R^6$ represents hydrogen or $C_{1-2}$alkyl).

In one embodiment of the present invention $X^1$ represents —O— or —NHC(O)—.

In one embodiment of the present invention $X^1$ represents —O—.

According to another aspect of the present invention $X^1$ represents —O— or a direct bond.

In one embodiment of the present invention $R^1$ is selected from one of the three groups:
(i) $Q^1X^1$ wherein $Q^1$ and $X^1$ are as defined hereinbefore;
(ii) $Q^{15}W^3$ wherein $Q^{15}$ and $W^3$ are as defined hereinbefore; and
(iii) $Q^{21}W^4C_{1-5}alkylX^1$— wherein $Q^{21}$, $W^4$ and $X^1$ are as defined hereinbefore;
and/or $R^1$ represents oxo, hydroxy, $C_{1-2}$alkoxymethyl, amino, halogeno, $C_{1-2}$alkyl, $C_{1-2}$alkoxy, trifluoromethyl, cyano, nitro, $C_{2-3}$alkanoyl.

According to one aspect of the present invention $R^1$ represents methyl, ethyl, trifluoromethyl or halogeno.

According to another aspect of the present invention $R^1$ represents methyl, fluoro, chloro or bromo.

According to another aspect of the present invention $R^1$ represents methyl or fluoro.

In one embodiment of the present invention n is 3.
In one embodiment of the present invention n is 2.
In one embodiment of the present invention n is 1.
In one embodiment of the present invention n is 0.
In one embodiment of the present invention n is 0, 1 or 2.
In one embodiment of the present invention m is 1 or 2.
In one embodiment of the present invention m is 1.
In one embodiment of the present invention m is 2.

In one embodiment of the present invention $X^3$ represents —O—, —S—, —SO—, —$SO_2$—, —$SO_2NR^{19}$— or —$NR^{21}$— (wherein $R^{19}$ and $R^{21}$ each independently represents hydrogen, $C_{1-2}$alkyl or $C_{1-2}$alkoxyethyl).

In one embodiment of the present invention $X^3$ represents —O— or —$NR^2$— (wherein $R^{21}$ represents hydrogen or $C_{1-2}$alkyl).

In one embodiment of the present invention $X^3$ represents —O—.

In one embodiment of the present invention $X^4$ and $X^5$ which may be the same or different each represents —O—, —S— or —$NR^{27}$— (wherein $R^{27}$ represents hydrogen, $C_{1-2}$alkyl or $C_{1-2}$alkoxyethyl).

In one embodiment of the present invention $X^4$ and $X^5$ which may be the same or different each represents —O— or —NH—.

In one embodiment of the present invention $X^4$ and $X^5$ each represents —O—.

In one embodiment of the present invention $X^6$ represents —O—, —S— or $NR^{38}$— (wherein $R^{38}$ represents hydrogen, $C_{1-2}$alkyl or $C_{1-2}$alkoxyethyl).

In one embodiment of the present invention $X^6$ represents —O— or —$NR^{38}$— (wherein $R^{38}$ represents hydrogen or $C_{1-2}$alkyl).

In one embodiment of the present invention $X^6$ represents —O—.

In one embodiment of the present invention $X^1$ represents —O—, —S— or —$NR^{43}$— (wherein $R^{43}$ represents hydrogen, $C_{1-2}$alkyl or $C_{1-2}$alkoxyethyl).

In one embodiment of the present invention $X^7$ represents —O— or —$NR^{43}$— (wherein $R^{43}$ represents hydrogen or $C_{1-2}$alkyl).

In one embodiment of the present invention $X^7$ represents —O—.

In one embodiment of the present invention $X^8$ represents —O—, —S— or —$NR^{48}$— (wherein $R^{48}$ represents hydrogen, $C_{1-2}$alkyl or $C_{1-2}$alkoxyethyl).

In one embodiment of the present invention $X^8$ represents —O— or —$NR^{48}$— (wherein $R^{48}$ represents hydrogen or $C_{1-2}$alkyl).

In one embodiment of the present invention $X^8$ represents —O—.

In one embodiment of the present invention $X^9$ represents —O—, —S— or —$NR^{53}$— (wherein $R^{53}$ represents hydrogen, $C_{1-2}$alkyl or $C_{1-2}$alkoxyethyl).

In one embodiment of the present invention $X^9$ represents —O— or —$NR^{53}$— (wherein $R^{53}$ represents hydrogen or $C_{1-2}$alkyl).

In one embodiment of the present invention $X^9$ represents —O—.

In one embodiment of the present invention $R^{28}$ is pyrrolidinyl, piperazinyl, piperidinyl, imidazolidinyl, 1,3-dioxolan-2-yl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, morpholino and thiomorpholino, which cyclic group may bear one or more substituents selected from $C_{1-3}$alkyl).

In one embodiment of the present invention $R^{28}$ is pyrrolidinyl, piperazinyl, piperidinyl, 1,3-dioxolan-2-yl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl.

In one embodiment of the present invention $R^{29}$ is phenyl, pyridyl, imidazolyl, thiazolyl or triazolyl group which group may bear 1 or 2 substituents selected from oxo, hydroxy, halogeno, $C_{1-4}$alkyl, $C_{1-4}$alkoxy, cyano and —NR$^{32}$C(O)R$^{33}$ (wherein $R^{32}$ and $R^{33}$ are each independently selected from hydrogen and $C_{1-4}$alkyl).

In one embodiment of the present invention $R^{54}$ and $R^{55}$ are each selected from pyrrolidinyl, piperazinyl, piperidinyl, imidazolidinyl, morpholino and thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl and a group —(—O—)$_f$—($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, morpholino and thiomorpholino, which cyclic group may bear one or more substituents selected from $C_{1-3}$alkyl).

In one embodiment of the present invention $R^2$ is selected from one of the five groups:
(i) $Q^1X^1$ wherein $Q^1$ and $X^1$ are as defined hereinbefore;
(ii) $Q^{15}W^3$ wherein $Q^{15}$ and $W^3$ are as defined hereinbefore;
(iii) $Q^{21}W^4C_{1-5}$alkyl$X^1$— wherein $Q^{21}$, $W^4$ and $X^1$ are as defined hereinbefore;
(iv) $Q^{28}C_{1-5}$alkyl$X^1$—, $Q^{28}C_{2-5}$alkenyl$X^1$— or $Q^{28}C_{2-5}$alkynyl$X^1$— wherein $Q^{28}$ and $X^1$ are as defined hereinbefore; and
(v) $Q^{29}Cl\_5$alkyl$X^1$—, $Q^{29}C_{2-5}$alkenyl$X^1$— or $Q^{29}C_{2-5}$alkynyl$X^1$— wherein $Q^{29}$ and $X^1$ are as defined hereinbefore;
and/or $R^2$ represents 6,7-methylenedioxy, 6,7-ethylenedioxy, hydroxy, $C_{1-3}$alkyl, amino or $R^5X^1$— [wherein $X^1$ is as hereinbefore defined and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 2-(ethylamino)ethyl, 2-(N,N-dimethylamino)ethyl, 2-(N,N-diethylamino)ethyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 2-(methylpiperidino)ethyl, 2-(ethylpiperidino)ethyl, 2-((2-methoxyethyl)piperidino)ethyl, 2-((2-methylsulphonyl)ethylpiperidino)ethyl, 3-((2-methylsulphonyl)ethylpiperidino)propyl, (1-cyanomethylpiperidin-3-yl)methyl, (1-cyanomethylpiperidin-4-yl)methyl, 2-(1-cyanomethylpiperidin-3-yl)ethyl, 2-(1-cyanomethylpiperidin-4-yl)ethyl, 3-(1-cyanomethylpiperidin-3-yl)propyl, 3-(1-cyanomethylpiperidin-4-yl)propyl, ((2-methoxyethyl)piperidin-3-yl)methyl, ((2-methoxyethyl)piperidin-4-yl)methyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, (pyrrolidin-2-yl)methyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomnorpholinoethyl, 3-thiomorpholinopropyl, 2-(1,1-dioxothiomnorpholino)ethyl, 3-(1,1-dioxothiomorpholino)propyl, 2-(2-methoxyethoxy)ethyl, 2-(4-methylpiperazin-1-yl)ethyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropyl)sulphonyl)-N-methyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-morpholinoethyl)piperidin-4-ylmethyl, 1-(2-thiomorpholinoethyl)piperidin-4-ylmethyl, 3-inorpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-(1-methylpiperazin-4-yl)-2-hydroxypropyl, (2R)-3-(1-dimethylpiperazin-4-yl)-2-hydroxypropyl or (2S)-3-(1-methylpiperazin-4-yl)-2-hydroxypropyl].

In one embodiment of the present invention $R^2$ is selected from one of the three groups:
(i) $Q^1X^1$ wherein $Q^1$ and $X^1$ are as defined hereinbefore;
(ii) $Q^{15}W^3$ wherein $Q^{15}$ and $W^3$ are as defined hereinbefore; and
(iii) $Q^2W^4C_{1-5}$alkyl$X^1$— wherein $Q^{21}$, $W^4$ and $X^1$ are as defined hereinbefore;
and/or $R^2$ represents hydroxy, $C_{1-3}$alkyl, amino or $R^5X^1$— [wherein $X^1$ is as hereinbefore defined and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylauino)ethyl, 2-(ethylamino)ethyl, 2-(N,N-dimethylamino)ethyl, 2-(N,N-diethylamino)ethyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 2-(methylpiperidino)ethyl, 2-(ethylpiperidino)ethyl, 2-((2-methoxyethyl)piperidino)ethyl, 2-((2-methylsulphonyl)ethylpiperidino)ethyl, 3-((2-methylsulphonyl)ethylpiperidino)propyl, (1-cyanomethylpiperidin-3-yl)methyl, (1-cyanomethylpiperidin-4-yl)methyl, 2-(1-cyanomethylpiperidin-3-yl)ethyl, 2-(1-cyanomethylpiperidin-4-yl)ethyl, 3-(1-cyanomethylpiperidin-3-yl)propyl, 3-(1-cyanomethylpiperidin-4-yl)propyl, ((2-methoxyethyl)piperidin-3-yl)methyl, ((2-methoxyethyl)

piperidin-4-yl)methyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, (pyrrolidin-2-yl)methyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-morpholinoethyl)piperidin-4-ylmethyl, 1-(2-thiomorpholinoethyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-(1-methylpiperazin-4-yl)-2-hydroxypropyl, (2R)-3-(1-methylpiperazin-4-yl)-2-hydroxypropyl or (2S)-3-(1-methylpiperazin-4-yl)-2-hydroxypropyl].

In one embodiment of the present invention $R^2$ is selected from one of the five groups: (i) $Q^1X^1$ wherein $Q^1$ and $X^1$ are as defined hereinbefore;
(ii) $Q^{15}W^3$ wherein $Q^{15}$ and $W^3$ are as defined hereinbefore;
(iii) $Q^{21}W^4C_{1-5}$alkyl$X^1$— wherein $Q^{21}$, $W^4$ and $X^1$ are as defined hereinbefore;
(iv) $Q^{28}C_{1-5}$alkyl$X^1$—, $Q^{28}C_{2-5}$alkenyl$X^1$— or $Q^{28}C_{2-5}$alkynyl$X^1$— wherein $Q^{28}$ and $X^1$ are as defined hereinbefore; and
(v) $Q^{29}C_{1-5}$alkyl$X^1$—, $Q^{29}C_{2-5}$alkenyl$X^1$— or $Q^{29}C_{2-5}$alkynyl$X^1$— wherein $Q^{29}$ and $X^1$ are as defined hereinbefore;
and/or $R^2$ represents 6,7-methylenedioxy, 6,7-ethylenedioxy, hydroxy, $C_{1-3}$alkyl, amino or $R^5X^1$— [wherein $X^1$ is —O— and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 2-(ethylamino)ethyl, 2-(N,N-dimethylamino)ethyl, 2-(N,N-diethylamino)ethyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 2-(methylpiperidino)ethyl, 2-(ethylpiperidino)ethyl, 2-((2-methoxyethyl)piperidino)ethyl, 2-((2-methylsulphonyl)ethylpiperidino)ethyl, 3-((2-methylsulphonyl)ethylpiperidino)propyl, (1-cyanomethylpiperidin-3-yl)methyl, (1-cyanomethylpiperidin-4-yl)methyl, 2-(1-cyanomethylpiperidin-3-yl)ethyl, 2-(1-cyanomethylpiperidin-4-yl)ethyl, 3-(1-cyanomethylpiperidin-3-yl)propyl, 3-(1-cyanomethylpiperidin-4-yl)propyl, ((2-methoxyethyl)piperidin-3-yl)methyl, ((2-methoxyethyl)piperidin-4-yl)methyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, (pyrrolidin-2-yl)methyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-morpholinoethyl)piperidin-4-ylmethyl, 1-(2-thiomorpholinoethyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-(1-methylpiperazin- 4-yl)-2-hydroxypropyl, (2R)-3-(1-methylpiperazin-4-yl)-2-hydroxypropyl or (2S)-3-(1-methylpiperazin-4-yl)-2-hydroxypropyl].

In one embodiment of the present invention $R^2$ is selected from one of the three groups:
(i) $Q^1X^1$ wherein $Q^1$ and $X^1$ are as defined hereinbefore;
(ii) $Q^{15}W^3$ wherein $Q^{15}$ and $W^3$ are as defined hereinbefore; and
(iii) $Q^{21}W^4C_{1-5}$alkyl$X^1$— wherein $Q^{21}$, $W^4$ and $X^1$ are as defined hereinbefore;
and/or $R^2$ represents hydroxy, $C_{1-3}$alkyl, amino or $R^5X^1$— [wherein $X^1$ is —O— and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 2-(ethylamino)ethyl, 2-(N,N-dimethylamino)ethyl, 2-(N,N-diethylamino)ethyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 2-(methylpiperidino)ethyl, 2-(ethylpiperidino)ethyl, 2-((2-methoxyethyl)piperidino)ethyl, 2-((2-methylsulphonyl)ethylpiperidino)ethyl, 3-((2-methylsulphonyl)ethylpiperidino)propyl, (1-cyanomethylpiperidin-3-yl)methyl, (1-cyanomethylpiperidin-4-yl)methyl, 2-(1-cyanomethylpiperidin-3-yl)ethyl, 2-(1-cyanomethylpiperidin-4-yl)ethyl, 3-(1-cyanomethylpiperidin-3-yl)propyl, 3-(1-cyanomethylpiperidin-4-yl)propyl, ((2-methoxyethyl)piperidin-3-yl)methyl, ((2-methoxyethyl)piperidin-4-yl)methyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, (pyrrolidin-2-yl)methyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothioinorpholino)propyl, 2-(2-methoxyethoxy)ethyl, 2-(4-methylpiperazin-1-yl)ethyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-morpholinoethyl)piperidin-4-ylmethyl, 1-(2-thiomorpholinoethyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-(1-methylpiperazin-4-yl)-2-hydroxypropyl, (2R)-3-(1-methylpiperazin-4-yl)-2-hydroxypropyl or (2S)-3-(1-methylpiperazin-4-yl)-2-hydroxypropyl].

In one embodiment of the present invention $R^2$ substituents are at the 6- and/or 7-positions of the quinazoline ring.

In one embodiment of the present invention $R^2$ is selected from one of the five groups:
(i) $Q^1X^1$ wherein $Q^1$ and $X^1$ are as defined hereinbefore;
(ii) $Q^{15}W^3$ wherein $Q^{15}$ and $W^3$ are as defined hereinbefore;
(iii) $Q^{21}W^4C_{1-5}$alkyl$X^1$— wherein $Q^{21}$, $W^4$ and $X^1$ are as defined hereinbefore;
(iv) $Q^{28}C_{1-5}$alkyl$X^1$—, $Q^{28}C_{2-5}$alkenyl$X^1$— or $Q^{28}C_{2-5}$alkynyl$X^1$— wherein $Q^{28}$ and $X^1$ are as defined hereinbefore; and
(v) $Q^{29}C_{1-5}$alkyl$X^1$—, $Q^{29}C_{2-5}$alkenyl$X^1$— or $Q^{29}C_{2-5}$alkynyl$X^1$— wherein $Q^{29}$ and $X^1$ are as defined hereinbefore;
and/or $R^2$ represents methoxy, or $R^2$ represents 6,7-methylenedioxy or 6,7-ethylenedioxy.

In one embodiment of the present invention $R^2$ is selected from one of the five groups:
(i) $Q^1X^1$ wherein $Q^1$ and $X^1$ are as defined hereinbefore;
(ii) $Q^{15}W^3$ wherein $Q^{15}$ and $W^3$ are as defined hereinbefore;
(iii) $Q^{21}W^4C_{1-5}$alkyl$X^1$— wherein $Q^{21}$, $W^4$ and $X^1$ are as defined hereinbefore;
(iv) $Q^{28}C_{1-5}$alkyl$X^1$—, $Q^{28}C_{2-5}$alkenyl$X^1$— or $Q^{28}C_{2-5}$alkynyl$X^1$— wherein $Q^{28}$ and $X^1$ are as defined hereinbefore; and
(v) $Q^{29}C_{1-5}$alkyl$X^1$—, $Q^{29}C_{2-5}$alkenyl$X^1$— or $Q^{29}C_{2-5}$alkynyl$X^1$— wherein $Q^{29}$ and $X^1$ are as defined hereinbefore;
and/or $R^2$ represents methoxy.

In one embodiment of the present invention $R^2$ is selected from one of the three groups:
(i) $Q^1X^1$ wherein $Q^1$ and $X^1$ are as defined hereinbefore;
(ii) $Q^{15}W^3$ wherein $Q^{15}$ and $W^3$ are as defined hereinbefore; and
(iii) $Q^{21}W^4C_{1-5}$alkyl$X^1$— wherein $Q^{21}$, $W^4$ and $X^1$ are as defined hereinbefore; and/or $R^2$ represents methoxy.

In one embodiment of the present invention $R^2$ is $Q^1X^1$ wherein $Q^1$ and $X^1$ are as defined hereinbefore and/or $R^2$ represents methoxy.

In one embodiment of the present invention $R^2$ is $Q^{15}W^3$ wherein $Q^{15}$ and $W^3$ are as defined hereinbefore and/or $R^2$ represents methoxy.

In one embodiment of the present invention $R^2$ is $Q^{21}W^4C_{1-5}$alkyl$X^1$— wherein $Q^{21}$, $W^4$ and $X^1$ are as defined hereinbefore and/or $R^2$ represents methoxy.

In one embodiment of the present invention $R^2$ is $Q^{28}C$—, alkyl$X^1$—, $Q^{28}C_{2-5}$alkenyl$X^1$— or $Q^{28}C_{2-5}$alkynyl$X^1$— wherein $Q^{28}$ and $X^1$ are as defined hereinbefore and/or $R^2$ represents methoxy.

In one embodiment of the present invention $R^2$ is $Q^{29}C_{1-5}$alkyl$X^1$—, $Q^{29}C_{2-5}$alkenyl$X^1$— or $Q^{29}C_{2-5}$alkynyl$X^1$— wherein $Q^{29}$ and $X^1$ are as defined hereinbefore and/or $R^2$ represents methoxy.

In one embodiment of the present invention $R^2$ is 6,7-methylenedioxy or 6,7-ethylenedioxy.

According to another aspect of the present invention there are provided compounds of the formula I.

According to another aspect of the present invention there are provided compounds of the formula Ia:

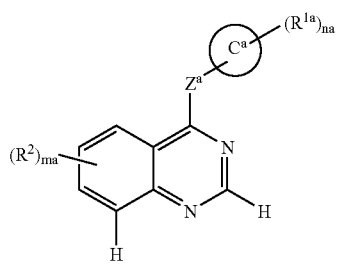

(Ia)

[wherein:
ring $C^a$ is indolyl, indazolyl or azaindolyl;
$R^{1a}$ is selected from oxo, hydroxy, $C_{1-2}$alkoxymethyl, amino, halogeno, $C_{1-3}$alkyl, $C_{1-3}$alkoxy, trifluoromethyl, cyano, nitro, $C_{1-3}$alkanoyl,
(i) $Q^1 X^1$ wherein $Q^1$ and $X^1$ are as defined hereinbefore, (ii) $Q^{15} W^3$ wherein $Q^{15}$ and $W^3$ are as defined hereinbefore,
(iii) $Q^{21} W^4 C_{1-5}$alkyl$X^1$— wherein $Q^{21}$, $W^4$ and $X^1$ are as defined hereinbefore;
$R^2$ is as defined hereinbefore;
ma is 0, 1, 2 or 3;
$Z^a$ is —O— or —S—;
and na is 0, 1 or 2;
with the proviso that at least one $R^2$ is selected from (i), (ii), (iii), (iv) or (v) as defined hereinbefore in the definitions of $R^2$, and/or $R^{1a}$ is selected from (i), (ii) and (iii) as defined hereinbefore,
or $R^2$ is 6,7-methylenedioxy or 6,7-ethylenedioxy; and salts thereof, and prodrugs thereof for example esters, amides and sulphides, preferably esters and amides.

According to another aspect of the present invention there are provided compounds of the formula II:

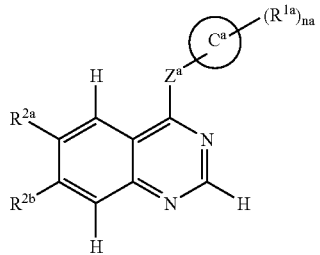

(II)

[wherein:
ring $C^a$ is indolyl, indazolyl or azaindolyl;
$R^{1a}$ is selected from oxo, hydroxy, $C_{1-2}$alkoxymethyl, amino, halogeno, $C_{1-3}$alkyl, $C_{1-3}$alkoxy, trifluoromethyl, cyano, nitro, $C_{1-3}$alkanoyl,
(i) $Q^1 X^1$ wherein $Q^1$ and $X^1$ are as defined hereinbefore;
(ii) $Q^{15} W^3$ wherein $Q^{15}$ and $W^3$ are as defined hereinbefore; and
(iii) $Q^{21} W^4 C_{1-5}$alkyl$X^1$— wherein $Q^{21}$, $W^4$ and $X^1$ are as defined hereinbefore;
$R^{2a}$, and $R^{2b}$, are each independently selected from hydrogen, hydroxy, halogeno, cyano, nitro, trifluoromethyl, $C_{1-3}$alkyl, $C_{1-3}$alkoxy, $C_{1-3}$alkylsulphanyl, —$NR^{3a}R^{4a}$ (wherein $R^{31}$ and $R^{4a}$, which may be the same or different, each represents hydrogen or $C_{1-3}$alkyl),
(i) $Q^1 X^1$ wherein $Q^1$ and $X^1$ are as defined hereinbefore,
(ii) $Q^{15} W^3$ wherein $Q^{15}$ and $W^3$ are as defined hereinbefore,
(iii) $Q^{21} W^4 C_{1-5}$alkyl$X^1$— wherein $Q^{21}$, $W^4$ and $X^1$ are as defined hereinbefore,
(iv) $Q^{28} C_{1-5}$alkyl$X^1$—, $Q^{28} C_{2-5}$alkenyl$X^1$— or $Q^{28} C_{2-5}$alkynyl$X^1$— wherein $Q^{28}$ and $X^1$ are as defined hereinbefore or
(v) $Q^{29} C_{1-5}$alkyl$X^1$—, $Q^{29} C_{2-5}$alkenyl$X^1$— or $Q^{29} C_{2-5}$alkynyl$X^1$— wherein $Q^{29}$ and $X^1$ are as defined hereinbefore,
or $R^{2a}$ and $R^{2b}$ together form 6,7-methylenedioxy or 6,7-ethylenedioxy;
$Z^a$ is —O— or —S—;
and na is 0, 1 or 2;
with the proviso that at least one of $R^{2a}$ and $R^{2b}$ is selected from (i), (ii), (iii), (iv) or (v) as defined hereinbefore and/or $R^{1a}$ is selected from (i), (ii) and (iii) as defined hereinbefore, or $R^{2a}$ and $R^{2b}$ together form 6,7-methylenedioxy or 6,7-ethylenedioxy; and salts thereof, and prodrugs thereof for example esters, amides and sulphides, preferably esters and amides.

According to another aspect of the present invention there are provided compounds of the formula IIa:

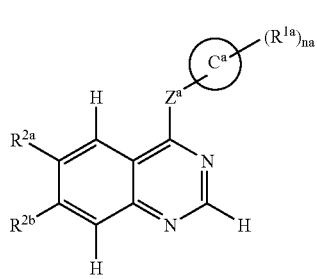

(IIa)

[wherein:
ring $C^a$ is indolyl, indazolyl or azaindolyl;
$R^{1a}$ is selected from oxo, hydroxy, $C_{1-2}$alkoxymethyl, amino, halogeno, $C_{1-3}$alkyl, $C_{1-3}$alkoxy, trifluoromethyl, cyano, nitro, $C_{1-3}$alkanoyl,
(i) $Q^1 X^1$ wherein $Q^1$ and $X^1$ are as defined hereinbefore;
(ii) $Q^{15} W^3$ wherein $Q^{15}$ and $W^3$ are as defined hereinbefore; and
(iii) $Q^{21} W^4 C_{1-5}$alkyl$X^1$— wherein $Q^{21}$, $W^4$ and $X^1$ are as defined hereinbefore;
$R^{2a}$ and $R^{2b}$, are each independently selected from hydrogen, hydroxy, halogeno, cyano, nitro, trifluoromethyl, $C_{1-3}$alkyl, $C_{1-3}$alkoxy, $C_{1-3}$alkylsulphanyl, —$NR^{3a}R^{4a}$ (wherein $R^{3a}$ and $R^{4a}$, which may be the same or different, each represents hydrogen or $C_{1-3}$alkyl),
(i) $Q^1 X^1$ wherein $Q^1$ and $X^1$ are as defined hereinbefore;
(ii) $Q^{15} W^3$ wherein $Q^{15}$ and $W^3$ are as defined hereinbefore; and
(iii) $Q^{21} W^4 C_{1-5}$alkyl$X^1$— wherein $Q^{21}$, $W^4$ and $X^1$ are as defined hereinbefore;
$Z^a$ is —O— or —S—;
and na is 0, 1 or 2;
with the proviso that at least one of $R^{2a}$ and $R^{2b}$ is selected from (i), (ii) and (iii) as defined hereinbefore and/or $R^{1a}$ is selected from (i), (ii) and (iii) as defined hereinbefore; and salts thereof, and prodrugs thereof for example esters, amides and sulphides, preferably esters and amides.

According to another aspect of the present invention there are provided compounds of the formula IIa as defined hereinbefore wherein at least one of $R^{2a}$ and $R^{2b}$ is selected from (i), (ii) and (iii) as defined hereinbefore.

In one embodiment of the present invention $Z^a$ is —O—.

In one embodiment of the present invention $C^a$ is indol-5-yl, indol-6-yl, 7-azaindol-5-yl, indazol-5-yl, indazol-6-yl.

In one embodiment of the present invention $C^a$ is indol-5-yl, 7-azaindol-5-yl or indazol-5-yl.

In one embodiment of the present invention $C^a$ is indol-5-yl.

In one embodiment of the present invention $C^a$ is 7-azaindol-5-yl.

In one embodiment of the present invention $R^{1a}$ is halogeno or $C_{1-3}$alkyl.

In one embodiment of the present invention $R^{1a}$ is fluoro or methyl.

In one embodiment of the present invention $R^{2a}$ is methoxy and $R^{2b}$ is selected from one of the five following groups:

(i) $Q^1X^1$ wherein $Q^1$ and $X^1$ are as defined hereinbefore;
(ii) $Q^{15}W^3$ wherein $Q^{15}$ and $W^3$ are as defined hereinbefore;
(ii) $Q^{21}W^4C_{1-5}$alkylX$^1$— wherein $Q^{21}$, $W^4$ and $X^1$ are as defined hereinbefore;
(iv) $Q^{28}C_{1-5}$alkylX$^1$—, $Q^{28}C_{2-5}$alkenylX$^1$— or $Q^{28}C_{2-5}$alkynylX$^1$— wherein $Q^{28}$ and $X^1$ are as defined hereinbefore; and
(v) $Q^{29}C_{1-5}$alkylX$^1$—, $Q^{29}C_{2-5}$alkenylX$^1$— or $Q^{29}C_{2-5}$alkynylX$^1$— wherein $Q^{29}$ and $X^1$ are as defined hereinbefore.

In one embodiment of the present invention $R^{2a}$ is methoxy and $R^{2b}$ is selected from one of the three following groups:

(i) $Q^1X^1$ wherein $Q^1$ and $X^1$ are as defined hereinbefore;
(ii) $Q^{15}W^3$ wherein $Q^{15}$ and $W^3$ are as defined hereinbefore; and
(iii) $Q^{21}W^4C_{1-5}$alkylX$^1$— wherein $Q^{21}$, $W^4$ and $X^1$ are as defined hereinbefore.

In another embodiment of the present invention $R^{2b}$ is methoxy and $R^{2a}$ is selected from one of the five following groups:

(i) $Q^1X^1$ wherein $Q^1$ and $X^1$ are as defined hereinbefore;
(ii) $Q^{15}W^3$ wherein $Q^{15}$ and $W^3$ are as defined hereinbefore;
(iii) $Q^{28}W^4C_{1-5}$alkylX$^1$— wherein $Q^{21}$, $W^4$ and $X^1$ are as defined hereinbefore;
(iv) $Q^{29}C_{1-5}$alkylX$^1$—, $Q^{28}C_{2-5}$alkenylX$^1$— or $Q^{28}C_{2-5}$alkynylX$^1$— wherein $Q^{28}$ and $X^1$ are as defined hereinbefore; and
(v) $Q^{29}C_{1-5}$alkylX$^1$—, $Q^{29}C_{2-5}$alkenylX$^1$— or $Q^{29}C_{2-5}$alkynylX$^1$— wherein $Q^{29}$ and $X^1$ are as defined hereinbefore.

In another embodiment of the present invention $R^{2b}$ is methoxy and $R^{2a}$ is selected from one of the three following groups:

(i) $Q^1X^1$ wherein $Q^1$ and $X^1$ are as defined hereinbefore;
(ii) $Q^{15}W^3$ wherein $Q^{15}$ and $W^3$ are as defined hereinbefore; and
(iii) $Q^{21}W^4C_{1-5}$alkylX$^1$— wherein $Q^{21}$, $W^4$ and $X^1$ are as defined hereinbefore.

According to another aspect of the present invention there are provided compounds of the formula IIb:

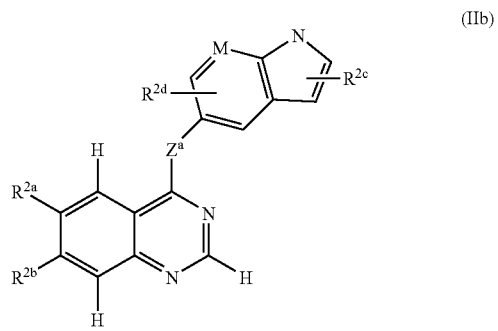

(IIb)

[wherein:
M is —CH— or —N—;
$R^{2c}$ is linked to a carbon atom of the 5-membered ring and is selected from hydrogen and methyl;
$R^{2d}$ is linked to a carbon atom of the 6-membered ring and is selected from hydrogen and fluoro;
$Z^a$, $R^{2a}$ and $R^{2b}$, are as defined hereinbefore;
with the proviso that at least one of $R^{2a}$ and $R^{2b}$ is selected from (i), (ii), (iii), (iv) and (v) as defined hereinbefore;
and salts thereof, and prodrugs thereof for example esters, amides and sulphides, preferably esters and amides.

According to another aspect of the present invention there are provided compounds of the formula IIc:

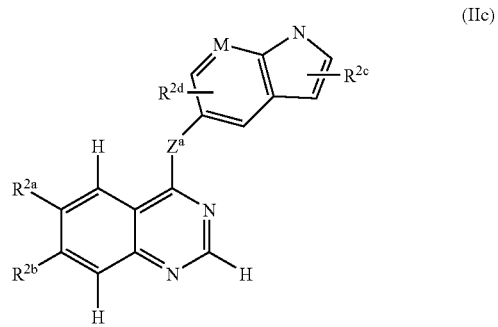

(IIc)

[wherein:
M is —CH— or —N—;
$R^{2c}$ is linked to a carbon atom of the 5-membered ring and is selected from hydrogen and methyl;
$R^{2d}$ is linked to a carbon atom of the 6-membered ring and is selected from hydrogen and fluoro;
$Z^a$, $R^{2a}$ and $R^{2b}$, are as defined hereinbefore;
with the proviso that at least one of $R^{2a}$ and $R^{2b}$ is selected from (i), (ii) and (iii) as defined hereinbefore;
and salts thereof, and prodrugs thereof for example esters, amides and sulphides, preferably esters and amides.

According to another aspect of the present invention there are provided compounds of the formula IId:

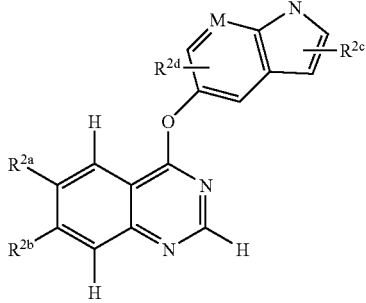

[wherein:
M is —CH— or —N—;
$R^{2c}$ is linked to a carbon atom of the 5-membered ring and is selected from hydrogen and methyl;
$R^{2d}$ is linked to a carbon atom of the 6-membered ring and is selected from hydrogen and fluoro;
one of $R^{2a}$ and $R^{2b}$ is methoxy and the other is $Q^1X^1$ wherein $X^1$ is as defined hereinbefore and $Q^1$ is selected from one of the following ten groups:
1) $Q^2$ (wherein $Q^2$ is a heterocyclic group selected from pyrrolidinyl, piperidinyl, piperazinyl,

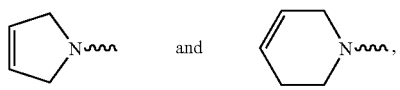

which heterocyclic group bears at least one substituent selected from $C_{2-5}$alkenyl, $C_{2-5}$alkynyl, $C_{1-4}$-fluoroalkyl, $C_{1-4}$alkanoyl, amino$C_{1-6}$alkanoyl, $C_{1-4}$alkylamino$C_{1-4}$alkanoyl, di($C_{1-4}$alkyl)amino$C_{1-6}$alkanoyl, $C_{1-4}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-4}$alkylsulphonyl and $C_{1-4}$-fluoroalkylsulphonyl and which heterocyclic group may optionally bear a further 1 or 2 substituents selected from $C_{2-5}$alkenyl, $C_{2-5}$alkynyl, $C_{1-4}$-fluoroalkyl, $C_{1-4}$alkanoyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-4}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-4}$alkylsulphonyl, $C_{1-4}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is selected from pyrrolidinyl, piperidinyl, piperazinyl,

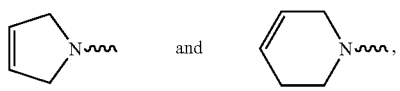

which heterocyclic group may bear one or more substituents selected from $C_{1-4}$alkyl)); 2) $C_{1-5}$alkyl$W^1Q^2$ (wherein $W^1$ represents —O—, —S—, —SO—, —SO$_2$—, —OC(O)—, —NQ$^3$C(O)—, —C(O)NQ$^4$-, —SO$_2$NQ$^5$-, —NQ$^6$SO$_2$— or —NQ$^7$- (wherein $Q^3$, $Q^4$, $Q^5$, $Q^6$ and $Q^7$ each independently represents hydrogen, $C_{1-2}$alkyl, $C_{1-2}$alkoxy$C_{2-3}$alkyl, $C_{2-5}$alkenyl, $C_{2-5}$alkynyl or $C_{1-4}$haloalkyl) and $Q^2$ is as defined hereinbefore;
3) $C_{1-5}$alkyl$Q^2$ (wherein $Q^2$ is as defined hereinbefore);
4) $C_{2-5}$alkenyl$Q^2$ (wherein $Q^2$ is as defined hereinbefore);
5) $C_{2-5}$alkynyl$Q^2$ (wherein $Q^2$ is as defined hereinbefore);
6) $C_{1-4}$alkyl$W^2C_{1-4}$alkyl$Q^2$ (wherein $W^2$ represents —O—, —S—, —SO—, —SO$_2$—, —NQ$^8$C(O)—, —C(O)NQ$^9$-, —SO$_2$NQ$^{10}$-, —NQ$^{11}$SO$_2$— or —NQ$^{12}$- (wherein $Q^8$, $Q^9$, $Q^{10}$, $Q^{11}$ and $Q^{12}$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl) and $Q^2$ is as defined hereinbefore);
7) $C_{2-5}$alkenyl$W^2C_{1-4}$alkyl$Q^2$ (wherein $W^2$ and $Q^2$ are as defined hereinbefore);
8) $C_{2-5}$alkynyl$W^2C_{1-4}$alkyl$Q^2$ (wherein $W^2$ and $Q^2$ are as defined hereinbefore);
9) $C_{1-4}$alkyl$Q^{13}$($C_{1-4}$alkyl)$_j$($W^2$)$_k$$Q^{14}$ (wherein $W^2$ is as defined hereinbefore, j is 0 or 1, k is 0 or 1, and $Q^{13}$ and $Q^{14}$ are each independently selected from pyrrolidinyl, piperidinyl, piperazinyl,

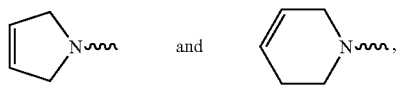

which heterocyclic group may bear 1, 2 or 3 substituents selected from $C_{2-5}$alkenyl, $C_{2-5}$alkynyl, $C_{1-4}$-fluoroalkyl, $C_{1-4}$alkanoyl, amino$C_{1-4}$alkanoyl, $C_{1-4}$alkylamino$C_{1-6}$alkanoyl, di($C_{1-4}$alkyl)amino$C_{1-6}$alkanoyl, $C_{1-4}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-4}$alkylsulphonyl, $C_{1-4}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is selected from pyrrolidinyl, piperidinyl, piperazinyl,

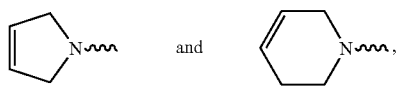

which heterocyclic group may bear one or more substituents selected from $C_{1-4}$alkyl), with the proviso that at least one of $Q^{13}$ and $Q^{14}$ bears at least one substituent selected from $C_{2-5}$alkenyl, $C_{2-5}$alkynyl, $C_{1-4}$-fluoroalkyl, $C_{1-4}$alkanoyl, amino$C_{1-6}$alkanoyl, $C_{1-4}$alkylamino$C_{1-6}$alkanoyl, di($C_{1-4}$ alkyl)amino$C_{1-6}$alkanoyl, $C_{1-4}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl, di($C_{1-4}$alkyl)carbamoyl, $C_{1-4}$alkylsulphonyl and $C_{1-4}$-fluoroalkylsulphonyl); and
10) $C_{1-4}$alkyl$Q^{13}C_{1-4}$alkanoyl$Q^{14}$, wherein $Q^{13}$ is as defined hereinbefore and is not hydrogen and $Q^{14n}$ is selected from pyrrolidinyl, piperidinyl, piperazinyl,

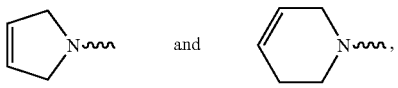

wherein $Q^{14n}$ is linked to $C_{1-6}$alkanoyl through a nitrogen atom;

and additionally wherein any $C_{1-5}$alkyl, $C_{2-5}$alkenyl or $C_{2-5}$alkynyl group in $Q^1X^1$—which is linked to $X^1$ may bear one or more substituents selected from hydroxy, halogeno and amino); and salts thereof, and prodrugs thereof for example esters, amides and sulphides, preferably esters and amides.

According to another aspect of the present invention there are provided compounds of the formula IIe:

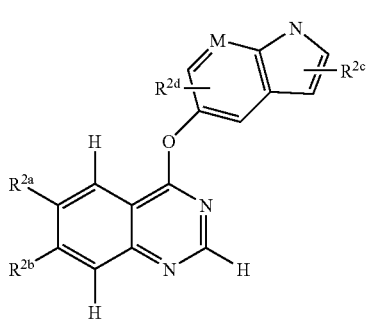

(IIe)

[wherein:

M is —CH— or —N—;

$R^{2c}$ is linked to a carbon atom of the 5-membered ring and is selected from hydrogen and methyl;

$R^{2d}$ is linked to a carbon atom of the 6-membered ring and is selected from hydrogen and fluoro;

one of $R^{2a}$ and $R^{2b}$ is methoxy and the other is $Q^1X^1$ wherein $X^1$ is as defined hereinbefore and $Q^1$ is selected from one of the following nine groups:

1) $Q^2$ (wherein $Q^2$ is a heterocyclic group selected from pyrrolidinyl, piperidinyl, piperazinyl,

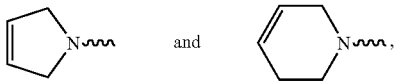

which heterocyclic group bears at least one substituent selected from $C_{2-5}$alkenyl, $C_{2-5}$alkynyl, $C_{1-4}$-fluoroalkyl, $C_{1-4}$alkanoyl, $C_{1-4}$-fluoroalkanoyl, $C_{1-4}$alkylsulphonyl and $C_{1-4}$-fluoroalkylsulphonyl and which heterocyclic group may optionally bear a further 1 or 2 substituents selected from $C_{2-5}$alkenyl, $C_{2-5}$alkynyl, $C_{1-4}$-fluoroalkyl, $C_{1-4}$alkanoyl, $C_{1-4}$-fluoroalkanoyl, $C_{1-4}$alkylsulphonyl, $C_{1-4}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylaminoC$_{1-4}$alkyl, di($C_{1-4}$alkyl)aminoC$_{1-4}$alkyl, $C_{1-4}$alkylaminoC$_{1-4}$alkoxy, di($C_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is selected from pyrrolidinyl, piperidinyl, piperazinyl,

which heterocyclic group may bear one or more substituents selected from $C_{1-4}$alkyl));

2) $C_{1-5}$alkylW$^1$Q$^2$ (wherein W$^1$ represents —O—, —S—, —SO—, —SO$_2$—, —OC(O)—, —NQ$^3$C(O)—, —C(O)NQ$^4$-, —SO$_2$NQ$^5$-, —NQ$^6$SO$_2$— or —NQ$^7$- (wherein Q$^3$, Q$^4$, Q$^5$, Q$^6$ and Q$^7$ each independently represents hydrogen, $C_{1-2}$alkyl, $C_{1-2}$alkoxyC$_{2-3}$alkyl, $C_{2-5}$alkenyl, $C_{2-5}$alkynyl or $C_{1-4}$haloalkyl) and Q$^2$ is as defined hereinbefore;

3) $C_{1-5}$alkylQ$^2$ (wherein Q$^2$ is as defined hereinbefore);

4) $C_{2-5}$alkenylQ$^2$ (wherein Q$^2$ is as defined hereinbefore);

5) $C_{2-5}$alkynylQ$^2$ (wherein Q$^2$ is as defined hereinbefore);

6) $C_{1-4}$alkylW$^2$C$_{1-4}$alkylQ$^2$ (wherein W$^2$ represents —O—, —S—, —SO—, —SO$_2$—, —NQ$^8$C(O)—, —C(O)NQ$^9$-, —SO$_2$NQ$^{10}$-, —NQ$^{11}$SO$_2$— or —NQ$^{12}$- (wherein Q$^8$, Q$^9$, Q$^{10}$, Q$^{11}$ and Q$^{12}$ each independently represents hydrogen, $C_{1-3}$alkyl, $C_{1-3}$alkoxyC$_{2-3}$alkyl, $C_{2-5}$alkenyl, $C_{2-5}$alkynyl or $C_{1-4}$haloalkyl) and Q$^2$ is as defined hereinbefore);

7) $C_{2-5}$alkenylW$^2$C$_{1-4}$alkylQ$^2$ (wherein W$^2$ and Q$^2$ are as defined hereinbefore);

8) $C_{2-5}$alkynylW$^2$C$_{1-4}$alkylQ$^2$ (wherein W$^2$ and Q$^2$ are as defined hereinbefore); and 9) $C_{1-4}$alkylQ$^{13}$(C$_{1-4}$alkyl)$_j$(W$^2$)$_k$Q$^{14}$ (wherein W$^2$ is as defined hereinbefore, j is 0 or 1, k is 0 or 1, and Q$^{13}$ and Q$^{14}$ are each independently selected from pyrrolidinyl, piperidinyl, piperazinyl, which heterocyclic group may bear 1, 2 or 3 substituents selected from $C_{2-5}$alkenyl, $C_{2-5}$alkynyl, $C_{1-4}$-fluoroalkyl, $C_{1-4}$alkanoyl, $C_{1-4}$-fluoroalkanoyl, $C_{1-4}$alkylsulphonyl, $C_{1-4}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylaminoC$_{1-4}$alkyl, di($C_{1-4}$alkyl)aminoC$_{1-4}$alkyl, $C_{1-4}$alkylaminoC$_{1-4}$alkoxy, di($C_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is selected from pyrrolidinyl, piperidinyl, piperazinyl, which heterocyclic group may bear one or more substituents selected from $C_{1-4}$alkyl), with the proviso that at least one of $Q^{13}$ and $Q^{14}$ bears at least one substituent selected from $C_{2-5}$alkenyl, $C_{2-5}$alkynyl, $C_{1-4}$-fluoroalkyl, $C_{1-4}$alkanoyl, $C_{1-4}$-fluoroalkanoyl, $C_{1-4}$alkylsulphonyl and $C_{1-4}$-fluoroalkylsulphonyl); and additionally wherein any $C_{1-5}$alkyl, $C_{2-5}$alkenyl or $C_{2-5}$alkynyl group in $Q^1X^1$—which is linked to $X^1$ may bear one or more substituents selected from hydroxy, halogeno and amino); and salts thereof, and prodrugs thereof for example esters, amides and sulphides, preferably esters and amides.

In one embodiment of the present invention one of $R^{2a}$ and $R^{2b}$ is methoxy and the other is $Q^1X^1$ wherein $X^1$ is —O— and $Q^1$ is selected from one of the following four groups:
1) $Q^2$ (wherein $Q^2$ is a heterocyclic group selected from pyrrolidinyl, piperidinyl, piperazinyl,

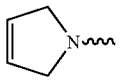 and 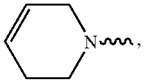, which heterocyclic group bears one substituent selected from $C_{2-5}$alkenyl, $C_{2-5}$alkynyl, $C_{1-4}$-fluoroalkyl, $C_{1-4}$alkanoyl, aminoC$_{1-6}$alkanoyl, $C_{1-4}$alkylaminoC$_{1-6}$alkanoyl, di($C_{1-4}$alkyl)aminoC$_{1-6}$alkanoyl, $C_{1-4}$-fluoroalkanoyl, carbamoyl, $C_{1-4}$alkylcarbaifoyl, di($C_{1-4}$alkyl)carbamoyl, carbamoylC$_{1-6}$alkyl, $C_{1-4}$alkylcarbamoylC$_{1-6}$alkyl, di($C_{1-4}$alkyl)carbamoylC$_{1-6}$alkyl, $C_{1-4}$alkylsulphonyl and $C_{1-4}$-fluoroalkylsulphonyl;
2) $C_{1-5}$alkylQ$^2$ (wherein $Q^2$ is as defined hereinbefore);
3) $C_{1-4}$alkylW$^2$C$_{1-4}$alkylQ$^2$ (wherein $W^2$ and $Q^2$ are as defined hereinbefore);
4) $C_{1-4}$alkylQ$^{13}$(C$_{1-4}$alkyl)$_j$(W$^2$)$_k$Q$^{14}$ (wherein $W^2$ is as defined hereinbefore, j is 0 or 1, k is 0 or 1, and $Q^{13}$ and $Q^{14}$ are each independently selected from pyrrolidinyl, piperidinyl, piperazinyl,

 and 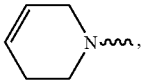, which heterocyclic group may bear 1, 2 or 3 substituents selected from $C_{2-5}$alkenyl, $C_{2-5}$alkynyl, $C_{1-4}$-fluoroalkyl, $C_{1-4}$alkanoyl, aminoC$_{1-6}$alkanoyl, $C_{1-4}$alkylaminoC$_{1-6}$alkanoyl, di($C_{1-4}$alkyl)aminoC$_{1-6}$alkanoyl, $C_{1-6}$-fluoroalkanoyl, carbamoyl, $C_{1-4}$alkylcarbamoyl, di($C_{1-4}$alkyl)carbamoyl, carbamoylC$_{1-6}$alkyl, $C_{1-4}$alkylcarbamoylC$_{1-6}$alkyl, di($C_{1-4}$alkyl)carbamoylC$_{1-6}$alkyl, $C_{1-4}$alkylsulphonyl, $C_{1-4}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl; with the proviso that at least one of $Q^{13}$ and $Q^{14}$ bears at least one substituent selected from $C_{2-5}$alkenyl, $C_{2-5}$alkynyl, $C_{1-4}$-fluoroalkyl, $C_{1-4}$alkanoyl, aminoC$_{1-6}$alkanoyl, $C_{1-4}$alkylaminoC$_{1-6}$alkanoyl, di($C_{1-4}$alkyl)aminoC$_{1-4}$alkanoyl, $C_{1-6}$-fluoroalkanoyl, carbamoyl, $C_{1-4}$alkylcarbamoyl, di($C_{1-4}$alkyl)carbamoyl, carbamoylC$_{1-6}$alkyl, $C_{1-4}$alkylcarbamoylC$_{1-6}$alkyl, di($C_{1-4}$alkyl)carbamoylC$_{1-6}$alkyl, $C_{1-4}$alkylsulphonyl and $C_{1-4}$-fluoroalkylsulphonyl); and additionally wherein any $C_{1-5}$alkyl, group in $Q^1X^1$— which is linked to $X^1$ may bear one or more substituents selected from hydroxy, halogeno and amino).

In one embodiment of the present invention one of $R^{2a}$ and $R^{2b}$ is methoxy and the other is $Q^1X^1$ wherein $X^1$ is —O— and $Q^1$ is selected from one of the following four groups:
1) $Q^2$ (wherein $Q^2$ is a heterocyclic group selected from pyrrolidinyl, piperidinyl, piperazinyl,

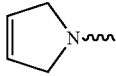 and 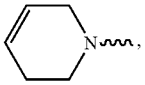, which heterocyclic group bears one substituent selected from $C_{2-5}$alkenyl, $C_{2-5}$alkynyl, $C_{1-4}$-fluoroalkyl, $C_{1-4}$alkanoyl, $C_{1-4}$-fluoroalkanoyl, $C_{1-4}$alkylsulphonyl and $C_{1-4}$-fluoroalkylsulphonyl;
2) $C_{1-5}$alkylQ$^2$ (wherein $Q^2$ is as defined hereinbefore);
3) $C_{1-4}$alkylW$^2$C$_{1-4}$alkylQ$^2$ (wherein $W^2$ and $Q^2$ are as defined hereinbefore);
4) $C_{1-4}$alkylQ$^{13}$(C$_{1-4}$alkyl)$_j$(W$^2$)$_k$Q$^{14}$ (wherein $W^2$ is as defined hereinbefore, j is 0 or 1, k is 0 or 1, and $Q^{13}$ and $Q^{14}$ are each independently selected from pyrrolidinyl, piperidinyl, piperazinyl,

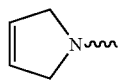 and 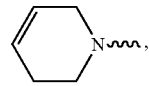, which heterocyclic group may bear 1, 2 or 3 substituents selected from $C_{2-5}$alkenyl, $C_{2-5}$alkynyl, $C_{1-4}$-fluoroalkyl, $C_{1-4}$alkanoyl, $C_{1-4}$-fluoroalkanoyl, $C_{1-4}$alkylsulphonyl, $C_{1-4}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl;
with the proviso that at least one of $Q^{13}$ and $Q^{14}$ bears at least one substituent selected from $C_{2-5}$alkenyl, $C_{2-5}$alkynyl, $C_{1-4}$-fluoroalkyl, $C_{1-4}$alkanoyl, $C_{1-4}$-fluoroalkanoyl, $C_{1-4}$alkylsulphonyl and $C_{1-4}$-fluoroalkylsulphonyl);
and additionally wherein any $C_{1-5}$alkyl, group in $Q^1X^1$— which is linked to $X^1$ may bear one or more substituents selected from hydroxy, halogeno and amino).

In one embodiment of the present invention one of $R^{2a}$ and $R^{2b}$ is methoxy and the other is $Q^1X^1$ wherein $X^1$ is —O— and $Q^1$ is selected from one of the following four groups:
1) $Q^2$ (wherein $Q^2$ is a heterocyclic group selected from pyrrolidinyl, piperidinyl, piperazinyl,

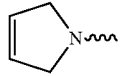 and 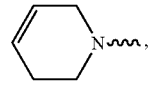, which heterocyclic group bears one substituent selected from $C_{2-5}$alkenyl, $C_{2-5}$alkynyl, $C_{1-4}$alkanoyl, aminoC$_{1-6}$alkanoyl, $C_{1-4}$alkylaminoC$_{1-6}$alkanoyl, di($C_{1-4}$alkyl)aminoC$_{1-4}$alkanoyl, $C_{1-6}$-fluoroalkanoyl, carbamoyl, $C_{1-4}$alkylcarbamoyl, di($C_{1-4}$alkyl)carbamoyl, carbamoylC$_{1-6}$alkyl, $C_{1-4}$alkylcarbamoylC$_{1-6}$alkyl, di($C_{1-4}$alkyl)carbamoylC$_{1-6}$alkyl, $C_{1-4}$alkylsulphonyl and $C_{1-4}$-fluoroalkylsulphonyl;
2) $C_{1-5}$alkylQ$^2$ (wherein $Q^2$ is as defined hereinbefore);
3) $C_{1-4}$alkylW$^2$C$_{1-4}$alkylQ$^2$ (wherein $W^2$ and $Q^2$ are as defined hereinbefore);
4) $C_{1-4}$alkylQ$^{13}$(C$_{1-4}$alkyl)$_j$(W$^2$)$_k$Q$^{14}$ (wherein $W^2$ is as defined hereinbefore, j is 0 or 1, k is 0 or 1, and $Q^{13}$ and $Q^{14}$ are each independently selected from pyrrolidinyl, piperidinyl, piperazinyl,

 and 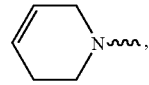, which heterocyclic group may bear 1, 2 or 3 substituents selected from $C_{2-5}$alkenyl, $C_{2-5}$alkynyl, $C_{1-4}$alkanoyl, aminoC$_{1-6}$alkanoyl, $C_{1-4}$alkylaminoC$_{1-6}$alkanoyl, di($C_{1-4}$alkyl)aminoC$_{6-4}$alkanoyl, $C_{1-6}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-4}$alkyl, $C_{1-4}$alkylsulphonyl, $C_{1-4}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl;

with the proviso that at least one of $Q^{13}$ and $Q^{14}$ bears at least one substituent selected from $C_{2-5}$alkenyl, $C_{2-5}$alkynyl, $C_{1-4}$alkanoyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-4}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-4}$alkylsulphonyl and $C_{1-4}$-fluoroalkylsulphonyl); and additionally wherein any $C_{1-5}$alkyl, group in $Q^1X^1$— which is linked to $X^1$ may bear one or more substituents selected from hydroxy, halogeno and amino).

In one embodiment of the present invention one of $R^{2a}$ and $R^{2b}$ is methoxy and the other is $Q^1X^1$ wherein $X^1$ is —O— and $Q^1$ is selected from one of the following four groups:

1) $Q^2$ (wherein $Q^2$ is a heterocyclic group selected from pyrrolidinyl, piperidinyl, piperazinyl,

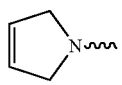 and 

which heterocyclic group bears one substituent selected from $C_{2-5}$alkenyl, $C_{2-5}$alkynyl, $C_{1-4}$alkanoyl, $C_{1-4}$-fluoroalkanoyl, $C_{1-4}$alkylsulphonyl and $C_{1-4}$-fluoroalkylsulphonyl;

2) $C_{1-5}$alkyl$Q^2$ (wherein $Q^2$ is as defined hereinbefore);

3) $C_{1-4}$alkyl$W^2C_{1-4}$alkyl$Q^2$ (wherein $W^2$ and $Q^2$ are as defined hereinbefore);

4) $C_{1-4}$alkyl$Q^{13}(C_{1-4}$alkyl$)_j(W^2)_kQ^{14}$ (wherein $W^2$ is as defined hereinbefore, j is 0 or 1, k is 0 or 1, and $Q^{13}$ and $Q^{14}$ are each independently selected from pyrrolidinyl, piperidinyl, piperazinyl,

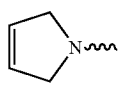 and 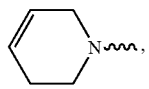

which heterocyclic group may bear 1, 2 or 3 substituents selected from $C_{2-5}$alkenyl, $C_{2-5}$alkynyl, $C_{1-4}$alkanoyl, $C_{1-4}$-fluoroalkanoyl, $C_{1-4}$alkylsulphonyl, $C_{1-4}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl; with the proviso that at least one of $Q^{13}$ and $Q^{14}$ bears at least one substituent selected from $C_{2-5}$alkenyl, $C_{2-5}$alkynyl, $C_{1-4}$alkanoyl, $C_{1-4}$fluoroalkanoyl, $C_{1-4}$alkylsulphonyl and $C_{1-4}$fluoroalkylsulphonyl);

and additionally wherein any $C_{1-5}$alkyl, group in $Q^1X^1$— which is linked to $X^1$ may bear one or more substituents selected from hydroxy, halogeno and amino).

According to another aspect of the present invention there are provided compounds of the formula IIf:

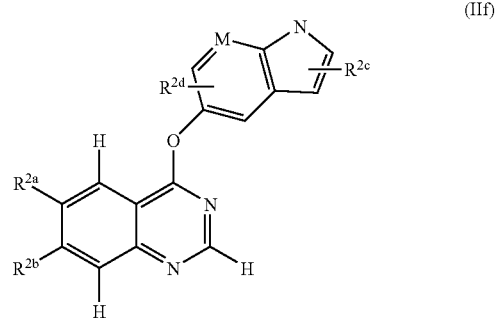

(IIf)

[wherein:
M is —CH— or —N—;
$R^{2c}$ is linked to a carbon atom of the 5-membered ring and is selected from hydrogen and methyl;
$R^{2d}$ is linked to a carbon atom of the 6-membered ring and is selected from hydrogen and fluoro;
$R^{2a}$ and $R^{2b}$ are each independently selected from methoxy, $Q^{15}W^3$ (wherein $Q^{15}$ and $W^3$ are as defined hereinbefore) and $Q^{21}W^4C_{1-5}$alkyl$X^1$— (wherein $Q^{21}$, $W^4$ and $X^1$ are as defined hereinbefore);
with the proviso that $R^{2a}$ and $R^{2b}$ cannot both be methoxy; and salts thereof, and prodrugs thereof for example esters, amides and sulphides, preferably esters and amides.

According to another aspect of the present invention there are provided compounds of the formula IIg:

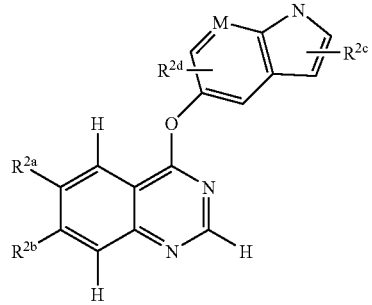

(IIg)

[wherein:
M is —CH— or —N—;
$R^{2c}$ is linked to a carbon atom of the 5-membered ring and is selected from hydrogen and methyl;
$R^{2d}$ is linked to a carbon atom of the 6-membered ring and is selected from hydrogen and fluoro;
$R^{2a}$ and $R^{2b}$ are each independently selected from methoxy, $Q^{15}W^3$ (wherein $W^3$ represents —NQ$^{16}$C(O)—, —C(O)NQ$^{17}$-, —SO$_2$NQ$^{18}$-, —NQ$^{19}$SO$_2$— or —NQ$^{20}$- (wherein $Q^{16}$, $Q^{17}$, $Q^{18}$, $Q^{19}$ and $Q^{20}$ each independently represents $C_{2-5}$alkenyl or $C_{2-5}$alkynyl), and $Q^{15}$ is $C_{2-5}$alkenyl or $C_{2-5}$alkynyl), and
$Q^{21}W^4C_{1-5}$alkyl$X^1$— (wherein $W^4$ represents —NQ$^{22}$C(O)—, —C(O)NQ$^{23}$-, —SO$_2$NQ$^{24}$-, —NQ$^{25}$SO$_2$— or —NQ$^{26}$- (wherein $Q^{22}$, $Q^{23}$, $Q^{24}$, $Q^{25}$ and $Q^{26}$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl), and $Q^{21}$ represents $C_{2-5}$alkenyl or $C_{2-5}$alkynyl, and $X^1$ is as defined hereinbefore); with the proviso that $R^{2a}$ and $R^{2b}$ cannot both be methoxy; and salts thereof, and prodrugs thereof for example esters, amides and sulphides, preferably esters and amides.

According to another aspect of the present invention there are provided compounds of the formula IIh:

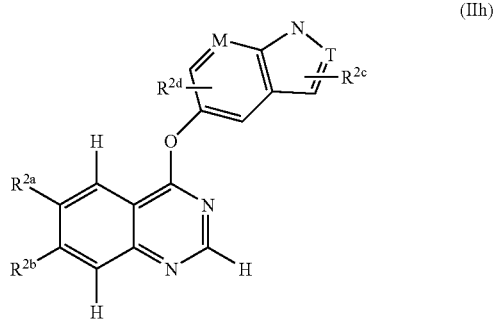

(IIh)

[wherein:

M and T each independently represents a carbon atom or a nitrogen atom with the proviso that M and T cannot both be nitrogen atoms;

$R^{2c}$ is linked to a carbon atom of the 5-membered ring and is selected from hydrogen and methyl;

$R^{2d}$ is linked to a carbon atom of the 6-membered ring and is selected from hydrogen and fluoro;

either $R^{2a}$ and $R^{2b}$ form 6,7-methylenedioxy or one of $R^{2a}$ and $R^{2b}$ is methoxy and the other is selected from one of the following four groups:

(a) $Q^1X^1$ wherein $X^1$ is —O— and $Q^1$ is selected from one of the following three groups:

1) $Q^2$ (wherein $Q^2$ is a heterocyclic group selected from pyrrolidinyl, piperidinyl and piperazinyl, which heterocyclic group bears one substituent selected from $C_{2-5}$alkenyl, $C_{2-5}$alkynyl, $C_{1-6}$fluoroalkyl, $C_{1-4}$alkanoyl, amino$C_{1-6}$alkanoyl, $C_{1-4}$alkylamino$C_{1-6}$alkanoyl, di($C_{1-4}$alkyl)amino$C_{1-4}$ alkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl and $C_{1-6}$alkylsulphonyl;

2) $C_{1-5}$alkyl$Q^2$ (wherein $Q^2$ is as defined hereinbefore); and

3) $C_{1-4}$alkyl$W^2C_{1-4}$alkyl$Q^2$ (wherein $W^2$ represents —O— and $Q^2$ is as defined hereinbefore); and additionally wherein any $C_{1-5}$alkyl group in $Q^1X^1$— which is linked to $X^1$ may bear one or more substituents selected from hydroxy);

(b) $Q^{21}W^4C_{1-5}$alkyl$X^1$— (wherein $X^1$ is —O—, $W^4$ is $NQ^{26}$ (wherein $Q^{26}$ is hydrogen or $C_{1-3}$alkyl) and $Q^{21}$ is $C_{2-5}$alkynyl);

(c) $Q^{28}C_{1-5}$alkyl$X^1$— wherein $X^1$ is —O— and $Q^{28}$ is an imidazolidinyl group which bears two oxo substituents and one $C_{1-6}$alkyl group which $C_{1-6}$alkyl group bears a hydroxy substituent on the carbon atom which is linked to the imidazolidinyl group; and (d) $Q^{29}C_{1-5}$alkyl$X^1$—wherein $X^1$ is —O— and $Q^{29}$ is a group 1,4-dioxa-8-azaspiro[4.5]dec-8-yl; and salts thereof, and prodrugs thereof for example esters, amides and sulphides, preferably esters and amides.

According to another aspect of the present invention there are provided compounds of the formula IIi:

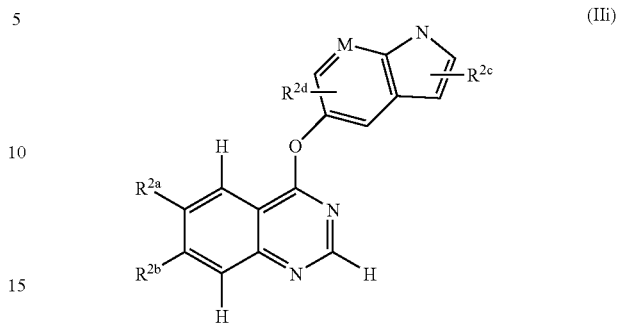

(IIi)

[wherein:

M is —CH— or —N—;

$R^{2c}$ is linked to a carbon atom of the 5-membered ring and is selected from hydrogen and methyl;

$R^{2d}$ is linked to a carbon atom of the 6-membered ring and is selected from hydrogen and fluoro;

one of $R^{2a}$ and $R^{2b}$ is methoxy and the other is selected from $Q^1X^1$— (wherein $X^1$ is —O— and $Q^1$ is $C_{1-5}$alkyl$Q^2$ (wherein $Q^2$ is a heterocyclic group selected from pyrrolidinyl, piperidinyl and piperazinyl, which heterocyclic group bears one substituent selected from $C_{2-5}$alkenyl, $C_{2-5}$alkynyl, $C_{1-4}$fluoroalkyl, $C_{1-4}$alkanoyl and $C_{1-4}$alkylsulphonyl)) and $Q^{21}W^4C_{1-5}$alkyl$X^1$— (wherein $X^1$ is —O—, $W^4$ is $NQ^{26}$ (wherein $Q^{26}$ is hydrogen or $C_{1-3}$alkyl) and $Q^{21}$ is $C_{2-5}$alkynyl);

and salts thereof, and prodrugs thereof for example esters, amides and sulphides, preferably esters and amides.

In one embodiment of the present invention $R^{2a}$ is methoxy. In one embodiment of the present invention $R^{2b}$ is selected from is selected from one of the following four groups:

(a) $Q^1X^1$ wherein $X^1$ is —O— and $Q^1$ is selected from one of the following three groups:

1) $Q^2$ (wherein $Q^2$ is a heterocyclic group selected from pyrrolidinyl, piperidinyl and piperazinyl, which heterocyclic group bears one substituent selected from $C_{2-5}$alkenyl, $C_{2-5}$alkynyl, $C_{1-6}$fluoroalkyl, $C_{1-6}$alkanoyl, amino$C_{1-6}$alkanoyl, $C_{1-4}$alkylamino$C_{1-6}$alkanoyl, di($C_{1-4}$alkyl)amino$C_{1-6}$ alkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl and $C_{1-6}$alkylsulphonyl;

2) $C_{1-5}$alkyl$Q^2$ (wherein $Q^2$ is as defined hereinbefore); and

3) $C_{1-4}$alkyl$W^2C_{1-4}$alkyl$Q^2$ (wherein $W^2$ represents —O— and $Q^2$ is as defined hereinbefore); and additionally wherein any $C_{1-5}$alkyl group in $Q^1X^1$— which is linked to $X^1$ may bear one or more substituents selected from hydroxy);

(b) $Q^{21}W^4C_{1-5}$alkyl$X^1$— (wherein $X^1$ is —O—, $W^4$ is $NQ^{26}$ (wherein $Q^{26}$ is hydrogen or $C_{1-3}$alkyl) and $Q^{21}$ is $C_{2-5}$alkynyl);

(c) $Q^{28}C_{1-5}$alkyl$X^1$— wherein $X^1$ is —O— and $Q^{28}$ is an imidazolidinyl group which bears two oxo substituents and one $C_{1-6}$alkyl group which $C_{1-6}$alkyl group bears a hydroxy substituent on the carbon atom which is linked to the imidazolidinyl group; and (d) $Q^{29}C_{1-5}$alkyl$X^1$—wherein $X^1$ is —O— and $Q^{29}$ is a group 1,4-dioxa-8-azaspiro[4.5]dec-8-yl. In one embodiment of the present invention $R^{2b}$ is selected from $Q^1X^1$— (wherein $X^1$ is —O— and $Q^1$ is $C_{1-5}$alkyl$Q^2$ (wherein $Q^2$ is a heterocyclic group selected from pyrrolidinyl, piperidinyl and piperazinyl, which heterocyclic group bears one substituent selected from C$_{2-5}$alkenyl, C$_{2-5}$alkynyl, C$_{1-4}$alkanoyl and C$_{1-4}$alkylsulphonyl)) and Q$^{21}$W$^4$C$_{1-5}$alkylX$^1$— (wherein X$^1$ is —O—, W$^4$ is NQ$^{26}$ (wherein Q$^{26}$ is hydrogen or C$_{1-3}$alkyl) and Q$^{21}$ is C$_{2-5}$alkenyl). Preferred compounds of the present invention include:

4-(7-azaindol-5-yloxy)-7-methoxy-6-(3-(4-methylsulphonylpiperazin-1-yl)propoxy)quinazoline,
6-(3-(4-acetylpiperazin-1-yl)propoxy)-4-(7-azaindol-5-yloxy)-7-methoxyquinazone,
4-[(4-fluoro-2-methyl-1H-indol-5-yl)oxy]-7-[(2S)-1-isobutyrylpyrrolidin-2-yl]methoxy)-6-methoxyquinazoline,
4-(7-azaindol-5-yloxy)-6-methoxy-7-[3-(4-carbamoylpiperazin-1-yl)propoxy]quinazoline,
6-[2-(4-acetylpiperazin-1-yl)ethoxy]-4-[(4-fluoro-1H-indol-5-yl)oxy]-7-methoxyquinazoline,
6-[(1-acetylpiperidin-4-yl)methoxy]-4-[(4-fluoro-1H-indol-5-yl)oxy]-7-methoxyquinazoline,
7-[2-(4-acetylpiperazin-1-yl)ethoxy]-4-(7-azaindol-5-yloxy)-6-methoxyquinazoine,
4-(7-azaindol-5-yloxy)-7-[3-(4-carbamoylmethyl)piperazin-1-yl)propoxy]-6-methoxyquinazoline,
4-(7-azaindol-5-yloxy)-7-{2-[4-(2-fluoroethyl)piperazin-1-yl]ethoxy}-6-methoxyquinazoline,
4-(7-azaindol-5-yloxy)-6-methoxy-7-[3-(4-prop-2-yn-1-ylpiperazin-1-yl)propoxy]quinazoline,
7-[1-(N,N-dimethylaminoacetyl)piperidin-4-ylmethoxy]-4-[(4-fluoro-2-methyl-1H-indol)-5-yloxy]-6-miethoxyquinazoline,
and salts thereof.

More preferred compounds of the present invention include:

6-(3-(4-acetylpiperazin-1-yl)propoxy)-4-(4-fluoro-2-methylindol-5-yloxy)-7-methoxyquinazoline,
7-(3-(4-acetylpiperazin-1-yl)propoxy)-4-(7-azaindol-5-yloxy)-6-methoxyquinazoline,
4-(7-azaindol-5-yloxy)-6-methoxy-7-(3-(4-methylsulphonylpiperazin-1-yl)propoxy)quinazoline,
4-(7-azaindol-5-yloxy)-6-methoxy-7-[2-(N-methyl-N-prop-2-yn-1-ylamino)ethoxy]quinazoline,
4-(4-fluoro-2-methylindol-5-yloxy)-7-methoxy-6-(3-(4-methylsulphonylpiperazin-1-yl)propoxy)quinazoline,
4-(4-fluoro-2-methylindol-5-yloxy)-6-methoxy-7-(3-(4-methylsulphonylpiperazin-1-yl)propoxy)quinazoline,
6-(3-(4-acetylpiperazin-1-yl)propoxy)-4-(4-fluoroindol-5-yloxy)-7-methoxyquinazoline,
7-[(1-acetylpiperidin-4-yl)methoxy]-4-[(4-fluoro-2-methyl-1H-indol-5-yl)oxy]-6-methoxyquinazoline,
7-[(2S)-1-acetylpyrrolidin-2-ylmethoxy]-4-[(4-fluoro-2-methyl-1H-indol-5-yl)oxy]-6-methoxyquinazoline,
7-[(2R)-1-acetylpyrrolidin-2-ylmethoxy]-4-[(4-fluoro-2-methyl-1H-indol-5-yl)oxy]-6-methoxyquinazoline,
4-[(4-fluoro-2-methyl-1H-indol-5-yl)oxy]-6-methoxy-7-[1-(2,2,2-trifluoroethyl)piperidin-4-ylmethoxy]quinazoline,
4-[(4-fluoro-2-methyl-1H-indol-5-yl)oxy]-6-methoxy-7-{3-[4-(2,2,2-trifluoroethyl)piperazin-1-yl]propoxy}quinazoline,
4-[(4-fluoro-2-methyl-1H-indol-5-yl)oxy]-6-methoxy-7-{3-[4-(2,2,2-trifluoroethyl)piperazin-1-yl]ethoxy}quinazoline,
7-{2-[4-(2-fluoroethyl)piperazin-1-yl]ethoxy}-4-[(4-fluoro-2-methyl-1H-indol-5-yl)oxy]-6-methoxyquinazoline,
7-(2-[2-(4-acetylpiperazin-1-yl)ethoxy]ethoxy-4-[(4-fluoro-2-methyl-1H-indol-5-yl)oxy]-6-inethoxyquinazoline,
4-[(4-fluoro-2-methyl-1H-indol-5-yl)oxy]-7-[(1-isobutyrylpiperidin-4-yl)methoxy]-6-methoxyquinazoline,
4-[(4-fluoro-2-methyl-1H-indol-5-yl)oxy]-7-{[(2R)-1-isobutyrylpyrrolidin-2-yl]methoxy}-6-methoxyquinazoline,
4-[(4-fluoro-2-methyl-1H-indol-5-yl)oxy]-6-methoxy-7-{[1-(methylsulfonyl)piperidin-4-yl]methoxy}quinazoline,
4-[(4-fluoro-2-methyl-1H-indol-5-yl)oxy]-6-methoxy-7-{[(2S)-1-(methylsulfonyl)pyrrolidin-2-yl]methoxy}quinazoline,
4-[(4-fluoro-2-methyl-1H-indol-5-yl)oxy]-6-methoxy-7-{[(2R)-1-(methylsulfonyl)pyrrolidin-2-yl]methoxy}quinazoline,
7-[3-(4-allylpiperazin-1-yl)propoxy]-4-(7-azaindol-5-yloxy)-6-methoxyquinazoline,
4-[(4-fluoro-2-methylindol-5-yl)oxy]-6-methoxy-7-{3-[4-(2-propynyl)piperazin-1-yl]propoxy}quinazoline,
7-{3-[4-(2-fluoroethyl)piperazin-1-yl]propoxy}-4-[(4-fluoro-2-methyl-1H-indol-5-yl)oxy]-6-methoxyquinazoline,
7-[3-(4-acetylpiperazin-1-yl)propoxy]-4-(1H-indol-5-yloxy)-6-methoxyquinazoline,
7-[(2S)-1-carbamoylpyrrolidin-2-ylmethoxy]-4-[(4-fluoro-2-methyl-1H-indol-5-yl)oxy]-6-methoxyquinazoline,
7-{3-[4-carbamoylpiperazin-1-yl]propoxy}-4-[(4-fluoro-2-methyl-1H-indol-5-yl)oxy]-6-methoxyquinazoline, 7-{3-[2,5-dioxo-4-(1-hydroxy-1-methylethyl)imidazolidin-1-yl]propoxy}-4-[(4-fluoro-2-methyl-1H-indol-5-yloxy]-6-methoxyquinazoline,
6-[(1-acetylpiperidin-4-yl)oxy]-4-[(4-fluoro-1H-indol-5-yl)oxy]-7-methoxyquinazoline,
4-[(4-fluoro-1H-indol-5-yl)oxy]-7-methoxy-6-{[1-(methylsulphonyl)piperidin-4-yl]oxy}quinazoline,
4-[(4-fluoro-2-methyl-1H-indol-5-yl)oxy]-6-methoxy-7-{2-[N-methyl-N-(2-propynyl)amino]ethoxy}quinazoline,
7-[3-(4-acetylpiperazin-1-yl)propoxy]-6-methoxy-4-[(2-methyl-1H-indol-5-yl)oxy]quinazoline,
7-[3-(4-acetylpiperazin-1-yl)propoxy]-4-[(4-fluoro-1H-indol-5-yl)oxy]-6-methoxyquinazoline,
7-[3-(4-carbamoylmethylpiperazin-1-yl)propoxy]-4-[(4-fluoro-2-methyl-1H-indol-5-yl)oxy]-6-methoxyquinazoline,
7-{3-[4-(2-fluoroethyl)piperazin-1-yl]propoxy}-6-methoxy-4-[(2-methyl-1H-indol-5-yl)oxy]quinazoline,
4-[(4-fluoro-2-methyl-1H-indol-5-yl)oxy]-7-{(2R)-2-hydroxy-3-[4-prop-2-yn-1-ylpiperazin-1-yl]propoxy}-6-dimethoxyquinazoline,
7-{(2R)-3-[(1,4-dioxa-8-azaspiro[4.5]dec-8-yl)]-2-hydroxypropoxy}-4-[(4-fluoro-2-methyl-1H-indol-5-yl)oxy]-6-methoxyquinazoline,
7-{(2R)-3-[4-acetylpiperazin-1-yl]-2-hydroxypropoxy}-4-[(4-fluoro-2-methyl-1H-indol-5-yl)oxy]-6-methoxyquinazoline, and salts thereof.

A particular compound of the present invention is 7-(3-(4-acetylpiperazin-1-yl)propoxy)-4-(4-fluoro-2-methylindol-5-yloxy)-6-methoxyquinazoline and salts thereof. A particular compound of the present invention is 7-[2-(4-acetylpiperazin-1-yl)ethoxy]-4-[(4-fluoro-2-methyl-1H-indol-5-yl)oxy]-6-methoxyquinazoline and salts thereof. Compounds of the present invention include 6-(3-(4-acetylpiperazin-1-yl)propoxy)-4-(4-fluoro-2-methylindol-5-yloxy)-7-methoxyquinazoline,
4-(7-azaindol-5-yloxy)-7-methoxy-6-(3-(4-methylsulphonylpiperazin-1-yl)propoxy)quinazoline,
6-(3-(4-acetylpiperazin-1-yl)propoxy)-4-(7-azaindol-5-yloxy)-7-methoxyquinazoline,
4-(7-azaindol-5-yloxy)-6-methoxy-7-(3-(4-methylsulphonylpiperazin-1-yl)propoxy)quinazoline, 4-(7-azaindol-5-yloxy)-6-methoxy-7-[2-(N-methyl-N-prop-2-yn-1-ylamino)ethoxy]quinazoline,
4-(4-fluoro-2-methylindol-5-yloxy)-7-methoxy-6-(3-(4-methylsulphonylpiperazin-1-yl)propoxy)quinazoline,
4-(4-fluoro-2-methylindol-5-yloxy)-6-methoxy-7-(3-(4-methylsulphonylpiperazin-1-yl)propoxy)quinazoline, and
6-(3-(4-acetylpiperazin-1-yl)propoxy)-4-(4-fluoroindol-5-yloxy)-7-methoxyquinazoline and salts thereof.

Compounds of the present invention include 7-(3-(4-acetylpiperazin-1-yl)propoxy)-4-(7-azaindol-5-yloxy)-6-methoxyquinazoline, and
7-(3-(4-acetylpiperazin-1-yl)propoxy)-4-(4-fluoro-2-methylindol-5-yloxy)-6-methoxyquinazoline
and salts thereof.

Another compound of the present invention is 4-(7-azaindol-5-yloxy)-7-(3-(4-(2-fluoroethyl)piperazin-1-yl)propoxy)-6-methoxyquinazoline
and salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1-6 carbon atoms, preferably 1-4 carbon atoms. The term "alkoxy" as used herein, unless stated otherwise includes "alkyl"-O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl"-O-groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C=O$, $C_1$alkanoyl is formyl and refers to CHO. Butanoyl refers to $CH_3$—$CH_2$—$CH_2$—$C(O)$, isobutyryl refers to $(CH_3)_2.CH$—$C(O)$. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2-5 carbon atoms, preferably 3-4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2-5 carbon atoms, preferably 3-4 carbon atoms. Unless stated otherwise the term "haloalkyl" refers to an alkyl group as defined hereinbefore which bears one or more halogeno groups, such as for example trifluoromethyl.

In this specification the term azaindolyl refers to the moiety (1H-pyrrolo[2,3-b]pyridinyl) and an analogous convention applies to similar groups. For example 7-azaindol-5-Y1 is (1H-pyrrolo[2,3-b]pyridin-5-yl) and is the group:

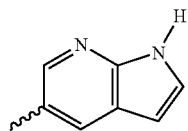

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated that compounds of the formula I or a salt thereof may possess an asymmetric carbon atom. Such an asymmetric carbon atom is also involved in the tautomerism described above, and it is to be understood that the present invention encompasses any chiral form (including both pure enantiomers, scalemic and racemic mixtures) as well as any tautomeric form which inhibits VEGF receptor tyrosine kinase activity, and is not to be limited merely to any one tautomeric form or chiral form utilised within the formulae drawings. It is to be understood that the invention encompasses all optical and diastereomers which inhibit VEGF receptor tyrosine kinase activity. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ration 50:50.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^6C(O)$—, it is the nitrogen atom bearing the $R^6$ group which is attached to the quinazoline ring and the carbonyl (C(O)) group is attached to $R^5$, whereas when $X^1$ is, for example, a group of formula —$C(O)NR^7$—, it is the carbonyl group which is attached to the quinazoline ring and the nitrogen atom bearing the $R^7$ group is attached to $R^5$. A similar convention applies to the other two atom $X^1$ linking groups such as —$NR^9SO_2$— and —$SO_2NR^8$—. When $X^1$ is —$NR^{10}$— it is the nitrogen atom bearing the $R^{10}$ group which is linked to the quinazoline ring and to $R^5$. An analogous convention applies to other groups. It is further to be understood that when $X^1$ represents —$NR^{10}$— and $R^{10}$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^5$ is, for example, a group of formula $C_{1-3}$alkyl$X^9C_{1-3}$alkyl$R^{29}$, it is the terminal $C_{1-3}$alkyl moiety which is linked to $X^1$, similarly when $R^5$ is, for example, a group of formula $C_{2-5}$alkenyl$R^{28}$ it is the $C_{2-5}$alkenyl moiety which is linked to $X^1$ and an analogous convention applies to other groups. When $R^5$ is a group 1-$R^{29}$prop-1-en-3-yl it is the first carbon to which the group $R^{29}$ is attached and it is the third carbon which is linked to $X^1$ and an analogous convention applies to other groups.

For the avoidance of any doubt, it is to be understood that in a compound of the formula I when $R^5$ is, for example, $R^{28}$ and $R^{28}$ is a pyrrolidinyl ring which bears a group —(—O—)$_f$ ($C_{1-4}$alkyl)$_g$ringD, it is the —O— or $C_{1-4}$alkyl which is linked to the pyrrolidinyl ring, unless f and g are both 0 when it is ring D which is linked to the pyrrolidinyl ring and an analogous convention applies to other groups.

For the avoidance of any doubt, it is to be understood that when $R^{29}$ carries a $C_{1-4}$aminoalkyl substituent it is the $C_{1-4}$alkyl moiety which is attached to $R^{29}$ whereas when $R^{29}$ carries a $C_{1-4}$alkylamino substituent it is the amino moiety which is attached to $R^{29}$ and an analogous convention applies to other groups.

For the avoidance of any doubt, it is to be understood that when $R^{28}$ carries a $C_{1-4}$alkoxy$C_{1-4}$alkyl substituent it is the $C_{1-4}$alkyl moiety which is attached to $R^{28}$ and an analogous convention applies to other groups.

For the avoidance of any doubt, it is to be understood that when $Q^1$ is a group $C_{1-5}$alkyl$W^1Q^2$ it is the $C_{1-5}$alkyl group which is linked to $X^1$ which is in turn linked to the quinazoline ring. Similarly when $Q^1$ is a group $C_{2-5}$alkenyl$Q^2$ it is the $C_{2-5}$alkenyl group which is linked to $X^1$ which is in turn linked to the quinazoline ring. An analogous convention applies to similar groups.

For the avoidance of any doubt, it is to be understood that when $R^2$ is a group $Q^{15}W^3$ it is the $W^3$ group which is linked to the quinazoline ring.

For the avoidance of any doubt, it is to be understood that when $R^2$ is a group $Q^2W^4C_{1-5}$alkyl$X^1$ it is the $X^1$ group which is linked to the quinazoline ring.

For the avoidance of any doubt, it is to be understood that when $R^2$ is a group $Q^{28}Cl_{-5}$alkyl$X^1$ it is the $X^1$ group which is linked to the quinazoline ring and an analogous convention applies to similar groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as herein defined) may be prepared by any process known to be applicable to the preparation of chemically-related compounds. Such processes include, for example, those illustrated in International Patent Application Number WO 00/47212 and in European Patent Applications Publication Nos. 0520722, 0566226, 0602851 and 0635498. Such processes also include, for example, solid phase synthesis. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus, the following processes (a) to (f) and (i) to (vi) constitute further features of the present invention.
Synthesis of Compounds of Formula I
(a) Compounds of the formula I and salts thereof may be prepared by the reaction of a compound of the formula III:

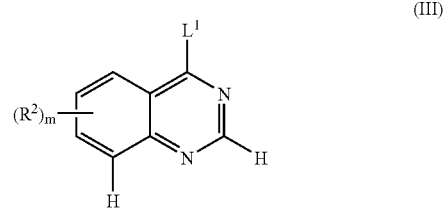

(wherein $R^2$ and m are as defined hereinbefore and $L^1$ is a displaceable moiety), with a compound of the formula IV:

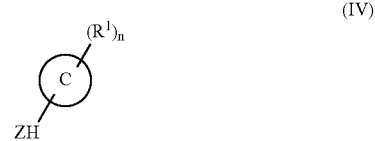

(wherein ring C, $R^1$, Z and n are as defined hereinbefore) to obtain compounds of the formula I and salts thereof. A convenient displaceable moiety $L^1$ is, for example, a halogeno, alkoxy (preferably $C_{1-4}$alkoxy), aryloxy, alkylsulphanyl, arylsulphanyl, alkoxyalkylsulphanyl or sulphonyloxy group, for example a chloro, bromo, methoxy, phenoxy, methylsulphanyl, 2-methoxyethylsulphanyl, methanesulphonyloxy or toluene-4-sulphonyloxy group.

The reaction is advantageously effected in the presence of a base. Such a base is, for example, an organic amine base such as, for example, pyridine, 2,6-lutidine, collidine, 4-dimethylaiinopyridine, triethylamine, morpholine, N-methylmorpholine or diazabicyclo[5.4.0]undec-7-ene, tetramethylguanidine or for example, an alkali metal or alkaline earth metal carbonate or hydroxide, for example sodium carbonate, potassium carbonate, calcium carbonate, cesium carbonate, sodium hydroxide or potassium hydroxide. Alternatively such a base is, for example, an alkali metal hydride, for example sodium hydride, or an alkali metal or alkaline earth metal amide, for example sodium amide, sodium bis(trmethylsilyl)amide, potassium amide or potassium bis(trimethylsilyl)amide. The reaction is preferably effected in the presence of an inert solvent or diluent, for example an ether such as tetrahydrofuran or 1,4-dioxan, an aromatic hydrocarbon solvent such as toluene, or a dipolar aprotic solvent such as N,N-dunethylformamide, N,N-dimethylacetamide, N-methylpyrrolidin-2-one or dimethyl sulphoxide. The reaction is conveniently effected at a temperature in the range, for example, 10 to 150° C., preferably in the range 20 to 90° C.

Where $R^1$ or $R^2$ contains a heterocyclic ring with a substituent it is possible to add the substituent after process (a) above using standard procedures of organic chemistry. Thus for example a compound of formula III as defined hereinbefore but wherein $R^2$ contains an unsubstituted heterocyclic ring may be reacted with a compound of formula IV as defined hereinbefore to give an intermediate compound in which $R^2$ contains an unsubstituted heterocyclic ring. The intermediate compound can then be substituted on the heterocyclic ring in $R^2$ using standard organic chemistry techniques to give a final compound of formula I.

When it is desired to obtain the acid salt, the free base may be treated with an acid such as a hydrogen halide, for example hydrogen chloride, sulphuric acid, a sulphonic acid, for example methane sulphonic acid, or a carboxylic acid, for example acetic or citric acid, using a conventional procedure.

(b) Production of those compounds of formula I and salts thereof wherein at least one $R^2$ is $R^5X^1$, $Q^1X^1$, $Q^{15}W^3$ or $Q^{21}W^4C_{1-5}alkylX^1$, wherein $R^5$, $Q^1$, $Q^{15}$, $W^1$, $Q^{21}$ and $W^4$ are as defined hereinbefore, and $X^1$ is —O—, —S—, —OC(O)— or —NR$^{10}$— (wherein $R^{10}$ independently represents hydrogen, $C_{1-3}$alkyl or $C_{1-3}$alkoxy$C_{2-3}$alkyl) can be achieved by the reaction, conveniently in the presence of a base (as defined hereinbefore in process (a)) of a compound of the formula V:

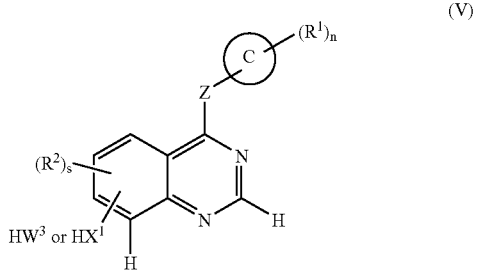

(wherein ring C, Z, $W^3$, $R^1$, $R^2$ and n are as hereinbefore defined and $X^1$ is as hereinbefore defined in this section and s is an integer from 0 to 2) with one of the compounds of the formulae VIa-d:

| | |
|---|---|
| $R^5$-$L^1$ | (VIa) |
| $Q^1$-$L^1$ | (VIb) |
| $Q^{15}$-$L^1$ | (VIc) |
| $Q^{21}$-$W^4$—$C_{1-5}$alkyl-$L^1$ | (VId) |

(wherein $R^5$, $Q^1$, $Q^{15}$, $Q^{21}$ and $W^4$ and $L^1$ are as hereinbefore defined), $L^1$ is a displaceable moiety for example a halogeno or sulphonyloxy group such as a bromo, methanesulphonyloxy or toluene-4-sulphonyloxy group, or $L^1$ may be generated in situ from an alcohol under standard Mitsunobu conditions ("Organic Reactions", John Wiley & Sons Inc, 1992, vol 42, chapter 2, David L Hughes). The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(c) Compounds of the formula I and salts thereof wherein at least one $R^2$ is $R^5X^1$, $Q^1X^1$, $Q^{15}W^3$ or $Q^{21}W^4C_{1-5}alkylX^1$, wherein $R^5$, $Q^1$, $Q^{15}$, $W^3$, $Q^{21}$ and $W^4$ are as defined hereinbefore, and $X^1$ is —O—, —S—, —OC(O)— or —NR$^{10}$— (wherein $R^{10}$ represents hydrogen, $C_{1-3}$alkyl or $C_{1-3}$alkoxy$C_{2-3}$alkyl) may be prepared by the reaction of a compound of the formula VII:

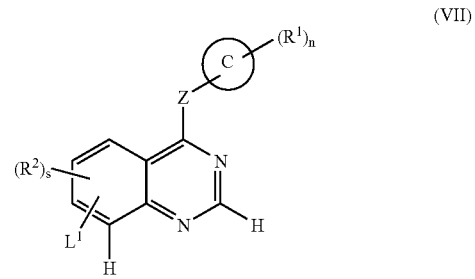

with one of the compounds of the formulae VIIIa-d:

| | |
|---|---|
| $R^5$-$X^1$-H | (VIIIa) |
| $Q^1$-$X^1$-H | (VIIIb) |
| $Q^{15}$-$W^3$—H | (VIIIc) |
| $Q^{21}$-$W^4$—$C_{1-5}$alkyl-$X^1$-H | (VIIId) |

(wherein $L^1$, $R^1$, $R^2$, $R^5$, $Q^1$, $Q^{15}$, $W^3$, $Q^{21}$, $W^4$, ring C, Z, n and s are all as hereinbefore defined and $X^1$ is as hereinbefore defined in this section). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(d) Compounds of the formula I and salts thereof wherein at least one $R^2$ is $R^5X'$, $Q^1X^1$, $Q^{21}W^4C_{1-5}alkylX^1$, $Q^{28}C_{1-5}alkylX^1$ or $Q^{29}C_{1-5}alkylX^1$ wherein $X^1$ is as hereinbefore, $R^5$ is $C_{1-5}alkylR^{113}$, wherein $R^{113}$ is selected from one of the following nine groups:

1) $X^{19}C_{1-3}$alkyl (wherein $X^{19}$ represents —O—, —S—, —SO$_2$—, —NR$^{114}$C(O)— or —NR$^{115}$SO$_2$— (wherein $R^{114}$ and $R^{115}$ which may be the same or different are each hydrogen, $C_{1-3}$alkyl or $C_{1-3}$alkoxy$C_{2-3}$alkyl);

2) NR$^{116}$R$^{117}$ (wherein $R^{116}$ and $R^{117}$ which may be the same or different are each hydrogen, $C_{1-3}$alkyl or $C_{1-3}$alkoxy$C_{2-3}$alkyl);

3) $X^{20}C_{1-5}alkylX^5R^{22}$ (wherein $X^{20}$ represents —O—, —S—, —SO$_2$—, —NR$^{118}$C(O)—, —NR$^{119}$SO$_2$— or —NR$^{120}$- (wherein $R^{118}$, $R^{119}$, and $R^{120}$ which may be the same or different are each hydrogen, $C_{1-3}$alkyl or $C_{1-3}$alkoxy$C_{2-3}$alkyl) and $X^5$ and $R^{22}$ are as defined hereinbefore);

4) $R^{28}$ (wherein $R^{28}$ is as defined hereinbefore);

5) $X^{21}R^{29}$ (wherein $X^{21}$ represents —O—, —S—, —SO$_2$—, —NR$^{121}$C(O)—, —NR$^{122}$SO$_2$—, or —NR$^{123}$- (wherein $R^{121}$, $R^{122}$, and $R^{123}$ which may be the same or different are each hydrogen, $C_{1-3}$alkyl or $C_{1-3}$alkoxy$C_{2-3}$alkyl) and $R^{29}$ is as defined hereinbefore); and 6) $X^{22}C_{1-5}alkylR^{29}$ (wherein $X^{22}$ represents —O—, —S—, —SO$_2$—, —NR$^{124}$C(O)—, —NR$^{125}$SO$_2$— or —NR$^{126}$— (wherein $R^{14}$, $R^{125}$ and $R^{126}$ each independently represents hydrogen, $C_{1-3}$alkyl or $C_{1-3}$alkoxy$C_{2-3}$alkyl) and $R^{29}$ is as defined hereinbefore);

7) $R^{29}$ (wherein $R^{29}$ is as defined hereinbefore);
8) $X^{22}C_{1-4}alkylR^{28}$ (wherein $X^{22}$ and $R^{28}$ are as defined hereinbefore); and
9) $R^{54}(C_{1-4}alkyl)_q(X^9)_rR^{55}$ (wherein q, r, $X^9$, $R^{54}$ and $R^{55}$ are as defined hereinbefore);
$Q^1$ is $C_{1-5}alkylQ^{27}$ wherein $Q^{27}$ is selected from:
10) $W^1Q^2$ (wherein $W^1$ and $Q^2$ are as defined hereinbefore);
11) $Q^2$ (wherein $Q^2$ is as defined hereinbefore);
12) $W^2C_{1-4}alkylQ^2$ (wherein $W^2$ and $Q^2$ are as defined hereinbefore);
13) $Q^{13}(C_{1-4}alkyl)_j(W^2)_kQ^{14}$ (wherein $W^2$, j, k, $Q^{13}$ and $Q^{14}$ are as defined hereinbefore); and
14) $Q^{13}(C_{1-4}alkanoyl)Q^{14n}$ (wherein $Q^{13}$ and $Q^{14n}$ are as defined hereinbefore), and
$Q^{21}$, $W^4$, $Q^{28}$ and $Q^{29}$ are as defined hereinbefore,
may be prepared by reacting a compound of the formula IX:

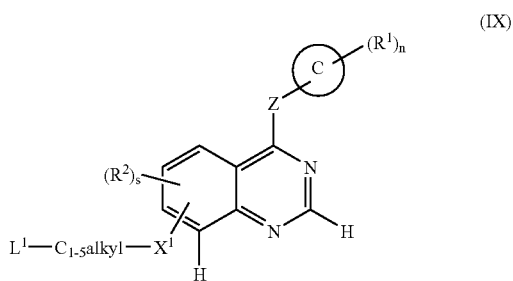

(wherein $L^1$, $X^1$, $R^1$, $R^2$, ring C, Z, n and s are as hereinbefore defined) with one of the compounds of the formulae Xa-e:

| | |
|---|---|
| $R^{113}$-H | (Xa) |
| $Q^{27}$-H | (Xb) |
| $Q^{21}$-$W^4$—H | (Xc) |
| $Q^{28}$-H | (Xd) |
| $Q^{29}$-H | (Xe) |

(wherein $R^{113}$, $Q^{27}$, $Q^{28}$, $Q^{29}$, $Q^{21}$ and $W^4$ are as defined hereinbefore) to give a compound of the formula I or salt thereof. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Processes (a), (b) and (d) are preferred over process (c).
Processes (a) and (b) are the more preferred.

(e) The production of those compounds of the formula I and salts thereof wherein one or more of the substituents $(R^2)_m$ is represented by —$NR^{127}R^{128}$, where one (and the other is hydrogen) or both of $R^{127}$ and $R^{128}$ are $C_{1-3}alkyl$, may be effected by the reaction of compounds of formula I wherein the substituent $(R^2)_m$ is an amino group and an alkylating agent, preferably in the presence of a base as defined hereinbefore. Such alkylating agents are C,3alkyl moieties bearing a displaceable moiety as defined hereinbefore such as $C_{1-3}alkyl$ halides for example $C_{1-3}alkyl$ chloride, bromide or iodide. The reaction is preferably effected in the presence of an inert solvent or diluent (as defined hereinbefore in process (a)) and at a temperature in the range, for example, 10 to 100° C., conveniently at about ambient temperature. The production of compounds of formula I and salts thereof wherein one or more of the substituents $R^2$ is an amino group may be effected by the reduction of a corresponding compound of formula I wherein the substituent(s) at the corresponding position(s) of the quinazoline group is/are a nitro group(s). The reduction may conveniently be effected as described in process (i) hereinafter. The production of a compound of formula I and salts thereof wherein the substituent(s) at the corresponding position(s) of the quinazoline group is/are a nitro group(s) may be effected by the processes described hereinbefore and hereinafter in processes (a-d) and (i-v) using a compound selected from the compounds of the formulae (I-XXII) in which the substituent(s) at the corresponding position(s) of the quinazoline group is/are a nitro group(s).

(f) Compounds of the formula I and salts thereof wherein $X^1$ is —SO— or —$SO_2$— may be prepared by oxidation from the corresponding compound in which $X^1$ is —S— or —SO— (when $X^1$ is —$SO_2$— is required in the final product). Conventional oxidation conditions and reagents for such reactions are well known to the skilled chemist.

Synthesis of Intermediates (i) The compounds of formula III and salts thereof in which $L^1$ is halogeno may for example be prepared by halogenating a compound of the formula XI:

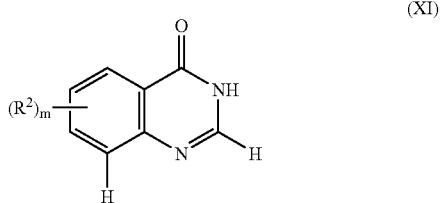

wherein $R^2$ and m are as hereinbefore defined).

Convenient halogenating agents include inorganic acid halides, for example thionyl chloride, phosphorus(III)chloride, phosphorus(V)oxychloride and phosphorus(V)chloride. The halogenation reaction may be effected in the presence of an inert solvent or diluent such as for example a halogenated solvent such as methylene chloride, trichloromethane or carbon tetrachloride, or an aromatic hydrocarbon solvent such as benzene or toluene, or the reaction may be effected without the presence of a solvent. The reaction is conveniently effected at a temperature in the range, for example 10 to 150° C., preferably in the range 40 to 100° C.

The compounds of formula XI and salts thereof may, for example, be prepared by reacting a compound of the formula XII:

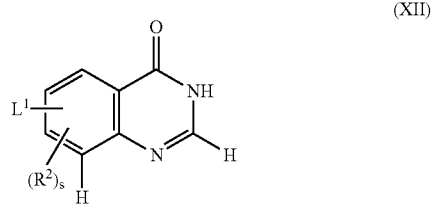

(wherein $R^2$, s and $L^1$ are as hereinbefore defined) with one of the compounds of formulae VIIIa-d as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

Compounds of formula XI and salts thereof wherein at least one $R^2$ is $R^5X'$, $Q^1X^1$, $Q^{15}W^3$ or $Q^{21}W^4C_{1-5}alkylX^1$, wherein $R^5$, $Q^1$, $Q^{15}$, $W^3$, $Q^{21}$ and $W^4$ are as defined hereinbefore, and wherein $X^1$ is —O—, —S—, —SO—, —SO$_2$—, —C(O)—, —C(O)NR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxyC$_{2-3}$alkyl), may for example also be prepared by the reaction of a compound of the formula XIII:

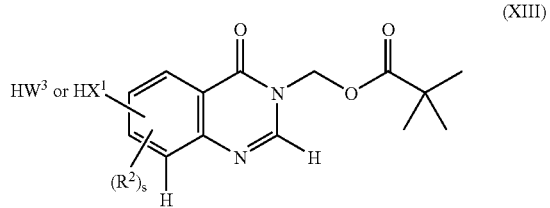

(XIII)

(wherein $R^2$, $W^3$ and s are as hereinbefore defined and $X^1$ is as hereinbefore defined in this section) with one of the compounds of formulae VIa-d as hereinbefore defined. The reaction may for example be effected as described for process (b) hereinbefore. The pivaloyloxymethyl group can then be cleaved by reacting the product with a base such as, for example, aqueous ammonia, triethylamine in water, an alkali metal or alkaline earth metal hydroxide or alkoxide, preferably aqueous ammonia, aqueous sodium hydroxide or aqueous potassium hydroxide, in a polar protic solvent such as an alcohol, for example methanol or ethanol. The reaction is conveniently effected at a temperature in the range 20 to 100° C., preferably in the range 20 to 50° C.

The compounds of formula XI and salts thereof may also be prepared by cyclising a compound of the formula XIV:

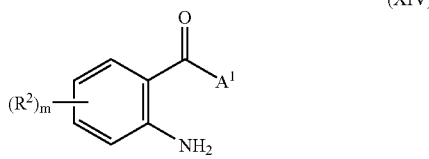

(XIV)

(wherein $R^2$ and m, are as hereinbefore defined, and $A^1$ is an hydroxy, alkoxy (preferably $C_{1-4}$alkoxy) or amino group) whereby to form a compound of formula XI or salt thereof. The cyclisation may be effected by reacting a compound of the formula XIV, where $A^1$ is an hydroxy or alkoxy group, with formamide or an equivalent thereof effective to cause cyclisation whereby a compound of formula XI or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XI may also be prepared by cyclising a compound of the formula XIV, where $A^1$ is an amino group, with formic acid or an equivalent thereof effective to cause cyclisation whereby a compound of formula XI or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethyl ether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XIV and salts thereof may for example be prepared by the reduction of the nitro group in a compound of the formula XV:

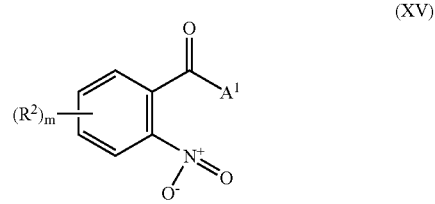

(XV)

(wherein $R^2$, m and $A^1$ are as hereinbefore defined) to yield a compound of formula XIV as hereinbefore defined. The reduction of the nitro group may conveniently be effected by any of the procedures known for such a transformation. The reduction may be carried out, for example, by stirring a solution of the nitro compound under hydrogen at 1 to 4 atmospheres pressure in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound under hydrogen at 2 atmospheres pressure in the presence of the activated metal and a solvent or diluent such as a mixture of water and alcohol, for example methanol or ethanol, at a temperature in the range, for example 50 to 150° C., conveniently at about 70° C.

Compounds of the formula XV and salts thereof may for example be prepared by the reaction of a compound of the formula XVI:

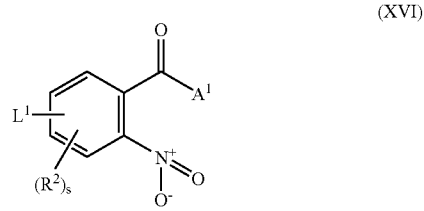

(XVI)

(wherein $R^2$, s, $L^1$ and $A^1$ are as hereinbefore defined) with one of the compounds of formulae VIIIa-d as hereinbefore defined to give a compound of the formula XV. The reaction of the compounds of formulae XVI and VIIIa-d is conveniently effected under conditions as described for process (c) hereinbefore.

Compounds of formula XV and salts thereof wherein at least one $R^2$ is $R^5X'$, $Q^1X^1$, $Q^{13}W^3$ or $Q^{21}W^4C_{1-5}alkylX^1$, wherein $R^1$, $Q^1$, $Q^{15}$, $W^3$, $Q^{21}$ and $W^4$ are as defined hereinbefore, and wherein $X^1$ is —O—, —S—, —SO$_2$—, —C(O)—, —C(O)NR$^7$—, —SO$_2$NR$^8$— or —NR$^{10}$— (wherein R$^7$, R$^8$ and R$^{10}$ each independently represents hydrogen, C$_{1-3}$alkyl or C$_{1-3}$alkoxyC$_{2-3}$alkyl), may for example also be prepared by the reaction of a compound of the formula XVII:

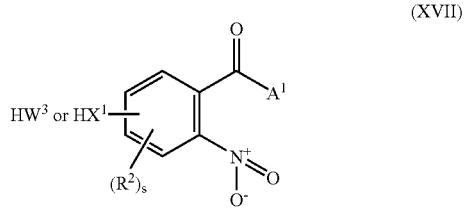

(XVII)

(wherein R$^2$, s and A$^1$ are as hereinbefore defined and X$^1$ is as hereinbefore defined in this section) with one of the compounds of formulae VIa-d as hereinbefore defined to yield a compound of formula XV as hereinbefore defined. The reaction of the compounds of formulae XVII and VIa-d is conveniently effected under conditions as described for process (b) hereinbefore.

The compounds of formula III and salts thereof wherein at least one R$^2$ is R$^5$X$^1$ and wherein X$^1$ is —CH$_2$— may be prepared for example as described above from a compound of the formula XV (in which R$^2$ is —CH$_3$) or XIII (in which HX$^1$— is —CH$_3$), by radical bromination or chlorination to give a —CH$_2$Br or —CH$_2$Cl group which may then be reacted with a compound of the formula R$^5$—H under standard conditions for such substitution reactions.

The compounds of formula III and salts thereof wherein at least one R$^2$ is R$^5$X$^1$ and wherein X$^1$ is a direct bond may be prepared for example as described above from a compound of the formula XI, wherein the R$^5$ group is already present in the intermediate compounds (for example in a compound of the formula XV) used to prepare the compound of formula XI.

The compounds of formula III and salts thereof wherein at least one R$^2$ is R$^5$X$^1$ and wherein X$^1$ is —NR$^6$C(O)— or —NR$^9$SO$_2$— may be prepared for example from a compound of the formula XIII in which HX$^1$— is an —NHR$^6$— or —NHR$^9$— group (prepared for example from an amino group (later functionalised if necessary) by reduction of a nitro group) which is reacted with an acid chloride or sulfonyl chloride compound of the formula R$^5$COCl or R$^5$SO$_2$Cl.

The compounds of formula III and salts thereof wherein at least one R$^2$ is R$^5$X$^1$, Q$^1$X$^1$, Q$^{15}$W$^3$ or Q$^{21}$W$^4$C$_{1-5}$alkylX$^1$, wherein R$^5$, Q$^1$, Q$^{15}$, W$^3$, Q$^{21}$ and W$^4$ are as defined hereinbefore, and wherein X$^1$ is —O—, —S—, —SO$_2$—, —OC(O)—, —C(O)NR$^7$—, —SO$_2$NR$^8$— or —NR$^{10}$— (wherein R$^7$, R$^8$ and R$^{10}$ each independently represents hydrogen, C$_{1-3}$alkyl or C$_{1-3}$alkoxyC$_{2-3}$alkyl), may also be prepared for example by reacting a compound of the formula XVIII:

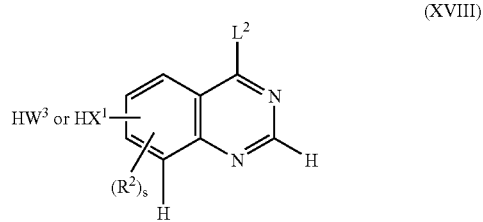

(XVIII)

(wherein R$^2$, W$^3$ and s are as hereinbefore defined, X$^1$ is as hereinbefore defined in this section and L$^2$ represents a displaceable protecting moiety) with one of the compounds of formulae VIa-d as hereinbefore defined, whereby to obtain a compound of formula III in which L$^1$ is represented by L$^2$.

A compound of formula XVIII is conveniently used in which L$^2$ represents a phenoxy group which may if desired carry up to 5 substituents, preferably up to 2 substituents, selected from halogeno, nitro and cyano. The reaction may be conveniently effected under conditions as described for process (b) hereinbefore.

The compounds of formula XVIII and salts thereof may for example be prepared by deprotecting a compound of the formula XIX:

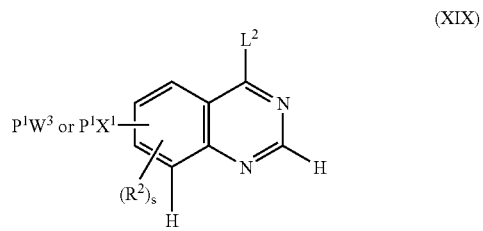

(XIX)

(wherein R$^2$, W$^3$, s and L$^2$ are as hereinbefore defined, PI is a protecting group and X$^1$ is as hereinbefore defined in the section describing compounds of the formula XVIII). The choice of protecting group PI is within the standard knowledge of an organic chemist, for example those included in standard texts such as "Protective Groups in Organic Synthesis" T. W. Greene and R. G. M. Wuts, 2nd Ed. Wiley 1991, including N-sulphonyl derivatives (for example, p-toluenesulphonyl), carbamates (for example, t-butyl carbonyl), N-alkyl derivatives (for example, 2-chloroethyl, benzyl) and amino acetal derivatives (for example benzyloxymethyl). The removal of such a protecting group may be effected by any of the procedures known for such a transformation, including those reaction conditions indicated in standard texts such as that indicated hereinbefore, or by a related procedure. Deprotection may be effected by techniques well known in the literature, for example where P$^1$ represents a benzyl group deprotection may be effected by hydrogenolysis or by treatment with trifluoroacetic acid.

One compound of formula III may if desired be converted into another compound of formula III in which the moiety L$^1$ is different. Thus for example a compound of formula III in which L$^1$ is other than halogeno, for example optionally substituted phenoxy, may be converted to a compound of formula III in which L$^1$ is halogeno by hydrolysis of a compound of formula III (in which L$^1$ is other than halogeno) to yield a compound of formula XI as hereinbefore defined, followed by introduction of halide to the compound of formula XI, thus obtained as hereinbefore defined, to yield a compound of formula III in which L$^1$ represents halogen.

(ii) Compounds of formula IV and salts thereof in which ring C is indolyl may be prepared by any of the methods known in the art, such as for example those described in "Indoles Part I", "Indoles Part II", 1972 John Wiley & Sons Ltd and "Indoles Part III" 1979, John Wiley & Sons Ltd, edited by W. J. Houlihan.

Examples of the preparation of indoles are given in Examples 1 and 10 hereinafter.

Compounds of formula IV and salts thereof in which ring C is quinolinyl may be prepared by any of the methods known in the art, such as for example those described in "The Chemistry of Heterocyclic Compounds: Quinolines Parts I, II and III", 1982 (Interscience publications) John Wiley & Sons Ltd, edited by G. Jones, and in "Comprehensive Heterocyclic Chemistry Vol II by A. R. Katritzky", 1984 Pergamon Press, edited by A. J. Boulton and A McKillop.

Compounds of formula IV and salts thereof in which ring C is indazolyl may be prepared by any of the methods known in the art, such as for example those described in Petitcoles, Bull. Soc. Chim. Fr. 1950, 466 and Davies, J. Chem. Soc. 1955, 2412.

Compounds of formula IV and salts thereof in which ring C is azaindolyl may be prepared by any of the methods known in the art, such as for example those described in Heterocycles 50, (2), 1065-1080, 1999. They may also be made according to the process in Example 2 hereinafter.

In Heterocycles 50, (2), 1065-1080, 1999 a process is described, shown in Scheme 1 hereinafter, wherein 7-azaindole is halogenated to give 3,3,5-tribromo-2-oxo-1,3-dihydropyrrolo[2,3-b]pyridine (12). 12 is then treated with zinc in acetic acid to give 5-broio-2-oxo-1,3-dihydropyrrolo[2,3-b]pyridine (13) and 13 is then treated via two steps to give 5-bromo-7-azaindole (14). This synthesis is shown in Scheme 1:

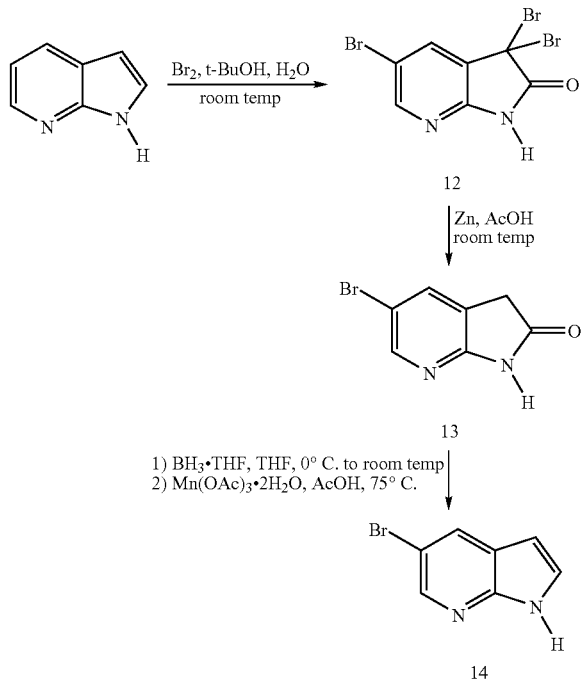

Surprisingly we have found that it is better to synthesise the 5-bromo-7-azaindole by three steps outlined in Scheme 2:

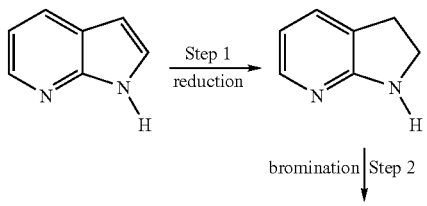

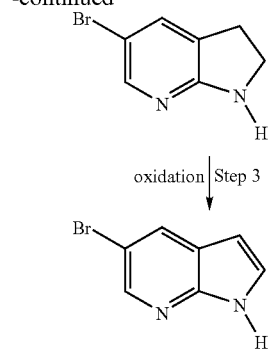

Scheme 2 is surprisingly better than Scheme 1. Scheme 2 requires smaller quantities of reagent and is more adaptable for large scale manufacture because it is cheaper, more efficient and more environmentally friendly than Scheme 1.

Step 1:

The reduction may be carried out by any of the procedures known for such a transformation. The reduction may be carried out, for example, by treating a solution of 7-azaindole in an alcohol, for example ethanol, or another solvent for example decahydronaphthalene, with wet Raney Nickel and then stirring the mixture in a hydrogen atmosphere under pressure, for example at 5 atmospheres pressure, at 50 to 150° C., preferably at about 95° C., over a period of time, for example 2 days, to give, after purification, 7-azaindoline.

Step 2:

The bromination may be carried out by any of the procedures known for such a reaction. The bromination may be carried out, for example, by mixing 7-azaindoline, p-toluene sulphonic acid monohydrate and 1,3-dibromo-5,5-dimethylhydantoin in methylene chloride and stirring the mixture at for example ambient temperature for a period of time, for example 3 hours. Extraction and purification gives 5-bromo-7-azaindoline.

Step 3:

The oxidation may be carried out by any of the procedures known for such a transformation. The oxidation may be carried out, for example, by mixing 5-bromo-7-azaindoline and precipitated, active manganese (IV) oxide in toluene, then heating the mixture at 50 to 150° C., preferably at about 90° C. to give 5-bromo-7-azaindole.

In Heterocycles 50, (2), 1065-1080, 1999 the 5-bromo-7-azaindole (986 mg, 5.0 mmol) is dissolved, under an inert atmosphere, in a mixture of DMF (32 ml) and methanol (20 ml). To this solution is added successively sodium methoxide (14.3 g, 265 mmol) and copper(I) bromide (1.43 g, 10.0 mmol) at ambient temperature. The mixture is heated at reflux for 2.5 hours to give, after extraction and purification, 5-methoxy-7-azaindole (530 mg, 72%).

We have found that the yield for this reaction is surprisingly and significantly increased from 72% to 97% if the reagents are used in proportionately smaller quantities including for example a different solvent mixture. Thus in Example 2 hereinafter:

"A solution of 5-bromo-7-azaindole (8.6 g, 44 mmol), copper (1) bromide (12.6 g, 88 mmol) and sodium methoxide (100 g, 1.85 mol) in a mixture of "degassed" DMF (260 mls) and methanol (175 mils) was stirred at ambient temperature in a nitrogen atmosphere, and then heated at reflux for 3.5 hours."

After extraction and partial purification this gave crude solid, 5-methoxy-7-azaindole (6.3 g, 97%), which was taken through the next step without further purification.

The 5-hydroxy-7-azaindole may be generated from the 5-methoxy-7-azaindole by the following process.

Adding boron tribromide in methylene chloride to a solution of 5-methoxy-7-azaindole in methylene chloride cooled at about −30° C. Leaving the mixture to warm up to ambient temperature and stirring it for a period of time, for example overnight. Pouring the mixture onto ice and water and adjusting the pH of the aqueous phase to about 6. Separating the organic phase and further extracting the aqueous phase with ethyl acetate. Combining the organic phases washing them with brine, drying them, for example over magnesium sulphate, and then evaporating them. The residue may then be purified, for example by column chromatography eluting with increasingly polar mixtures of methylene chloride and methanol to give 5-hydroxy-7-azaindole.

Alternatively the 5-methoxy-7-azaindole may be suspended in methylene chloride, stirred in a nitrogen atmosphere, cooled in a cold water bath and a 1.0 M solution of boron tribromide in methylene chloride added dropwise over a period of time, for example 30 minutes. The mixture is then allowed to stir at ambient temperature for a period of time, for example 4 hours, before being quenched by taking the solution to about pH7, for example by the dropwise addition of 5N sodium hydroxide. The resulting 2 phase mixture is allowed to separate and the organic phase collected and evaporated in vacuo. The residue may be treated with the aqueous phase from above, the mixture adjusted to about pH7 once more and subjected to a continuous ethyl acetate extraction over a period of time for example 18 hours. The resulting ethyl acetate suspension is then evaporated in vacuo to give a product which may be purified, for example by column chromatography using Kieselgel 60 silica and methylene chloride/methanol/880 ammonium hydroxide (100/8/1) solvent to give 5-hydroxyazaindole.

(ii) Compounds of formula V as hereinbefore defined and salts thereof may be made by deprotecting the compound of formula XX:

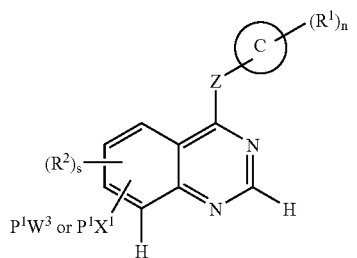

(XX)

(wherein ring C, Z, $R^1$, $R^2$, $P^1$, $W^3$, n and s are as hereinbefore defined and $X^1$ is as hereinbefore defined in the section describing compounds of the formula V) by a process for example as described in (i) above.

Compounds of the formula XX and salts thereof may be made by reacting compounds of the formulae XIX and IV as hereinbefore defined, under the conditions described in (a) hereinbefore, to give a compound of the formula XX or salt thereof.

(iv) Compounds of the formula VII and salts thereof may be made by reacting a compound of the formula XXI:

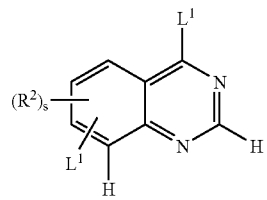

(XXI)

(wherein $R^2$, s and each $L^1$ are as hereinbefore defined and the $L^1$ in the 4-position and the other $L^1$ in a further position on the quinazoline ring may be the same or different) with a compound of the formula IV as hereinbefore defined, the reaction for example being effected by a process as described in (a) above.

(v) Compounds of formula IX as defined hereinbefore and salts thereof may for example be made by the reaction of compounds of formula V as defined hereinbefore with compounds of the formula XXII:

$$L^1\text{-}C_{1\text{-}5}\text{alkyl-}L^1 \qquad \qquad (XXII)$$

(wherein $L^1$ is as hereinbefore defined) to give compounds of formula IX or salts thereof. The reaction may be effected for example by a process as described in (b) above.

(vi) Intermediate compounds wherein $X^1$ is —SO— or —$SO_2$— may be prepared by oxidation from the corresponding compound in which $X^1$ is —S— or —SO— (when $X^1$ is —$SO_2$— is required in the final product). Conventional oxidation conditions and reagents for such reactions are well known to the skilled chemist.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein are novel and these are provided as a further feature of the invention. The preparation of these compounds is as described herein and/or is by methods well known to persons skilled in the art of organic chemistry.

For example the intermediates 7-benzyloxy-4-(4-fluoro-2-methylindol-5-yloxy)-6-methoxyquinazoline and 4-(4-fluoro-2-methylindol-5-yloxy)-7-hydroxy-6-methoxyquinazoline, which are both described in Example 7, are novel and each may be used in the manufacture of compounds of the present invention and of compounds of WO 00/47212. 7-Benzyloxy-4-(4-fluoro-2-methylindol-5-yloxy)-6-methoxyquinazoiine and 4-(4-fluoro-2-methylindol-5-yloxy)-7-hydroxy-6-methoxyquinazoline may each be used in the manufacture of compounds which inhibit angiogenesis and/or increased vascular permeability.

According to one embodiment of the present invention there is provided 7-benzyloxy-4-(4-fluoro-2-methylindol-5-yloxy)-6-methoxyquinazoline or a salt thereof.

According to one embodiment of the present invention there is provided 4-(4-fluoro-2-methylindol-5-yloxy)-7-hydroxy-6-methoxyquinazoline or a salt thereof.

According to one embodiment of the present invention there is provided the use of 7-benzyloxy-4-(4-fluoro-2-methylindol-5-yloxy)-6-methoxyquinazoline or a salt thereof in the manufacture of a compound of the present invention or a compound of WO 00/47212.

According to one embodiment of the present invention there is provided the use of 4-(4-fluoro-2-methylindol-5-yloxy)-7-hydroxy-6-methoxyquinazoline or a salt thereof in the manufacture of a compound of the present invention or a compound of WO 00/47212.

The identification of compounds which inhibit angiogenesis and/or increased vascular permeability, which potently inhibit the tyrosine kinase activity associated with the VEGF receptor KDR and are selective for KDR over Flt-1, which have less extended plasma pharmacokinetics and which are inactive or only weakly active in the hERG assay, is desirable and is the subject of the present invention.

These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF, FGF or EGF receptor cytoplasmic domains may be obtained by total gene synthesis (Edwards M, International Biotechnology Lab 5(3), 19-25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt-1 (Genbank accession number X51602), a 1.7 kb DNA fragment encoding most of the cytoplasmic domain, commencing with methionine 783 and including the termination codon, described by Shibuya et al (Oncogene, 1990, 5: 519-524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF R1 receptor, Genbank accession number X51803) may be cloned and expressed in a similar manner.

For expression of cFlt-1 tyrosine kinase activity, Sf21 cells were infected with plaque-pure cFlt-1 recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microlitres of 40 mM manganese(II) chloride containing 8 µM adenosine-5'-triphosphate (ATP) was added to all test wells except "blank" control wells which contained manganese(II)chloride without ATP. To start the reactions 50 µl of freshly diluted enzyme was added to each well and the plates were incubated at ambient temperature for 20 minutes. The liquid was then discarded and the wells were washed twice with PBST. One hundred microlitres of mouse IgG antiphosphotyrosine antibody (Upstate Biotechnology Inc. product 05-321), diluted 1 in 6000 with PBST containing 0.5% w/v bovine serum albumin (BSA), was added to each well and the plates were incubated for 1 hour at ambient temperature before discarding the liquid and washing the wells twice with PBST. One hundred microlitres of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at ambient temperature before discarding the liquid and washing the wells twice with PBST. One hundred microlitres of 2,2'-azino-bis(3-ethylbenzthiazolie-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20-60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 µg/ml heparin+1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$.

On day 4 the cultures were pulsed with 1 μCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cprn, was used to measure inhibition of growth factor-stimulated cell proliferation by compounds.

(c) In Vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1\times10^6$ CaLu-6 cells/mouse in 100 μl of a 50% (v/v) solution of Matrigel in serum free culture medium. Ten days after cellular implant, mice were allocated to groups of 8-10, so as to achieve comparable group mean volumes. Tumours were measured using vernier calipers and volumes were calculated as: $(l\times w)\times\sqrt{(l\times w)}\times(\pi/6)$, where l is the longest diameter and w the diameter perpendicular to the longest. Test compounds were administered orally once daily for a minimum of 21 days, and control animals received compound diluent. Tumours were measured twice weekly. The level of growth inhibition was calculated by comparison of the mean tumour volume of the control group versus the treatment group using a Student T test and/or a Mann-Whitney Rank Sum Test. The inhibitory effect of compound treatment was considered significant when $p<0.05$.

(d) hERG-encoded Potassium Channel Inhibition Test

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% Ml senun-free supplement (Egg Technologies; product number 70916) and 0.4 mg/ml Geneticin G418 (Sigina-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at ambient temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of –80 in V (set by the amplifier), and appropriate adjustment of series resistance and capacitance controls, electrophysiology software (Clampex, Axon Instruments) was used to set a holding potential (–80 mV) and to deliver a voltage protocol. This protocol was applied every 15 seconds and consisted of a 1 s step to +40 mV followed by a 1 s step to –50 mV. The current response to each imposed voltage protocol was low pass filtered by the amplifier at 1 kHz. The filtered signal was then acquired, on line, by digitizing this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| $MgCl_2$ | 1 | 1 |
| $CaCl_2$ | — | 1.8 |
| HEPES | 10 | 10 |
| glucose | — | 10 |
| $Na_2ATP$ | 5 | — |
| EGTA | 5 | — |

| Parameter | Pipette | Bath |
|---|---|---|
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to –50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency ($IC_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Plasma pharmacokinetics may be assessed by measuring plasma half-life in vivo. The longer the plasma half-life in vivo the more extended are the plasma pharmacokinetics.

Compounds of the present invention have less extended plasma pharmacokinetics than compounds of WO 00/47212. Compounds of the present invention have shorter half-lives in vivo than compounds of WO 00/47212.

Plasma half-life in vivo may be determined by standard methods which are well-known in the art of plasma pharmacokinetics. Any species may be used and the plasma half-life determined by standard methodology, for example plasma half-life may be measured in rat, dog, monkey or human.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5-5000 mg per square metre body area of the animal, i.e. approximately 0.1-100 mg/kg. A unit dose in the range, for example, 1-10 mg/kg, preferably 1-50 mg/kg is envisaged and this normally provides a therapeutically-effective dose. A unit dose form such as a tablet or capsule will usually contain, for example 1-250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 0.1-50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:
(i) other antiangiogenic agents such as those which inhibit the effects of vascular endothelial growth factor, (for example the anti-vascular endothelial cell growth factor antibody bevacizumab [Avastin™], and those that work by different mechanisms from those defined hereinbefore (for example linomide, inhibitors of integrin αvβ3 function, angiostatin, razoxin, thalidomide), and including vascular targeting agents (for example combretastatin phosphate and compounds disclosed in International Patent Applications WO00/40529, WO 00/41669, WO01/92224, WO02/04434 and WO02/08213 and the vascular damaging agents described in International Patent Application Publication No. WO 99/02166 the entire disclosure of which document is incorporated herein by reference, (for example N-acetylcolchinol-O-phosphate)); (ii) cytostatic agents such as antioestrogens (for example tamoxifen, toreinifene, raloxifene, droloxifene, iodoxyfene), oestrogen receptor down regulators (for example fulvestrant), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide, buserelin), inhibitors of 5α-reductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor), such inhibitors include growth factor antibodies, growth factor receptor antibodies, (for example the anti-erbb2 antibody trastuzumab [Herceptin™] and the anti-erbb1 antibody cetuximab [C225]), farnesyl transferase inhibitors, tyrosine kinase inhibitors for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)) and serine/threonine kinase inhibitors); and
(iii) antiproliferative/antineoplastic drugs and combinations thereof, as used in medical oncology, such as antimetabolites (for example antifolates like methotrexate, fluoropyrimidines like 5-fluorouracil, tegafur, purine and adenosine analogues, cytosine arabinoside); antitumour antibiotics (for example anthracyclines like adriamycin, bleomycin, doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine, vinblastine, vindesine, vinorelbine, and taxoids like taxol, taxotere); topoisomerase inhibitors (for example epipodophyllotoxins like etoposide and teniposide, amsacrine, topotecan, camptothecin and also irinotecan); also enzymes (for example asparaginase); and thymidylate synthase inhibitors (for example raltitrexed);
and additional types of chemotherapeutic agent include:
(iv) biological response modifiers (for example interferon);
(v) antibodies (for example edrecolomab);

(vi) antisense therapies, for example those which are directed to the targets listed above, such as ISIS 2503, an anti-ras antisense;

(vii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

For example such conjoint treatment may be achieved by way of the simultaneous, sequential or separate administration of a compound of formula I as defined hereinbefore, and a vascular targeting agent described in WO 99/02166 such as N-acetylcolchinol-O-phosphate (Example 1 of WO 99/02166).

It is known from WO 01/74360 that antiangiogenics can be combined with antihypertensives. A compound of the present invention can also be administered in combination with an antihypertensive. An antihypertensive is an agent which lowers blood pressure, see WO 01/74360 which is incorporated herein by reference.

Thus according to the present invention there is provided a method of treatment of a disease state associated with angiogenesis which comprises the administration of an effective amount of a combination of a compound of the present invention or a pharmaceutically acceptable salt thereof and an anti-hypertensive agent to a warm-blooded animal, such as a human being.

According to a further feature of the present invention there is provided the use of a combination of a compound of the present invention or a pharmaceutically acceptable salt thereof and an anti-hypertensive agent for use in the manufacture of a medicament for the treatment of a disease state associated with angiogenesis in a warm-blooded mammal, such as a human being.

According to a further feature of the present invention there is provided a pharmaceutical composition comprising a compound of the present invention or a pharmaceutically acceptable salt thereof and an anti-hypertensive agent for the treatment of a disease state associated with angiogenesis in a warm-blooded mammal, such as a human being.

According to a further aspect of the present invention there is provided a method for producing an anti-angiogenic and/or vascular permeability reducing effect in a warm-blooded animal, such as a human being, which comprises administering to said animal an effective amount of a combination of a compound of the present invention or a pharmaceutically acceptable salt thereof and an anti-hypertensive agent.

According to a further aspect of the present invention there is provided the use of a combination of a compound of the present invention or a pharmaceutically acceptable salt thereof and an anti-hypertensive agent for the manufacture of a medicament for producing an anti-angiogenic and/or vascular permeability reducing effect in a warm-blooded mammal, such as a human being.

Preferred antihypertensive agents are calcium channel blockers, angiotensin converting enzyme inhibitors (ACE inhibitors), angiotensin II receptor antagonists (A-II antagonists), diuretics, beta-adrenergic receptor blockers (β-blockers), vasodilators and alpha-adrenergic receptor blockers (α-blockers). Particular antihypertensive agents are calcium channel blockers, angiotensin converting enzyme inhibitors (ACE inhibitors), angiotensin II receptor antagonists (A-II antagonists) and beta-adrenergic receptor blockers (β-blockers), especially calcium channel blockers.

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation including age-related macular degeneration. Cancer may affect any tissue and includes leukaemia, multiple myeloma and lymphoma. In particular such compounds of the invention are expected to slow advantageously the growth of primary and recurrent solid tumours of, for example, the colon, breast, prostate, lungs and skin. More particularly such compounds of the invention are expected to inhibit any form of cancer associated with VEGF including leukaemia, multiple myeloma and lymphoma and also, for example, the growth of those primary and recurrent solid tumours which are associated with VEGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:—

(i) evaporations were carried out by rotary evaporation in vacuo and work-up procedures were carried out after removal of residual solids such as drying agents by filtration;

(ii) operations were carried out at ambient temperature, that is in the range 18-25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; qui, quintet;

(vii) intermediates were not generally fully characterised and purity was assessed by thin layer chromatography (TLC), high-performance liquid chromatography (HPLC), infra-red (1R) or NMR analysis;

(viii) HPLC were run under 2 different conditions:
1) on a TSK Gel super ODS 2 μM 4.6 mm×5 cm column, eluting with a gradient of methanol in water (containing 1% acetic acid) 20 to 100% in 5 minutes. Flow rate 1.4 nm/minute. Detection: U.V. at 254 nm and light scattering detections;
2) on a TSK Gel super ODS 2 μM 4.6 mm×5 cm column, eluting with a gradient of methanol in water (containing 1% acetic acid) 0 to 100% in 7 minutes. Flow rate 1.4 ml/minute. Detection: U.V. at 254 nm and light scattering detections.

(ix) petroleum ether refers to that fraction boiling between 40-60° C.

(x) the following abbreviations have been used:—

| DMF | N,N-dimethylformamide |
|---|---|
| DMSO | dimethylsulphoxide |
| TFA | trifluoroacetic acid |
| THF | tetrahydrofuran |
| DEAD | diethyl azodicarboxylate |
| DMA | dimethylacetamide |
| DMAP | 4-dimethylaminopyridine |
| LC/MS | HPLC coupled to mass spectrometry |

EXAMPLE 1

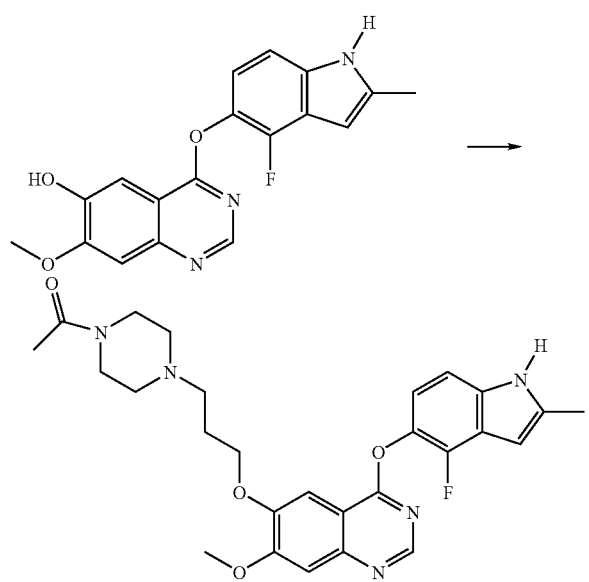

Diethyl azodicarboxylate (0.178 g, 1.02 mmol) was added to a solution of 4-(4-fluoro-2-methylindol-5-yloxy)-6-hydroxy-7-methoxyquinazoline (0.267 g, 0.787 mmol), triphenylphosphine (0.31 g, 1.18 mmol) and 3-(4-acetylpiperazin-1-yl)propan-1-ol (0.176 g, 0.945 mmol) in methylene chloride (10 nm). After stirring for 15 minutes at ambient temperature, further triphenylphosphine (0.062 mg, 0.236 mmol) and diethyl azodicarboxylate (0.041 mg, 0.3 mmol) were added. After stirring for 1 hour at ambient temperature, the mixture was poured onto a column of silica and eluted with increasingly polar mixtures of ethyl acetate and methylene chloride followed by methylene chloride and methanol. The fractions containing the expected product were combined and evaporated. The residue was triturated under diethyl ether and the solid was filtered, washed with ether and dried under vacuum to give 6-(3-(4-acetylpiperazin-1-yl)propoxy)-4-(4-fluoro-2-methylindol-5-yloxy)-7-methoxyquinazoline 0.210 g, 60%).

$^1$H NMR Spectrum: (DMSOd$_6$, CF$_3$COOD) 2.1 (s, 3H), 2.35 (m, 2H), 2.45 (s, 3H), 3.0 (m, 2H), 3.2 (r, 1H), 3.4 (dd, 2H), 3.5 (m, 1H), 3.65 (d, 2H), 4.1 (m, 1H), 4.15 (s, 3H), 4.45 (dd, 2H), 4.55 (d, 1H), 6.3 (s, 0.3H, partly exchanged), 7.05 (dd, 1H), 7.28 (d, 1H), 7.6 (s, 1H), 7.9 (s, 1H), 9.2 (s, 1H)

MS-ESI: 508.5 [M+H]$^+$

The starting material was prepared as follows:

A suspension of 1-acetylpiperazine (3.85 g, 30 mmol), potassium carbonate (8.3 g, 60 mmol) and 3-bromo-1-propanol (4 ml, 45 mmol) in acetonitrile (30 ml) was heated and stirred at 80° C. for 5 hours. After cooling, the mixture was filtered and the filtrate was evaporated. The residue was purified by column chromatography, eluting with increasingly polar mixtures of methylene chloride and ethanol. The fractions containing the expected product were combined and evaporated to give 3-(4-acetylpiperazin-1-yl)propan-1-ol (3.15 g, 56%).

$^1$H NMR Spectrum (CDCl$_3$): 1.7 (m, 2H), 2.08 (s, 3H), 2.45 (m, 4H), 2.6 (dd, 2H), 3.45 (dd, 2H), 3.6 (dd, 2H), 3.78 (dd, 2H), 4.6 (br s, 1H)

MS-ESI: 187 [M+H]+

A solution of 6-benzyloxy-4-chloro-7-methoxyquinazoline (0.39 g, 1.33 mmol), (EP1153920 production examples 28-30), 4-fluoro-5-hydroxy-2-methylindole (0.24 g, 1.43 mmol) and cesium carbonate (1.2 g, 4 mmol) in DMF (4 ml) was stirred at 95° C. for 45 minutes. After cooling, the mixture was filtered and the filtrate was evaporated under vacuum The residue was purified by column chromatography eluting with increasingly polar mixtures of methylene chloride and ethyl acetate to give 6-benzyloxy-4-(4-fluoro-2-methylindol-5-yloxy)-7-methoxyquinazoline (0.213 g, 37%).

$^1$H NMR Spectrum: (DMSO d$_6$) 2.42 (s, 3H), 4.05 (s, 3H), 5.3 (s, 2H), 6.25 (s, 1H), 7.0 (dd, 1H), 7.18 (d, 1H), 7.35-7.6 (m, 6H), 7.8 (s, 1H), 8.55 (s, 1H)

MS-ESI: 430 [M+H]+

A solution of 6-benzyloxy-4-(4-fluoro-2-methylindol-5-yloxy)-7-methoxyquinazoline (1.32 g, 3 mmol), ammonium formate (1.94 g, 30 mmol) and 10% palladium on carbon (0.2 g) in DMF (15 ml) containing water (2 ml) was stirred at ambient temperature for 1 hour. The mixture was filtered and the filtrate was evaporated. The residue was triturated under diethyl ether, filtered, washed with diethyl ether followed by water and dried under vacuum over P$_2$O$_5$ overnight to give 4-(4-fluoro-2-methylindol-5-yloxy)-6-hydroxy-7-methoxyquinazoline (1 g, 100%).

$^1$H NMR Spectrum: (DMSO-d$_6$) 2.35 (s, 3H), 4.0 (s, 3H), 6.25 (s, 1H), 7.0 (m, 1H), 7.15 (d, 1H), 7.4 (s, 1H), 7.6 (s, 1H), 8.0 (s, 1H), 8.55 (s, 1H)

MS-ESI: 340 [M+H]+

To a solution of 2-fluoro-4-nitroanisole (9.9 g, 58 mmol) and 4-chlorophenoxyacetonitrile (10.7 g, 64 mmol) in DMF (50 ml) cooled at −15° C. was added potassium tert-butoxide (14.3 g, 127 mmol) in DMF (124 ml). After stirring for 30 minutes at −15° C., the mixture was poured onto cooled 1N hydrochloric acid. The mixture was extracted with ethyl acetate. The organic layer was washed with 1N sodium hydroxide, brine, dried (MgSO$_4$) and evaporated. The residue was purified by column chromatography eluting with methylene chloride. The fractions containing the expected product were combined and evaporated. The residue was dissolved in ethanol (180 ml) and acetic acid (24 ml) containing 10% palladium on charcoal (600 mg) and the mixture was hydrogenated under 3 atmospheres pressure for 2 hours. The mixture was filtered, and the volatiles were removed under vacuum. The residue was partitioned between ethyl acetate and water. The organic layer was separated, and washed with saturated sodium hydrogen carbonate followed by brine, dried ($MgSO_4$) and evaporated. The residue was purified by column chromatography eluting with methylene chloride to give a mixture of 4-fluoro-5-methoxyindole and 6-fluoro-5-methoxyindole (5.64 g, 59%) in a ratio 1/2.

$^1$H NMR Spectrum (DMSO-$d_6$) 3.85 (s, 3H); 6.38 (s, 1H, 6-Fluoro); 6.45 (s, 1H; 4-Fluoro); 6.9-7.4 (m, 3H)

A solution of 4-fluoro-5-methoxyindole and 6-fluoro-5-methoxyindole in a ratio ½ (496 mg, 3 μmmol), di-tertbutyl dicarbonate (720 mg, 3.3 mmol) in acetonitrile (12 ml) containing DMAP (18 mg, 0.15 mmol) was stirred at ambient temperature for 24 hours. The volatiles were removed under vacuum The residue was dissolved in ethyl acetate, washed with 1N hydrochloric acid, followed by water, brine, dried ($MgSO_4$) and evaporated to give a mixture of 4-fluoro-5-methoxy-1-tert-butoxycarbonylindole and 6-fluoro-5-methoxy-1-tert-butoxycarbonylindole in a ratio 1/2 (702 mg, 88%).

$^1$H NMR Spectrum: (DMSOd$_6$) 1.65 (s, 9H); 3.9 (s, 3H); 6.6 (d, 1H, 6-fluoro); 6.72 (d, 1H, 4-fluoro); 7.2 (t, 1H, 6-fluoro); 7.4 (d, 1H, 4-fluoro); 7.62 (d, 1H, 6-fluoro); 7.68 (d, 1H, 4-fluoro); 7.78 (s, 1H, 4-fluoro); 7.85 (s, 1H, 6-fluoro)

To a solution of 4-fluoro-5-methoxy-1-tert-butoxycarbonylindole and 6-fluoro-5-methoxy-1-tert-butoxycarbonylindole in a ratio 1/2 (8.1 g, 30.5 mmol) in THF (100 ml) cooled at −65° C. was added tert-butyllithium (1.7 M) (23 ml, 35.7 mmol). After stirring for 4 hours at −70° C., methyl iodide (8.66 g, 61 mmol) was added and the mixture was left to warm-up to ambient temperature. Water was added and the mixture was extracted with ether. The organic layer was washed with water, brine, dried ($MgSO_4$) and evaporated and was used directly in the next step.

The crude product was dissolved in methylene chloride (100 ml) and TFA (25 ml) was added. After stirring for 1 hour at ambient temperature, the volatiles were removed under vacuum The residue was dissolved in ethyl acetate and the organic layer was washed with 1N sodium hydroxide, followed by water, brine, dried ($MgSO_4$) and evaporated. The residue was purified by column chromatography, eluting with ethyl acetate/petroleum ether (3/7) to give 6-fluoro-5-methoxy-2-methylindole (1.6 g) and 4-fluoro-5-methoxy-2-methylindole (0.8 g, 48

6-fluoro-5-methoxy-2-methylindole

MS-ESI: 180 [MH]+
$^1$H NMR Spectrum: (DMSOd$_6$) 2.35 (s, 3H); 3.8 (s, 3H); 6.05 (s, 1H); 7.1 (s, 1H); 7.12 (s, 1H); 10.8 (s, 1H)

4-fluoro-5-methoxy-2-methylindole

MS-ESI: 180 [MH]$^+$
$^1$H NMR Spectrum: (DMSO-$d_6$) 2.35 (s, 3H); 3.8 (s, 3H); 6.15 (s, 1H); 6.9 (t, 1H); 7.05 (d, 1H); 11.0 (s, 1H)

To a solution of 4-fluoro-5-methoxy-2-methylindole (709 mg, 3.95 mmol) in methylene chloride (9 in) cooled at −30° C. was added a solution of boron tribromide (2.18 g, 8.7 mmol) in methylene chloride (1 ml). After stirring for 1 hour at ambient temperature, the mixture was poured onto water and was diluted with methylene chloride. The pH of the aqueous layer was adjusted to 6. The organic layer was separated, washed with water, brine, dried ($MgSO_4$) and evaporated. The residue was purified by column chromatography, eluting with ethyl acetate/petroleum ether (3/7) to give 4-fluoro-5-hydroxy-2-methylindole (461 mg, 70%).

MS-ESI: 166 [MH]$^+$
$^1$H NMR Spectrum: (DMSOd$_6$) 2.35 (s, 3H); 6.05 (s, 1H); 6.65 (dd, 1H); 6.9 (d, 1H); 8.75 (s, 1H); 10.9 (s, 1H)
$^{13}$C NMR Spectrum: (DMSO-$d_6$) 13.5; 94.0; 106.0; 112; 118.5; 132; 136; 136.5; 142.5

Alternatively the 4-fluoro-5-hydroxy-2-methylindole may be prepared as follows:

To a suspension of sodium hydride (5.42 g, 226 mmol) (prewashed with pentane) in THF (100 ml) cooled at 10° C. was added ethyl acetoacetate (29.4 g, 226 mmol) while keeping the temperature below 15° C. After completion of addition, the mixture was further stirred for 15 minutes and cooled to 5° C. A solution of 1,2,3-trifluoro-4-nitrobenzene (20 g, 113 mmol) in THF (150 ml) was added while keeping the temperature below 5° C. The mixture was then left to warm up to ambient temperature and stirred for 24 hours. The volatiles were removed under vacuum and the residue was partitioned between ethyl acetate and 2N aqueous hydrochloric acid. The organic layer was washed with water, brine, dried ($MgSO_4$) and evaporated. The residue was dissolved in concentrated hydrochloric acid (650 ml) and acetic acid (600 ml) and the mixture was refluxed for 15 hours. After cooling, the volatiles were removed under vacuum and the residue was partitioned between aqueous sodium hydrogen carbonate (5%) and ethyl acetate. The organic layer was washed with sodium hydrogen carbonate, water, brine, dried ($MgSO_4$) and evaporated. The residue was purified by column chromatography eluting with ethyl acetate/petroleum ether (75/25) to give 3-acetylmethyl-1,2-difluoro-4-nitrobenzene (17.5 g, 72%).

$^1$H NMR Spectrum: (CDCl$_3$) 2.4 (s, 3H); 4.25 (s, 2H); 7.25 (dd, 1H); 8.0 (dd, 1H)

A solution of 3-acetylmethyl-1,2-difluoro-4-nitrobenzene (500 mg, 2.3 mmol) in methylene chloride (5 ml) containing montmorillonite K10 (1 g) and trimethyl orthoformate (5 ml) was stirred for 24 hours at ambient temperature. The solid was filtered, washed with methylene chloride and the filtrate was evaporated to give 1,2-difluoro-3-(2,2-dimethoxypropyl)-4-nitrobenzene (534 mg, 88%).

$^1$H NMR Spectrum: (CDCl$_3$) 1.2 (s, 3H); 3.2 (s, 6H); 3.52 (s, 2H); 7.18 (dd, 1H); 7.6 (m, 1H)

To a solution of benzyl alcohol (221 mg, 2.05 mmol) in DMA (1.5 nl) was added 60% sodium hydride (82 mg, 2.05 mmol). The mixture was stirred for 1 hour at ambient temperature. A solution of 1,2-difluoro-3-(2,2-dimethoxypropyl)-4-nitrobenzene (534 mg, 2.05 mmol) in DMA (1.5 ml) was added and the mixture was stirred for 3 hours at ambient temperature. The mixture was diluted with 1N hydrochloric acid (10 ml) and extracted with ethyl acetate. The organic layer was evaporated and the residue was dissolved in THF (2 ml) and 6N hydrochloric acid (0.3 ml) was added. The mixture was stirred for 1 hour at ambient temperature and the solvents were removed under vacuum The residue was partitioned between ethyl acetate and water. The organic layer was separated, washed with brine, dried ($MgSO_4$) and evaporated. The solid was triturated with ether, filtered, washed with ether and dried under vacuum to give 3-acetylmethyl-1-benzyloxy-2-fluoro-4-nitrobenzene (350 mg, 56

$^1$H NMR Spectrum: (CDCl$_3$) 2.35 (s, 3H); 4.25 (s, 2H); 5.25 (s, 2H); 7.0 (dd, 1H); 7.32-7.5 (m, 5H); 8.0 (dd, 1H)

A solution of 3-acetylmethyl-1-benzyloxy-2-fluoro-4-nitrobenzene (300 mg, 0.99 mmol) in ethanol (10 ml) and acetic acid (1 ml) containing 10% palladium on charcoal (30 mg) was hydrogenated at 2 atmospheres pressure for 2 hours. The mixture was filtered and the filtrate was evaporated. The residue was dissolved in ethyl acetate and the organic layer was washed with aqueous sodium hydrogen carbonate, brine and evaporated to give 4-fluoro-5-hydroxy-2-methylindole. The residue was purified by column chromatography eluting with ethyl acetate/petroleum ether (3/7) to give 4-fluoro-5-hydroxy-2-methylindole (63 mg, 30%). Analytical data as above.

Alternatively the 4-fluoro-5-methoxy-2-methylindole can be prepared as follows:

A solution of sodium methoxide (freshly prepared from sodium (1.71 g) and methanol (35 ml)) was added to a solution of 1,2-difluoro-3-(2,2-dimethoxypropyl)-4-nitrobenzene (16.2 g, 62 mmol), (prepared as described above), in methanol (200 ml) cooled at 5° C. The mixture was left to warm to ambient temperature and was stirred for 3 days. The volatiles were removed under vacuum and the residue was partitioned between ethyl acetate and 2N hydrochloric acid (1 mA). The organic layer was concentrated to a total volume of 100 ml and THF (100 ml) and 6N hydrochloric acid (25 ml) were added. The mixture was stirred for 1 hour at ambient temperature. The volatiles were removed under vacuum and the residue was partitioned between ethyl acetate and water. The organic layer was separated, washed with water, brine, dried (MgSO$_4$) and evaporated. The residue was purified by column chromatography eluting with ethyl acetate/petroleum ether (3/7) to give 3-acetylmethyl-2-fluoro-1-methoxy-4-nitrobenzene (12.7 g, 90%).

MS-ESI: 250 [MNa]+

$^1$H NMR Spectrum: (CDCl$_3$) 2.38 (s, 3H); 4.0 (s, 3H); 4.25 (s, 2H); 7.0 (dd, 1H); 8.05 (d, 1H)

To a solution of 3-acetylmethyl-2-fluoro-1-methoxy-4-nitrobenzene (11.36 g, 50 mmol) in acetone (200 ml) was added 4M aqueous ammonium acetate (700 ml) followed by a solution of titanium trichloride (15% in water, 340 ml) dropwise. The mixture was stirred for 10 minutes at ambient temperature and the mixture was extracted with ether. The organic layer was washed with 0.5N aqueous sodium hydroxide followed by water, brine, dried (MgSO$_4$) and the volatiles were removed under vacuum. The residue was purified by column chromatography eluting with methylene chloride to give 4-fluoro-5-methoxy-2-methylindole (8.15 g, 90%).

$^1$H NMR Spectrum: (DMSO) 2.35 (s, 3H); 3.8 (s, 3H); 6.1 (s, 1H); 6.85 (dd, 1H); 7.02 (d, 1H)

Cleavage of 4-fluoro-5-methoxy-2-methylindole with boron tribromide to give 4-fluoro-5-hydroxy-2-methylindole is described above.

EXAMPLE 2

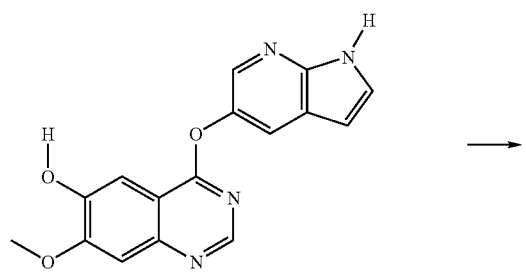

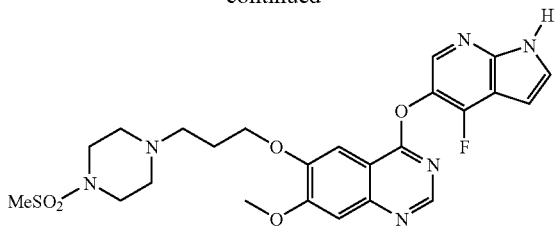

Diethyl azodicarboxylate (0.09 g, 0.518 mmol) was added dropwise to a solution of 4-(7-azaindol-5-yloxy)-6-hydroxy-7-methoxyquinazoline (0.133 g, 0.432 mmol), triphenylphosphine (0.17 g, 0.647 mmol) and 3-(4-methylsulphonylpiperazin-1-yl)propan-1-ol (0.115 g, 0.519 mmol) in DMF (4 ml) and the mixture was stirred at ambient temperature for 1 hour. The volatiles were removed under vacuum and the residue was purified by column chromatography using increasingly polar mixtures of ethyl acetate and methylene chloride followed by methylene chloride and methanol. The fractions containing the expected product were combined and evaporated. The solid was then repurified by preparative LC/MS eluting with acetonitrile/water (containing 1% acetic acid). The fractions containing the expected product were combined and evaporated. The residue was dissolved in aqueous sodium hydrogen carbonate and methylene chloride. The organic phase was separated and dried over magnesium sulphate and evaporated. The residue was triturated under diethyl ether, filtered, washed with ether and dried under vacuum over P$_2$O$_5$ to give 4-(7-azaindol-5-yloxy)-7-methoxy-6-(3-(4-methylsulphonylpiperazin-1-yl)propoxy)quinazoline (0.09, 40%).

$^1$H NMR Spectrum: (DMSOd$_6$, CF$_3$COOD) 2.3 (m, 2H), 3.05 (s, 3H), 3.1-3.3 (m, 4H), 3.4 (dd, 2H), 3.7 (d, 2H), 3.8 (d, 2H), 4.1 (s, 3H), 4.4 (dd, 2H), 6.6 (d, 1H), 7.55 (s, 1H), 7.65 (d, 1H), 7.8 (s, 1H), 8.1 (s, 1H), 8.3 (s, 1H), 9.0 (s, 1H)

MS-ESI: 513 [M+H]+

The starting material was prepared as follows:

Methanesulphonyl chloride (2.28 ml) was added dropwise to a solution of 1-(tert-butoxycarbonyl)piperazine (5 g) in methylene chloride (90 ml) containing triethylamine (4.5 µl). The solution was stirred at ambient temperature for 24 hours. The solution was poured onto cooled water and extracted with methylene chloride. The organic phase was separated, washed with brine and dried over magnesium sulphate and evaporated to give tert-butyl 4-(methylsulphonyl)piperazine-1-carboxylate (7 g).

$^1$H NMR Spectrum: (CDCl$_3$) 1.45 (s, 9H), 2.75 (s, 3H), 3.15 (m, 4H), 3.5 (m, 4H)

A solution of tert-butyl 4-(methylsulphonyl)piperazine-1-carboxylate (7 g) in methylene chloride (150 ml) containing TFA (35 ml) was stirred for 2 hours at ambient temperature. The volatiles were removed under vacuum and the resultant residue was partitioned between methylene chloride and 2N aqueous sodium hydroxide. The organic phase was separated and washed with brine, dried over magnesium sulphate and evaporated to give 1-(methylsulphonyl)piperazine (2.18 g).

$^1$H NMR Spectrum: (CDCl$_3$) 2.9 (s, 3H), 3.0 (m, 4H), 3.2 (m, 2H)

A suspension of 1-(methylsulphonyl)piperazine (3 g, 18.3 mmol), 3-bromopropan-1-ol (3.3 g, 23.8 mmol) and potassium carbonate (3.28 g, 23.8 mmol) in acetonitrile (20 ml) was stirred at 70° C. for 4 hours. After cooling, the mixture was filtered and the filtrate was evaporated. The residue was purified by column chromatography eluting with increasingly polar mixtures of methanol and methylene chloride to give 3-(4-methylsulphonylpiperazin-1-yl)propan-1-ol (2.93 g, 72%).

$^1$H NMR Spectrum: (CDCl$_3$) 1.72 (m, 2H), 2.55-2.7 (m, 6H), 2.75 (s, 3H), 3.25 (m, 4H), 3.75 (dd, 2H)

MS-ESI: 223 [M+H]+

A solution of 7-azaindole (20.0 g, 169 mmol) in ethanol (200 ml) was treated with wet Raney Nickel (4 g, 50% water) and stirred in a hydrogen atmosphere at 5 atmospheres pressure at 95° C. over 2 days. The reaction mixture was filtered through diatomaceous earth and the filtrate evaporated under vacuum The residue was purified by column chromatography eluting with ethyl acetate followed by increasingly polar mixtures of methylene chloride and methanol (saturated with ammonia) to give 7-azaindoline (12.1 g, 79%).

$^1$H NMR Spectrum: (CDCl$_3$) 3.06 (t, 2H), 3.61 (t, 2H), 4.48 (br s, 1H), 6.50 (m, 1H), 7.25 (m, 1H), 7.81 (d, 1H)

A solution of 7-azaindoline (22.7 g, 189 mmol), p-toluene sulphonic acid monohydrate (2.95 g, 15 mmol) and 1,3-dibromo-5,5-dimethylhydantoin (27.4 g, 96 mmol) in methylene chloride (1500 µl) was stirred at ambient temperature for 3 hours. The reaction solution was then decanted from a black polymeric material; washed with 0.2 M sodium thiosulphate (4×250 mls) followed by brine and dried over magnesium sulphate. The filtrate was evaporated under vacuum to give a black solid which was extracted with boiling ethyl acetate (2×800 mls and 2×500 mls). The combined extracts were heated at reflux for a few minutes with decolorizing charcoal, filtered and evaporated under vacuum to give 5-bromo-7-azaindoline (16.6 g, 44%).

$^1$H NMR Spectrum: (CDCl$_3$) 3.07 (t, 2H), 3.64 (t, 2H), 4.52 (s, 1H), 7.31 (d, 1H), 7.84 (d, 1H)

A mixture of 5-bromo-7-azaindoline (15.6 g, 78 mmol) and precipitated, active manganese (IV) oxide (21.9 g, 252 mmol) in toluene (300 mls) was heated at 90° C. for 1 hour and the hot solution filtered through a pad of diatomaceous earth. The diatomaceous earth and manganese residues were washed with acetone and these washings added to the toluene filtrate. Evaporation of the filtrate under vacuum gave 5-bromo-7-azaindole (12.1 g, 78%).

$^1$H NMR spectrum: (CDCl$_3$) 6.47 (m, 1H), 7.36 (m, 1H), 8.08 (d, 1H), 8.35 (d, 1H), 9.89 (s, 1H)

A solution of 5-bromo-7-azaindole (8.6 g, 44 mmol), copper (I) bromide (12.6 g, 88 mmol) and sodium methoxide (100 g, 1.85 mol) in a mixture of "degassed" DMF (260 mls) and methanol (175 mls) was stirred at ambient temperature in a nitrogen atmosphere, and then heated at reflux for 3.5 hours. The mixture was concentrated to about half its original volume, cooled in a cold water bath and treated dropwise with water causing an exotherm. The resulting suspension was evaporated under vacuum to give a brown solid which was then treated with water followed by ammonium hydroxide. The aqueous phase was extracted with ethyl acetate and the combined extracts were washed with dilute ammonium hydroxide until no blue colour was seen in the aqueous washings. The ethyl acetate solution was washed with brine, dried over MgSO$_4$, filtered and evaporated under vacuum This crude solid, 5-methoxy-7-azaindole (6.3 g, 97%), was taken through the next step without further purification.

Boron tribromide (0.506 µl, 5.35 mmol) in methylene chloride (1 ml) was added to a solution of 5-methoxy-7-azaindole (0.36 g, 2.43 mmol) in methylene chloride (25 ml) cooled at −30° C. The mixture was left to warm up to ambient temperature and was stirred overnight. The mixture was poured onto ice and water and the pH of the aqueous phase was adjusted to 6. The organic phase was separated and the aqueous phase was further extracted with ethyl acetate. The organic phases were combined, washed with brine, dried over magnesium sulphate and evaporated. The residue was purified by column chromatography eluting with increasingly polar mixtures of methylene chloride and methanol to give 5-hydroxy-7-azaindole (0.23 g, 71%).

$^1$H NMR Spectrum: (DMSO-d$_6$) 6.25 (s, 1H), 7.25 (s, 1H), 7.35 (s, 1H), 7.85 (s, 1H), 9.05 (br s, 1H)

MS-ESI: 135 [M+H]+

A solution of 6-benzyloxy-4-chloro-7-methoxyquinazoline (0.449 g, 1.49 mmol), (EP1153920 production examples 28-30), 5-hydroxy-7-azaindole (0.22 g, 1.64 mmol) and potassium carbonate (0.28 g, 2.02 mmol) in DMF (5 ml) was stirred at 95° C. for 3 hours. The mixture was filtered and the filtrate was evaporated and dried overnight under vacuum. The residue was triturated under methylene chloride and ethyl acetate and the solid was filtered and dried under vacuum to give 4-(7-azaindol-5-yloxy)-6-benzyloxy-7-methoxyquinazoline (0.36 g, 60%).

$^1$H NMR spectrum (DMSO-d$_6$): 4.05 (s, 3H), 5.35 (s, 2H), 6.5 (s, 1H), 7.35-7.5 (m, 4H), 7.5-7.6 (m, 3H), 7.8 (s, 1H), 7.95 (s, 1H), 8.2 (s, 1H), 8.55 (s, 1H)

MS-ESI: 399 [M+H]+

A solution of 4-(7-azaindol-5-yloxy)-6-benzyloxy-7-methoxyquinazoline (0.36 g, 0.873 mmol), ammonium formate (0.55 g, 8.73 mmol) and 10% palladium on carbon (0.05 g) in DMF (7 ml) containing water (0.3 ml) was stirred at ambient temperature for 1 hour. The mixture was filtered and the filtrate was evaporated. The residue was triturated under diethyl ether and the solid was filtered, washed with ether and dried under vacuum. The solid was triturated under water, filtered, washed with water and dried under vacuum over P$_2$O$_5$ to give 4-(7-azaindol-5-yloxy)-6-hydroxy-7-methoxyquinazoline (0.26 g, 85%).

$^1$H NMR Spectrum: (DMSO-d$_6$) 4.05 (s, 3H), 6.5 (d, 1H), 7.4 (s, 1H), 7.6 (m, 2H), 7.95 (s, 1H), 8.2 (s, 1H), 8.5 (s, 1H)

MS-ESI: 307 [M−H]

EXAMPLE 3

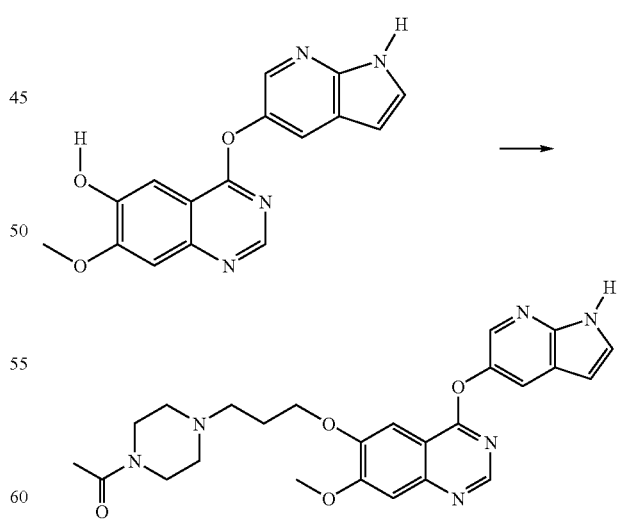

Using an analogous procedure to that described for the preparation of Example 2,4-(7-azaindol-5-yloxy)-6-hydroxy-7-methoxyquinazoline (0.133 g, 0.432 mmol), (prepared as described for the starting material in Example 2), was reacted with 3-(4-acetylpiperazin-1-yl)propan-1-ol (0.097, 0.51 mmol), (prepared as described for the starting material in Example 1 or Example 7), to give 6-(3-(4-acetylpiperazin-1-yl)propoxy)-4-(7-azaindol-5-yloxy)-7-methoxyquinazoline (0.11 g, 53%).

$^1$H NMR Spectrum: (DMSOd$_6$, CF$_3$COOD) 2.08 (s, 3H), 2.3 (m, 2H), 2.9-3.1 (m, 2H), 3.1-3.25 (m, 1H), 3.35 (dd, 2H), 3.45 (m, 1H), 3.6 (d, 2H), 4.0-4.05 (m, 1H), 4.1 (s, 3H), 4.4 (dd, 2H), 4.5 (d, 1H), 6.6 (d, 1H), 7.6 (s, 1H), 7.68 (d, 1H), 7.85 (s, 1H), 8.1 (s, 1H), 8.38 (s, 1H), 9.1 (s, 1H)

MS-ESI: 477 [M+H]+

EXAMPLE 4

A solution of 7-(3-(4-acetylpiperazin-1-yl)propoxy)-4-chloro-6-methoxyquinazoline (0.285 g, 0.753 mmol), 5-hydroxy-7-azaindole (0.111 g, 0.828 mmol), (prepared as described for the starting material in Example 2), and potassium carbonate (0.114 g, 0.828 mmol) in DMF (1.6 ml) was stirred and heated at 95° C. under nitrogen for 3 hours. The mixture was cooled and filtered and the filtrate was evaporated. The residue was purified by column chromatography eluting with increasingly polar mixtures of methylene chloride and methanol (saturated with ammonia). The fractions containing the expected product were combined and evaporated and the residue was triturated under diethyl ether, filtered and dried under vacuum to give 7-(3-(4-acetylpiperazin-1-yl)propoxy)-4-(7-azaindol-5-yloxy)-6-methoxyquinazoline (0.225 g, 62%).

$^1$NMR Spectrum: (DMSOd$_6$) 1.98 (s, 3H), 1.98 (m, 2H), 2.35 (dd, 2H), 2.4 (dd, 2H), 2.5 (m, 2H), 3.41 (m, 4H), 4.0 (s, 3H), 4.25 (dd, 2H), 6.47 (d, 1H), 7.38 (s, 1H), 7.55 (dd, 1H), 7.6 (s, 1H), 7.9 (d, 1H), 8.18 (d, 1H), 8.5 (s, 1H)

MS-ESI: 477.6 [M+H]+

The starting material was prepared as follows:

A mixture of 2-amino-4-benzyloxy-5-methoxybenzamide (10 g, 0.04 mol), (J. Med. Chem. 1977, vol 20, 146-149), and Gold's reagent (7.4 g, 0.05 mol) in dioxane (100 ml) was stirred and heated at reflux for 24 hours. Sodium acetate (3.02 g, 0.037 mol) and acetic acid (11.65 ml, 0.029 mol) were added to the reaction mixture and it was heated for a further 3 hours. The mixture was evaporated, water was added to the residue, the solid was filtered off, washed with water and dried (MgSO$_4$). Recrystallisation from acetic acid gave 7-benzyloxy-6-methoxy-3,4-dihydroquinazolin-4-one (8.7 g, 84%).

10% Palladium on carbon (8.3 g) was added to a suspension of 7-benzyloxy-6-methoxy-3,4-dihydroquinazolin-4-one (50 g, 0.177 mol) in dimethylformamide (800 ml) under nitrogen. Ammonium formate (111.8 g, 1.77 mol) was then added in portions over 5 minutes. The reaction mixture was stirred for one hour at ambient temperature then heated to 80° C. for a further hour. The reaction mixture was filtered hot through diatomaceous earth and the residues washed with dimethylformamide. The filtrate was then concentrated and the residue suspended in water. The pH was adjusted to 7.0 using 2M sodium hydroxide and the resulting mixture was stirred at ambient temperature for one hour. The solid was filtered, washed with water and dried over phosphorus pentoxide yielding 7-hydroxy-6-methoxy-3,4-dihydroquinazolin-4-one as a white solid (20.52 g, 60%).

$^1$H NMR Spectrum: (DMSOd$_6$) 3.85 (s, 3H), 6.95 (s, 1H), 7.40 (s, 1H), 7.85 (s, 1H)

MS-ESI: 193 [M+H]+

Pyridine (20 ml) was added to a suspension of 7-hydroxy-6-methoxy-3,4-dihydroquinazolin-4-one (20.5 g, 107 mmol) in acetic anhydride (150 ml, 1.6 mol). The reaction mixture was heated to 120° C. for three hours, during which time the solid dissolved. The reaction mixture was allowed to cool then poured into ice-water (900 ml). The reaction mixture was stirred for one hour then the solid was removed by filtration and dried over phosphorus pentoxide yielding 7-acetoxy-6-methoxy-3,4-dihydroquinazolin-4-one as a white solid (20.98 g, 84%).

$^1$H NMR Spectrum: (DMSOd$_6$) 2.25 (s, 3H), 3.85 (s, 3H), 7.40 (s, 1H), 7.60 (s, 1H), 8.00 (s, 1H)

MS-ESI: 235 [M+H]+

7-Acetoxy-6-methoxy-3,4-dihydroquinazolin-4-one (1 g, 4.3 mmol) was suspended in thionyl chloride (10.5 ml). One drop of dimethylformamide was added and the reaction was heated to 80° C. for two hours, during which time the solid dissolved. The reaction mixture was cooled and the thionyl chloride was removed in vacuo. The residue was azeotroped with toluene before being suspended in methylene chloride. A solution of 10% ammonia in methanol (40 ml) was added and the reaction mixture was heated to 80° C. for 15 minutes. After cooling the solvents were removed in vacuo and the residue redissolved in water (10 ml) and the pH adjusted to 7.0 with 2M hydrochloric acid. The resulting solid was filtered, washed with water and dried over phosphorus pentoxide yielding 4-chloro-7-hydroxy-6-methoxyquinazoline as a white solid (680 mg, 75%).

$^1$H NMR Spectrum: (DMSOd$_6$) 4.00 (s, 3H), 7.25 (s, 1H), 7.35 (s, 1H), 8.75 (s, 1H)

MS-ESI: 211-213 [M+H]+

Diethyl azodicarboxylate (0.243 g, 1.396 mmol) was added dropwise to a solution of 4-chloro-7-hydroxy-6-methoxyquinazoline (0.245 g, 1.16 mmol), triphenylphosphine (0.396 g, 1.51 mmol) and 3-(4-acetylpiperazin-1-yl)propan-1-ol (0.238 g, 1.28 mmol), (prepared as described for the starting material in Example 1 or Example 7). After stirring at ambient temperature for 1 hour, the mixture was poured onto silica and eluted with increasingly polar mixtures of methylene chloride and methanol to give 7-(3-(4-acetylpiperazin-1-yl)propoxy)-4-chloro-6-methoxyquinazoline (0.29 g, 66%).

$^1$H NMR Spectrum: (DMSOd$_6$) 2.0 (s, 3H), 2.0 (m, 21), 2.35 (dd, 2H), 2.4 (dd, 2H), 2.5 (dd, 2H), 3.45 (m, 4H), 4.02 (s, 3H), 4.3 (dd, 2H), 7.4 (s, 1H), 7.5 (s, 1H), 8.9 (s, 1H)

MS-ESI: 379-381 [M+H]+

EXAMPLE 5

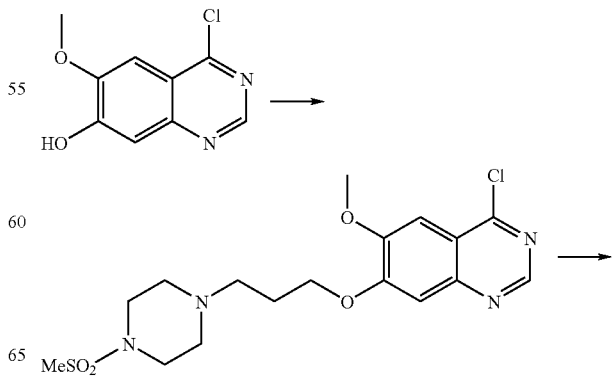

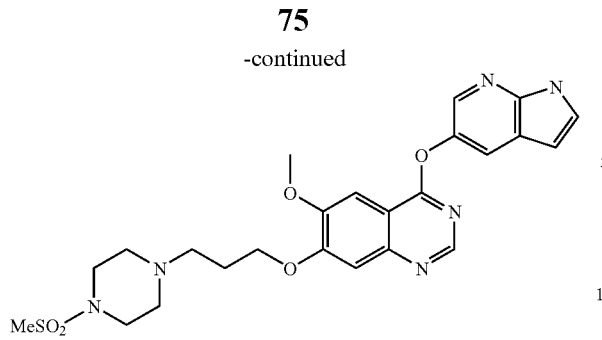

A suspension of 4-chloro-6-methoxy-7-(3-(4-methylsulphonylpiperazin-1-yl)propoxy)quinazoline (0.25 g, 0.66 mmol), 5-hydroxy-7-azaindole (0.089 g, 0.663 mmol), (prepared as described for the starting material in Example 2), and potassium carbonate (0.091 g, 0.66 mmol) in DMF (3 ml) was stirred at 85° C. for 3 hours. The mixture was filtered and the filtrate was purified by preparative LCtMS eluting with acetonitrile/water (containing 1% acetic acid). The fractions containing the expected product were combined and evaporated. The residue was dissolved in methylene chloride and washed with 0.5N aqueous ammonia followed by brine, dried (MgSO$_4$) and evaporated. The residue was triturated under diethyl ether, filtered and dried under vacuum to give 4-(7-azaindol-5-yloxy)-6-methoxy-7-(3-(4-methylsulphonylpiperazin-1-yl)propoxy)quinazoline (0.138 g, 45%).

$^1$H NMR Spectrum: (DMSOd$_6$) 2.02 (m, 2H), 2.52 (m, 6H), 2.9 (s, 3H), 3.15 (m, 4H), 4.02 (s, 3H), 4.3 (dd, 2H), 6.5 (d, 1H), 7.4 (s, 1H), 7.6 (d, 1H), 7.65 (s, 1H), 7.95 (d, 1H), 8.2 (s, 1H), 8.52 (s, 1H)

MS-ESI: 513.5 [M+H]+

The starting material was prepared as follows:

Using an analogous procedure to that described for the preparation of the starting material in Example 4,4-chloro-7-hydroxy-6-methoxyquinazoline (0.25 g, 1.19 mmol), (prepared as described for the starting material in Example 4), was reacted with 3-(4-methylsulphonylpiperazin-1-yl)propan-1-ol (0.29 g, 1.3 mmol), (prepared as described in Example 2), to give 4-chloro-6-methoxy-7-(3-(4-methylsulphonylpiperazin-1-yl)propoxy)quinazoline (0.339 g, 69%).

$^1$H NMR Spectrum: (DMSOd$_6$) 2.0 (m, 2H), 2.5 (m, 6H), 2.85 (s, 3H), 3.1 (m 4H), 4.0 (s, 3H), 4.3 (dd, 2H), 7.4 (s, 1H), 7.42 (s, 1H), 8.85 (s, 1H)

MS-ESI: 415-417 [M+H]+

EXAMPLE 6

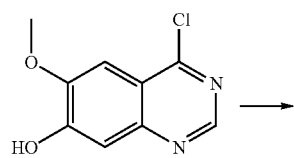

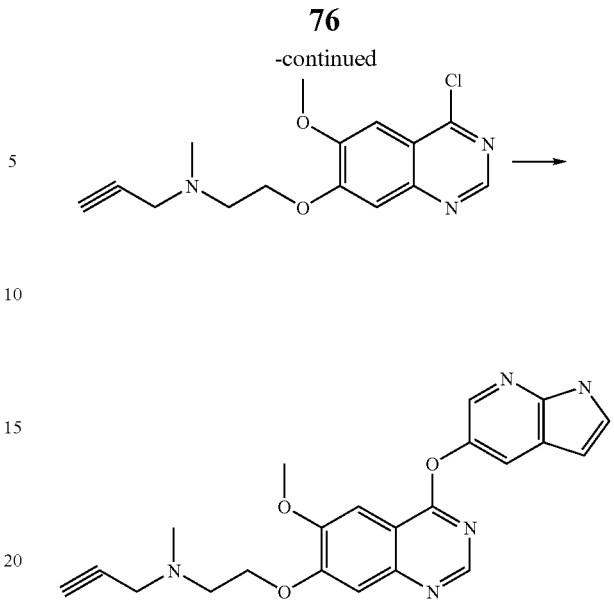

Using an analogous procedure to that described for the preparation of Example 5, 4-chloro-6-methoxy-7-[2-(N-methyl-N-prop-2-yn-1-ylamino)ethoxy]quinazoline (0.25 g, 0.817 mmol) was reacted with 5-hydroxy-7-azaindole (0.12 g, 0.899 mmol), (prepared as described for the starting material in Example 2), to give 4-(7-azaindol-5-yloxy)-6-methoxy-7-[2-(N-methyl-N-prop-2-yn-1-ylamino)ethoxy]quinazoline (0.156 g, 47%).

$^1$H NMR Spectrum: (DMSOd$_6$) 2.35 (s, 3H), 2.9 (dd, 2H), 3.2 (dd, 1H), 3.45 (d, 2H), 4.02 (s, 3H), 4.31 (dd, 2H), 6.5 (d, 1H), 7.45 (s, 1H), 7.6 (dd, 1H), 7.65 (s, 1H), 7.95 (d, 1H), 8.2 (d, 1H), 8.52 (s, 1H)

MS-ESI: 404 [M+H]+

The starting material was prepared as follows:

6N Aqueous sodium hydroxide (4.2 ml) was added to a solution of 2-(methylamino)ethanol (1.42 g, 18.9 mmol), propargyl bromide in toluene (1.5 g, 12.6 mmol;

1.6 ml) in dioxane (8 ml). After stirring overnight at ambient temperature, the mixture was partitioned between water and ethyl acetate. The organic phase was separated, washed with brine, dried with magnesium sulphate and evaporated. The residue was purified by column chromatography eluting with increasingly polar mixtures of methylene chloride and methanol to give 2-(N-methyl-N-prop-2-yn-1-ylamino)ethanol (0.794 g, 56%).

$^1$H NMR Spectrum: (CDCl$_3$) 2.2 (dd, 1H), 2.3 (s, 3H), 2.58 (dd, 2H), 3.35 (d, 2H), 3.6 (dd, 2H)

Diethyl azodicarboxylate (0.297 g, 1.71 mmol) was added to a solution of 4-chloro-7-hydroxy-6-methoxyquinazoline (0.3 g, 1.42 mmol), (prepared as described for the starting material in Example 4), triphenylphosphine (0.485 g, 1.85 mmol) and 2-(N-methyl-N-prop-2-yn-1-ylamino)ethanol (0.177 g, 1.56 mmol) in methylene chloride (8 ml). The mixture was stirred for 2 hours at ambient temperature and poured onto a column of silica and eluted with increasingly polar mixtures of methylene chloride and ethyl acetate followed by ethyl acetate to give 4-chloro-6-methoxy-7-[2-(N-methyl-N-prop-2-yn-1-ylamino)ethoxy]quinazoline (0.341 g, 78%).

¹H NMR Spectrum: (DMSOd₆) 2.33 (s, 3H), 2.87 (t, 2H), 3.17 (t, 1H), 3.44 (d, 2H), 4.02 (s, 3H), 4.33 (t, 2H), 7.41 (s, 1H), 7.51 (s, 1H), 8.89 (s, 1H)

EXAMPLE 7

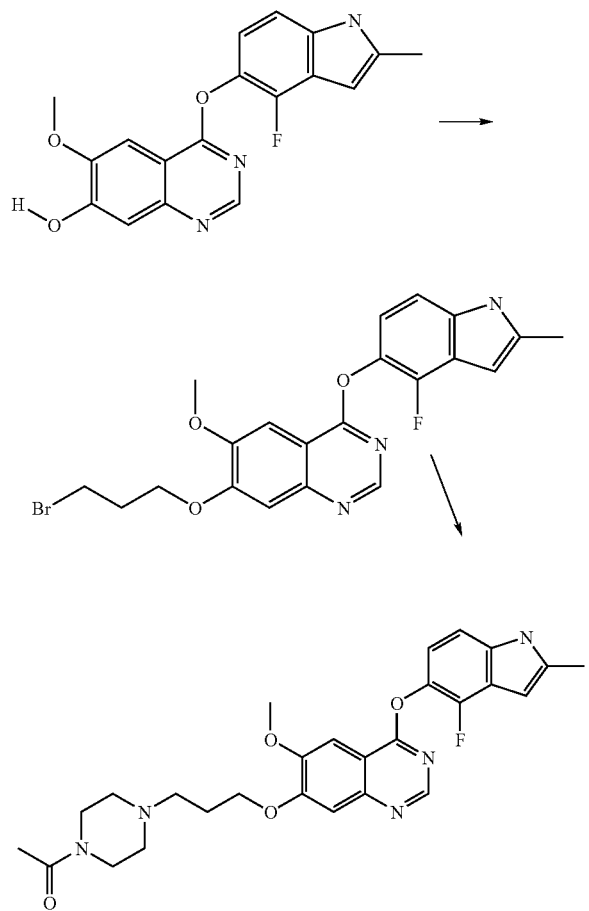

A solution of 7-(3-bromopropoxy)-4-(4-fluoro-2-methylindol-5-yloxy)-6-methoxyquinazoline (0.25 g, 0.543 mmol) and 1-acetylpiperazine (0.208 g, 1.63 mmol) in DMF (4 ml) was stirred at 80° C. for 2.5 hours. The volatiles were removed under vacuum and the residue was purified by column chromatography eluting with increasingly polar mixtures of methylene chloride and methanol. The fractions containing the expected product were combined and evaporated. The residue was triturated under diethyl ether and the resulting solid was filtered, washed with diethyl ether and dried under vacuum to give 7-(3-(4-acetylpiperazin-1-yl)propoxy)-4-(4-fluoro-2-methylindol-5-yloxy)-6-methoxyquinazoline (0.25 g, 0.543 mmol).

¹H NMR Spectrum: (DMSOd₆) 1.98 (s, 3H), 2.0 (m, 2H), 2.4 (s, 3H), 2.4 (m, 4H), 2.55 (t, 2H), 3.45 (dd, 4H), 4.0 (s, 3H), 4.3 (t, 2H), 6.22 (s, 1H), 6.98 (dd, 1H), 7.15 (d, 1H), 7.4 (s, 1H), 7.62 (s, 1H), 8.48 (s, 1H), 10.98 (br s, 1H)

MS-ESI: 508 [M+H]+

The starting material was prepared as follows:

A mixture of 7-benzyloxy-6-methoxy-3,4-dihydroquinazolin-4-one (2.82 g, 0.01 mol), (prepared as described for the starting material in Example 4), thionyl chloride (40 ml) and DMF (0.28 ml) was stirred and heated at reflux for 1 hour. The mixture was evaporated, the residue was taken up in toluene and evaporated to dryness to give 7-benzyloxy-4-chloro-6-methoxyquinazoline hydrochloride (3.45 g).

7-Benzyloxy-4-chloro-6-methoxyquinazoline hydrochloride (3.35 g) was dissolved in methylene chloride (250 ml) and washed with aqueous sodium hydrogen carbonate until the pH of the aqueous solution was adjusted to pH8. The organic layer was washed with brine, dried (MgSO₄) and evaporated to give 7-benzyloxy-4-chloro-6-methoxyquinazoline free base (2.9 g, 96%).

A suspension of 7-benzyloxy-4-chloro-6-methoxyquinazoline free base (10 g, 33.2 mmol), 4-fluoro-5-hydroxy-2-methylindole (5.9 g, 35.7 mmol), (prepared as described for the starting material in Example 1), and potassium carbonate (9.2 g, 66.6 mmol) in NMP (100 ml) was stirred at 95° C. for 1 hour. After cooling, the mixture was partitioned between ethyl acetate and aqueous sodium hydrogen carbonate. The organic layer was separated, washed with brine and dried over magnesium sulphate and evaporated under vacuum. The residue was triturated under acetonitrile and the suspension was cooled. The precipitate was filtered and dried under vacuum to give 7-benzyloxy-4-(4-fluoro-2-methylindol-5-yloxy)-6-methoxyquinazoline (8.2 g, 57%).

¹H NMR Spectrum: (DMSOd₆): 2.4 (s, 3H), 4.0 (s, 3H), 5.35 (s, 2H), 6.22 (s, 1H), 6.95 (dd, 1H), 7.15 (d, 1H), 7.3-7.55 (m, 6H), 7.51 (s, 1H), 8.5 (s, 1H)

A suspension of 7-benzyloxy-4-(4-fluoro-2-methylindol-5-yloxy)-6-methoxyquinazoline (8.2 g, 19.1 mmol), ammonium formate (12 g, 190 mmol) in DMF (50 ml) containing 10% palladium on carbon (2 g) was stirred at ambient temperature for 1.5 hours. The mixture was diluted with ethyl acetate and filtered over diatomaceous earth. A solid precipitated out of the filtrate. The solid was filtered off. The filtrate was washed with aqueous sodium hydrogen carbonate, followed by brine and dried over magnesium sulphate. The volatiles were removed under vacuum. The residual solid was combined with the solid previously isolated from the filtrate and was then triturated with acetonitrile under cooling. The precipitate was filtered, washed with acetonitrile followed by diethyl ether and dried under vacuum to give 4-(4-fluoro-2-methylindol-5-yloxy)-7-hydroxy-6-methoxyquinazoline (6.48 g, quant.).

¹H NMR Spectrum: (DMSOd₆) 2.4 (s, 3H), 3.98 (s, 3H), 6.22 (s, 1H), 6.95 (dd, 1H), 7.15 (d, 1H), 7.2 (s, 1H), 7.58 (s, 1H), 8.38 (s, 1H)

Diethyl azodicarboxylate (557 µl, 3.53 mmol) was added to a solution of 4-(4-fluoro-2-methylindol-5-yloxy)-7-hydroxy-6-methoxyquinazoline (1 g, 2.95 mmol), triphenylphosphine (1.15 g, 4.42 mmol) and 3-bromo-1-propanol (293 ul, 3.24 mmol) in methylene chloride (25 ml). The mixture was stirred at ambient temperature for 1 hour and the residue was purified by column chromatography eluting with increasingly polar mixtures of methylene chloride and methanol. The fractions containing the expected product were combined and evaporated. The residue was triturated under diethyl ether and the solid was filtered, washed with diethyl ether and evaporated to give 7-(3-bromopropoxy)-4-(4-fluoro-2-methylindol-5-yloxy)-6-methoxyquinazoline (1.35 g, 100%).

¹H NMR Spectrum: (DMSOd₆) 2.4 (m, 2H), 2.45 (s, 3H), 3.75 (dd, 2H), 4.05 (s, 3H), 4.35 (dd, 2H), 6.25 (s, 1H), 7.0 (dd, 1H), 7.2 (d, 1H), 7.45 (s, 1H), 7.65 (s, 1H), 8.55 (s, 1H), 9.0 (br s, 1H)

MS-ESI: 460-462 [M+H]+

Alternatively 7-[3-(4-acetylpiperazin-1-yl)propoxy]-4-[(4-fluoro-2-methyl-1H-indol-5-yl)oxy]-6-methoxyquinazoline may be prepared as follows:

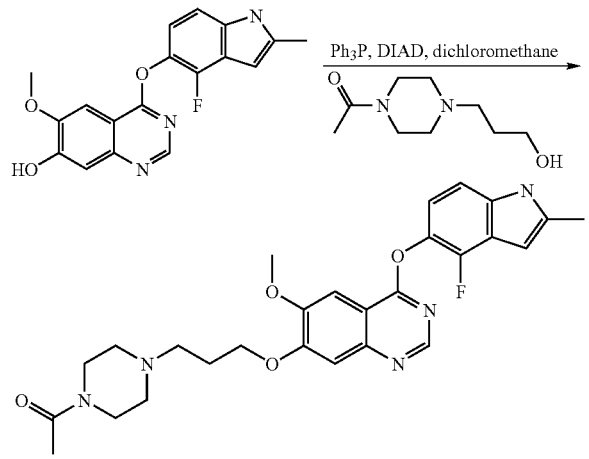

4-[(4-Fluoro-2-methyl-1H-indol-5-yl)oxy]-7-hydroxy-6-methoxyquinazoline (14 g, 41.3 mmol), (prepared as described for the starting material in this example hereinbefore), 3-(4-acetylpiperazin-1-yl)propan-1-ol (9.2 g, 49.5 mmol) and triphenylphosphine (12.9 g, 49.5 mmol) were stirred together in methylene chloride (210 ml). Diisopropyl azodicarboxylate (9.75 ml, 49.5 mmol) was added dropwise and an ice/water bath was used to keep the temperature of the reaction mixture between 15 and 18° C. After the end of addition the reaction mixture was allowed to warm to ambient temperature and stirred for 3 hours. The mixture was filtered and concentrated under reduced pressure and the resulting viscous oil dissolved in acetone (280 ml) and stirred for 45 minutes. The solid that formed was filtered off and dried under vacuum. The solid was purified by chromatography eluting with methylene chloride/methanol (saturated with ammonia) (96/4) to give 7-[3-(4-acetylpiperazin-1-yl)propoxy]-4-[(4-fluoro-2-methyl-1H-indol-5-yl)oxy]-6-methoxyquinazoline (12.5 g, 60%) as a white solid.

MS and NMR details are given hereinbefore.

The starting material was prepared as follows:

1-Acetylpiperazine (15.0 g, 117 mmol) was dissolved in acetonitrile (200 ml) and potassium carbonate (40.4 g, 293 mmol) was added followed by 3-bromo-1-propanol (10.6 ml, 117 mmol). The mixture was heated at reflux for 2.5 hours, cooled, filtered and concentrated under reduced pressure. The resulting viscous oil was cooled in ice for 3 hours and the crystalline product that formed was suspended in diethyl ether and filtered off. The hydroscopic solid was dried under vacuum ($P_2O_5$) overnight to give 3-(4-acetylpiperazin-1-yl)propan-1-ol (17.3 g, 90%) as a pale yellow solid.

$^1$H NMR Spectrum: ($CDCl_3$) 1.75 (m, 2H); 2.08 (s, 3H); 2.51 (m, 4H); 2.65 (t, 2H); 3.47 (br t, 2H); 3.64 (br t, 2H); 3.82 (t, 2H)

MS-ESI: 187 [M+H]+

Alternatively 7-[3-(4-acetylpiperazin-1-yl)propoxy]-4-[(4-fluoro-2-methyl-1H-indol-5-yl)oxy]-6-methoxyquinazoline may be prepared as follows:

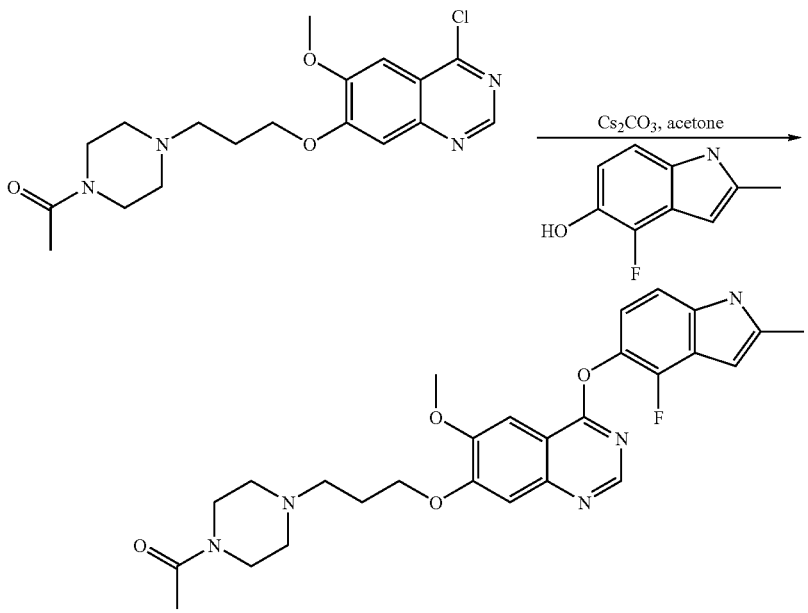

A mixture of 7-[3-(4-acetylpiperazin-1-yl)propoxy]-4-chloro-6-methoxyquinazoline (20.0 g, 52.3 mmol), 4-fluoro-5-hydroxy-2-methylindole (10.5 g, 63.3 mmol), (prepared as described for the starting material in Example 1), and cesium carbonate (34.4 g, 106 mmol) in acetone (500 ml) was heated at reflux for 4 hours. The mixture was cooled and allowed to stand overnight. The mixture was filtered and the solid suspended in water and re-filtered and dried under vacuum. The solid was purified by column chromatography eluting with methylene chloride/methanol (saturated with ammonia) (95/5) to give 7-[3-(4-acetylpiperazin-1-yl)propoxy]-4-[(4-fluoro-2-methyl-1H-indol-5-yl)oxy]-6-methoxyquinazoline (20.4 g, 77%) as a white solid.

MS and NMR details are given hereinbefore.

The starting material was prepared as follows:

4-Chloro-7-hydroxy-6-methoxyquinazoline (3 g, 14.2 mmol), (prepared as described for the starting material in Example 4), 3-(4-acetylpiperazin-1-yl)propan-1-ol (3.2 g, 17.1 mmol), (prepared as described for the starting material in this example hereinbefore), and triphenylphosphine (4.5 g, 17.1 mmol) were stirred together in dichloromethane (140 ml). Diisopropyl azodicarboxylate (3.4 ml, 17.1 mmol) was added dropwise and an ice/water bath used to keep the temperature of the reaction mixture below 10° C. After the addition, the reaction mixture was allowed to warm to ambient temperature and stirred overnight. The mixture was concentrated under reduced pressure. Column chromatography of the residue (2:1 iso-hexane:ethyl acetate then 3%-5% methanol/dichloromethane) gave 7-[3-(4-acetylpiperazin-1-yl)propoxy]-4-chloro-6-methoxyquinazoline (3.96 g, 74%) as a white solid.

$^1$H NMR Spectrum: (DMSOd$_6$) 1.98 (m, 5H); 2.34 (m, 2H); 2.40 (m, 2H); 2.46 (t, 2H); 3.43 (m, 4H); 4.01 (s, 3H); 4.29 (t, 2H); 7.40 (s, 1H); 7.46 (s, 1H); 8.87 (s, 1H)

MS-ESI 379.1 and 381.1 [MH]+

Alternatively 7-[3-(4-acetylpiperazin-1-yl)propoxy]-4-[(4-fluoro-2-methyl-1H-indol-5-yl)oxy]-6-methoxyquinazoline may be prepared as follows:

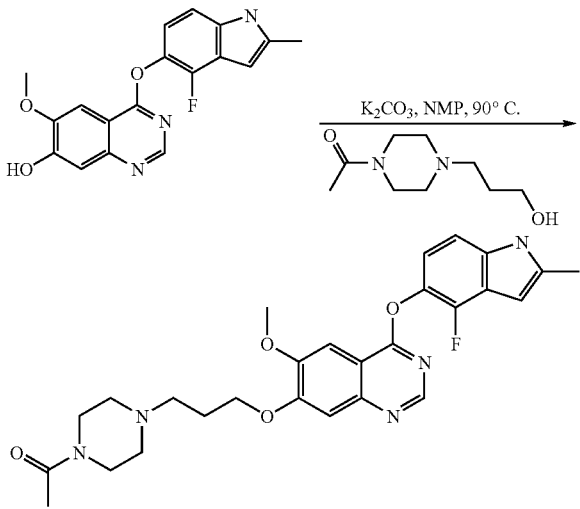

4-[(4-Fluoro-2-methyl-1H-indol-5-yl)oxy]-7-hydroxy-6-methoxyquinazoline (250 mg, 0.74 mmol), (prepared as described for the starting material in this example hereinbefore), and potassium carbonate (112 mg, 0.81 mmol) were stirred together in N-methylpyrrolidinone (3 ml). 1-Acetyl-4-(3-chloropropoxy)piperazine (166 mg, 0.81 mmol) in N-methylpyrrolidinone (1 ml) was added and the mixture heated at 90° C. for 3 hours. The mixture was cooled, filtered and concentrated under reduced pressure. The residue was purified by column chromatography eluting with methylene chloride/methanol (saturated with ammonia) (97/3) to give 7-[3-(4-acetylpiperazin-1-yl)propoxy]-4-[(4-fluoro-2-methyl-1H-indol-5-yl)oxy]-6-methoxyquinazoline (268 mg, 71%) as a white solid.

MS and NMR details are given hereinbefore.

The starting material was prepared as follows:

A mixture of 1-acetylpiperazine (1.0 g, 7.8 mmol), 1-bromo-3-chloropropane (772 μl, 7.8 mmol) and potassium carbonate (2.7 g, 19.5 mmol) in acetonitrile (150 ml) was heated at reflux for 2 hours. The mixture was cooled, filtered and concentrated under reduced pressure. The residue was purified by column chromatography eluting with methylene chloride/methanol (98/2) to give 1-acetyl-4-(3-chloropropoxy)piperazine (656 mg, 41%) as a colourless oil.

$^1$H NMR Spectrum: (CDCl$_3$) 1.95 (m, 2H); 2.08 (s, 3H); 2.42 (m, 4H), 2.51 (t, 2H); 3.46 (t, 2H); 3.61 (t, 4H)

EXAMPLE 8

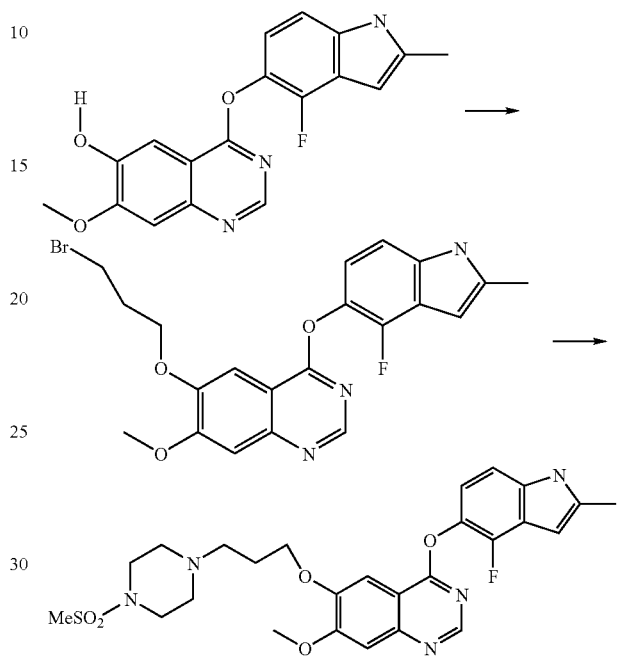

A solution of 6-(3-bromopropoxy)-4-(4-fluoro-2-methylindol-5-yloxy)-7-methoxyquinazoline (0.3 g, 0.652 mmol) and 1-(methylsulphonyl)piperazine (0.322 g, 1.95 mmol), (prepared as described for the starting material in Example 2), in DMF (4 ml) was stirred at 80° C. for 2.5 hours. The volatiles were removed under vacuum and the residue was purified by column chromatography eluting with increasingly polar mixtures of methylene chloride and methanol. The fractions containing the expected product were combined and evaporated. The residue was triturated under diethyl ether and the resulting solid was filtered, washed with diethyl ether and dried under vacuum to give 4-(4-fluoro-2-methylindol-5-yloxy)-7-methoxy-6-(3-(4-methylsulphonylpiperazin-1-yl)propoxy)quinazoline (0.08 g, 23%).

$^1$H NMR Spectrum: (DMSOd$_6$ and CF$_3$COOD) 2.3 (m, 2H), 2.4 (s, 3H), 3.0 (s, 3H), 3.1-3.3 (m, 4H), 3.4 (dd, 2H), 3.7 (d, 2H), 3.8 (d, 2H), 4.1 (s, 3H), 4.4 (dd, 2H), 6.25 (s, 0.2H, partly exchanged), 7.0 (dd, 1H), 7.2 (d, 1H), 7.55 (s, 1H), 7.82 (s, 1H), 9.1 (s, 1H)

MS-ESI: 544 [M+H]+

The starting material was prepared as follows:

Diethyl azodicarboxylate (0.847 g, 4.86 mmol) was added to a solution of 4-(4-fluoro-2-methylindol-5-yloxy)-6-hydroxy-7-methoxyquinazoline (1.5 g, 4.42 mmol), (prepared as described for the starting material in Example 1), triphenylphosphine (1.74 g, 6.63 mmol) and 3-bromo-1-propanol (0.923 g, 6.63 mmol) in methylene chloride. After stirring for 1 hour at ambient temperature, triphenylphosphine (1.16 g) and DEAD (0.770 g) was added. After stirring for 30 minutes, the volatiles were removed under vacuum and the residue was purified by column chromatograhy eluting with increasingly polar mixtures of methylene chloride and ethyl acetate to give 6-(3-bromopropoxy)-4-(4-fluoro-2-methylindol-5-yloxy)-7-methoxyquinazoline (1.5 g, 73%).

¹H NMR Spectrum: (DMSOd₆) 2.4 (m, 2H), 2.45 (s, 3H), 3.75 (dd, 2H), 4.05 (s, 3H), 4.32 (dd, 2H), 6.25 (s, 1H), 7.02 (dd, 2H), 7.18 (d, 1H), 7.42 (s, 1H), 7.7 (s, 1H) 8.55 (s, 1H)
MS-ESI: 460-462 [M+H]+

EXAMPLE 9

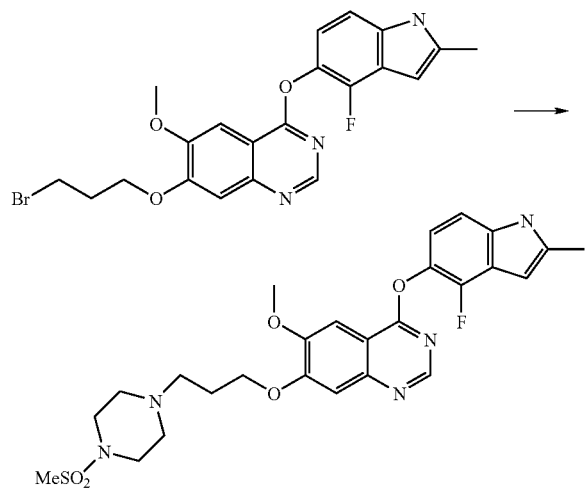

Using an analogous procedure to that described for the preparation of Example 8,7-(3-bromopropoxy)-4-(4-fluoro-2-methylindol-5-yloxy)-6-methoxyquinazoline (0.25 g, 0.54 mmol), (prepared as described for the starting material in Example 7), was reacted with 1-methylsulphonylpiperazine (0.268 g, 163 mmol), (prepared as described for the starting material in Example 2), in DMF to give 4-(4-fluoro-2-methylindol-5-yloxy)-6-methoxy-7-(3-(4-methylsulphonylpiperazin-1-yl)propoxy)quinazoline (0.14 g, 47%).

¹H NMR Spectrum: (DMSOd₆, CF₃COOD) 2.35 (m, 2H), 2.4 (s, 3H), 3.02 (s, 3H), 3.1-3.3 (m, 4H), 3.4 (dd, 2H), 3.7 (d, 2H), 3.8 (d, 2H), 4.08 (s, 3H), 4.4 (dd, 2H), 6.25 (s, 0.2H, partly exchanged), 7.0 (dd, 1H), 7.2 (d, 1H), 7.58 (s, 1H), 7.82 (s, 1H), 9.1 (s, 1H)

MS-ESI: 544 [M+H]+

EXAMPLE 10

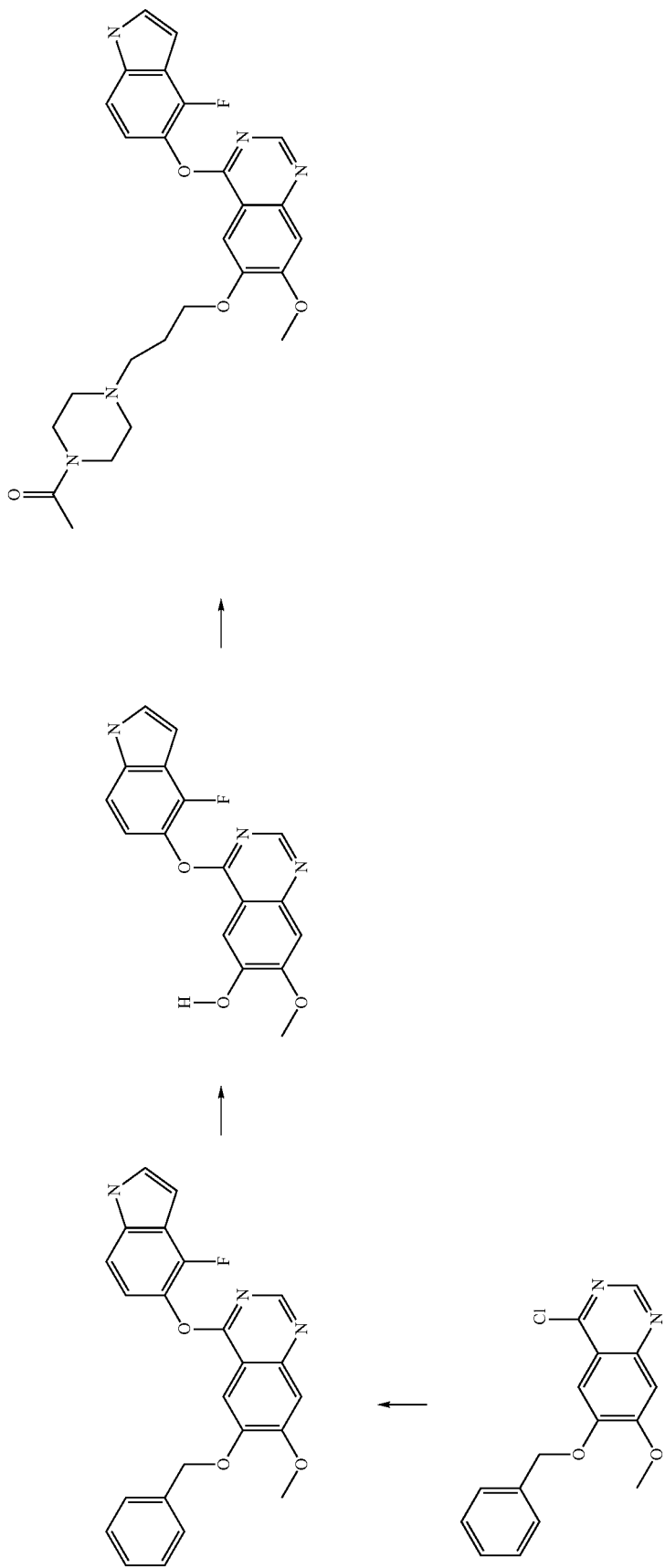

Diethyl azodicarboxylate (117 μl, 0.738 mmol) was added dropwise to a solution of 4-(4-fluoroindol-5-yloxy)-6-hydroxy-7-methoxyquinazoline (0.2 g, 0.615 mmol), triphenylphosphine (0.242 g, 0.92 mmol) and 3-(4-acetylpiperazin-1-yl)propan-1-ol (0.137 g, 0.738 mmol), (prepared as described for the starting material in Example 1 or Example 7), in methylene chloride (5 ml). After stirring at ambient temperature for 1 hour, triphenylphosphine (0.032 g), 3-(4-acetylpiperazin-1-yl)propan-1-ol (0.022 g) and diethyl azodicarboxylate (20 μl) were added. The mixture was stirred for 1 hour at ambient temperature and evaporated under vacuum. The residue was purified by column chromatography, eluting with increasingly polar mixtures of methylene chloride and ethyl acetate followed by methylene chloride and methanol. The fractions containing the expected product were combined and evaporated. The residue was repurified by preparative LC/MS eluting with increasingly polar mixtures of acetonitrile and water (containing 1% acetic acid). The fractions containing the expected product were combined and evaporated. The residue was triturated under diethyl ether and pentane and the residue was filtered, washed with diethyl ether and dried under vacuum to give 6-(3-(4-acetylpiperazin-1-yl) propoxy)-4-(4-fluoroindol-5-yloxy)-7-methoxyquinazoline (0.057 g, 19%).

$^1$H NM Spectrum: (DMSOd$_6$, CF$_3$COOD) 2.05 (s, 3H), 2.3 (m, 2H), 2.9-3.1 (m, 2H), 3.15 (m, 1H), 3.35 (dd, 2H), 3.45 (m, 1H), 3.6 (d, 2H), 4.05 (m, 1H), 4.1 (s, 3H), 4.4 (dd, 2H), 4.5 (d, 1H), 6.55 (d, 1H), 7.15 (dd, 1H), 7.38 (d, 1H), 7.5 (d, 1H), 7.58 (s, 1H), 7.85 (s, 1H), 9.12 (s, 1H)

MS-ESI: 494 [M+H]+

The starting material was prepared as follows

A mixture of 6-benzyloxy-4-chloro-7-methoxyquinazoline (0.88 g, 2.9 mmol), (EP1153920 production examples 28-30), 4-fluoro-5-hydroxyindole (0.53 g, 3.5 mmol) and potassium carbonate (0.607 g, 4.39 mmol) in DMF (18 ml) was stirred at 95° C. for 2 hours. After cooling, the mixture was filtered and the volatiles were removed under vacuum. The residue was purified by column chromatography eluting with increasingly polar mixtures of methylene chloride and ethyl acetate to give 6-benzyloxy-4-(4-fluoroindol-5-yloxy)-7-methoxyquinazoline (0.8 g, 67%).

$^1$H NMR Spectrum: (DMSOd$_6$) 4.05 (s, 3H), 5.35 (s, 2H), 6.6 (s, 1H), 7.1 (dd, 1H), 7.35 (d, 1H), 7.35-7.5 (m, 5H), 7.55 (d, 2H), 7.8 (s, 1H), 8.55 (s, 1H), 11.5 (br s, 1H)

MS-ESI: [M+H]+ 416

6-Benzyloxy-4-(4-fluoroindol-5-yloxy)-7-methoxyquinazoline (0.75 g, 1.8 mmol), ammonium formate (1.14 g, 18 mmol) and 10% palladium on carbon (115 mg) in DMF (8 ml) containing water (1.5 ml) was stirred at ambient temperature for 2.5 hours. The mixture was filtered over diatomaceous earth and the filtrate was evaporated. The residue was triturated under diethyl ether, filtered, washed with water, followed by diethyl ether and dried overnight over P$_2$O$_5$ to give 4-(4-fluoroindol-5-yloxy)-6-hydroxy-7-methoxyquinazoline (0.471 g, 80%).

$^1$H NMR Spectrum: (DMSOd$_6$) 4.02 (s, 3H), 6.55 (s, 1H), 7.1 (dd, 1H), 7.3 (d, 1H), 7.4 (s, 1H), 7.5 (dd, 1H), 7.6 (s, 1H), 8.48 (s, 1H)

MS-ESI: 326 [M+H]+

A mixture of 2-fluoro-4-nitrophenol (15 gr, 95.5 mmol) and benzyl bromide (18 g, 105 mmol) in acetone (125 ml) containing potassium carbonate (26.5 gr, 190 mmol) was heated at reflux for 2 hours. The volatiles were removed and the residue was partitioned between 2N hydrochloric acid and ethyl acetate. The organic layer was separated, washed with water, brine, dried (MgSO$_4$) and the volatiles were removed under vacuum. The solid was triturated with petroleum ether to give 2-fluoro-4-nitro-benzyloxybenzene (23 g, 97%).

$^1$H NMR Spectrum: (CDCl$_3$) 5.3 (s, 2H); 7.1 (t, 1H); 7.35-7.55 (m, 5H); 8.0 (m, 2H)

To a solution of potassium tert-butoxide (1.72 g, 15.4 mmol) in DMF (15 ml) cooled at −30° C., was added dropwise a solution of 2-fluoro-4-nitro-benzyloxybenzene (1.73 g, 7 mmol) and 4-chlorophenoxyacetonitrile (1.29 g, 7.7 mmol) while maintaining the temperature below −25° C. After completion of addition, the mixture was stirred for 30 minutes at −20° C. and then poured onto a mixture of cold 1N hydrochloric acid and ether. The organic layer was separated, washed with 1N sodium hydroxide, followed by water, brine, dried (MgSO$_4$). The volatiles were removed under vacuum and the residue was purified by column chromatography eluting with methylene chloride/petroleum ether (3/1) to give a mixture of 3-cyanomethyl-2-fluoro-4-nitrobenzyloxybenzene and 5-cyanomethyl-2-fluoro-4-nitrobenzyloxybenzene (1.2 g, 60%).

$^1$H NMR Spectrum: (DMSO-d$_6$) 4.22 (s, 2H, 3-cyanomethyl isomer); 4.3 (s, 2H, 5-cyanomethyl isomer); 5.32 (s, 2H, 5-cyanomethyl isomer); 5.36 (s, 2H, 3-cyanomethyl isomer); 7.3-7.7 (m, 6H); 8.1 (d, 1H, 3-cyanomethyl isomer); 8.2 (d, 1H, 5-cyanomethyl isomer)

A solution of a mixture of 3-cyanomethyl-2-fluoro-4-nitrobenzyloxybenzene and 5-cyanomethyl-2-fluoro-4-nitrobenzyloxybenzene (23 g, 80.4 mmol) in ethanol (220 ml) and acetic acid (30 ml) containing 10% palladium on charcoal (600 mg) was hydrogenated under 3 atmospheres pressure until hydrogen uptake ceased. The mixture was filtered and the filtrate was evaporated under vacuum. The residue was purified on column chromatography using a Prochrom® equipment eluting with methylene chloride/petroleum ether (20/80) to give 4-fluoro-5-hydroxyindole (2.48 g) and 6-fluoro-5-hydroxyindole (3.5 g).

4-fluoro-5-hydroxyindole $^1$H NMR Spectrum: (DMSOd$_6$) 6.32 (s, 1H); 6.75 (dd, 1H); 7.0 (d, 1H); 7.28 (dd, 1H); 8.8 (br s, 1H); 11.05 (br s, 1H)

6-fluoro-5-hydroxyindole $^1$H NMR Spectrum: (DMSOd$_6$) 6.25 (s, 1H); 7.0 (d, 1H); 7.12 (d, 1H); 7.2 (dd, 1H); 9.0 (br s, 1H)

EXAMPLE 11

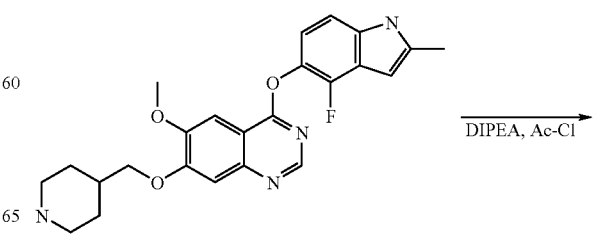

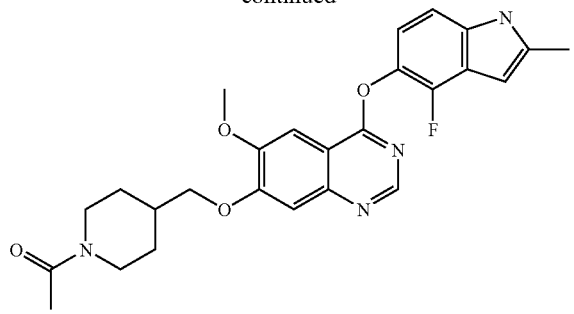

4-[(4-Fluoro-2-methyl-1H-indol-5-yl)oxy]-6-methoxy-7-(piperidin-4-ylmethoxy)quinazoline (150 mg, 0.34 mmol) was suspended in methylene chloride (5 ml), and diisopropylethylamine (72 µl, 0.41 mmol) and acetyl chloride (29 µl, 0.41 mmol) were added. The mixture was stirred for half an hour at ambient temperature, washed with saturated sodium hydrogen carbonate solution, dried (MgSO$_4$) and concentrated under reduced pressure. The solid was suspended in methanol and filtered off to give 7-[(1-acetylpipeidin-4-yl)methoxy]-4-[(4-fluoro-2-methyl-1H-indol-5-yl)oxy]-6-methoxyquinazoline (117 mg, 71%).

MS-ESI: 479.5 [MH]$^+$ $^1$H NMR Spectrum: (DMSOd$_6$) 1.22 (m, 2H); 1.83 (m, 2H); 1.99 (s, 3H); 2.13 (m, 1H); 2.40 (s, 3H); 2.58 (m, 1H); 3.06 (m, 1H), 3.85 (m, 1H); 3.98 (s, 3H); 4.08 (d, 2H); 4.40 (m, 1H); 6.22 (s, 1H); 6.96 (t, 1H); 7.14 (d, 1H); 7.38 (s, 1H); 7.59 (s, 1H); 8.48 (s, 1H); 11.29 (br s, 1H)

The starting material was prepared as follows:

While maintaining the temperature in the range 0-5° C., a solution of di-tert-butyl dicarbonate (41.7 g, 0.19 mol) in ethyl acetate (75 ml) was added in portions to a solution of ethyl 4-piperidinecarboxylate (30 g, 0.19 mol) in ethyl acetate (150 ml) cooled at 5° C. After stirring for 48 hours at ambient temperature, the mixture was poured onto water (300 ml). The organic layer was separated, washed successively with water (200 ml), 0.1N aqueous hydrochloric acid (200 ml), saturated sodium hydrogen carbonate (200 ml) and brine (200 ml), dried (MgSO$_4$) and evaporated to give ethyl 4-(1-(tert-butoxycarbonyl)piperidine)carboxylate (48 g, 98%).

$^1$H NMR Spectrum: (CDCl$_3$) 1.25 (t, 3H); 1.45 (s, 9H); 1.55-1.70 (m, 2H); 1.8-2.0 (d, 2H); 2.35-2.5 (m, 1H); 2.7-2.95 (t, 2H); 3.9-4.1 (br s, 2H); 4.15 (q, 2H)

A solution of 1M lithium aluminium hydride in THF (133 ml, 0.133 mol) was added in portions to a solution of ethyl 4-(1-(tert-butoxycarbonyl)piperidine)carboxylate (48 g, 0.19 mol) in dry THF (180 ml) cooled at 0° C. After stirring at 0° C. for 2 hours, water (30 ml) was added followed by 2N sodium hydroxide (10 ml). The precipitate was removed by filtration through diatomaceous earth and washed with ethyl acetate. The filtrate was washed with water, brine, dried (MgSO$_4$) and evaporated to give 1-(tert-butoxycarbonyl)-4-hydroxymethylpiperidine (36.3 g, 89%).

MS (EI): 215 [M.]+

$^1$H NMR Spectrum: (CDCl$_3$) 1.05-1.2 (m, 2H); 1.35-1.55 (m, 10H); 1.6-1.8 (m, 2H); 2.6-2.8 (t, 2H); 3.4-3.6 (t, 2H); 4.0-4.2 (br s, 2H)

Diisopropyl azodicarboxylate (139 µl, 0.71 mmol) was added to a mixture of 4-(4-fluoro-2-methylindol-5-yloxy)-7-hydroxy-6-methoxyquinazoline (200 mg, 0.59 mmol), (prepared as described for the starting material in Example 7), triphenylphosphine (186 mg, 0.71 mmol) and 1-(tert-butoxycarbonyl)-4-hydroxymethylpiperidine, (also known as tert-butyl 4-(hydroxymethyl)piperidine-1-carboxylate), (152 mg, 0.71 mmol) in methylene chloride (3 ml), cooled in an ice/water bath. The mixture was allowed to warm to ambient temperature and was stirred overnight. The mixture was concentrated under reduced pressure and the residue purified by column chromatography, eluting with 1% methanol/methylene chloride and 0.1% triethylamine to give tert-butyl 4-[(4-[(4-fluoro-2-methyl-1H-indol-5-yl)oxy]-6-methoxyquinazolin-7-yloxy)methyl]piperidine-1-carboxylate (293 mg containing 13.5 mol % triphenylphospine oxide, 86%).

MS-ESI: 537.6 [MH]$^+$ $^1$H NMR Spectrum: (DMSOd$_6$) 1.22 (m, 2H); 1.39 (s, 9H); 1.78 (m, 2H); 2.04 (m, 1H); 2.40 (s, 3H); 2.76 (m, 2H); 3.97 (m, 5H); 4.07 (d, 2H); 6.22 (s, 1H); 6.96 (t, 1H); 7.14 (d, 2H); 7.37 (s, 1H); 7.69 [m, 3.3H (1H+Ph$_3$PO)]; 8.47 (s, 1H); 11.29 (br s, 1H)

tert-Butyl 4-[(4-[(4-fluoro-2-methyl-1H-indol-5-yl)oxy]-6-methoxyquinazolin-7-yloxy)methyl]piperidine-1-carboxylate [285 mg (containing 13.5% triphenylphospine oxide), 0.49 mmol] was dissolved in 4M hydrogen chloride in dioxane (5 ml) and stirred at ambient temperature for 3 hours. The solvent was removed under reduced pressure and the solid suspended in methylene chloride and filtered off. The solid was dissolved in methanol and absorbed onto an Isolute SCX column which was washed through with methanol and then the product eluted with 7N ammonia in methanol. Concentration of the fractions gave 4-[(4-fluoro-2-methyl-1H-indol-5-yl)oxy]-6-methoxy-7-(piperidin-4-ylmethoxy)quinazoline (185 mg, 86%).

MS-ESI: 437.5 [MH]$^+$ $^1$H NMR Spectrum: (CDCl$_3$) 1.34 (m, 2H); 1.85-2.20 (m, 3H); 2.45 (s, 3H); 2.68 (m, 2H); 3.15 (m, 2H); 4.05 (m, 5H); 6.32 (s, 1H); 6.97 (t, 1H); 7.11 (d, 1H); 7.30 (s, 1H) 7.63 (s, 1H); 8.58 (s, 1H); 9.08 (br s, 1H)

EXAMPLE 12

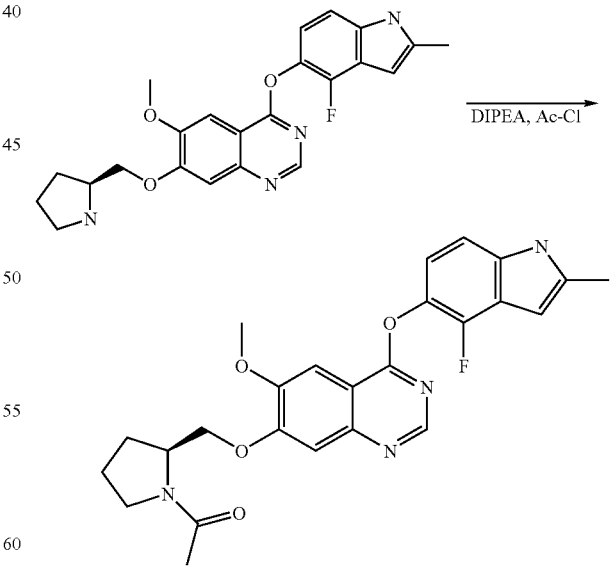

Using an analogous procedure to that described for the preparation of Example 11, 4-[(4-fluoro-2-methyl-1H-indol-5-yl)oxy]-6-methoxy-7-[(2S)-pyrrolidin-2-ylmethoxy]quinazoline (120 mg, 0.28 mmol) was reacted with acetyl chloride (24 µl, 0.34 mmol). The crude product was purified by column chromatography eluting with methanol/methylene chloride (2/98) to give 7-[(2S)-1-acetylpyrrolidin-2-ylmethoxy]-4-[(4-fluoro-2-methyl-1H-indol-5-yl)oxy]-6-methoxyquiinazoline (76 mg, 58%).

MS-ESI: 465.6 [MH]+

$^1$H NMR Spectrum: (100° C., DMSOd$_6$) 2.02 (m, 7H); 2.41 (s, 3H); 3.50 (m, 2H); 4.00 (s, 3H), 4.29 (m, 3H); 6.22 (s, 1H); 6.95 (t, 1H); 7.14 (d, 1H); 7.43 (s, 1H); 7.63 (s, 1H); 8.47 (s, 1H); 11.02 (br s, 1H)

The starting material was prepared as follows:

Using an analogous procedure to that described for the preparation of the starting material in Example 11, tert-butyl (2S)-2-(hydroxymethyl)pyrrolidine-1-carboxylate (142 mg, 0.71 mmol) was reacted with 4-(4-fluoro-2-methylindol-5-yloxy)-7-hydroxy-6-methoxyquinazoline (200 mg, 0.59 mmol), (prepared as described for the starting material in Example 7), and the product purified by column chromatography, eluting with methanol/methylene chloride (1/9) containing 0.1% triethylamine to give tert-butyl (2S)-2-[(4-[(4-fluoro-2-methyl-1H-indol-5-yl)oxy]-6-methoxyquinazolin-7-yloxy)methyl]pyrrolidine 1-carboxylate (178 mg, 58%).

MS-ESI: 523.3 [H]+

$^1$H NMR Spectrum: (DMSOd$_6$) 1.40 (s, 9H); 1.80 (m, 1H); 1.98 (m, 3H); 2.40 (s, 3H); 3.98 (s, 3H); 4.19 (m, 3H); 6.22 (s, 1H); 6.97 (t, 1H); 7.14 (d, 1H); 7.43 (br s, 1H); 7.59 (s, 1H); 8.48 (s, 1H); 11.29 (br s, 1H)

Using an analogous procedure to that described for the preparation of the starting material in Example 11, tert-butyl (2S)-2-[(4-[(4-fluoro-2-methyl-1H-indol-5-yl)oxy]-6-methoxyquinazoline-7-yloxy)methyl]pyrrolidine-1-carboxylate (170 mg, 0.33 mmol) was reacted with hydrogen chloride in dioxane. The solid was dissolved in methanol and absorbed onto an Isolute SCX column which was washed through with methanol and then the product was eluted with 7N ammonia in methanol to give 4-[(4-fluoro-2-methyl-1H-indol-5-yl)oxy]-6-methoxy-7-[(2S)-pyrrolidin-2-ylmethoxy]quinazoline (128 mg, 93%).

MS-ESI: 423.5 [MH]+

$^1$H NMR Spectrum: (DMSOd$_6$) 1.53 (m, 1H); 1.71 (m, 2H); 1.88 (m, 1H); 2.40 (s, 3H); 2.84 (m, 2H); 3.52 (m, 1H); 3.98 (s, 3H); 4.04 (d, 2H); 6.22 (s, 1H); 6.97 (t, 1H); 7.14 (d, 1H); 7.37 (s, 1H); 7.59 (s, 1H); 8.47 (s, 1H); 11.30 (br s, 1H)

EXAMPLE 13

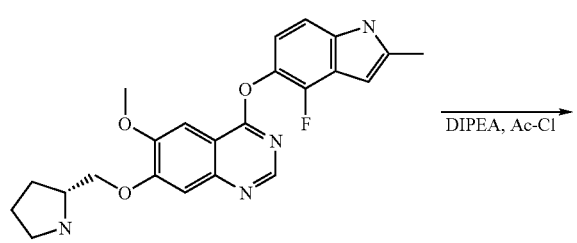

DIPEA, Ac-Cl

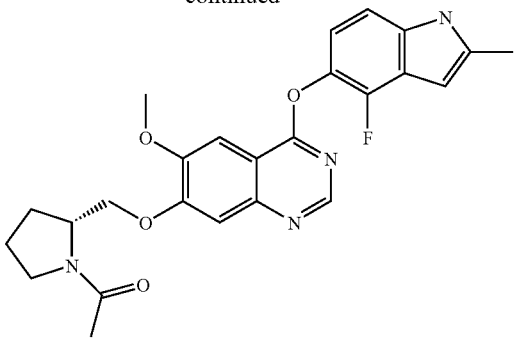

Using an analogous procedure to that described for the preparation of Example 11, 4-[(4-fluoro-2-methyl-1H-indol-5-yl)oxy]-6-methoxy-7-[(2R)-pyrrolidin-2-ylmethoxy]quinazoline (160 mg, 0.38 mmol) was reacted with acetyl chloride (32 μl, 0.46 mmol). The crude product was purified by column chromatography eluting with methanol/methylene chloride (2/98) to give 7-[(2R)-1-acetylpyrrolidin-2-ylmethoxy]-4-[(4-fluoro-2-methyl-1H-indol-5-yl)oxy]-6-methoxyquinazoline (82 mg, 46%).

MS-ESI: 465.6 [MH]+

$^1$H NMR Spectrum: (100° C., DMSO-d$_6$) 2.02 (m, 7H); 2.41 (s, 3H); 3.50 (m, 2H); 4.00 (s, 3H), 4.29 (m, 3H); 6.22 (s, 1H); 6.95 (t, 1H); 7.14 (d, 1H); 7.43 (s, 1H); 7.63 (s, 1H); 8.47 (s, 1H); 11.02 (br s, 1H)

The starting material was prepared as follows:

Using an analogous procedure to that described for the preparation of the starting material in Example 11, tert-butyl (2R)-2-(hydroxymethyl)pyrrolidine-1-carboxylate (1.48 g, 7.37 mmol) was reacted with 4-(4-fluoro-2-methylindol-5-yloxy)-7-hydroxy-6-methoxyquinazoline (1.0 g, 2.95 mmol), (prepared as described for the starting material in Example 7), and the product purified by column chromatography, eluting with methanol/methylene chloride (1/9) containing 0.1% triethylamine to give tert-butyl (2R)-2-[(4-[(4-fluoro-2-methyl-1H-indol-5-yl)oxy]-6-methoxyquinazolin-7-yloxy)methyl]pyrrolidine 1-carboxylate (970 mg, 62%).

MS-ESI: 523.3 [MH]+

$^1$H NMR Spectrum: (DMSOd$_6$) 1.40 (s, 9H); 1.80 (m, 1H); 1.98 (m, 3H); 2.40 (s, 3H); 3.98 (s, 3H); 4.19 (m, 3H); 6.22 (s, 1H); 6.97 (t, 1H); 7.14 (d, 1H); 7.43 (br s, 1H); 7.59 (s, 1H); 8.48 (s, 1H); 11.29 (br s, 1H)

Using an analogous procedure to that described for the preparation of the starting material in Example 11, tert-butyl (2R)-2-[(4-[(4-fluoro-2-methyl-1H-indol-5-yl)oxy]-6-methoxyquinazolin-7-yloxy)methyl]pyrrolidine-1-carboxylate (960 mg, 1.84 mmol) was reacted with hydrogen chloride in dioxane. The solid was dissolved in methanol and absorbed onto an Isolute SCX column which was washed through with methanol and then the product was eluted with 7N ammonia in methanol to give 4-[(4-fluoro-2-methyl-1H-indol-5-yl)oxy]-6-methoxy-7-[(2R)-pyrrolidin-2-ylmethoxy]quinazoline (480 mg, 62%).

MS-ESI: 423.5 [MH]+

$^1$H NMR Spectrum: (DMSOd$_6$) 1.53 (m, 1H); 1.71 (m, 2H); 1.88 (m, 1H); 2.40 (s, 3H); 2.84 (m, 2H); 3.52 (m, 1H); 3.98 (s, 3H); 4.04 (d, 2H); 6.22 (s, 1H); 6.97 (t, 1H); 7.14 (d, 1H); 7.37 (s, 1H); 7.59 (s, 1H); 8.47 (s, 1H); 11.30 (br s, 1H)

EXAMPLE 14

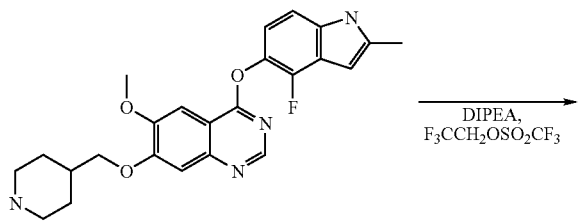

rated with diethyl ether and filtered to give 4-[(4-fluoro-2-methyl-1H-indol-5-yl)oxy]-6-methoxy-7-[1-(2,2,2-trifluoroethyl)pipexidin-4-ylmethoxy]quinazoline (93 mg, 44%).

MS-ESI: 519.1 [MH]$^+$ $^1$H NMR Spectrum: (DMSOd$_6$) 1.40 (m, 2H); 1.80 (m, 3H); 2.36 (m, 5H); 2.95 (br d, 2H); 3.14 (m, 2H); 3.98 (s, 3M); 4.06 (d, 2H); 6.22 (s, 1H); 6.96 (t, 1H); 7.14 (d, 1H); 7.36 (s, 1H); 7.58 (s, 1H); 8.48 (s, 1H); 11.29 (br s, 1H)

EXAMPLE 15

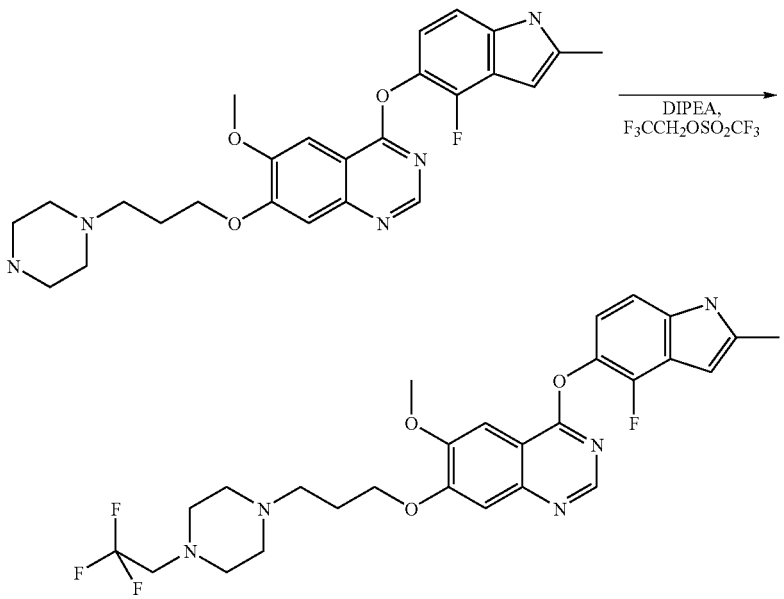

-continued

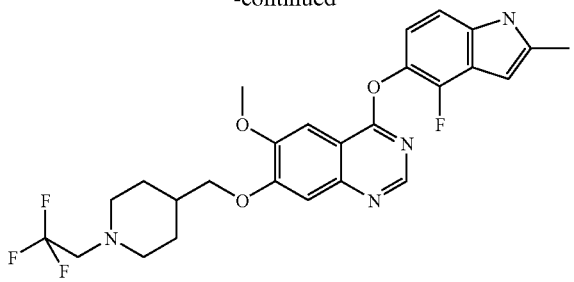

4-[(4-Fluoro-2-methyl-1H-indol-5-yl)oxy]-6-methoxy-7-(piperidin-4-ylmethoxy)quinazoline (180 mg, 0.41 mmol), (prepared as described for the starting material in Example 11), was suspended in tetrahydrofuran (15 ml), and diisopropylethylamine (108 µl, 0.45 mmol) and 2,2,2-trifluoroethyl trifluoromethanesulphonate (98 mg, 0.62 mmol) were added. The mixture was heated at reflux for 1.5 hours. Diisopropylethylamine (36 µl, 0.21 mmol) and 2,2,2-trifluoroethyl trifluoromethanesulphonate (45 mg, 0.21 mmol) were added and the mixture was heated at reflux for a further 2 hours. The mixture was concentrated under reduced pressure and column chromatography of the residue, eluting with 1% methanol/methylene chloride gave a sticky solid. This was tritu- Using an analogous procedure to that described for the preparation of Example 14, 4-[(4-fluoro-2-methyl-1H-indol-5-yl)oxy]-6-methoxy-7-(3-piperazin-1-ylpropoxy)quinazoline (250 mg, 0.54 mmol) was reacted with 2,2,2-trifluoroethyl trifluoromethanesulphonate (128 mg, 0.59 mmol) and purified by column chromatography, eluting with 5% methanol/methylene chloride to give a sticky solid. The sticky solid was dissolved in methanol and absorbed onto an Isolute SCX column. The column was washed with methanol and eluted with 7N ammonia in methanol. The product was triturated in ether/isohexane and filtered to give 4-[(4-fluoro-2-methyl-1H-indol-5-yl)oxy]-6-methoxy-7-{3-[4-(2,2,2-trifluoroethyl)piperazin-1-yl]propoxy}quinazoline (130 mg, 44%).

MS-ESI: 548.6 [MH]$^+$ $^1$H NMR Spectrum: (DMSOd$_6$) 1.95 (m, 2H); 2.40 (m, 9H); 2.62 (m, 4H); 3.12 (q, 2H); 3.97 (s, 3H); 4.22 (t, 2H); 6.22 (s, 1H); 6.96 (t, 1H); 7.14 (d, 1H); 7.36 (s, 1H); 7.58 (s, 1H); 8.47 (s, 1H); 11.29 (br s, 1H)

The starting material was prepared as follows:

A mixture of 1-tert-butoxycarbonylpiperazine (1.0 g, 5.37 mmol), 3-bromo-1-propanol (0.49 ml, 5.37 mmol) and potassium carbonate (1.86 g, 13.4 mmol) was heated at reflux in acetonitrile (10 ml) for 1.5 hours. The mixture was concentrated under reduced pressure and column chromatography of the residue, eluting with 2% methanol/methylene chloride, gave 1-tert-butoxycarbonyl-4-(3-hydroxypropyl)piperazine (1.2 g, 91%).

¹H NMR Spectrum: (CDCl₃) 1.46 (s, 9H); 1.74 (m, 2H); 2.46 (m, 4H); 2.61 (t, 2H); 3.43 (m, 4H); 3.80 (t, 2H)

Using an analogous procedure to that described for the preparation of the starting material in Example 11, 1-tert-butoxycarbonyl-4-(3-hydroxypropyl)piperazine (432 mg, 1.77 mmol) was reacted with 4-[(4-fluoro-2-methyl-1H-indol-5-yl)oxy]-7-hydroxy-6-methoxyquinazoline (500 mg, 1.47 mmol), (prepared as described for the starting material in Example 7). The product was purified by column chromatography, eluting with 2%-5% methanol/methylene chloride to give tert-butyl 4-[3-(4-[(4-fluoro-2-methyl-1H-indol-5-yl)oxy]-6-methoxyquinazolin-7-yloxy)propyl]piperazine-1-carboxylate (582 mg, 70%).

LC-MS (ESI) 1.67 min, 100%, 566.7 [MH]⁺

¹H NMR Spectrum: (DMSOd₆) 1.38 (s, 9H); 1.97 (m, 2H); 2.24-2.35 (m, 6H); 2.46 (s, 3H); 3.31 (m, 4H); 3.97 (s, 3H); 4.24 (t, 2H); 6.22 (s, 1H); 6.96 (t, 1H); 7.14 (d, 1H); 7.37 (s, 1H); 7.58 (s, 1H); 8.48 (s, 1H); 11.29 (br s, 1H)

Using an analogous procedure to that described for the preparation of the starting material in Example 11, tert-butyl 4-[3-(4-[(4-fluoro-2-methyl-1H-indol-5-yl)oxy]-6-methoxyquinazolin-7-yloxy)propyl]piperazine-1-carboxylate was reacted with hydrogen chloride in dioxane. The crude product was absorbed onto an Isolute SCX column, washing with methanol and eluting with 7N ammonia in methanol to give 4-[(4-fluoro-2-methyl-1H-indol-5-yl)oxy]-6-methoxy-7-(3-piperazin-1-ylpropoxy)quinazoline (96%) as a pale orange foam.

MS-ESI 466.5 [MH]⁺

¹H NMR Spectrum: (DMSOd₆) 1.96 (m, 2H); 2.30 (m, 4H); 2.40 (m, 5H); 2.69 (m, 4H), 3.97 (s, 3H); 4.23 (t, 2H); 6.22 (s, 1H); 6.96 (t, 1H); 7.13 (d, 1H); 7.37 (1H, s); 7.58 (s, 1H); 8.49 (s, 1H); 11.32 (br s, 1H)

EXAMPLE 16

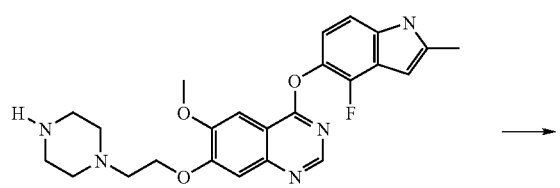

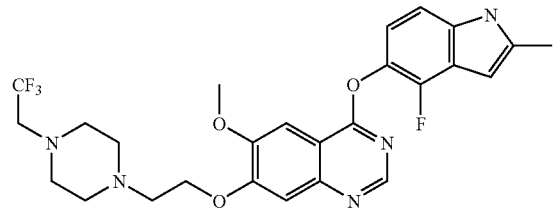

Using an analogous procedure to that described for the preparation of Example 14, 2,2,2-trifluoroethyl trifluoromethanesulphonate was reacted with 4-[(4-fluoro-2-methyl-1H-indol-5-yl)oxy]-6-methoxy-7-(2-piperazin-1-ylethoxy)quinazoline. The product was purified by column chromatography, eluting with 5% methanol/methylene chloride to give a sticky solid. The sticky solid was dissolved in methanol and absorbed onto an Isolute SCX column, washed with methanol and eluted with 7N ammonia in methanol. The product was concentrated from ether to give 4-[(4-fluoro-2-methyl-1H-indol-5-yl)oxy]-6-methoxy-7-{3-[4-(2,2,2-trifluoroethyl)piperazin-1-yl]ethoxy}qunazoline.

MS-ESI: 534.2 [MH]⁺

¹H NMR Spectrum: (DMSOd₆) 2.40 (s, 3H); 2.55 (m, 4H); 2.63 (m, 4H); 2.79 (t, 2H); 3.13 (q, 2H); 3.97 (s, 3H); 4.29 (t, 2H); 6.22 (s, 1H); 6.97 (t, 1H); 7.14 (d, 1H); 7.41 (s, 1H); 7.58 (s, 1H); 8.48 (s, 1H); 11.29 (br s, 1H)

EXAMPLE 17

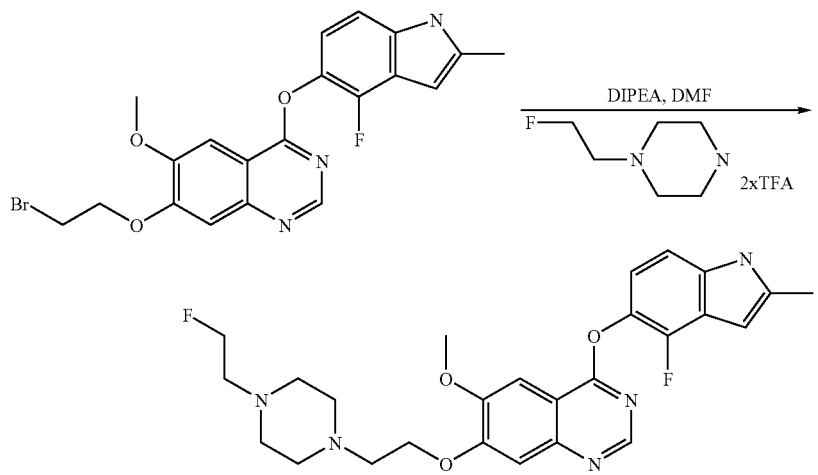

A mixture of 7-(2-bromoethoxy)-4-[(4-fluoro-2-methyl-1H-indol-5-yl)oxy]-6-methoxyquinazoline (150 mg, 0.36 mmol), 1-(2-fluoroethyl)piperazine di-trifluoroacetic acid salt (240 mg, 0.67 mmol) and diisopropylethylamine (293 μl, 1.68 mmol) in N,N-dimethylformamide (3 ml) was stirred overnight at ambient temperature. The mixture was diluted with ethyl acetate, washed with brine (×2), dried (MgSO$_4$) and concentrated under reduced pressure. Column chromatography of the residue, eluting with 4% methanol/methylene chloride gave 7-{2-[4-(2-fluoroethyl)piperazin-1-yl]ethoxy}-4-[(4-fluoro-2-methyl-1H-indol-5-yl)oxy]-6-methoxyquinazoline (50 mg, 30%).

MS-ESI: 498.6 [MH]$^+$ $^1$H NMR Spectrum: (DMSOd$_6$) 2.42 (s, 3H); 2.64 (t, 1H); 2.81 (t, 2H); 4.00 (s, 3H); 4.32 (t, 2H); 4.47 (t, 1H); 4.59 (t, 1H); 6.25 (s, 1H); 6.99 (t, 1H); 7.17 (d, 1H); 7.44 (s, 1H); 7.61 (s, 1H); 8.50 (s, 1H); 11.32 (br s, 1H)

The starting material was prepared as follows:

A suspension of 4-[(4-fluoro-2-methyl-1H-indol-5-yl)oxy]-7-hydroxy-6-methoxyquinazoline (530 mg, 1.56 mmol), (prepared as described for the starting material in Example 7), in methylene chloride (15 ml) was treated with triphenylphosphine (570 mg, 2.18 mmol), 2-bromoethanol (300 mg, 2.40 mmol) and diisopropyl azodicarboxylate (380 mg, 1.88 mmol) and the mixture stirred at ambient temperature for 2 hours. The crude reaction mixture was loaded onto a silica column and eluted using ethyl acetate as solvent. The relevant fractions were combined and evaporated under vacuum to give a residue, which was triturated with ether, filtered and dried. This gave 7-(2-bromoethoxy)-4-[(4-fluoro-2-methyl-1H-indol-5-yl)oxy]-6-methoxyquinazoline as a white solid (546 mg, 78%).

$^1$H NMR Spectrum: (DMSOd$_6$) 2.40 (s, 3H), 3.90 (t, 2H), 3.99 (s, 3H), 4.56 (t, 2H), 6.21 (s, 1H), 6.97 (t, 1H), 7.16 (d, 1H), 7.42 (s, 1H), 7.62 (s, 1H), 8.49 (s, 1H) and 11.29 (s, 1H)

MS (ESI): 446 and 448 (MH)$^+$

A mixture of 1-(tert-butoxycarbonyl)piperazine (Sg), 1-bromo-2-fluoroethane (5.11 g), potassium carbonate (9.26 g) and acetonitrile (60 ml) was stirred and heated to 60° C. for 4 hours. The reaction mixture was cooled to ambient temperature and filtered and the filtrate was evaporated. The residue was purified by column chomatography on silica using increasingly polar mixtures of isohexane and ethyl acetate as eluent. There was thus obtained 4-(tert-butoxycarbonyl)-1-(2-fluoroethyl)piperazine as a solid (3.7 g).

$^1$H NMR Spectrum: (DMSOd$_6$ and CD$_3$CO$_2$D) 1.37 (s, 9H), 2.34-2.4 (m, 4H), 2.56 (t, 1H), 2.67 (t, 1H), 3.25-3.34 (m, 4H), 4.42 (t, 1H), 4.58 (t, 1H)

Trifluoroacetic acid (20 ml) was added to a mixture of 4-(tert-butoxycarbonyl)-1-(2-fluoroethyl)piperazine (3.7 g), triethylsilane (8 ml) and methylene chloride (100 ml) and the resultant mixture was stirred at ambient temperature for 1.5 hours. The mixture was evaporated and the residue was triturated under diethyl ether. The solid so obtained was isolated, washed with diethyl ether and dried to give 1-(2-fluoroethyl)piperazine trifluoroacetic acid salt (6.0 g) as a solid.

$^1$H NMR Spectrum: (DMSOd$_6$ and CD$_3$CO$_2$D) 3.0-3.31 (m, 10H), 4.59 (m, 1H), 4.75 (m, 1H)

EXAMPLE 18

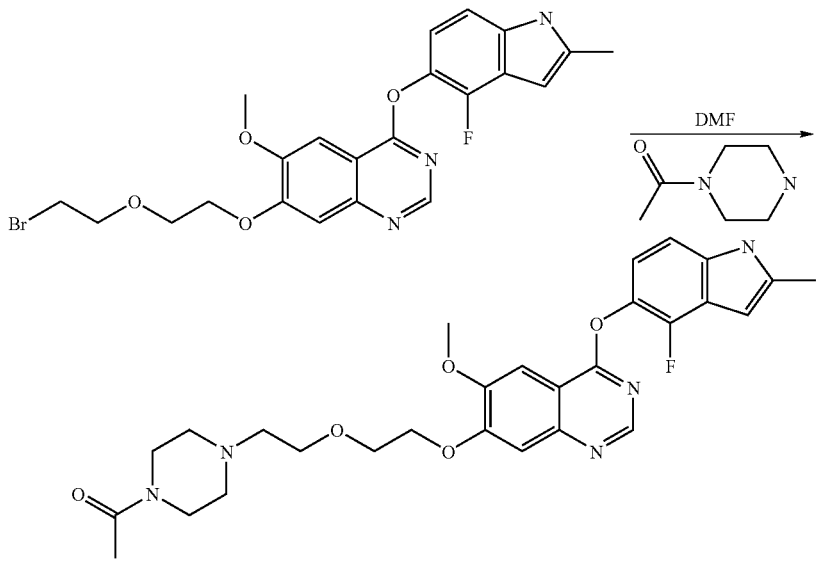

A mixture of 7-[2-(2-bromoethoxy)ethoxy]-6-methoxy-4-(4-fluoro-2-methylindol-5-yloxy)quinazoline (165 mg, 0.38 mmol) and 1-acetylpiperazine (129 mg, 1.01 mmol) in N,N-dimethylformamide (4 ml) was stirred overnight at ambient temperature. The mixture was diluted with ethyl acetate, washed with brine (×2), dried (MgSO$_4$) and concentrated under reduced pressure. Column chromatography of the residue, eluting with 5% 7N ammonia in methanol/methylene chloride gave 7-{2-[2-(4-acetylpiperazin-1-yl)ethoxy]ethoxy}-4-[(4-fluoro-2-methyl-1H-indol-5-yl)oxy]-6-methoxyquinazohine (130 mg, 72%).

MS-ESI: 538.6 [MH]$^+$ $^1$H NMR Spectrum: (DMSOd$_6$) 1.94 (s, 3H); 2.38 (m, 7H); 3.37 (m, 4H); 3.63 (t, 2H); 3.82 (br t, 2H); 3.98 (s, 3H); 4.33 (br t; 2H); 6.22 (s, 1H); 6.97 (t, 1H); 7.14 (d, 1H); 7.41 (s, 1H); 7.60 (s, 1H); 8.48 (s, 1H); 11.29 (brs, 1H)

The starting material was prepared as follows:

Using an analogous procedure to that described for the preparation of the starting material in Example 11, 2-(2-bromoethoxy)ethanol, (600 mg, 3.54 mmol) (J. Org. Chem., 7697, 58, 1993), was reacted with 4-[(4-fluoro-2-methyl-1H-indol-5-yl)oxy]-7-hydroxy-6-methoxyquinazoline (1.0 g, 2.95 mmol), (prepared as described for the starting material in Example 7). The crude product was purified by column chromatography, eluting with methanol/methylene chloride (1/98 followed by 2/98) to give the expected product contaminated by triphenylphosphine oxide. This was crystalised from methanol to give 7-[2-(2-bromoethoxy)ethoxy]-6-methoxy-4-(4-fluoro-2-methylindol-5-yloxy)quinazoline (675 mg, 47%).

MS-ESI: 492.4 [MH]$^+$ $^1$H NMR Spectrum: (DMSOd$_6$) 2.40 (s, 3H); 3.63 (t, 2H); 3.85 (t, 2H); 3.90 (br t, 2H), 3.98 (s, 3H); 4.34 (br t, 2H); 6.22 (s, 1H); 6.97 (t, 1H); 7.14 (d, 1H); 7.41 (s, 1H); 7.60 (s, 1H); 8.48 (s, 1H); 11.29 (br s, 1H)

EXAMPLE 19

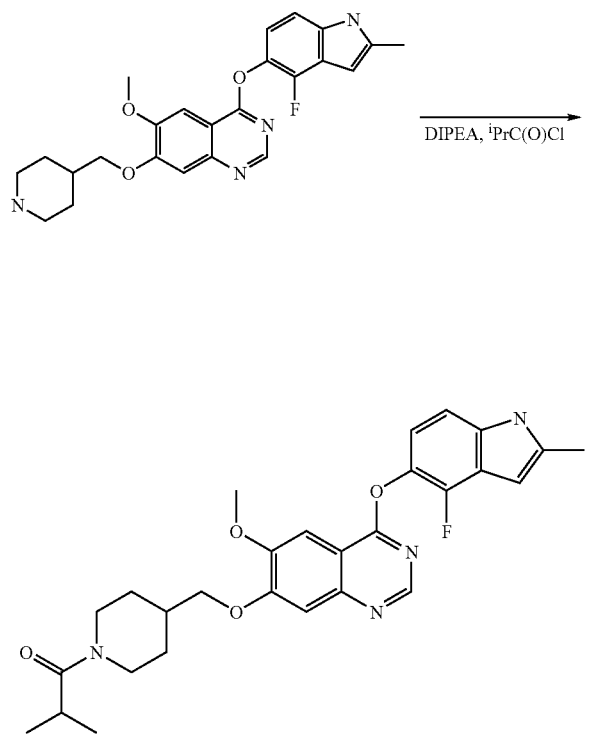

Diisopropylethylamine (72 μl, 0.41 mmol) and isobutyryl chloride (44 mg, 0.41 mmol), in methylene chloride (0.5 ml) were added to a suspension of 4-[(4-fluoro-2-methyl-1H-indol-5-yl)oxy]-6-methoxy-7-(piperidin-4-ylmethoxy) quinazoline (150 mg, 0.34 mmol), (prepared as described for the starting material in Example 11), in methylene chloride (4 ml). After a few minutes all the material had gone into solution. The mixture was stirred for 3 hours at ambient temperature, washed with saturated sodium hydrogen carbonate solution, dried (MgSO$_4$) and concentrated under reduced pressure. Column chromatography of the residue, eluting with 2% methanol/methylene chloride gave 4-[(4-fluoro-2-methyl-1H-indol-5-yl)oxy]-7-[(1-isobutyrylpiperidin-4-yl) methoxy]-6-methoxyquinazoline (90 mg, 52%).

MS-ESI: 507.5 [MH]$^+$ $^1$H NMR Spectrum: (DMSOd$_6$) 0.99 (d, 6H); 1.20 (m, 2H); 1.85 (br t, 2H); 2.13 (m, 1H); 2.40 (s, 3H); 2.58 (br t, 1H); 2.87 (m, 1H); 3.07 (br t, 1H); 3.98 (m, 4H); 4.08 (br d, 2H); 4.44 (br d, 1H); 6.22 (s, 1H); 6.96 (t, 1H); 7.14 (d, 1H); 7.37 (s, 1H); 7.58 (s, 1H); 8.48 (s, 1H); 11.29 (br s, 1H)

EXAMPLE 20

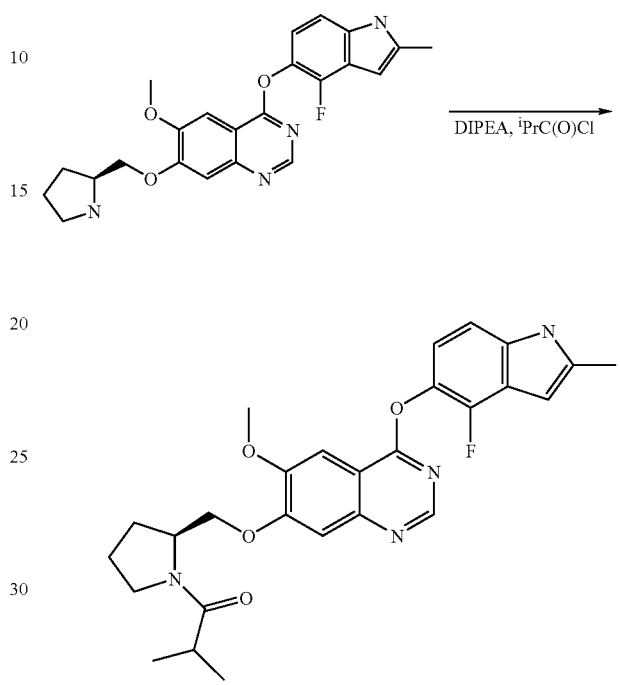

Using an analogous procedure to that described for the preparation of Example 19, 4-[(4-fluoro-2-methyl-1H-indol-5-yl)oxy]-6-methoxy-7-[(2S)-pyrrolidin-2-ylmethoxy] quinazoline (150 mg, 0.36 mmol), (prepared as described for the starting material in Example 12), was reacted with isobutyryl chloride (45 μl, 0.43 mmol). The product was purified by column chromatography, eluting with methanol/methylene chloride (2/98) to give 4-[(4-fluoro-2-methyl-1H-indol-5-yl)oxy]-7-{[(2S)-1-isobutyrylpyrrolidin-2-yl]methoxy}-6-methoxyquinazoline (95 mg, 54%).

MS-ESI: 493.2 [MH]$^+$ $^1$H NMR Spectrum: (100° C., DMSOd$_6$) 1.03 (m, 6H); 2.02 (m, 4H); 2.41 (s, 3H); 2.72 (m, 1H); 3.54 (m, 2H); 3.99 (s, 3H); 4.26 (m, 2H); 4.39 (m, 1H); 6.22 (s, 1H); 6.95 (t, 1H); 7.14 (d, 1H), 7.44 (s, 1H); 7.62 (s, 1H); 8.46 (s, 1H); 11.02 (br s, 1H)

EXAMPLE 21

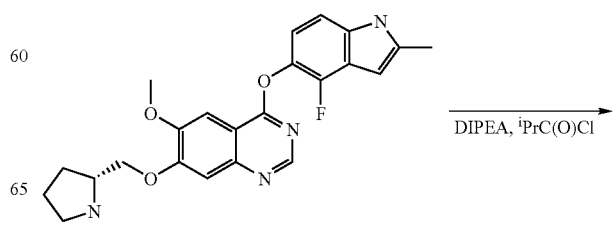

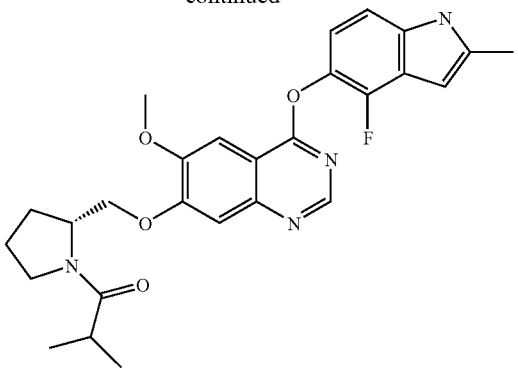

Using an analogous procedure to that described for the preparation of Example 19, 4-[(4-fluoro-2-methyl-1H-indol-5-yl)oxy]-6-methoxy-7-[(2R)-pyrrolidin-2-ylmethoxy]quinazoline (160 mg, 0.38 mmol), (prepared as described for the starting material in Example 13), was reacted with isobutyryl chloride (48 µl, 0.45 mmol). The product was purified by column chromatography, eluting with methanol/methylene chloride (2/98) to give 4-[(4-fluoro-2-methyl-1H-indol-5-yl)oxy]-7-([(2R)-1-isobutryipyrrofidin-2-yl]methoxy)-6-methoxyquinazoline (120 mg, 64%).

MS-ESI: 493.2 [MH]$^+$ $^1$H NMR Spectrum: (100° C., DMSOd$_6$) 1.03 (m, 6H); 2.02 (m, 4H); 2.41 (s, 3H); 2.72 (m, 1H); 3.54 (m, 2H); 3.99 (s, 3H); 4.26 (m, 2H); 4.39 (m, 1H); 6.22 (s, 1H); 6.95 (t, 1H); 7.14 (d, 1H), 7.44 (s, 1H); 7.62 (s, 1H); 8.46 (s, 1H); 11.02 (br s, 1H)

EXAMPLE 22

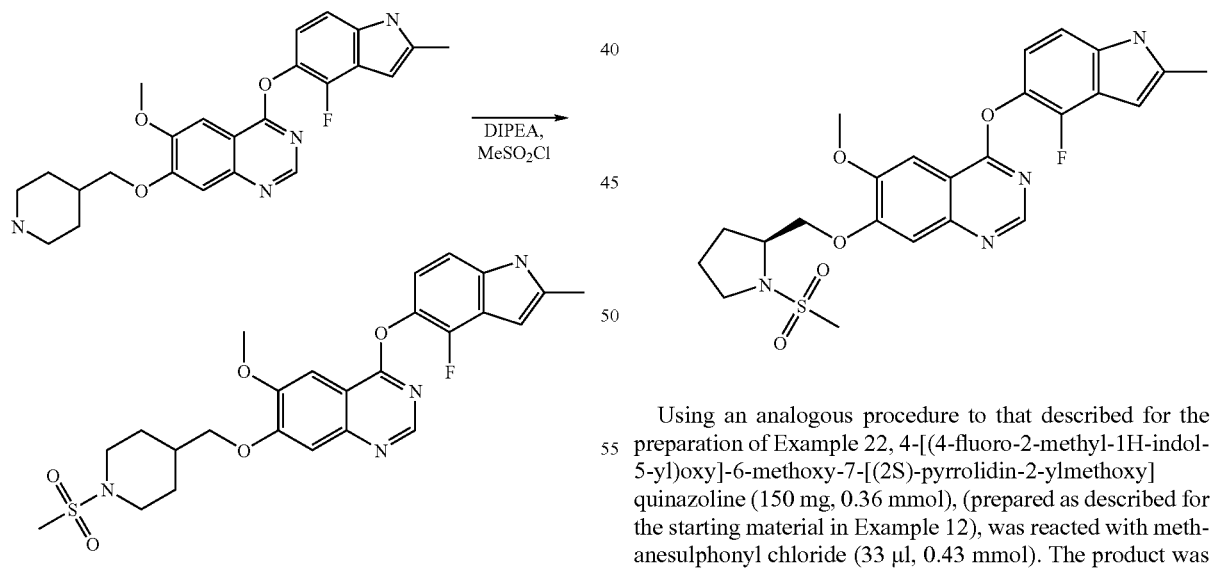

Diisopropylethylamine (72 µl, 0.41 mmol) and methanesulphonyl chloride (32 µl, 0.41 mmol) were added to a suspension of 4-[(4-fluoro-2-methyl-1H-indol-5-yl)oxy]-6-methoxy-7-(piperidin-4-ylmethoxy)quinazoline (150 mg, 0.34 mmol), (prepared as described for the starting material in Example 11), in methylene chloride (4 ml). After a few minutes all the material had gone into solution. The mixture was stirred for 3 hours at ambient temperature, washed with saturated sodium hydrogen carbonate solution, dried (MgSO$_4$) and concentrated under reduced pressure. The solid was suspended in methanol and filtered to give 4-[(4-fluoro-2-methyl-1H-indol-5-yl)oxy]-6-methoxy-7-{[1-(methylsulfonyl)piperidin-4-yl]methoxy}quinazoline (83 mg, 47%).

MS-ESI: 515.5 [MH]$^+$ $^1$H NMR Spectrum: (DMSOd$_6$) 1.41 (m, 2H); 1.95 (m, 3H); 2.40 (s, 3H); 2.77 (br t, 2H); 2.85 (s, 3H); 3.60 (br t, 2H); 3.98 (s, 3H); 4.12 (br d, 2H); 6.22 (s, 1H); 6.97 (t, 1H); 7.14 (d, 1H); 7.39 (s, 1H); 5.59 (s, 1H); 8.48 (s, 1H); 11.29 (br s, 1H)

EXAMPLE 23

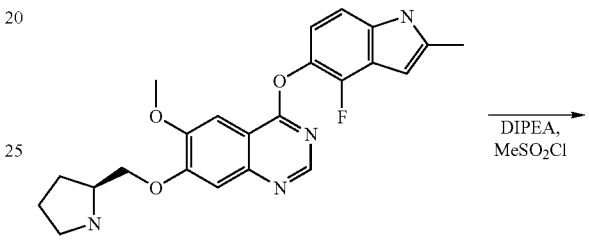

Using an analogous procedure to that described for the preparation of Example 22, 4-[(4-fluoro-2-methyl-1H-indol-5-yl)oxy]-6-methoxy-7-[(2S)-pyrrolidin-2-ylmethoxy]quinazoline (150 mg, 0.36 mmol), (prepared as described for the starting material in Example 12), was reacted with methanesulphonyl chloride (33 µl, 0.43 mmol). The product was purified by column chromatography, eluting with methanol/methylene chloride (2/98) to give 4-[(4-fluoro-2-methyl-1H-indol-5-yl)oxy]-6-methoxy-7-([(2S)-1-(methylsulfonyl)pyrrolidin-2-yl]methoxy)quinazoline (105 mg, 59%).

MS-ESI: 501.6 [MH]$^+$ $^1$H NMR Spectnim: (100° C., DMSOd$_6$) 2.02 (m, 4H); 2.41 (s, 3H); 3.38 (br t, 2H); 4.00 (s, 3H); 4.19 (m, 2H); 4.30 (dd, 1H); 6.22 (s, 1H); 6.96 (t, 1H); 7.14 (d, 1H); 7.40 (s, 1H); 7.64 (s, 1H); 8.47 (s, 1H); 11.02 (br s, 1H)

EXAMPLE 24

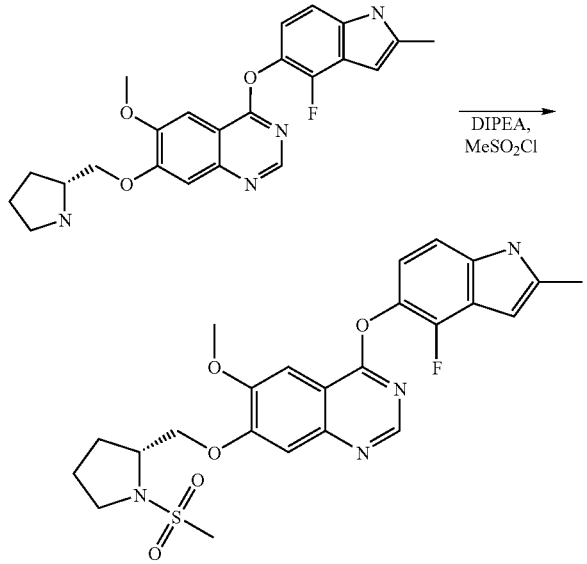

Using an analogous procedure to that described for the preparation of Example 22, 4-[(4-fluoro-2-methyl-1H-indol-5-yl)oxy]-6-methoxy-7-[(2R)-pyrrolidin-2-ylmethoxy]quinazoline (160 mg, 0.38 mmol), (prepared as described for the starting material in Example 13), was reacted with methanesulphonyl chloride (35 µl, 0.45 mmol). The product was purified by column chromatography, eluting with methanol/methylene chloride (2/98) to give 4-[(4-fluoro-2-methyl-1H-indol-5-yl)oxy]-6-methoxy-7-{[(2R)-1-(methylsulfonyl)pyrrolidin-2-yl]methoxy}quinazoline (108 mg, 57%).

MS-ESI: 501.6 [MH]+

$^1$H NMR Spectrum: (100° C., DMSOd$_6$) 2.02 (m, 4H); 2.41 (s, 3H); 3.38 (br t, 2H); 4.00 (s, 3H); 4.19 (m, 2H); 4.30 (dd, 1H); 6.22 (s, 1H); 6.96 (t, 1H); 7.14 (d, 1H); 7.40 (s, 1H); 7.64 (s, 1H); 8.47 (s, 1H); 11.02 (br s, 1H)

EXAMPLE 25

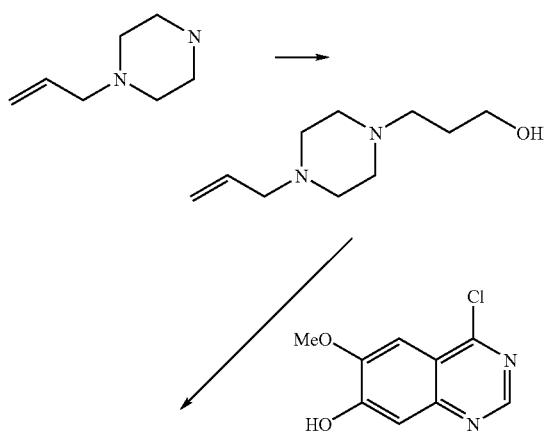

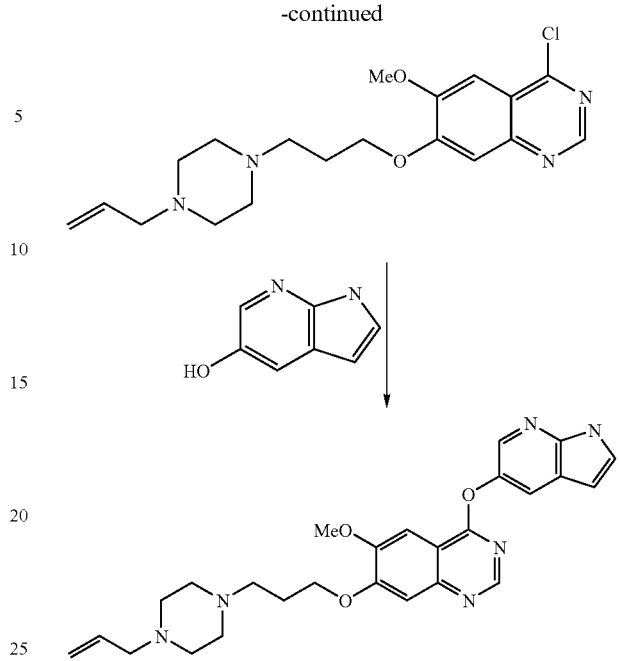

A mixture of 7-[3-(4-allylpiperazin-1-yl)propoxy]-4-chloro-6-methoxyquinazoline (288 mg, 0.76 mmol), 5-hydroxy-7-azaindole (113 mg, 0.84 mmol), (prepared as described for the starting material in Example 2), and potassium carbonate (116 mg, 0.84 mmol) in DMA (8 ml) was stirred at 85° C. for 3 hours and allowed to cool to ambient temperature. The mixture was filtered, the filtrate evaporated under vacuum and the residue purified by column chromatography eluting with methylene chloride/methanol (saturated with ammonia) (100/8/1). The volatiles were removed under vacuum to give a white solid which was triturated with diethyl ether, filtered and dried to give 7-[3-(4-allylpiperazin-1-yl)propoxy]-4-(7-azaindol-5-yloxy)-6-methoxyquinazoline (280 mg, 77%).

MS-ESI: 475 [MH]+

$^1$H NMR Spectrum: (CDCl$_3$) 2.14 (m, 2H); 2.53 (m, 8H); 2.59 (t, 2H), 3.03 (d, 2H); 4.07 (s, 3H); 4.29 (t, 2H); 5.20 (m, 2H); 5.89 (m, 1H); 6.55 (m, 1H); 7.35 (s, 1H); 7.40 (m, 1H); 7.61 (s, 1H); 7.86 (d, 1H); 8.30 (d, 1H); 8.60 (s, 1H); 9.68 (s, 1H).

The starting material was prepared as follows:

To a suspension of 4-chloro-7-hydroxy-6-methoxyquinazoline (300 mg, 1.43 mmol), (prepared as described for the starting material in Example 4), in methylene chloride (15 ml) was added triphenylphospbine (522 mg, 2.0 mmol), 3-(4-allylpiperazin-1-yl)propan-1-ol (288 mg, 1.57 mmol), (DE 2755707), and dusopropyl azodicarboxylate (336 µl, 1.71 mmol) and the mixture stirred at ambient temperature for 2 hours. The crude reaction mixture was loaded directly onto a silica chromatography column and eluted with methylene chloride/methanol (95/5). The volatile solvents were removed under vacuum to give 7-[3-(4-allylpiperazin-1-yl)propoxy]-4-chloro-6-methoxyquinazoline as an oil which crystallised on standing (480 mg, 89%).

MS-ESI: 377-379 [MH]+

$^1$H NMR Spectrum: (CDCl$_3$) 2.12 (m, 2H); 2.51 (m, 8H); 2.57 (t, 2H); 3.01 (d, 2H); 4.05 (s, 3H); 4.27 (t, 2H); 5.16 (m, 2H); 5.87 (m, 1H); 7.34 (s, 1H); 7.38 (s, 1H); 8.85 (s, 1H)

EXAMPLE 26

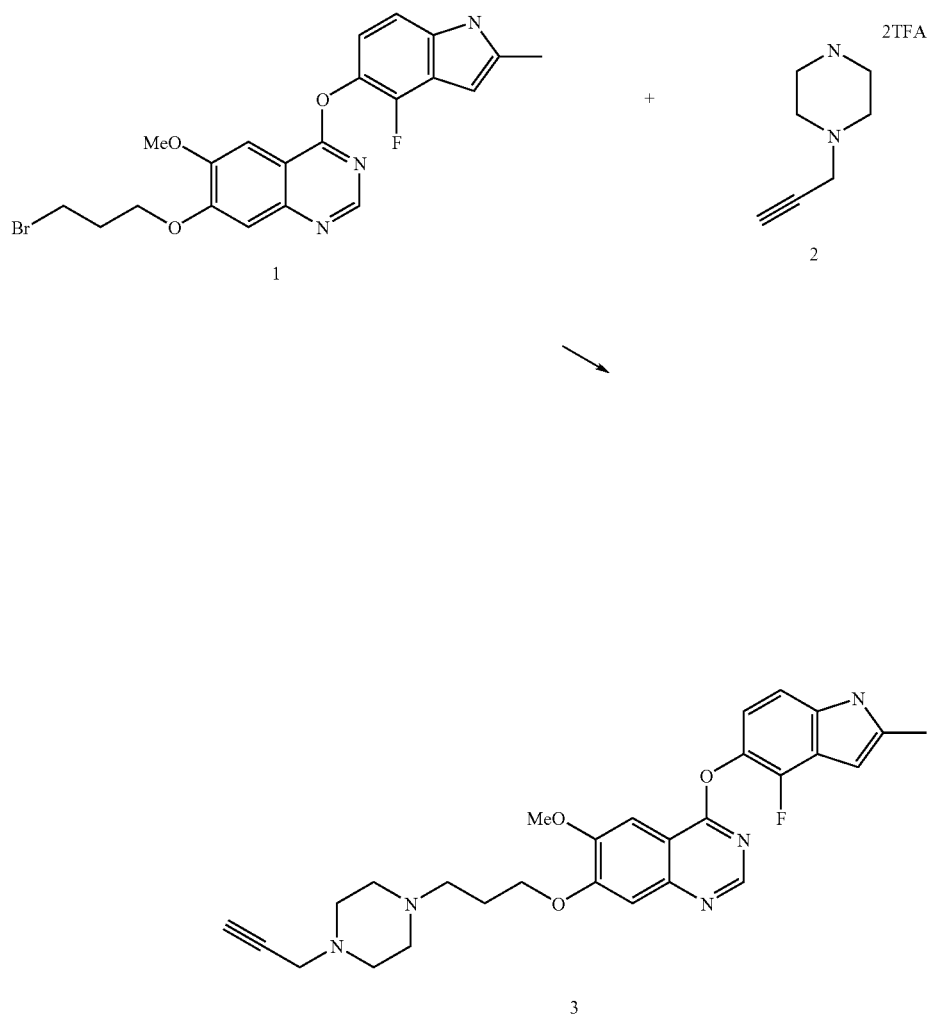

1-Prop-2-ynylpiperazine diTFA salt (329 mg, 0.94 mmol) and potassium carbonate (258 mg, 1.87 mmol) were added to a solution of 7-(3-bromopropoxy)-4-[(4-fluoro-2-methylindol-5-yl)oxy]-6-methoxyquinazoline (144 mg, 0.31 mmol), (prepared as described for the starting material in Example 7), in DMA (3.6 ml). The reaction mixture was stirred at 85° C. overnight before being filtered. The filtrate was concentrated under vacuum and the crude product was purified by column chromatography eluting with increasingly polar mixtures of ammonia/methanol in methylene chloride (1 to 7%). A second purification by column chromatography eluting with a mixture of methanol in methylene chloride (1/9) gave 4-[(4-fluoro-2-methylindol-5-yl)oxy]-6-methoxy-7-{3-[4-(2-propynyl)piperazin-1-yl]propoxy}quinazoline as a white solid (115 mg, 73%).

MS-ESI: 504 [MH]$^+$ $^1$H NMR Spectrum: (DMSOd$_6$) 1.96 (m, 2H); 2.39 (s, 3H); 2.42 (m, 2H); 2.45 (m, 4H); 3.09 (t, 1H); 3.22 (d, 2H); 3.28 (m, 4H); 3.97 (s, 3H); 4.22 (t, 2H); 6.22 (s, 1H); 6.96 (t, 1H); 7.14 (d, 1H); 7.36 (s, 1H); 7.58 (s, 1H); 8.47 (s, 1H); 11.29 (br s, 1H)

The starting material was prepared as follows:

Potassium carbonate (1.04 g, 7.5 mmol) and propargyl bromide (654 mg, 5.5 mmol) were added to a solution of tert-butyl-1-piperazinecarboxylate (931 mg, 5.0 mmol) in acetone (5 ml). The reaction mixture was heated at 60° C. for 1 hour, and then filtered to remove the inorganics. The solvent was removed under vacuum to give a crude product which was purified by column chromatography (10-30% ethyl acetate/hexane) yielding 4-propargylpiperazine-1-carboxylic acid tert-butyl ester (894 mg, 80%).

$^1$H NMR Spectrum: (CDCl$_3$) 1.46 (s, 9H); 2.25 (t, 1H); 2.51 (t, 4H); 3.31 (d, 2H); 3.47 (t, 4H)

Trifluoroacetic acid (5 ml, mmol) was added to a solution of 4-propargylpiperazine-1-carboxylic acid tert-butyl ester (559 mg, 2.5 mmol) in methylene chloride (2 ml). The reaction mixture was stirred at ambient temperature for 40 minutes before the solvent was removed under high vacuum. The residue was azeotroped with ethanol yielding 1-prop-2-yn-1-ylpiperazine di-trifluoroacetic salt (865 mg, 98%) as a white solid.

MS-EI125 [MH]$^+$ $^1$H NMR Spectrum: (DMSOd$_6$) 2.91 (t, 4H); 3.20 (t, 4H); 3.45 (t, 1H); 3.64 (d, 2H); 8.88 (br s, 1H)

EXAMPLE 27

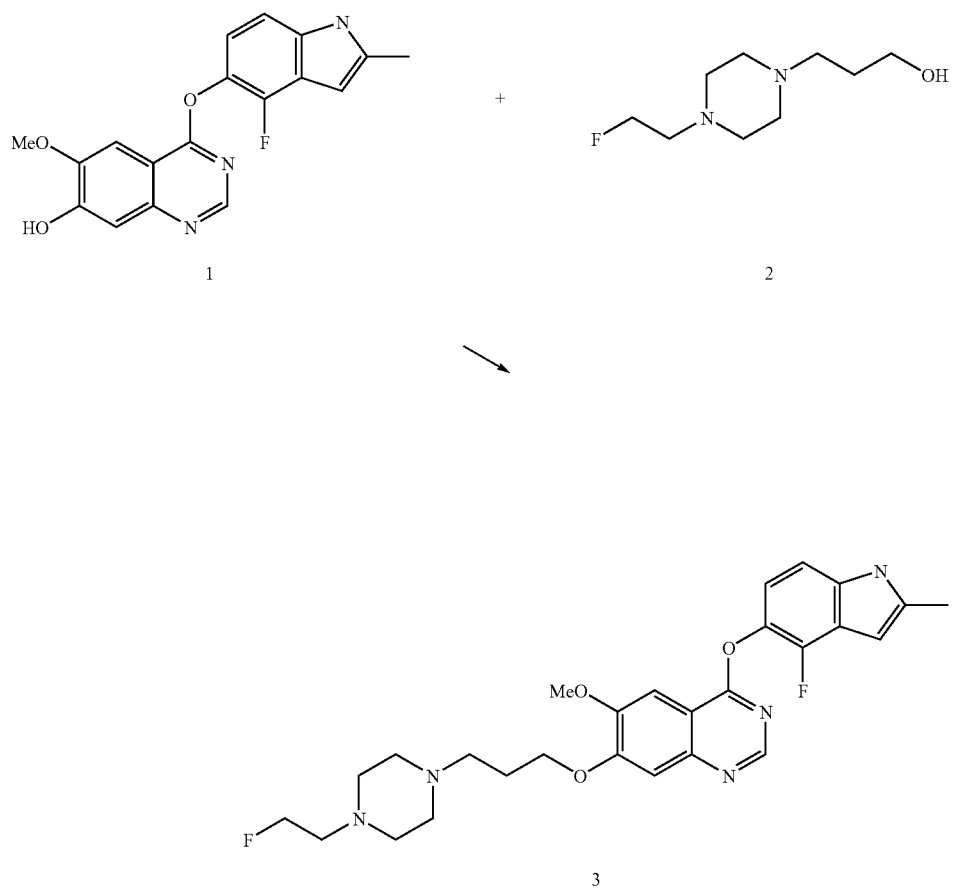

Diisopropyl azadicarboxylate (230 μl, 1.17 mmol) was added dropwise to a solution of 3-[4-(2-fluoroethyl)piperazin-1-yl]propan-1-ol (203 mg, 1.07 mmol), triphenylphosphine (357 mg, 1.36 mmol) and 4-[(4-fluoro-2-methyl-1H-indol-5-yl)oxy]-7-hydroxy-6-methoxyquinazoline (330 mg, 0.97 mmol), (prepared as described for the starting material in Example 7), in dichloromethane (8.5 ml). The reaction mixture was stirred at ambient temperature for 1.5 hours and then loaded directly onto a silica column, eluting with a mixture of methanol in methylene chloride (11/89) to give 7-{3-[4-(2-fluoroethyl)piperazin-1-yl]propoxy}-4-[(4-fluoro-2-methyl-1H-indol-5-yl)oxy]-6-methoxyquinazoline (413 mg, 83%) as a white solid.

MS-ESI: 512 [MH]$^+$ $^1$H NMR Spectrum: (DMSOd$_6$) 1.96 (m, 2H); 2.40 (s, 3H); 2.43 (m, 4H); 2.45 (m, 4H); 2.48 (m, 2H); 2.58 (dt, 2H); 3.97 (s, 3H); 4.23 (t, 2H); 4.50 (dt, 2H); 6.22 (s, 1H); 6.97 (t, 1H); 7.14 (d, 1H); 7.36 (s, 1H); 7.58 (s, 1H); 8.48 (s, 1H); 11.29 (br s, 1H)

The starting material was prepared as follows:

Potassium carbonate (1.85 g, 13.4 mmol) and 1-bromo-2-fluoroethane (440 Pl, 5.9 mmol) were added to a solution of tert-butyl-1-piperazinecarboxylate (1 g, 5.4 mmol) in acetonitrile (12 ml). The reaction mixture was stirred at 65° C. for 3.5 hours after which time more 1-bromo-2-fluoroethane (160 μl, 2.1 mmol) was added. The reaction was heated for a further 3 hours then filtered to remove the inorganic solids. The filtrate was concentrated and the crude product was purified using column chromatography eluting with ethyl acetate to give 4-(2-fluoroethyl)-piperazine-1-carboxylic acid tert-butyl ester (714 mg, 57%).

MS-ESI: 233 [MH]$^+$ $^1$H NMR Spectrum: (CDCl$_3$) 1.46 (s, 9H); 2.50 (t, 4H); 2.70 (dt, 2H); 3.45 (t, 4H); 4.57 (dt, 2H)

Trifluoroacetic acid (3 ml, 17.5 mmol) was added to a solution of 4-(2-fluoroethyl)-piperazine-1-carboxylic acid tert-butyl ester (350 mg, 1.5 mmol) in methylene chloride (12 ml). The reaction mixture was stirred at ambient temperature for 40 minutes, before the solvent was evaporated under high vacuum. The residue was azeotroped with toluene to give 1-(2-fluoroethyl)-piperazine diTFA salt (377 mg, 96%).

MS-EI: 133 [MH]$^+$ $^1$H NMR Spectrum: (DMSOd$_6$) 3.06 (s, 4H); 3.17 (m, 2H); 3.25 (m, 4H); 4.67 (dt, 2H); 9.03 (br s, 1H)

3-Bromopropan-1-ol (581 mg, 4.18 mmol) and potassium carbonate (2.88 g, 20.9 mmol) were added to a solution of 1-(2-fluoroethyl)-piperazine diTFA salt (1.5 g, 4.18 mmol) in acetonitrile (11 ml). The reaction mixture was stirred at 85° C. for 4 hours and then loaded directly onto a column and eluted with a mixture of methanol in methylene chloride (7/93) to give 3-[4-(2-fluoroethyl)piperazin-1-yl]propan-1-ol (721 mg, 91%).

MS-EI: 191 [MH]$^+$ $^1$H NMR Spectrum: (CDCl$_3$) 1.72 (m, 2H); 2.58 (m, 8H) 2.62 (m, 2H); 2.73 (t, 2H); 3.79 (t, 2H); 4.55 (dt, 2H)

EXAMPLE 28

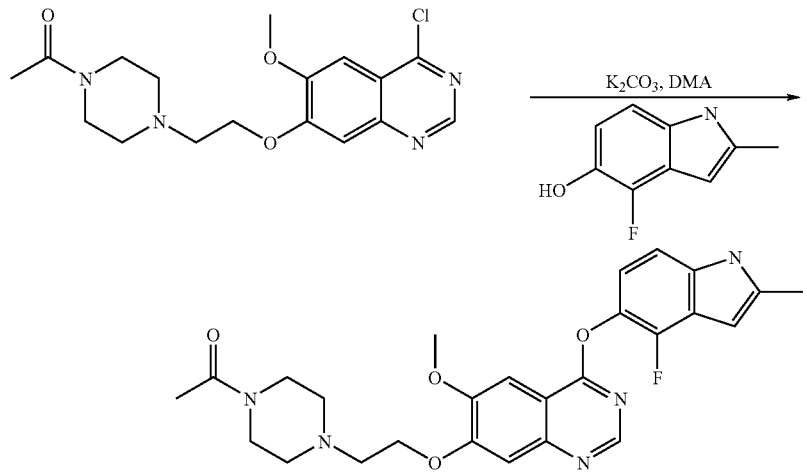

A mixture of 7-[2-(4-acetylpiperazin-1-yl)ethoxy]-4-chloro-6-methoxyquinazoline (12.24 g, 33.5 mmol), 4-fluoro-5-hydroxy-2-methylindole (5.54 g, 33.5 mmol), (prepared as described for the starting material in Example 1), and potassium carbonate (4.64 g, 33.5 mmol) was heated in N,N-dimethylacetamide (150 ml) at 85° C. for 4 hours. 4-Fluoro-5-hydroxy-2-methylindole (33 mg, 0.2 mmol) and potassium carbonate (108 mg, 57%) were added and the mixture heated for a further 1 hour at 85° C. and then stirred at ambient temperature overnight. The mixture was filtered and concentrated under reduced pressure. The residue was purified by column chromatography eluting with methylene chloride/methanol (95/5) to give a white solid which was suspended in acetone (150 ml) and heated at reflux for 1 hour. After cooling the mixture was filtered and the solid dried in air to give 7-[2-(4-acetylpiperazin-1-yl)ethoxy]-4-[(4-fluoro-2-methyl-1H-indol-5-yl)oxy]-6-methoxyquinazoline (10 g, 60%) as a white solid.

$^1$H NMR Spectrum: (DMSOd$_6$) 2.00 (s, 3H); 2.42 (s, 3H); 2.52 (t, 2H); 2.56 (br t, 2H); 2.85 (t, 2H); 3.45 (m, 4H); 4.00 (s, 3H); 4.35 (t, 2H); 6.25 (s, 1H), 6.99 (t, 1H); 7.17 (d, 1H); 7.45 (s, 1H); 7.62 (s, 1H); 8.51 (s, 1H); 11.32 (br s, 1H)

MS-ESI: 494.3 [M+H]$^+$

The starting material was prepared as follows:

A suspension of 4-chloro-7-hydroxy-6-methoxyquinazoline (222 mg, 1.05 mmol), (prepared as described for the starting material in Example 4), in methylene chloride (12 ml) was treated with triphenylphosphine (389 mg, 1.48 mmol), 2-(4-acetylpiperazin-1-yl)ethanol (200 mg, 1.16 mmol) and diisopropyl azodicarboxylate (255 mg, 1.26 mmol) and the mixture stirred at ambient temperature for 2.5 hours. The crude reaction mixture was loaded onto a silica column and eluted using methylene chloride/methanol (saturated with ammonia) (92/8). The relevant fractions were combined and evaporated under vacuum to give a residue, which was triturated with acetone, filtered and dried. This gave 7-[2-(4-acetylpiperazin-1-yl)ethoxy]-4-chloro-6-methoxyquinazoline as a white solid (240 mg, 62%).

$^1$H NMR Spectrum: (DMSOd$_6$) 1.97 (s, 3H), 2.50 (m, 4H), 2.82 (t, 2H), 3.41 (m, 4H), 3.98 (s, 3H), 4.32 (t, 2H), 7.38 (s, 1H), 7.48 (s, 1H), 8.85 (s, 1H)

MS-ESI: 365 (MH)+

Alternatively 7-[2-(4-acetylpiperazin-1-yl)ethoxy]-4-[(4-fluoro-2-methyl-1H-indol-5-yl)oxy]-6-methoxyquinazoline may be prepared as follows:

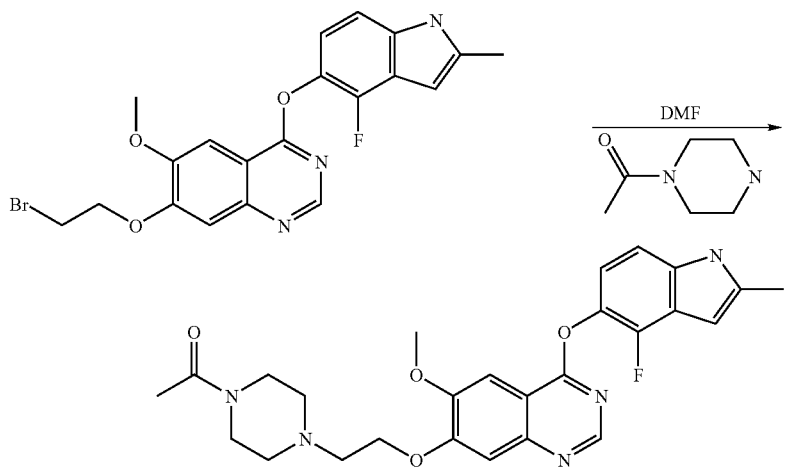

A mixture of 7-(2-bromoethoxy)-4-[(4-fluoro-2-methyl-1H-indol-5-yl)oxy]-6-methoxyquinazoline (310 mg of a sample containing triphenylphosphine oxide (approx. 12% w/w), 0.61 mmol) and 1-acetylpiperazine (258 mg, 2.02 mmol) in N,N-dimethylformamide (5 ml) was stirred at ambient temperature overnight and then concentrated under reduced pressure. The residue was purified by column chromatography eluting with methylene chloride/methanol (95/5) to give 7-[2-(4-acetylpiperazin-1-yl)ethoxy]-4-[(4-fluoro-2-methyl-1H-indol-5-yl)oxy]-6-methoxyquinazoline (202 mg, 67%) as a white solid.

MS and NMR details are given hereinbefore.

The starting material was prepared as follows:

A suspension of 4-[(4-fluoro-2-methyl-1H-indol-5-yl)oxy]-7-hydroxy-6-methoxyquinazoline (530 mg, 1.56 mmol), (prepared as described for the starting material in Example 7), in methylene chloride (15 ml) was treated with triphenylphosphine (570 mg, 2.18 mmol), 2-bromoethanol (300 mg, 2.40 mmol) and diisopropyl azodicarboxylate (380 mg, 1.88 mmol) and the mixture stirred at ambient temperature for 2 hours. The crude reaction mixture was loaded onto a silica column and eluted using ethyl acetate as solvent. The relevant fractions were combined and evaporated under vacuum to give a residue, which was triturated with ether, filtered and dried. This gave 7-(2-bromoethoxy)-4-[(4-fluoro-2-methyl-1H-indol-5-yl)oxy]-6-methoxyquinazoline as a white solid (546 mg, 78%).

$^1$H NMR Spectrum: (DMSOd$_6$) 2.40 (s, 3H), 3.90 (t, 2H), 3.99 (s, 3H), 4.56 (t, 2H), 6.21 (s, 1H), 6.97 (t, 1H), 7.16 (d, 1H), 7.42 (s, 1H), 7.62 (s, 1H), 8.49 (s, 1H), 11.29 (s, 1H)

MS (ESI): 446 and 448 (MH)$^+$

Alternatively 7-[2-(4-acetylpiperazin-1-yl)ethoxy]-4-[(4-fluoro-2-methyl-1H-indol-5-yl)oxy]-6-methoxyquinazoline may be prepared as follows:

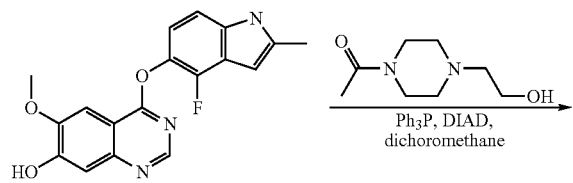

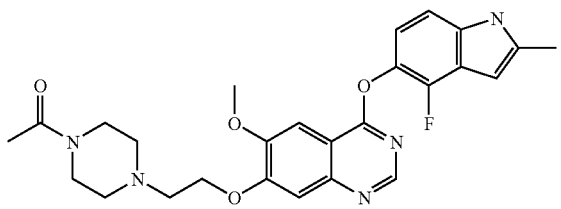

4-[(4-Fluoro-2-methyl-1H-indol-5-yl)oxy]-7-hydroxy-6-methoxyquinazoline (300 mg, 0.88 mmol), (prepared as described for the starting material in Example 7), 2-(4-acetylpiperazin-1-yl)ethanol (183 mg, 1.06 mmol) and triphenylphosphine (278 mg, 1.06 mmol) were stirred together in dichloromethane (10 ml) and the mixture cooled in an ice/water bath. Diisopropyl azodicarboxylate (2091, 1.06 mmol) was added and the mixture stirred for 1.5 hours. A further one mole equivalent of 2-(4-acetylpiperazin-1-yl)ethanol (172 mg, 1 mmol), triphenylphosphine (262 mg, 1 mmol) and diisopropyl azodicarboxylate (197 µl, 1 mmol) were added and the mixture stirred for a further 1 hour. The volatiles were removed under vacuum and the residue was purified by column chromatography eluting with methylene chloride/methanol (95/5) to give a crude solid that was further purified by preparative HPLC to give 7-[2-(4-acetylpiperazin-1-yl)ethoxy]-4-[(4-fluoro-2-methyl-1H-indol-5-yl)oxy]-6-methoxyquinazoline (75 mg, 17%).

MS and NMR details are given hereinbefore.

The starting material was prepared as follows:

A mixture of 1-acetylpiperazine (2.5 g, 19.5 mmol), 2-bromoethanol (1.38 ml, 19.5 mmol) and potassium carbonate (6.7 g, 48.8 mmol) in acetonitrile (30 ml) was heated at reflux for 3 hours. The mixture was cooled, filtered and concentrated under reduced pressure. The residue was purified by column chromatography eluting with methylene chloride/methanol (9/1) to give 2-(4-acetylpiperazin-1-yl)ethanol (1.89 g, 56%) as a colourless oil.

$^1$H NMR Spectrum: (CDCl$_3$) 2.09 (s, 3H); 2.50 (m, 4H); 2.57 (t, 2H); 3.48 (t, 2H); 3.63 (m, 4H)

Alternatively 7-[2-(4-acetylpiperazin-1-yl)ethoxy]-4-[(4-fluoro-2-methyl-1H-indol-5-yl)oxy]-6-methoxyquinazoline may be prepared as follows:

A mixture of 4-[(4-fluoro-2-methyl-1H-indol-5-yl)oxy]-7-hydroxy-6-methoxyquinazoline (250 mg, 0.74 mmol), 1-acetyl-4-(2-chloroethyl)piperazine (144 mg, 0.81 mmol) and potassium carbonate (12 mg, 0.81 mmol) in N-methylpyrrolidinone (6 ml) was heated at 90° C. for 2 hours. The mixture was cooled and water added. After 30 minutes the solid was filtered off and dried under vacuum. The residue was purified by column chromatography eluting with methylene chloride/methanol (saturated with ammonia) (96/4) to give 7-[2-(4-acetylpiperazin-1-yl)ethoxy]-4-[(4-fluoro-2-methyl-1H-indol-5-yl)oxy]-6-methoxyquinazoline (310 mg, 58%) as a white solid.

MS and NMR details are given hereinbefore.

The starting material was prepared as follows:

2-(4-Acetylpiperazin-1-yl)ethanol (500 mg, 2.90 mmol), (prepared as described for the starting material in this example hereinbefore), was dissolved in methylene chloride (10 ml) and triethylamine (445 µl, 3.19 mmol) and 4-toluenesulphonyl chloride (609 mg, 3.19 mmol) were added and the mixture was stirred at ambient temperature overnight. The mixture was washed with brine, dried (MgSO$_4$) and concentrated under reduced pressure. The residue was purified by column chromatography eluting with methylene chloride/methanol (98/2) to give 1-acetyl-4-(2-chloroethyl)piperazine (300 mg, 54%) as an oil.

$^1$H NMR Spectrum: (CDCl$_3$) 2.08 (s, 3H); 2.48 (br t, 2H); 2.52 (br t, 2H); 2.75 (t, 2H); 3.48 (br t, 2H); 3.59 (t, 2H); 3.63 (br t, 2H)

EXAMPLE 29

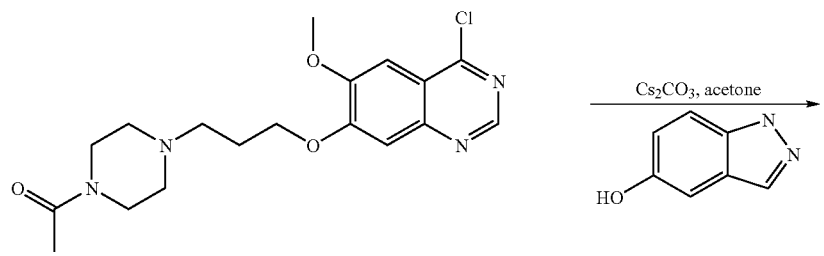

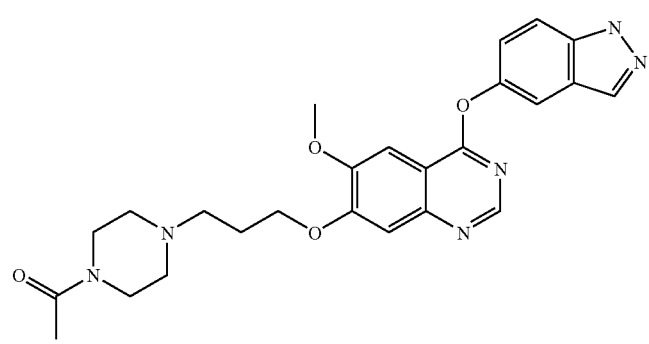

A mixture of 7-[3-(4-acetylpiperazin-1-yl)propoxy]-4-chloro-6-methoxyquinazoline (235 mg, 0.62 mmol), (prepared as described for the starting material in Example 7), 5-hydroxyindazole (100 mg, 0.75 mmol) and cesium carbonate (303 mg, 0.93 mmol) in acetone (15 ml) was heated at reflux for 1.25 hours. The mixture was cooled, filtered and the filtrate concentrated under reduced pressure. The residue was purified by column chromatography eluting with methylene chloride/methanol (saturated with ammonia) (96/4). The residue was further purified by preparative HPLC to give 7-[3-(4-acetylpiperazin-1-yl)propoxy]-4-(1H-indazol-5-yloxy)-6-methoxyquinazoline (127 mg, 43%) as a white foam.

$^1$H NMR Spectrum: (DMSOd$_6$) 1.98 (m, 5H); 2.33 (m, 2H); 2.39 (m, 2H); 2.48 (t, 2H); 3.42 (m, 4H); 3.97 (s, 3H); 4.24 (t, 2H); 7.26 (dd, 1H); 7.36 (s, 1H); 7.60 (m, 2H); 7.65 (d, 1H); 8.07 (s, 1H); 8.48 (s, 1H); 13.15 (br s, 1H)

MS-ESI: 477.6 [M+H]$^+$

The starting material was prepared as follows:

5-Methoxyindazole (1.7 g, 11.5 mmol), (Tetrahedron, 1994, 50, 3529), was dissolved in methylene chloride (35 ml) and cooled in an ice/water bath. Boron tribromide (57.4 ml of a 1M solution in methylene chloride, 57.4 mmol) was added over 10 minutes and then the mixture allowed to warm to ambient temperature. The mixture was stirred for 2 hours and then re-cooled in an ice/water bath. 2N Sodium hydroxide was slowly added until pH8. The precipitated solid was filtered off and dried under vacuum at 60° C. overnight. The residue was purified by column chromatography eluting with methylene chloride/methanol (95/5) to give 5-hydroxyindazole (11.0 g, 65%) as a brown solid.

$^1$H NMR Spectrum: (DMSOd$_6$) 6.87 (dd, 1H); 6.95 (d, 1H); 7.32 (d, 1H); 7.81 (s, 1H); 8.99 (s, 1H); 12.69 (s, 1H)

MS-ESI: 135 [M+H]$^+$

EXAMPLE 30

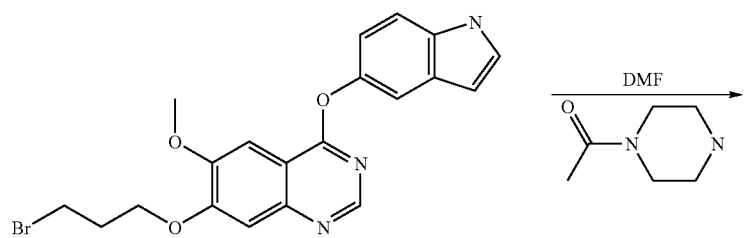

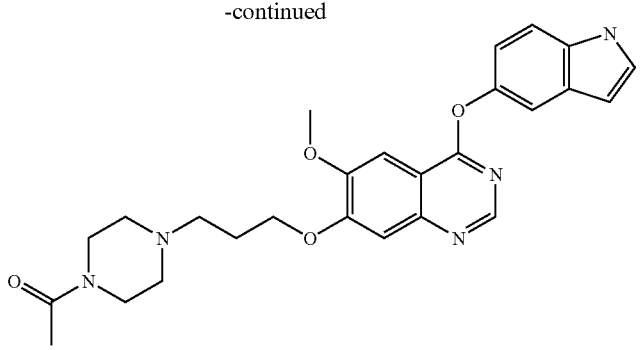

A mixture of 7-(3-bromopropoxy)-4-(1H-indol-5-yloxy)-6-methoxyquinazoline (200 mg, 0.47 mmol), (WO 00/47212 A1, Example 314), and 1-acetylpiperazine (180 mg, 1.40 mmol) in N,N-dimethylformamide (4 ml) was stirred at ambient temperature for 3 hours. The mixture was diluted with ethyl acetate and washed with brine (×2), dried (MgSO$_4$) and concentrated under reduced pressure. Column chromatography of the residue (5% methanol/dichloromethane) gave 7-[3-(4-acetylpiperazin-1-yl)propoxy]-4-(1H-indol-5-yloxy)-6-methoxyquinazoline (109 mg, 49%) as a white solid.

$^1$H NMR Spectrum: (DMSOd$_6$) 1.97 (m, 5H); 2.32 (m, 2H); 2.39 (m, 2H); 2.48 (t, 2H); 3.42 (m, 4H); 3.97 (s, 3H); 4.24 (t, 2H); 6.43 (s, 1H); 6.96 (dd, 1H); 7.35 (s, 1H); 7.42 (m, 3H); 7.58 (s, 1H); 8.46 (s, 1H); 11.17 (br s, 1H)

MS-ESI: 476.6 [MH]$^+$

EXAMPLE 31

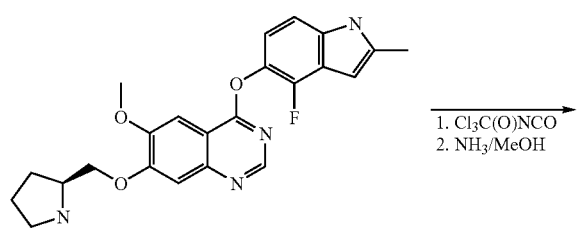 1. Cl$_3$C(O)NCO
2. NH$_3$/MeOH

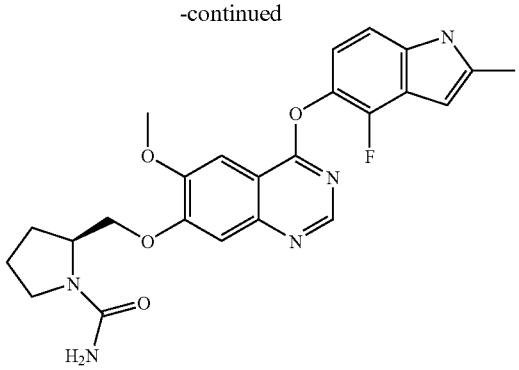

4-[(4-Fluoro-2-methyl-1H-indol-5-yl)oxy]-6-methoxy-7-[(2S)-pyrrolidin-2-ylmethoxy]quinazoline (60 mg, 0.14 mmol), (prepared as described for the starting material in Example 12), was dissolved in pyridine (3 ml) and cooled to 0° C. Trichloroacetyl isocyanate (17 μl, 0.14 mmol) was added and the mixture stirred for 2 hours. The solvent was removed under reduced pressure and the residue dissolved in 7N ammonia in methanol and stirred at ambient temperature overnight and then at 50° C. for 2 hours. The solvent was removed under reduced pressure. Column chromatography of the residue (2% to 5% methanol/dichloromethane) gave 7-[(2S)-1-carbamoylpyrrolidin-2-ylmethoxy]-4-[(4-fluoro-2-methyl-1H-indol-5-yl)oxy]-6-methoxyquinazoline (40 mg, 69%) as a yellow solid.

$^1$H NMR Spectrum: (DMSOd$_6$) 1.80-2.50 (m, 4H); 2.40 (s, 3H); 3.25 (m, 2H); 3.99 (s, 3H); 4.17 (m, 3H); 5.85 (s, 2H); 6.22 (s, 1H); 6.97 (t, 1H); 7.14 (d, 1H); 7.44 (s, 1H); 7.59 (s, 1H); 8.47 (s, 1H); 11.29 (br s, 1H)

MS-ESI: 466.5 [MH]$^+$

EXAMPLE 32

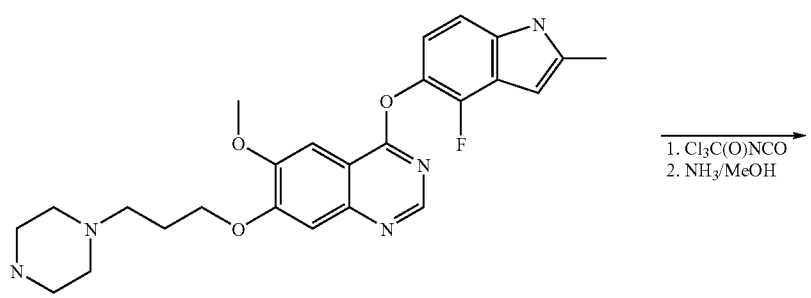 1. Cl$_3$C(O)NCO
2. NH$_3$/MeOH

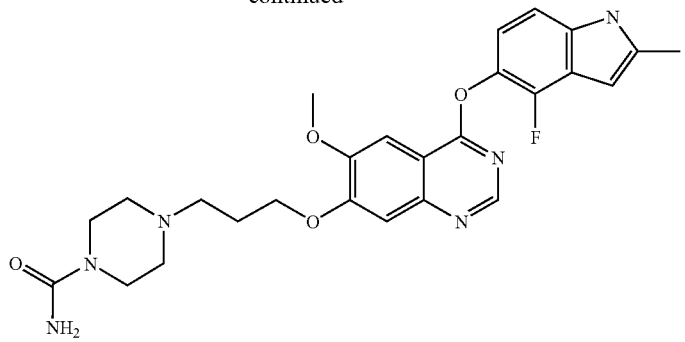

4-[(4-Fluoro-2-methyl-1H-indol-5-yl)oxy]-6-methoxy-7-(3-piperazin-1-ylpropoxy)quinazoline (240 mg, 0.52 mmol), (prepared as described for the starting material in Example 15), was dissolved in pyridine (5 ml) and cooled to 0° C. Trichloroacetyl isocyanate (61 μl, 0.52 mmol) was added and the mixture stirred at ambient temperature for 1 hour. The mixture was concentrated under reduced pressure and the residue dissolved in 7N ammonia in methanol and stirred at 45° C. for 2.5 hours. Aqueous ammonia (1 ml) was added and the mixture was stirred at 60° C. for 1.5 hours and then at ambient temperature overnight. The solvent was removed under reduced pressure. Column chromatography of the residue using methylne chloride/methanol (90/10) followed by methylene chloride/methanol (saturated with ammonia) (90/10) gave a solid which was suspended in methanol and filtered to give 7-(3-[4-carbamoylpiperazin-1-yl]propoxy)-4-[(4-fluoro-2-methyl-1H-indol-5-yl)oxy]-6-methoxyquinazoline (120 mg, 46%) as a pale yellow solid.

$^1$H NMR Spectrum: (DMSOd$_6$) 1.98 (m, 2H); 2.32 (m, 4H); 2.40 (s, 3H); 2.48 (t, 2H); 3.28 (m, 4H); 3.97 (s, 3H); 4.24 (t, 2H); 5.88 (s, 2H); 6.22 (s, 1H); 6.97 (t, 1H); 7.14 (d, 1H); 7.37 (s, 1H); 7.58 (s, 1H); 8.48 (s, 1H); 11.29 (br s, 1H)

MS-ESI: 509.6 [MH]$^+$

EXAMPLE 33

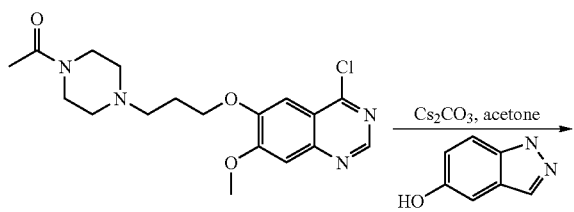

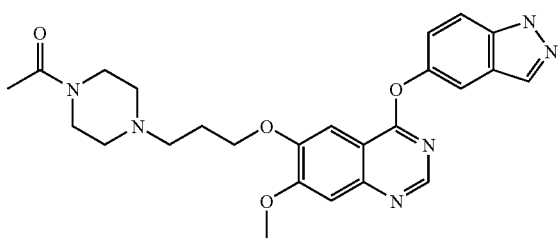

A mixture of 6-[3-(4-acetylpiperazin-1-yl)propoxy]-4-chloro-7-methoxyquinazoline (235 mg, 0.62 mmol), 5-hydroxyindazole (100 mg, 0.75 mmol), (prepared as described for the starting material in Example 29), and cesium carbonate (303 mg, 0.93 mmol) in acetone (20 ml) was heated at reflux for 2 hours. The mixture was filtered and the filtrate concentrated under reduced pressure. The residue was purified by column chromatography eluting with methylene chloride/methanol (95/5) to give 6-[3-(4-acetylpiperazin-1-yl)propoxy]-4-(1H-indazol-5-yloxy)-7-methoxyquinazoline (200 mg, 68%) as a pale green solid.

$^1$H NMR Spectrum: (DMSOd$_6$) 1.95 (s, 3H); 2.00 (m, 2H); 2.34 (br t, 2H); 2.41 (br t, 2H); 2.4 (t, 2H); 2.5 (m, 2H); 3.42 (m, 4H); 4.01 (s, 3H); 4.25 (t, 2H); 7.29 (dd, 1H); 7.39 (s, 1H); 7.63 (m, 2H); 7.68 (d, 1H); 8.09 (s, 1H); 8.51 (s, 1H); 13.18 (br s, 1H)

MS-ESI: 477.6 [MH]$^+$

The starting material was prepared as follows:

6-Acetoxy-4-chloro-7-methoxyquinazoline (10.0 g, 39.6 mmol), (WO 01/04102, Table VI examples), was added in portions to a stirred 7N methanolic ammonia solution (220 ml) and the mixture cooled to 10° C. in an ice/water bath. Initially the solid dissolved to give a yellow solution which then deposited a yellow precipitate. After stirring for one hour the precipitate was filtered off, washed with diethyl ether and dried thoroughly under high vacuum to give 4-chloro-6-hydroxy-7-methoxyquinazoline (5.65 g, 67.8%).

$^1$H NMR Spectrum: (DMSOd$_6$) 3.96 (s, 3H); 7.25 (s, 1H); 7.31 (s, 1H); 8.68 (s, 1H)

MS-ESI: 211 [M+H]$^+$

Diethyl azodicarboxylate (991 mg, 5.7 mmol) was added dropwise to a solution of 4-chloro-6-hydroxy-7-methoxyquinazoline (1 g, 4.75 mmol), 3-(4-acetylpiperazin-1-yl) propan-1-ol (972 mg, 5.22 mmol), (prepared as described for the starting material in Example 1 or Example 7), and triphenylphosphine (1.74 g, 6.65 mmol) in methylene chloride (25 ml). The mixture was stirred at ambient temperature for 2 hours. The solution was poured onto silica and eluted with methylene chloride, followed by methylene chloride/methanol (97/3 followed by 92/8). The fractions containing the expected product were combined and evaporated to give 6-[3-(4-acetylpiperazin-1-yl)propoxy]-4-chloro-7-methoxyquinazoline (1.3 g, 72%).

NMR Spectrum: (DMSOd$_6$) 2.0 (s, 3H), 2.05 (m, 2H), 2.35 (m, 2H), 2.4 (m, 2H), 2.5 (m, 2H), 2.45 (m, 4H), 4.02 (s, 3H), 4.2 (m, 2H), 7.4 (s, 1H), 7.5 (s, 1H), 8.9 (s, 1H)

MS-ESI: 379 [M+H]+

EXAMPLE 34

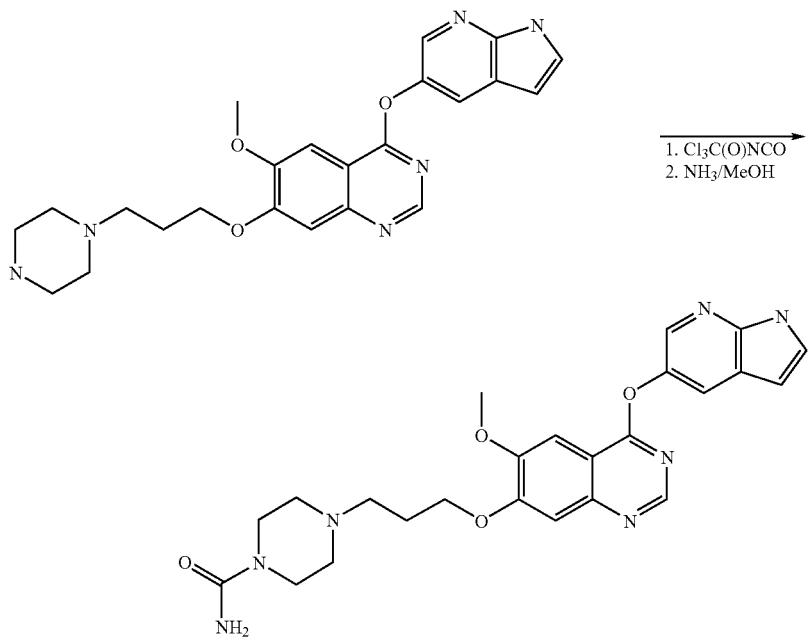

4-(7-Azaindol-5-yloxy)-6-methoxy-7-(3-piperazin-1-yl-propoxy)quinazoline (200 mg, 0.46 mmol) was dissolved in pyridine (5 ml) and cooled to 0° C. Trichloroacetyl isocyanate (55 µl, 0.46 mmol) was added and the mixture stirred at ambient temperature for 3 hours. The mixture was concentrated under reduced pressure and the residue dissolved in 7N ammonia in methanol and stirred at ambient temperature for 20 hours. The solvent was removed under reduced pressure and the residue was purified by column chromatography eluting with methylene chloride/methanol (90/10) to give 4-(7-azaindol-5-yloxy)-6-methoxy-7-[3-(4-carbamoylpiperazin-1-yl)propoxy]quinazoline (95 mg, 43%) as a white solid.

$^1$H NMR Spectrum: (DMSOd$_6$) 2.01 (m, 2H); 2.35 (br t, 4H); 2.48 (t, 2H); 3.3 (m, 4H); 4.01 (s, 3H); 4.27 (t, 2H); 5.91 (s, 2H); 6.50 (dd, 1H); 7.40 (s, 1H); 7.57 (t, 1H); 7.64 (s, 1H); 7.93 (d, 1H); 8.20 (d, 1H); 8.51 (s, 1H); 11.78 (br s, 1H)

MS-ESI: 478.6 [MH]$^+$

The starting material was prepared as follows 4-Chloro-7-hydroxy-6-methoxyquinazoline (1.7 g, 0.08 mmol), (prepared as described for the starting material in Example 4), tert-butyl 4-(3-hydroxypropyl)piperazine-1-carboxylate (20.17 g, 8.89 mmol), (prepared as described for the starting material in Example 15), and triphenylphosphine (2.97 g, 11.3 mmol) were added to dichloromethane (42.5 ml). Diisopropyl azodicarboxylate (1.91 ml, 9.70 mmol) was added and the reaction mixture stirred at ambient temperature for 1.5 hours and then concentrated under reduced pressure. The residue was purified by column chromatography eluting with methylene chloride/methanol (95/5 followed by 92/8) to give the product containing a single impurity. A second column chromatography eluting with methylene chloride/methanol (saturated with ammonia) (96/4) gave tert-butyl 4-{3-[(4-chloro-6-methoxyquinazolin-7-yl)oxy]propyl}piperazine-1-carboxylate (3.0 g, 99%) as a white solid.

$^1$H NMR Spectrum: (CDCl$_3$) 1.46 (s, 9H); 2.12 (m, 2H); 2.42 (t, 4H); 2.57 (t, 2H); 3.44 (t, 4H); 4.05 (s, 3H); 4.29 (t, 2H); 7.35 (s, 1H); 7.38 (s, 1H); 8.85 (s, 1H)

MS-ESI: 437.1, 439.0 [MH]$^+$ tert-Butyl 4-{3-[(4-chloro-6-methoxyquinazolin-7-yl)oxy]propyl}piperazine-1-carboxylate (2.0 g, 4.42 mmol) was dissolved in N,N-dimethylacetamide (60 ml) and 5-hydroxy-7-azaindole (651 mg, 4.86 mmol), (prepared as described for the starting material in Example 2), and potassium carbonate (671 mg, 4.86 mmol) added. The reaction mixture was heated at 85° C. for 3 hours. The mixture was cooled, filtered and concentrated under reduced pressure. Column chromatography of the residue (8-10% methanol/dichloromethane) gave 4-(7-azaindol-5-yloxy)-7-{3-[4-(tert-butoxycarbonyl)piperazin-1-yl]propoxy}-6-methoxyquinazoline (2.0 g, 85%) as a white solid.

$^1$H NMR Spectrum: (CDCl$_3$) 1.47 (s, 9H); 2.14 (m, 2H); 2.44 (t, 4H); 2.59 (t, 2H); 3.45 (t, 4H); 4.07 (s, 3H); 4.29 (t, 2H); 6.55 (m, 1H); 7.36 (s, 1H); 7.41 (m, 1H); 7.61 (s, 1H); 7.86 (d, 1H); 8.30 (d, 1H); 8.61 (s, 1H); 9.80 (br s, 1H)

MS-ESI: 535.0 [MH]$^+$ 4-(7-Azaindol-5-yloxy)-7-{3-[4-(tert-butoxycarbonyl)piperazin-1-yl]propoxy}-6-methoxyquinazoline (1.9 g, 3.55 mmol) was suspended in dichloromethane (60 ml) and trifluoroacetic acid (2 ml) added dropwise. All solid dissolved at this point giving an orange solution which was stirred for 3 hours at ambient temperature. More trifluoroacetic acid (4 ml) was added and the mixture stirred overnight. The mixture was concentrated under reduced pressure and the residue concentrated from dichloromethane (×3) and toluene to remove trifluoroacetic acid. The residue was dissolved in methanol, placed on an Isolute SCX column, washed with methanol and then eluted with 7N ammonia in methanol. The product was then purified by column chromatography eluting with methylene chloride/methanol (saturated with ammonia) (95/5 followed by 93/7) to give 4-(7-azaindol-5-yloxy)-6-methoxy-7-(3-piperazin-1-ylpropoxy)quinazoline (660 mg, 43%) as a white foam.

$^1$H NMR Spectrum: (DMSOd$_6$) 1.95 (m, 2H); 2.30 (m, 4H); 2.41 (t, 2H); 2.68 (t, 4H); 3.97 (s, 3H), 4.22 (t, 2H); 6.46

(d, 2H); 7.36 (s, 1H); 7.55 (d, 1H); 7.60 (s, 1H); 7.90 (d, 1H); 8.17 (d, 1H); 8.48 (s, 1H); 11.76 (br s, 1H)

MS-ESI: 435.6 [MH]+

EXAMPLE 35

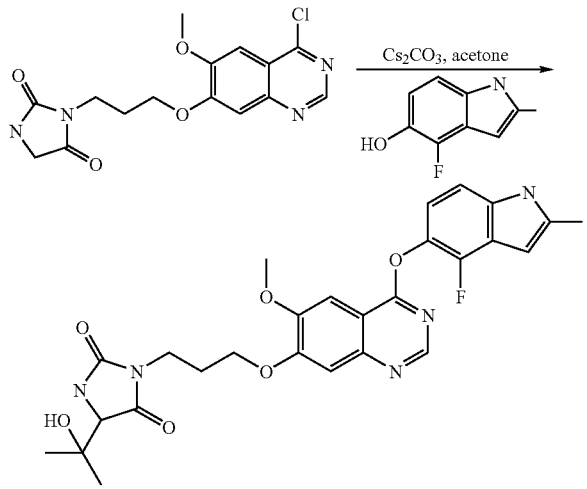

A mixture of 4-chloro-7-[3-(2,5-dioxoimidazolidin-1-yl)propoxy]-6-methoxyquinazoline (200 mg, 0.57 mmol), 4-fluoro-5-hydroxy-2-methylindole (113 mg, 0.68 mmol), (prepared as described for the starting material in Example 1), and caesium carbonate (279 mg, 0.86 mmol) in acetone (15 ml) was heated at reflux for 4 hours. The mixture was cooled, filtered and the filtrate concentrated under reduced pressure. The residue was purified by column chromatography eluting with methylene chloride/methanol (97/3 followed by 95/5) to give 7-{3-[2,5-dioxo-4-(1-hydroxy-1-methylethyl)imidazolidin-1-yl]propoxy}-4-[(4-fluoro-2-methyl-1H-indol-5-yloxy]-6-methoxyquinazoline (87 mg, 28%) as a brown foam.

$^1$H NMR Spectrum: (DMSOd$_6$) 1.17 (s, 3H); 1.22 (s, 3H); 2.06 (m, 2H); 2.42 (s, 3H); 3.57 (t, 2H); 3.84 (d, 1H); 4.01 (s, 3H); 4.21 (t, 2H); 4.78 (s, 1H); 6.25 (s, 1H); 6.99 (t, 1H); 7.16 (d, 1H); 7.33 (s, 1H); 7.62 (s, 1H); 8.19 (s, 1H); 8.50 (s, 1H); 11.32 (br s, 1H)

MS-ESI: 538.6 [M+H]+

The starting material was prepared as follows:

Imidazolidine-2,4-dione (1.0 g, 9.99 mmol), 3-benzyloxypropan-1-ol (1.91 ml, 12.0 mmol) and triphenylphosphine (3.1 g, 12.0 mmol) were stirred in methylene chloride (20 ml) and cooled to 0° C. Diisopropyl azodicarboxylate (2.36 µl, 12.0 mmol) in dichloromethane (5 ml) was slowly added and the mixture stirred at ambient temperature overnight. The mixture was washed with water, dried (MgSO$_4$) and concentrated under reduced pressure. The residue was purified by column chromatography eluting with methylene chloride/methanol (98/2) to give 3-(3-benzyloxypropyl)imidazolidine-2,4-dione (1.3 g, 53%, containing 7% w/w triphenylphosphine oxide) as a pale yellow solid.

$^1$H NMR Spectrum: (DMSOd$_6$) 1.76 (m, 2H); 3.40 (m, 4H); 3.83 (d, 2H); 4.41 (s, 2H); 7.31 (m, 5H); 7.94 (br s, 1H)

3-(3-Benzyloxypropyl)imidazolidine-2,4-dione (1.3 g, 5.26 mmol) was dissolved in methanol (15 ml) and the system purged with nitrogen. 10% Palladium on carbon (130 mg, 10% by mass) and a few drops of glacial acetic acid were added and the mixture stirred under a hydrogen atmosphere (1 atmosphere) for 3 days. The mixture was filtered and concentrated under reduced pressure. The residue was purified by column chromatography eluting with methylene chloride/methanol (98/2 to 95/5) to give 3-(3-hydroxypropyl)imidazolidine-2,4-dione (606 mg, 73%) as a viscous oil which crystallised on standing.

$^1$H NMR Spectrum: (DMSOd$_6$) 1.65 (m, 2H); 3.39 (m, 4H); 3.88 (s, 2H); 4.44 (t, 1H); 7.96 (br s, 1H)

A mixture of 4-chloro-7-hydroxy-6-methoxyquinazoline (665 mg, 3.16 mmol), (prepared as described for the starting material in Example 4), 3-(3-hydroxypropyl)imidazolidine-2,4-dione (600 mg, 3.79 mmol) and triphenylphosphine in dichloromethane (15 ml) was stirred and cooled to 0° C. Diisopropyl azodicarboxylate (747 µl, 3.79 mmol) in dichloromethane (5 ml) was added and the mixture stirred at ambient temperature for 3 hours. Initially all material went into solution but later a precipitate formed. The mixture was concentrated and the solid residue suspended in methanol, filtered and dried in air to give 4-chloro-7-[3-(2,5-dioxoimidazolidin-1-yl)propoxy]-6-methoxyquinazoline (765 mg, 69%) as a pale yellow solid.

$^1$H NMR Spectrum: (DMSOd$_6$) 2.09 (m, 2H); 3.58 (t, 2H); 3.88 (d, 2H); 4.02 (s, 3H); 4.25 (t, 2H); 7.39 (s, 1H), 7.41 (s, 1H); 7.99 (br s, 1H); 8.87 (s, 1H)

MS-ESI: 351.5 and 353.5 [MH]+

EXAMPLE 36

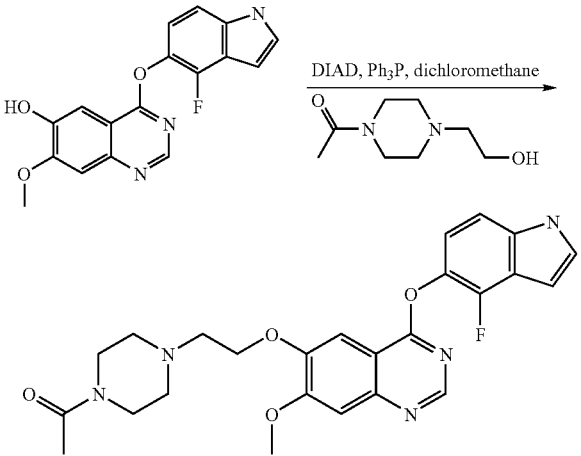

A mixture of 4-[(4-fluoro-1H-indol-5-yl)oxy]-6-hydroxy-7-methoxyquinazoline (260 mg, 0.80 mmol), (prepared as described for the starting material in Example 10), 2-(4-acetylpiperazin-1-yl)ethanol (165 mg, 0.96 mmol), (prepared as described for the starting material in Example 28), and triphenylphosphine (252 mg, 0.96 mmol) in dichloromethane (15 ml) was stirred and cooled in an ice/water bath. Diisopropyl azodicarboxylate (189 µl, 0.96 mmol) was added. The mixture was stirred for 3 hours and then a further 0.5 mole equivalent of 2-(4-acetylpiperazin-1-yl)ethanol, triphenylphosphine and diisopropyl azodicarboxylate were added. The mixture was stirred for a further 1 hour and then concentrated under reduced pressure. The residue was purified by column chromatography eluting with methylene chloride/methanol (95/5) to give 6-[2-(4-acetylpiperazin-1-yl)ethoxy]-4-[(4-fluoro-1H-indol-5-yl)oxy]-7-methoxyquinazoline (260 mg, 68%) as a white solid.

¹H NMR Spectrum: (DMSOd₆) 1.98 (s, 3H); 2.45 (m, 2H); 2.55 (m, 2H); 2.83 (t, 2H); 3.43 (m, 4H); 4.00 (s, 3H); 4.33 (t, 2H); 6.55 (s, 1H); 7.09 (t, 1H); 7.30 (d, 1H); 7.41 (s, 1H); 7.48 (t, 1H); 7.70 (s, 1H); 8.51 (s, 1H); 11.52 (br s, 1H)

MS-ESI: 480.1 [MH]⁺

EXAMPLE 37

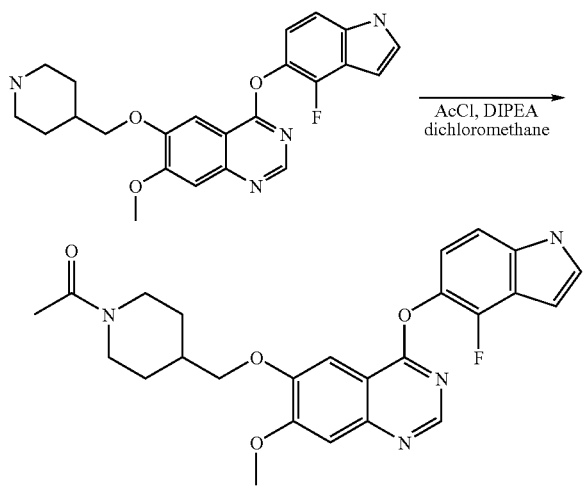

4-[(4-Fluoro-1H-indol-5-yl)oxy]-7-methoxy-6-(piperidin-4-ylmethoxy)quinazoline (210 mg, 0.50 mmol) was suspended in dichloromethane (7 ml) and diisopropylethylamine (104 µl, 0.60 mmol) and acetyl chloride (42 µl, 0.60 mmol) were added. All solid material went into solution. The mixture was stirred at ambient temperature overnight. The mixture was washed with brine, followed by saturated aqueous sodium hydrogen carbonate, dried (MgSO₄) and concentrated under reduced pressure. The residue was purified by column chromatography eluting with methylene chloride/methanol (98/2) to give 6-[(1-acetylpipendin-4-yl)methoxy]-4-[(4-fluoro-1H-indol-5-yl)oxy]-7-methoxyquinazoline (146 mg, 63%) as a white foam.

¹H NMR Spectrum: (DMSOd₆) 1.14-1.36 (m, 2H); 1.85 (m, 2H); 2.01 (s, 3H); 2.12 (m, 1H); 2.61 (br t, 1H); 3.09 (br t, 1H); 3.87 (br d, 1H); 4.01 (s, 3H); 4.09 (d, 2H); 4.41 (br d, 1H); 6.55 (s, 1H); 7.09 (t, 1H); 7.30 (d, 1H); 7.41 (s, 1H); 7.47 (t, 1H); 7.63 (s, 1H); 8.51 (s, 1H); 11.49 (br s, 1H)

MS-ESI: 465.1 [MH]⁺

The starting material was prepared as follows:

A mixture of 4-[(4-fluoro-1H-indol-5-yl)oxy]-6-hydroxy-7-methoxyquinazoline (250 mg, 0.77 mmol), (prepared as described for the starting material in Example 10), tert-butyl 4-(hydroxymethyl)piperidine-1-carboxylate (199 mg, 0.92 mmol), (prepared as described for the starting material in Example 11), and triphenylphosphine (242 mg, 0.92 mmol) in dichloromethane (15 ml) was stirred and cooled to 0° C. Diisopropyl azodicarboxylate (182 µl, 0.92 mmol) in dichloromethane (2 ml) was added. The mixture was stirred for 3 hours and then a further 0.5 mole equivalent of tert-butyl 4-(hydroxymethyl)piperidine-1-carboxylate, triphenylphosphine and diisopropyl azodicarboxylate added. The mixture was stirred for 1 hour and then concentrated under reduced pressure. The residue was purified by column chromatography eluting with ethyl acetate/hexane (1/1) followed by methylene chloride/methanol (99/1) to give 6-[1-(tert-butoxycarbonyl)piperidin-4-yl]methoxy-4-[(4-fluoro-1H-indol-5-yl) oxy]-7-methoxyquinazoline (306 mg containing 10% w/w triphenylphosphine oxide) which was used without further purification in the next step.

MS-ESI: 523.1 [MH]⁺

6-[1-(tert-Butoxycarbonyl)piperidin-4-yl]methoxy-4-[(4-fluoro-1H-indol-5-yl)oxy]-7-methoxyquinazoline (306 mg containing 10% w/w triphenylphosphine oxide) was dissolved in 1,4-dioxane (5 ml) and 4M hydrogen chloride in 1,4-dioxane (5 ml) was added. The mixture was stirred at ambient temperature for 2.5 hours and then concentrated under reduced pressure. The residue was dissolved in methanol and adsorbed onto an Isolute SCX column, washed with methanol and then eluted with 7N ammonia in methanol to give 4-[(4-fluoro-1H-indol-5-yl)oxy]-7-methoxy-6-(piperidin-4-ylmethoxy)quinazoline (215 mg, 66% over two steps).

¹H NMR Spectrum: (DMSOd₆) 1.24 (m, 2H); 1.75 (br d, 2H); 1.93 (m, 1H); 2.98 (br d, 2H); 4.01 (m, 5H); 6.55 (s, 1H); 7.09 (t, 1H), 7.30 (d, 1H); 7.40 (s, 1H); 7.47 (t, 1H), 7.61 (s, 1H); 8.50 (s, 1H); 11.50 (s, 1H)

MS-ESI: 423.1 [MH]⁺

EXAMPLE 38

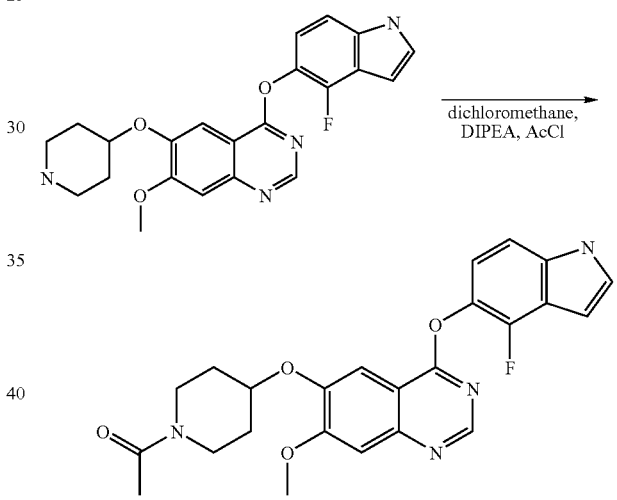

4-[(4-Fluoro-1H-indol-5-yl)oxy]-7-methoxy-6-(piperidin-4-yloxy)quinazoline (215 mg, 0.53 mmol) was suspended in dichloromethane (10 ml) and diisopropylethylamine (110 µl, 0.63 mmol) and acetyl chloride (45 µl, 0.63 mmol) were added. The mixture was stirred at ambient temperature for 3 hours. The mixture was washed with brine, followed by aqueous sodium hydrogen carbonate, dried (MgSO₄) and concentrated under reduced pressure. The residue was purified by column chromatography eluting with methylene chloride/methanol (98/2) to give 6-[(1-acetylpipenidin-4-yl)oxy]-4-[(4-fluoro-1H-indol-5-yl)oxy]-7-methoxyquinazoline (128 mg, 54%) as a white foam.

¹H NMR Spectrum: (DMSOd₆) 1.67 (m, 1H); 1.79 (m, 1H), 2.09 (m, 5H); 3.35 (m, 1H); 3.47 (m, 1H); 3.76 (m, 1H); 3.93 (m, 1H); 4.06 (s, 3H); 5.00 (m, 1H); 6.61 (s, 1H); 7.16 (t, 1H); 7.63 (d, 1H); 7.49 (s, 1H); 7.53 (t, 1H); 7.82 (s, 1H); 8.57 (s, 1H); 11.55 (br s, 1H)

MS-ESI: 451.1 [MH]⁺

The starting material was prepared as follows:

4-[(4-Fluoro-1H-indol-5-yl)oxy]-6-hydroxy-7-methoxyquinazoline (700 mg, 2.15 mmol), (prepared as described for the starting material in Example 10), tert-butyl 4-hydroxypiperidine-1-carboxylate (520 mg, 2.58 mmol) and triphenylphosphine (677 mg, 2.58 mmol) were stirred in dichloromethane (20 ml) and cooled to 0° C. Diisopropyl azodicarboxylate (508 µl, 2.58 mmol) in dichloromethane (3 ml) was added and the mixture stirred at ambient temperature overnight. The mixture was filtered and concentrated under reduced pressure. The residue was purified by column chromatography eluting with ethyl acetate/isohexane (1/1) followed by methylene chloride/methanol (99/1) to give 6-[(1-tert-butoxycarbonyl)piperidin-4-yloxy]-4-[(4-fluoro-1H-indol-5-yl)oxy]-7-methoxyquinazoline (933 mg containing 35% w/w triphenylphosphine oxide) which was used directly in the next step without further purification.

MS-ESI: 509.2 [MH]+

6-[(1-tert-Butoxycarbonyl)piperidin-4-yloxy]-4-[(4-fluoro-1H-indol-5-yl)oxy]-7-methoxyquinazoline (933 mg containing 35% w/w triphenylphosphine oxide) was dissolved in 1,4-dioxane (5 ml) and 4M hydrogen chloride in 1,4-dioxane (10 ml) was added. The mixture was stirred at ambient temperature for 1 hour and then concentrated under reduced pressure. The residue was dissolved in methanol and adsorbed onto an Isolute SCX column, washed with methanol and then eluted with 7N ammonia in methanol to give 4-[(4-fluoro-1H-indol-5-yl)oxy]-7-methoxy-6-(piperidin-4-yloxy)quinazolne (430 mg, 49% over two steps), approximately 86% pure. Used without finther purification.

MS-ESI: 409.1 [MH]+

EXAMPLE 39

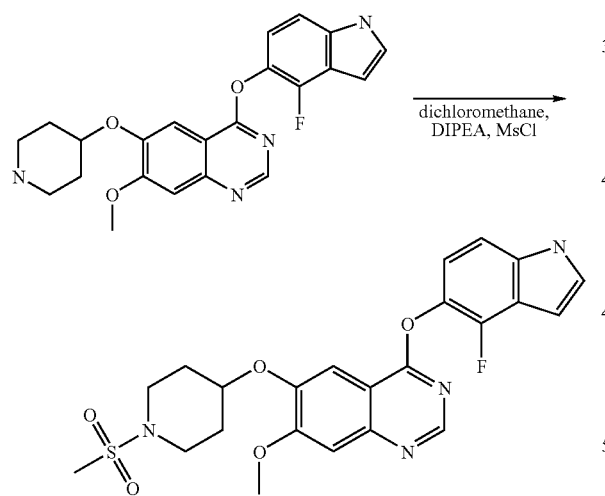

4-[(4-Fluoro-1-indol-5-yl)oxy]-7-methoxy-6-(piperidin-4-yloxy)quinazoline (215 mg, 0.53 mmol), (prepared as described for the starting material in Example 38), was suspended in dichloromethane (10 ml) and diisopropylethylamine (110 µl, 0.63 mmol) and methane sulphonyl chloride (49 µl, 0.63 mmol) were added. All solid material went into solution. The mixture was stirred at ambient temperature for 3 hours. The mixture was washed with brine, followed by aqueous sodium hydrogen carbonate, dried (MgSO4) and concentrated under reduced pressure. The residue was purified by column chromatography eluting with methylene chloride/methanol (98/2) to give 4-[(4-fluoro-1H-indol-5-yl)oxy]-7-methoxy-6-{[1-(methylsulphonyl)piperidin-4-yl]oxy}quinazoline (168 mg, 66%) as a white foam.

1H NMR Spectrum: (DMSOd6) 1.85 (m, 2H); 2.12 (m, 2H); 2.91 (s, 3H); 3.19 (m, 2H); 3.43 (m, 2H); 4.02 (s, 3H); 4.87 (m, 1H); 6.55 (s, 1H); 7.10 (t, 1H); 7.30 (d, 1H); 7.44 (s, 1H); 7.47 (t, 1H); 7.76 (s, 1H); 8.52 (s, 1H); 11.49 (s, 1H)

MS-ESI: 487.1 [MH]+

EXAMPLE 40

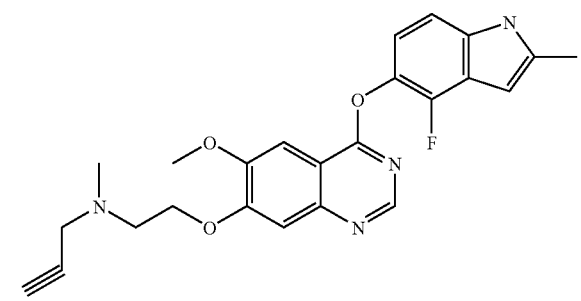

A stirred solution of 7-(2-bromoethoxy)-4-[(4-fluoro-2-methyl-1H-indol-5-yl)oxy]-6-methoxyquinazoline (250 mg, 0.56 mmol), (prepared as described for the starting material in Example 17), in DMF (2.5 ml) was treated with N-methyl-propargylamine (116 mg, 1.68 mmol) and stirred at ambient temperature overnight. The solvent was evaporated under vacuum and the residue purified by column chromatography eluting with methylene chloride/methanol (saturated with ammonia) (92/8). The relevant fractions were combined and evaporated under vacuum to give 4-[(4-fluoro-2-methyl-1H-indol-5-yl)oxy]-6-methoxy-7-(2-[N-methyl-N-(2-propynyl)amino]ethoxy)quinazoline as a white solid. (165 mg, 68%).

1H NMR Spectrum: (DMSOd6): 2.32 (s, 3H), 2.40 (s, 3H), 2.86 (t, 2H), 3.14 (s, 1H), 3.42 (d, 2H), 3.98 (s, 3H), 4.30 (t, 2H), 6.21 (s, 1H), 6.96 (t, 1H), 7.14 (d, 1H), 7.40 (s, 1H), 7.60 (s, 1H), 8.50 (s, 1H), and 11.29 (s, 1H)

MS-ESI: 435 [M+H]+

EXAMPLE 41

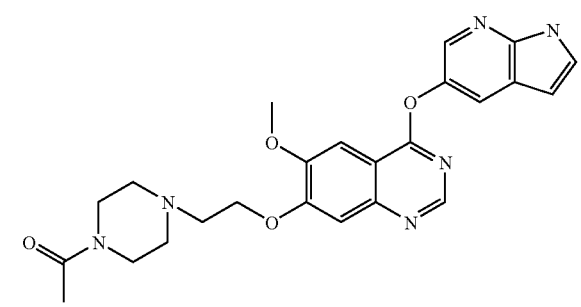

A mixture of 7-[2-(4-acetylpiperazin-1-yl)ethoxy]-4-chloro-6-methoxyquinazoline (224 mg, 0.61 mmol), (prepared as described for the starting material in Example 28), 5-hydroxy-7-azaindole (91 mg, 0.68 mmol), (prepared as described for the starting material in Example 2), and potassium carbonate (94 mg, 0.68 mmol) in DMA (5 ml) was stirred at 85° C. for 2 hours, allowed to cool to ambient temperature and the solvent evaporated under vacuum. The residue was purified by column chromatography eluting with methylene chloride/methanol (saturated with ammonia) (95/

5) to give a white solid. This was triturated with acetone, filtered and dried to give 7-[2-(4-acetylpiperazin-1-yl)ethoxy]-4-(7-azaindol-5-yloxy)-6-methoxyquinazoline (227 mg, 80%)

$^1$H NMR Spectrum: (CDCl$_3$) 2.03 (s, 3H), 2.57 (m, 4H), 2.91 (t, 2H), 3.43 (t, 2H), 3.59 (t, 2H), 3.99 (s, 3H), 4.29 (t, 2H), 6.48 (m, 1H), 7.27 (s, 1H), 7.33 (t, 1H), 7.55 (s, 1H), 7.78 (d, 1H), 8.22 (d, 1H), 8.54 (s, 1H) and 9.59 (s, 1H)

MS-ESI: 463 [M+H]$^+$

EXAMPLE 42

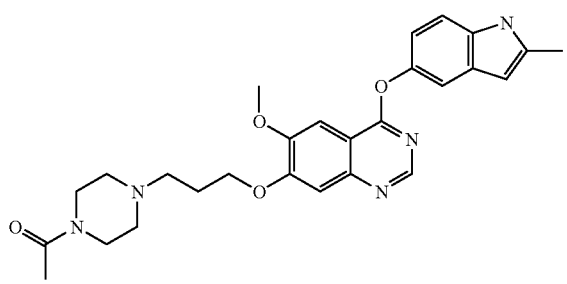

A mixture of 7-[3-(4-acetylpiperazin-1-yl)propoxy]-4-chloro-6-methoxyquinazoline (190 mg, 0.50 mmol), (prepared as described for the starting material in Example 4), 5-hydroxy-2-methylindole (81 mg, 0.55 mmol), (WO 00/47212, Example 48), and potassium carbonate (76 mg, 0.55 mmol) in DMA (6 ml) was stirred at 85° C. for 3 hours, allowed to cool to ambient temperature and the solvent evaporated under vacuum. The residue was purified by column chromatography eluting with methylene chloride/methanol (saturated with ammonia) (92/8) to give a white solid. This was triturated with a mixture of ether and acetone, filtered and dried to give 7-[3-(4-acetylpiperazin-1-yl)propoxy]-6-methoxy-4-[(2-methyl-1H-indol-5-yl)oxy]quinazoline (130 mg, 53%).

$^1$H NMR Spectrum: (CDCl$_3$) 2.02 (s, 3H), 2.09 (m, 2H), 2.39 (s, 3H), 2.41 (m, 4H), 2.54 (t, 2H), 3.40 (m, 2H), 3.57 (m, 2H), 3.98 (s, 3H), 4.22 (t, 2H), 6.17 (s, 1H), 6.90 (dd, 1H), 7.24 (m, 3H), 7.56 (s, 1H), 8.00 (br s, 1H) and 8.52 (s, 1H)

MS-ESI: 490 [M+H]$^+$

EXAMPLE 43

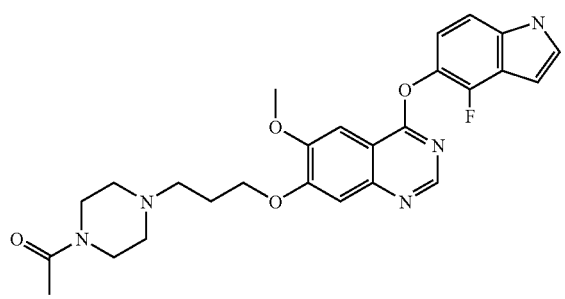

A mixture of 7-[3-(4-acetylpiperazin-1-yl)propoxy]-4-chloro-6-methoxyquinazoline (190 mg, 0.50 mmol), (prepared as described for the starting material in Example 4), 4-fluoro-5-hydroxyindole (83 mg, 0.55 mmol), (WO 00/47212, Example 242), and potassium carbonate (76 mg, 0.55 mmol) in DMA (6 ml) was stirred at 85° C. for 3 hours, allowed to cool to ambient temperature and the solvent evaporated under vacuum. The residue was purified by column chromatography eluting with methylene chloride/methanol (saturated with ammonia) (92/8) to give a white solid. This was triturated with acetone, filtered and dried to give 7-[3-(4-acetylpiperain-1-yl)propoxy]-4-[(4-fluoro-1H-indol-5-yl)oxy]-6-methoxyquinazoline (75 mg, 30%).

$^1$H NMR Spectrum: (CDCl$_3$) 2.03 (s, 3H), 2.06 (m, 2H), 2.40 (m, 4H), 2.53 (t, 2H), 3.40 (m, 2H), 3.58 (m, 2H), 4.00 (s, 3H), 4.22 (t, 2H), 6.60 (m, 1H), 7.05 (m, 1H), 7.17 (m, 2H), 7.30 (s, 1H), 7.58 (s, 1H), 8.44 (br s, 1H) and 8.56 (s, 1H)

MS-ESI: 494 [M+H]$^+$

EXAMPLE 44

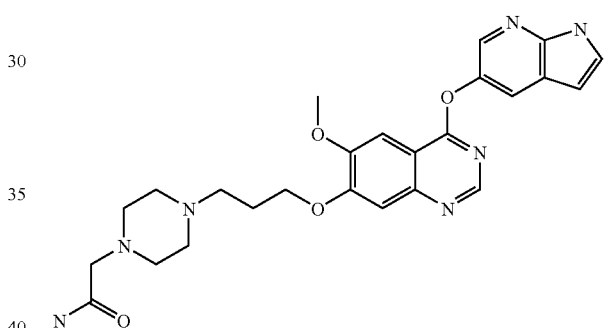

A mixture of 4-(7-azaindol-5-yloxy)-6-methoxy-7-(3-piperazin-1-ylpropoxy)quinazoline (87 mg, 0.2 mmol), (prepared as described for the starting material in Example 34), iodoacetamide (41 mg, 0.22 mmol) and N,N-diisopropylethylamine (26 mg, 0.22 mmol) in acetonitrile (5 ml) was stirred at reflux for 1 hour and allowed to cool to ambient temperature. The crude reaction mixture was loaded onto a silica column and eluted using methylene chloride/methanol (saturated with ammonia) (92/8) solvent. The relevant fractions were combined and evaporated under vacuum to give a residue which was triturated with acetone, filtered and dried to give 4-(7-azaindol-5-yloxy)-7-[3-(4-carbamoylmethyl)piperazin-1-yl)propoxy]-6-methoxyquinazoline (62 mg, 63%).

$^1$H NMR Spectrum: (CDCl$_3$) 2.07 (m, 2H), 2.51 (m, 10H), 2.96 (s, 2H), 4.00 (s, 3H), 4.22 (t, 2H), 5.57 (br s, 1H), 6.48 (m, 1H), 6.96 (br s, 1H), 7.28 (s, 1H), 7.33 (m, 1H), 7.54 (s, 1H), 7.78 (d, 1H); 8.21 (d, 1H); 8.53 (s, 1H) and 9.37 (s, 1H)

MS-ESI: 492 [M+H]$^+$

EXAMPLE 45

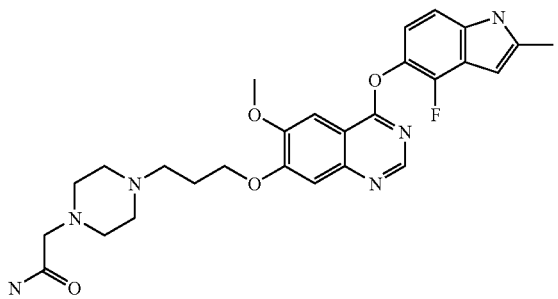

A mixture of 4-[(4-fluoro-2-methyl-1H-indol-5-yl)oxy]-6-methoxy-7-(3-piperazin-1-ylpropoxy)quinazoline (370 mg, 0.8 mmol), (prepared as described for the starting material in Example 15), iodoacetamide (162 mg, 0.88 mmol) and N,N-diisopropylethylanmine (230 mg, 1.80 mmol) in acetonitrile (10 ml) was stirred at reflux for 1 hour and allowed to cool to ambient temperature. The solvent was removed under vacuum and the residue purified by column chromatography eluting with methylene chloride/methanol (saturated with ammonia) (92/8) solvent. The relevant fractions were combined and evaporated under vacuum to give a solid which was triturated with acetone, filtered and dried to give 7-[3-(4-carbamoylmethylpiperazin-1-yl)propoxy]-4-[(4-fluoro-2-methyl-1H-indol-5-yl)oxy]-6-methoxyquinazoline (132 mg, 32%).

$^1$H NMR Spectrum: (CDCl$_3$) 2.06 (m, 2H), 2.39 (s, 3H), 2.51 (m, 10H), 2.95 (s, 2H), 3.99 (s, 3H), 4.21 (t, 2H), 5.33 (br s, 1H), 6.28 (m, 1H), 6.93 (m, 2H), 7.03 (d, 1H), 7.27 (s, 1H), 7.56 (s, 1H), 8.05 (br s, 1H), 8.53 (s, 1H)

MS-ESI: 523 [M+H]$^+$

EXAMPLE 46

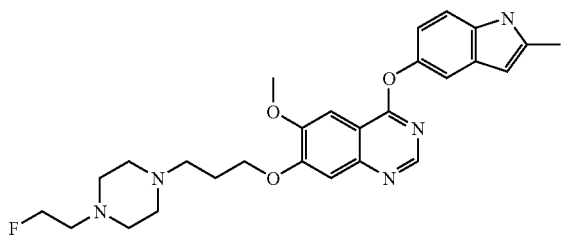

A solution of 4-chloro-7-{3-[4-(2-fluoroethyl)piperazin-1-yl]propoxy}-6-methoxyquinazoline (240 mg, 0.63 mmol) in DMA (5 ml) was treated with potassium carbonate (96 mg, 0.69 mmol) and 5-hydroxy-2-methylindole (102 mg, 0.69 mmol), (WO 00/47212, Example 48), and stirred at 85° C. for 4 hours. The mixture was cooled and the solvent evaporated under vacuum to give a residue which was purified by column chromatography eluting with methylene chloride/methanol (saturated with ammonia) (92/8). Evaporation of the relevant fractions gave an oil which crystallised on trituration with ether to give 7-{3-[4-(2-fluoroethyl)piperazin-1-yl]propoxy}-6-methoxy-4-[(2-methyl-1H-indol-5-yl)oxy]quinazoline (150 mg, 48%).

$^1$H NMR Spectrum: (CDCl$_3$) 2.06 (m, 2H), 2.39 (s, 3H), 2.51 (m, 10H), 2.60 (t, 1H), 2.67 (t, 1H), 3.97 (s, 3H), 4.20 (t, 2H), 4.44 (t, 1H), 4.56 (t, 1H), 6.17 (s, 1H), 6.90 (m, 1H), 7.26 (m, 3H), 7.54 (s, 1H), 7.92 (br s, 1H), 8.53 (s, 1H)

MS-ESI: 494 [M+H]$^+$

The starting material was prepared as follows:—

A suspension of 4-chloro-7-hydroxy-6-methoxyquinazoline (202 mg, 0.96 mmol), (prepared as described for the starting material in Example 4), in methylene chloride (10 ml) was treated with triphenylphosphine (352 mg, 1.35 mmol), 3-[4-(2-fluoroethyl)piperazin-1-yl]propan-1-ol (200 mg, 1.06 mmol), (prepared as described for the starting material in Example 27), and diisopropyl azodicarboxylate (226 mg, 1.15 mmol) and the mixture stirred at ambient temperature for 2 hours. The crude reaction mixture was loaded onto a silica column and eluted using methylene chloride/methanol (95/5). The relevant fractions were combined and evaporated under vacuum to give 4-chloro-7-{3-[4-(2-fluoroethyl)piperazin-1-yl]propoxy}-6-methoxyquinazoline (208 mg, 57%) as a white solid.

$^1$H NMR Spectrum: (CDCl$_3$) 2.12 (t, 2H), 2.57 (m, 10H), 2.66 (t, 1H), 2.75 (t, 1H), 4.05 (s, 3H), 4.28 (t, 2H), 4.49 (t, 1H), 4.65 (t, 1H), 7.35 (s, 1H), 7.38 (s, 1H), 8.85 (s, 1H)

MS-ESI: 383 [M+H]$^+$

EXAMPLE 47

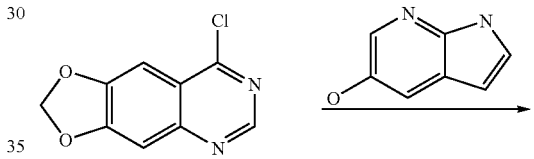

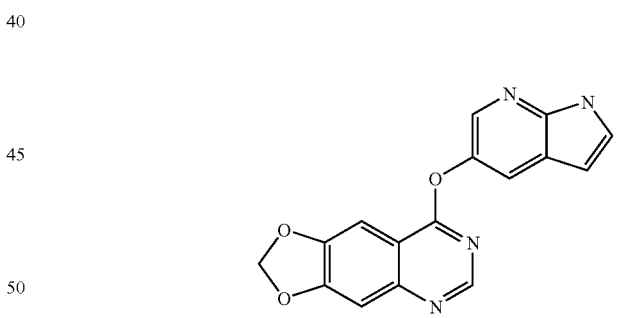

8-Chloro[1,3]dioxolo[4,5-g]quinazoline (100 mg, 0.48 mmol), (WO 9749688), was dissolved in dimethylacetamide (2.5 ml). 5-Hydroxy-7-azaindole (71 mg, 0.53 mmol), (prepared as described for the starting material in Example 2), and potassium carbonate (73 mg, 0.53 mmol) were added and the mixture heated to 85° C. for 3 hours. The reaction mixture was cooled, filtered and concentrated. The resulting residue was purified by column chromatography eluting with methylene chloride/methanol (91/9) to yield 4-(7-azaindol-5-yloxy)-6,7-methylenedioxyquinazoline (92 mg, 63%).

$^1$H NMR Spectrum: (DMSOd$_6$) 6.30 (s, 2H), 6.45 (d, 1H), 7.35 (s, 1H), 7.55 (t, 1H), 7.65 (s, 1H), 7.90 (d, 1H), 8.15 (d, 1H), 8.45 (s, 1H), 11.75 (br s, 1H)

MS-ESI: 307 [M+H]+

EXAMPLE 48

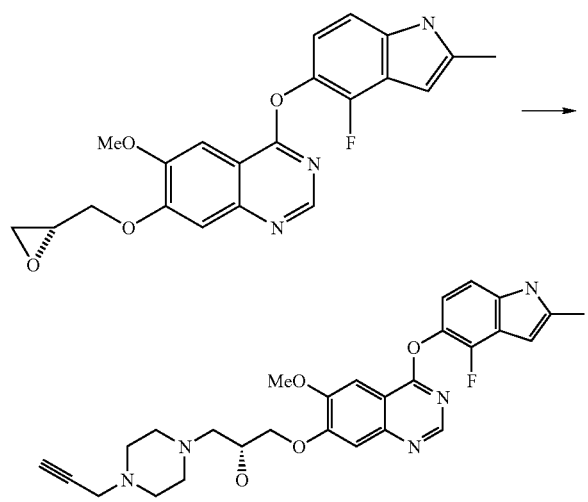

4-[(4-Fluoro-2-methyl-1H-indol-5-yl)oxy]-6-methoxy-7-[(2R)-oxiran-2-ylmethoxy]quinazoline (200 mg, 0.5 mmol) was dissolved in dimethylformamide (2 ml) and added to a solution of 1-prop-2-yn-1-ylpiperazine di-trifluoracetic acid salt (535 mg, 1.5 mmol), (prepared as described for the starting material in Example 26), and potassium carbonate (414 mg, 3 mmol) in dimethylformamide (3 ml). The reaction was heated to 60° C. and left overnight. The reaction mixture was cooled, filtered and concentrated. The resulting residue was purified by column chromatography eluting with methylene chloride/methanol (saturated with ammonia) (94/6) to give 4-[(4-fluoro-2-methyl-1H-indol-5-yl)oxy]-7-{(2R)-2-hydroxy-3-[4-prop-2-yn-1-ylpiperazin-1-yl]propoxy}-6-methoxyquinazoline (200 mg, 76%).

$^1$H NMR Spectrum: (DMSO-d$_6$) 2.35 (s, 3H), 2.40 (m, 10H), 3.05 (t, 1H), 3.20 (d, 2H), 4.00 (s, 3H), 4.05 (m, 2H), 4.20 (m, 1H), 4.90 (d, 1H), 6.20 (s, 1H), 6.95 (dd, 1H), 7.15 (d, 1H), 7.40 (s, 1H), 7.60 (s, 1H), 8.45 (s, 1H), 11.30 (br s, 1H)

MS-ESI: 520 [M+H]+

The starting material was prepared as follows:

4-(4-Fluoro-2-methylindol-5-yloxy)-7-hydroxy-6-methoxyquinazoline (339 mg, 1 mmol), (prepared as described for the starting material in Example 7), was dissolved in dimethylacetamide (5 ml) under nitrogen. (2R) Glycidyl tosylate (285 mg, 1.25 mmol) and potassium carbonate (345 mg, 2.5 mmol) were added and the reaction stirred at ambient temperature for 2.5 hours, then warmed to 40° C. and left overnight. The solvent was removed under vacuum and the residue partitioned between water and dichloromethane. The organic phase was washed with brine and dried (Na$_2$SO$_4$). The residue was purified by column chromatography, eluting with methylene chloride/methanol (97/3) to give 4-[(4-Fluoro-2-methyl-1H-indol-5-yl)oxy]-6-methoxy-7-[(2R)-oxiran-2-ylmethoxy]quinazoline (339 mg, 85%).

$^1$H NMR Spectrum: (DMSOd$_6$) 2.40 (s, 3H), 2.75 (m, 1H), 2.90 (m, 1H), 3.40 (m, 1H), 4.00 (s, 3H), 4.05 (m, 1H), 4.60 (m, 1H), 6.20 (s, 1H), 6.95 (dd, 1H), 7.15 (d, 1H), 7.40 (s, 1H), 7.60 (s, 1H), 8.45 (s, 1H), 11.30 (br s, 1H)

MS-ESI: 396 [M+H]+.

EXAMPLE 49

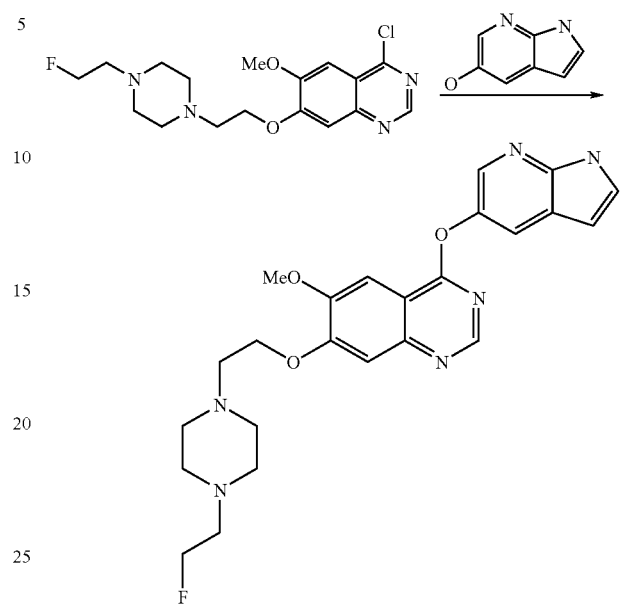

4-Chloro-7-{2-[4-(2-fluoroethyl)piperazin-1-yl]ethoxy}-6-methoxyquinazoline (172 mg, 0.47 mmol) was dissolved in dimethylacetamide (5 ml). 5-Hydroxy-7-azaindole (69 mg, 0.51 mmol), (prepared as described for the starting material in Example 2), and potassium carbonate (71 mg, 0.51 mmol) were added and the mixture heated to 85° C. for 4 hours. The reaction mixture was cooled, filtered and concentrated. The resulting residue was purified by column chromatography eluting with methylene chloride/methanol (saturated with ammonia) (94/6). The fractions containing the expected product were evaporated under vacuum and the residue was suspended in acetone, filtered and dried under vacuum to give 4-(7-azaindol-5-yloxy)-7-(2-[4-(2-fluoroethyl)piperazin-1-yl]ethoxy)-6-methoxyquinazoline (123 mg, 56%).

$^1$H NMR Spectrum: (CDCl$_3$) 2.60 (m, 4H), 2.65 (m, 4H), 2.75 (t, 2H), 3.00 (t, 2H), 4.05 (s, 3H), 4.35 (t, 2H), 4.50 (t, 1H), 4.65 (t, 1H), 6.55 (d, 1H), 7.35 (s, 1H), 7.40 (t, 1H), 7.60 (s, 1H), 7.85 (d, 1H), 8.30 (d, 1H), 8.60 (s, 1H), 9.70 (br s, 1H)

MS-ESI: 467 [M+H]+

The starting material was prepared as follows:

1-(2-Fluoroethyl)piperazine diTFA salt (464 mg, 1.29 mmol), (prepared as described for the starting material in Example 27), was dissolved in acetonitrile (3.5 ml). Potassium carbonate (889 mg, 6.44 mmol) and 2-bromoethanol (95 µl, 1.34 mmol) were added and the mixture heated to 85° C. and left overnight. More bromoethanol (95 µl, 1.34 mmol) was added and the reaction mixture heated at 85° C. for a further 2 hours. The reaction mixture was cooled, filtered and concentrated. The residue was purified by column chromatography eluting with methylene chloride/methanol (saturated with ammonia) (92/8) to give 2-[4-(2-fluoroethyl)piperazin-1-yl]ethanol (151 mg, 66%).

$^1$H NMR Spectrum: (CDCl$_3$) 2.60 (m, 10H), 2.65 (t, 1H), 2.75 (t, 1H), 3.60 (t, 2H), 4.45 (t, 1H), 4.65 (t, 1H)

MS-ESI: 177 [M+H]+

4-Chloro-7-hydroxy-6-methoxyquinazoline (146 mg, 0.69 mmol), (prepared as described for the starting material in Example 4), was suspended in dichloromethane (7.5 ml). Triphenylphosphine (254 mg, 0.97 mmol) and 2-[4-(2-fluoroethyl)piperazin-1-yl]ethanol (134 mg, 0.76 mmol) were added. Diisopropyl azadicarboxylate (165 μl, 0.83 mmol) was then added dropwise. The reaction mixture was stirred for 2.25 hours at ambient temperature and then loaded directly onto a silica column and eluted with methylene chloride/methanol (92/8) to give 4-chloro-7-{2-[4-(2-fluoroethyl)piperazin-1-yl]ethoxy}-6-methoxyquinazoline (172 mg, 67%).

¹H NMR Spectrum: (CDCl₃) 2.65 (10H, m), 2.95 (2H, t), 4.05 (3H, s), 4.30 (2H, t), 4.50 (1H, t), 4.65 (1H, t), 7.30 (1H, s), 7.40 (1H, s), 8.85 (1H, s)

MS-ESI: 369 and 371 [M+H]+

EXAMPLE 50

¹H NMR Spectrum (CDCl₃) 1.70 (m, 2H), 2.25 (t, 1H), 2.60 (m, 10H), 3.25 (d, 2H), 3.80 (t, 2H)

MS-ESI: 183 [M+H]+

4-Chloro-7-hydroxy-6-methoxyquinazoline (300 mg, 1.42 mmol), (prepared as described for the starting material in Example 4), was suspended in dichloromethane (15 ml). Triphenylphosphine (523 mg, 2 mmol) and 3-(4-prop-2-yn-1-ylpiperazin-1-yl)propan-1-ol (267 mg, 1.46 mmol) were added. Diisopropyl azadicarboxylate (340 μl, 1.71 mmol) was then added dropwise. The reaction mixture was stirred for 1.25 hours at ambient temperature and then loaded directly onto a silica column, and eluted with methylene chloride/methanol (90/8 followed by 90/10) to give 4-chloro-6-methoxy-7-[3-(4-prop-2-yn-1-ylpiperazin-1-yl)propoxy]quinazoline (409 mg, 77%).

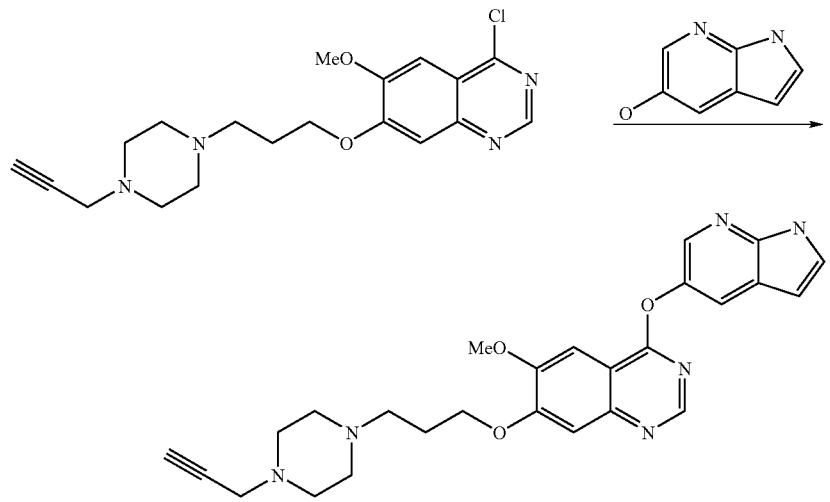

4-Chloro-6-methoxy-7-[3-(4-prop-2-yn-1-ylpiperazin-1-yl)propoxy]quinazoline (300 mg, 0.8 mmol) was dissolved in dimethylacetamide (10 ml). 5-Hydroxy-7-azaindole (118 mg, 0.88 mmol), (prepared as described for the starting material in Example 2), and potassium carbonate (122 mg, 0.88 mmol) were added and the mixture heated to 85° C. for 1.5 hours. The reaction mixture was cooled, filtered and concentrated. The resulting residue was preabsorbed on silica and eluted with methylene chloride/methanol (saturated with ammonia) (90/10) to give 4-(7-azaindol-5-yloxy)-6-methoxy-7-[3-(4-prop-2-yn-1-ylpiperazin-1-yl)propoxy]quinazoline (288 mg, 76%).

¹H NMR Spectrum: (DMSO-d₆) 1.95 (m, 2H), 2.45 (m, 10H), 3.10 (t, 1H), 3.25 (d, 2H), 4.00 (s, 3H), 4.20 (t, 2H), 6.45 (d, 1H), 7.35 (s, 1H), 7.55 (t, 1H), 7.60 (s, 1H), 7.90 (d, 1H), 8.20 (d, 1H), 8.50 (s, 1H), 11.75 (br s, 1H)

MS-ES: 473 (M+H)+

The starting material was prepared as follows:

1-Prop-2-yn-1-ylpiperazine diTFA salt (704 mg, 2 mmol), (prepared as described for the starting material in Example 26), was dissolved in acetonitrile (5 ml). Potassium carbonate (1.38 g, 10 mmol) and 3-bromopropan-1-ol (180 μL, 2 mmol) were added and the mixture heated to 85° C. for 6.5 hours. The reaction mixture was cooled, filtered and concentrated to give an oil. This was triturated with diethyl ether to give a white solid, which was partitioned between dichloromethane and water. The organic phase was then dried (MgSO₄) and concentrated to give 3-(4-prop-2-yn-1-ylpiperazin-1-yl)propan-1-ol (286 mg, 79%).

¹H NMR Spectrum: (DMSO-d₆) 1.95 (m, 2H), 2.45 (m, 10H), 3.10 (t, 1H), 3.20 (d, 2H), 4.00 (s, 3H), 4.25 (t, 2H), 7.35 (s, 1H), 7.40 (s, 1H), 8.80 (s, 1H)

MS-ESI: 375 and 377 [M+H]+Examnile 51

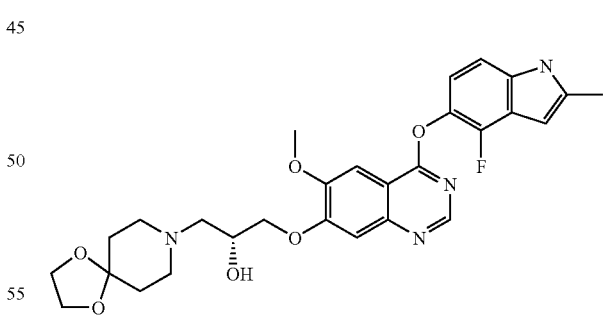

A mixture of 4-[(4-fluoro-2-methyl-1H-indol-5-yl)oxy]-6-methoxy-7-[(2R)-oxiran-2-ylmethoxy]quinazoline (200 mg, 0.506 mmol), (prepared as described for the starting material in Example 48), and 1,4-dioxa-8-azaspiro[4.5]decane (195 μl, 1.52 mmol) in DMF (3 ml) was stirred at 70° C. under argon for 3 hours. The volatiles were removed under vacuum and the residue was purified by column chromatography eluting with methylene chloride/methanol (95/5 followed by 90/10). The fractions containing the expected product were combined and evaporated to dryness. The residue was triturated with diethyl ether, filtered and dried under vacuum to give 7-{(2R)-3-[(1,4-dioxa-8-azaspiro[4.5]dec-8-yl)]-2-hydroxypropoxy}-4-[(4-fluoro-2-methyl-1H-indol-5-yl)oxy]-6-methoxyquinazoline (190 mg, 70%).

$^1$H NMR Spectrum: (DMSOd$_6$) 1.65 (t, 4H); 2.43 (s, 3H); 2.49-2.64 (m, 6H); 3.87 (s, 4H); 4.01 (s, 3H); 4.05 (br s; 1H); 4.13 (dd, 1H); 4.26 (dd, 1H); 4.97 (d, 1H); 6.26 (s, 1H); 7.01 (dd, 1H); 7.18 (d, 1H); 7.44 (s, 1H); 7.63 (s, 1H); 8.52 (s, 1H); 11.31 (s, 1H)

MS-ESI: 539.5 [M+H]$^+$

EXAMPLE 52

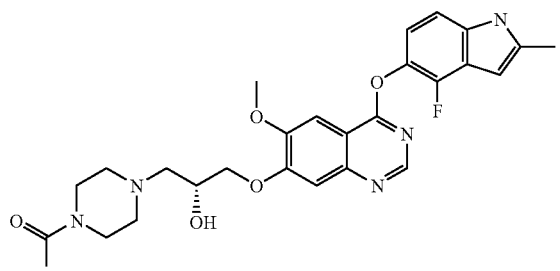

Using an analogous procedure to that described for the preparation of Example 51, 4-[(4-fluoro-2-methyl-1H-indol-5-yl)oxy]-6-methoxy-7-[(2R)-oxiran-2-ylmethoxy]quinazoline (200 mg, 0.506 mmol), (prepared as described for the starting material in Example 48), was reacted with 1-acetylpiperazine (195 mg, 1.51 mmol) to give 7-{(2R)-3-[4-acetylpiperazin-1-yl]-2-hydroxypropoxy}-4-[(4-fluoro-2-methyl-1H-indol-5-yl)oxy]-6-methoxyquinazoline (175 mg, 66%).

$^1$H NMR Spectrum: (DMSOd$_6$) 2.00 (s, 3H); 2.43 (s, 3H); 2.35-2.60 (m, 6H); 3.40-3.52 (m, 4H); 4.02 (s, 3H); 4.11 (br s, 1H); 4.15 (dd, 1H); 4.27 (dd, 1H); 5.05 (d, 1H); 6.26 (s, 1H); 7.01 (dd, 1H); 7.18 (d, 1H); 7.46 (s, 1H); 7.63 (s, 1H); 8.52 (s, 1H); 11.36 (s, 1H)

MS-ESI: 524.5 [M+H]$^+$

EXAMPLE 53

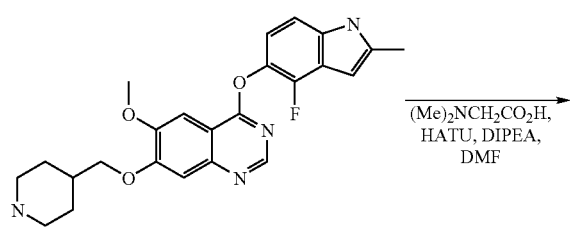

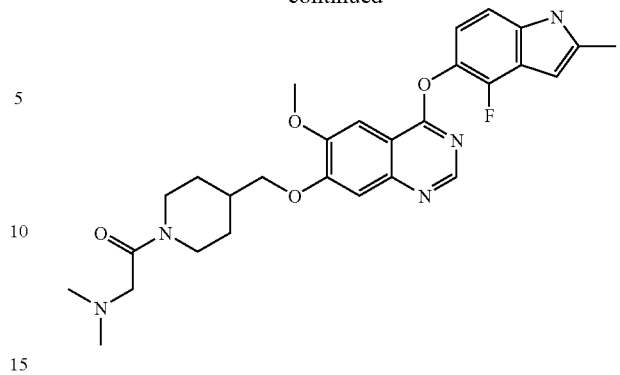

4-[(4-Fluoro-2-methyl-1H-indol)-5-yloxy]-6-methoxy-7-(piperidin-4-ylmethoxy)quinazoline (500 mg, 1.15 mmol), (prepared as described for the starting material in Example 11), N,N-dimethylglycine (142 mg, 1.37 mmol) and O-(7-azabenzotriazol-1-yl)-N,N,N',N'-tetramethyluronium hexafluorophosphate (HATU) (523 mg, 1.37 mmol) were stirred in N,N-dimethylformamide (4 ml) and N,N-diisopropylethylamine (399 µl, 2.29 mmol) was added. The mixture was stirred for 1 hour, diluted with ethyl acetate, washed with brine followed by 2N aqueous sodium hydroxide. The organic layer was dried (MgSO$_4$) and concentrated under reduced pressure. The residue was purified by column chromatography eluting with methylene chloride/methanol (saturated with ammonia) (98/2) to give 7-[1-(N,N-dimethylaminoacetypipeidin-4-ylmethoxy]-4-[(4-fluoro-2-methyl-1H-indol)-5-yloxy]-6-methoxyquinazoline (455 mg, 76%) as a white foam.

MS-ESI: 522.1 [MH]$^+$ $^1$H NMR Spectrum: (DMSOd$_6$) 1.33 (m, 2H); 1.87 (br d, 2H); 2.22 (m, 7H); 2.44 (s, 3H); 2.65 (br t, 1H); 3.10 (m, 3H); 4.02 (s, 3H); 4.12 (m, 3H); 4.43 (br d, 1H); 6.27 (s, 1H); 7.01 (t, 1H); 7.18 (d, 1H); 7.42 (s, 1H); 7.63 (s, 1H); 8.52 (s, 1H); 11.34 (br s, 1H)

EXAMPLE 54

The following illustrate representative pharmaceutical dosage forms containing the compound of formula I, or a pharmaceutically acceptable salt thereof (hereafter compound X), for therapeutic or prophylactic use in humans:

| (a) | |
|---|---|
| Tablet I | mg/tablet |
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) | |
|---|---|
| Tablet II | mg/tablet |
| Compound X | 50 |
| Lactose Ph. Eur | 223.75 |
| Croscarmellose sodium | 6.0 |
| Maize starch | 15.0 |

(b)

| Tablet II | mg/tablet |
|---|---|
| Polyvinylpyrrolidone (5% w/v paste) | 2.25 |
| Magnesium stearate | 3.0 |

(c)

| Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

(d)

| Capsule | mg/capsule |
|---|---|
| Compound X | 10 |
| Lactose Ph. Eur | 488.5 |
| Magnesium stearate | 1.5 |

(e)

| Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

(f)

| Injection II | 10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

(g)

| Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)-(c) may be enteric coated by conventional means, for example to provide a coating of cellulose acetate phthalate.

The invention claimed is:

1. A compound selected from:
 4-[(4-fluoro-2-methyl-1H-indol-5-yl)oxy]-7-{[(2S)-1-isobutyrylpyrrolidin-2-yl]methoxy}-6-methoxyquinazoline,
 6-[2-(4-acetylpiperazin-1-yl)ethoxy]-4-[(4-fluoro-1H-indol-5-yl)oxy]-7-methoxyquinazoline,
 6-[(1-acetylpiperidin-4-yl)methoxy]-4-[(4-fluoro-1H-indol-5-yl)oxy]-7-methoxyquinazoline,
 7-[1-(N,N-dimethylaminoacetyl)piperidin-4-ylmethoxy]-4-[(4-fluoro-2-methyl-1H-indol)-5-yloxy]-6-methoxyquinazoline,
 6-(3-(4-acetylpiperazin-1-yl)propoxy)-4-(4-fluoro-2-methylindol-5-yloxy)-7-methoxyquinazoline,
 4-(4-fluoro-2-methylindol-5-yloxy)-7-methoxy-6-(3-(4-methylsulphonylpiperazin-1-yl)propoxy)quinazoline,
 4-(4-fluoro-2-methylindol-5-yloxy)-6-methoxy-7-(3-(4-methylsulphonylpiperazin-1-yl)propoxy)quinazoline,
 6-(3-(4-acetylpiperazin-1-yl)propoxy)-4-(4-fluoroindol-5-yloxy)-7-methoxyquinazoline,
 7-[(1-acetylpiperidin-4-yl)methoxy]-4-[(4-fluoro-2-methyl-1H-indol-5-yl)oxy]-6-methoxyquinazoline,
 7-[(2S)-1-acetylpyrrolidin-2-ylmethoxy]-4-[(4-fluoro-2-methyl-1H-indol-5-yl)oxy]-6-methoxyquinazoline,
 7-[(2R)-1-acetylpyrrolidin-2-ylmethoxy]-4-[(4-fluoro-2-methyl-1H-indol-5-yl)oxy]-6-methoxyquinazoline,
 7-{2-[2-(4-acetylpiperazin-1-yl)ethoxy]ethoxy}-4-[(4-fluoro-2-methyl-1H-indol-5-yl)oxy]-6-methoxyquinazoline,
 4-[(4-fluoro-2-methyl-1H-indol-5-yl)oxy]-7-[(1-isobutyrylpiperidin-4-yl)methoxy]-6-methoxyquinazoline,
 4-[(4-fluoro-2-methyl-1H-indol-5-yl)oxy]-7-{[(2R)-1-isobutyrylpyrrolidin-2-yl]methoxy}-6-methoxyquinazoline;
 4-[(4-fluoro-2-methyl-1H-indol-5-yl)oxy]-6-methoxy-7-{[1-(methylsulfonyl)piperidin-4-yl]methoxy}quinazoline,
 4-[(4-fluoro-2-methyl-1H-indol-5-yl)oxy]-6-methoxy-7-{[(2S)-1-(methylsulfonyl)pyrrolidin-2-yl]methoxy}quinazoline,
 4-[(4-fluoro-2-methyl-1H-indol-5-yl)oxy]-6-methoxy-7-{[(2R)-1-(methylsulfonyl)pyrrolidin-2-yl]methoxy}quinazoline,
 4-[(4-fluoro-2-methylindol-5-yl)oxy]-6-methoxy-7-{3-[4-(2-propynyl)piperazin-1-yl]propoxy}quinazoline;
 7-[3-(4-acetylpiperazin-1-yl)propoxy]-4-(1H-indol-5-yloxy)-6-methoxyquinazoline,
 7-[(2S)-1-carbamoylpyrrolidin-2-ylmethoxy]-4-[(4-fluoro-2-methyl-1H-indol-5-yl)oxy]-6-methoxyquinazoline;
 7-{3-[4-carbamoylpiperazin-1-yl]propoxy}-4-[(4-fluoro-2-methyl-1H-indol-5-yl)oxy]-6-methoxyquinazoline,
 7-{3-[2,5-dioxo-4-(1-hydroxy-1-methylethyl)imidazolidin-1-yl]propoxy}-4-[(4-fluoro-2-methyl-1H-indol-5-yloxy]-6-methoxyquinazoline,
 6-[(1-acetylpiperidin-4-yl)oxy]-4-[(4-fluoro-1H-indol-5-yl)oxy]-7-methoxyquinazoline,
 4-[(4-fluoro-1H-indol-5-yl)oxy]-7-methoxy-6-{[1-(methylsulphonyl)piperidin-4-yl]oxy}quinazoline;
 4-[(4-fluoro-2-methyl-1H-indol-5-yl)oxy]-6-methoxy-7-{2-[N-methyl-N-(2-propynyl)amino]ethoxy}quinazoline,
 7-[3-(4-acetylpiperazin-1-yl)propoxy]-6-methoxy-4-[(2-methyl-1H-indol-5-yl)oxy]quinazoline,
 7-[3-(4-acetylpiperazin-1-yl)propoxy]-4-[(4-fluoro-1H-indol-5-yl)oxy]-6-methoxyquinazoline, 7-[3-(4-carbamoylmethylpiperazin-1-yl)propoxy]-4-[(4-fluoro-2-methyl-1H-indol-5-yl)oxy]-6-methoxyquinazoline, 4-[(4-fluoro-2-methyl-1H-indol-5-yl)oxy]-7-{(2R)-2-hydroxy-3-[4-prop-2-yn-1-ylpiperazin-1-yl]propoxy}-6-methoxyquinazoline, 7-{(2R)-3-[(1,4-dioxa-8-azaspiro[4.5]dec-8-yl)]-2-hydroxypropoxy}-4-[(4-fluoro-2-methyl-1H-indol-5-yl)oxy]-6-methoxyquinazoline, 7-{(2R)-3-[4-acetylpiperazin-1-yl]-2-hydroxypropoxy}-4-[(4-fluoro-2-methyl-1H-indol-5-yl)oxy]-6-methoxyquinazoline, or a salt thereof.

2. A compound 7-(3-(4-acetylpiperazin-1-yl)propoxy)-4-(4-fluoro-2-methylindol-5-yloxy)-6-methoxyquinazoline or a salt thereof.

3. A compound 7-[2-(4-acetylpiperazin-1-yl)ethoxy]-4-[(4-fluoro-2-methyl-1H-indol-5-yl)oxy]-6-methoxyquinazoline or a salt thereof.

4. A compound 7-benzyloxy-4-(4-fluoro-2-methylindol-5-yloxy)-6-methoxyquinazoline or a salt thereof.

5. A compound 4-(4-fluoro-2-methylindol-5-yloxy)-7-hydroxy-6-methoxyquinazoline or a salt thereof.

6. A process for the preparation of a compound as claimed in claim 4 which comprises:
(i) halogenating 7-benzyloxy-6-methoxy-3,4-dihydroquinazolin-4-one to give 7-benzyloxy-4-chloro-6-methoxyquinazoline hydrochloride;
(ii) optionally, converting 7-benzyloxy-4-chloro-6-methoxyquinazoline hydrochloride to 7-benzyloxy-4-chloro-6-methoxyquinazoline free base; and
(iii) reacting 7-benzyloxy-4-chloro-6 methoxyquinazoline free base or 7-benzyloxy-4-chloro-6-methoxyquinazoline hydrochloride with 4-fluoro-5-hydroxy-2-methylindole to give 7-benzyloxy-4-(4-fluoro-2-methylindol-5-yloxy)-6-methoxyquinazoline.

7. A process for the preparation of a compound as claimed in claim 5 which comprises:
(i) halogenating 7-benzyloxy-6-methoxy-3,4-dihydroquinazolin-4-one to give 7-benzyloxy-4-chloro-6-methoxyquinazoline hydrochloride;
(ii) optionally, converting 7-benzyloxy-4-chloro-6-methoxyquinazoline hydrochloride to 7-benzyloxy-4-chloro-6-methoxyquinazoline free base;
(iii) reacting 7-benzyloxy-4-chloro-6-methoxyquinazoline free base or 7-benzyloxy-4-chloro-6-methoxyquinazoline hydrochloride with 4-fluoro-5-hydroxy-2-methylindole to give 7-benzyloxy-4-(4-fluoro-2-methylindol-5-yloxy)-6-methoxyquinazoline; and
(iv) reducing 7-benzyloxy-4-(4-fluoro-2-methylindol-5-yloxy)-6-methoxyquinazoline to give 4-(4-fluoro-2-methylindol-5-yloxy)-7-hydroxy-6-methoxyquinazoline.

\* \* \* \* \*